(12) United States Patent
Peter et al.

(10) Patent No.: US 11,613,754 B2
(45) Date of Patent: Mar. 28, 2023

(54) TOXIC RNAI ACTIVE SEED SEQUENCES FOR KILLING CANCER CELLS

(71) Applicant: Northwestern University, Evanston, IL (US)

(72) Inventors: Marcus E. Peter, Chicago, IL (US); William E. Putzbach, Lombard, IL (US); Andrea E. Murmann, Chicago, IL (US); Monal Patel, Des Plaines, IL (US); Quan Gao, Chicago, IL (US)

(73) Assignee: Northwestern University, Evanston, IL (US)

( * ) Notice: Subject to any disclaimer, the term of this patent is extended or adjusted under 35 U.S.C. 154(b) by 430 days.

(21) Appl. No.: 15/900,392

(22) Filed: Feb. 20, 2018

(65) Prior Publication Data

US 2018/0320187 A1  Nov. 8, 2018

Related U.S. Application Data

(60) Provisional application No. 62/596,457, filed on Dec. 8, 2017, provisional application No. 62/531,991, filed on Jul. 13, 2017, provisional application No. 62/461,042, filed on Feb. 20, 2017.

(51) Int. Cl.
| | |
|---|---|
| C12N 15/113 | (2010.01) |
| A61P 35/00 | (2006.01) |
| C12N 15/11 | (2006.01) |
| A61K 47/69 | (2017.01) |
| A61K 47/64 | (2017.01) |
| A61K 31/713 | (2006.01) |

(52) U.S. Cl.
CPC ........ *C12N 15/1138* (2013.01); *A61K 31/713* (2013.01); *A61K 47/64* (2017.08); *A61K 47/6931* (2017.08); *A61P 35/00* (2018.01); *C12N 15/11* (2013.01); *C12N 15/111* (2013.01); *C12N 15/113* (2013.01); *C12N 2310/122* (2013.01); *C12N 2310/14* (2013.01); *C12N 2310/141* (2013.01); *C12N 2310/531* (2013.01); *C12N 2320/10* (2013.01); *C12N 2320/52* (2013.01)

(58) Field of Classification Search
CPC ... C12N 15/1138; C12N 15/11; C12N 15/113; C12N 2310/122; C12N 2310/14; A61K 31/713; A61K 47/6931; A61P 35/00
See application file for complete search history.

(56) References Cited

U.S. PATENT DOCUMENTS

| | | | | |
|---|---|---|---|---|
| 7,718,629 B2* | 5/2010 | Bumcrot | ........... | C12N 15/1138 536/23.1 |
| 2008/0038308 A1* | 2/2008 | Miller | ................ | C12N 15/1137 536/24.5 |
| 2009/0217399 A1* | 8/2009 | Stern | ...................... | C12N 15/86 435/375 |
| 2010/0297242 A1* | 11/2010 | Park | ....................... | A61K 47/60 977/773 |
| 2015/0344887 A1 | 12/2015 | Song et al. | | |

FOREIGN PATENT DOCUMENTS

EP   3128008 A2   2/2017

OTHER PUBLICATIONS

Lawrence, MS, et al. Nature (2013), 499(7457):214-218. (Year: 2013).*
Kamola, P.J., et al., "The siRNA non-seed region and its target sequences are auxiliary determinants of off-target effects", PloS Comput Biol., 2015, vol. 11, No. 12, pp. 1-17.
Petri, S., et al., "Increased siRNA duplex stability correlates with reduced off-target and elevated on-target effects", RNA, 2011, vol. 17, No. 4, pp. 737-749.
International Search Report and Written Opinion for PCT/US2018/018801 dated Jun. 7, 2018.
Agostini M, Knight RA. (2014). miR-34: from bench to bedside. Oncotarget. 5:872-81.
Baek D, Villen J, Shin C, Camargo FD, Gygi SP, Bartel DP. (2008). The impact of microRNAs on protein output. Nature. 455:64-71.
Balatti V, Pekarky Y, Rizzotto L, Croce CM. (2013). miR deregulation in CLL. Adv Exp Med Biol. 792:309-25.
Beg MS, Brenner AJ, Sachdev J, Borad M, Kang YK, Stoudemire J, Smith S, Bader AG, Kim S, Hong DS. (2017). Phase I study of MRX34, a liposomal miR-34a mimic, administered twice weekly in patients with advanced solid tumors. Invest New Drugs. 35:180-8.
Bernstein E, Caudy AA, Hammond SM, Hannon GJ. (2001). Role for a bidentate ribonuclease in the initiation step of RNA interference. Nature. 409:363-6.
Birmingham A, Anderson EM, Reynolds A, Ilsley-Tyree D, Leake D, Fedorov Y, Baskerville S, Maksimova E, Robinson K, Karpilow J, Marshall WS, Khvorova A. (2006). 3' UTR seed matches, but not overall identity, are associated with RNAi off-targets. Nat Methods. 3:199-204.
Bramsen JB, Laursen MB, Nielsen AF, Hansen TB, Bus C, Langkjaer N, Babu BR, Hojland T, Abramov M, Van Aerschot A, Odadzic D, Smicius R, Haas J, Andree C, Barman J, Wenska M, Srivastava P, Zhou C, Honcharenko D, Hess S, Muller E, Bobkov GV, Mikhailov SN, Fava E, Meyer TF, Chattopadhyaya J, Zerial M, Engels JW, Herdewijn P, Wengel J, Kjems J. (2009). A large-scale chemical modification screen identifies design rules to generate siRNAs with high activity, high stability and low toxicity. Nucleic Acids Res. 37:2867-81.

(Continued)

Primary Examiner — J. E. Angell
(74) Attorney, Agent, or Firm — Quarles & Brady LLP

(57) ABSTRACT

Disclosed are polynucleotides, compositions, and methods related to RNA interference (RNAi). The disclosed polynucleotides, compositions, and methods may be utilized for treating diseases and disorders through RNAi. Particular disclosed are toxic RNAi active seed sequences and methods of using toxic RNAi active sequences for killing cancer cells. The disclosed toxic RNAi active seed sequences preferentially target and inhibit the expression of multiple essential genes for cell survival and/or growth through a process called "death-induced by survival gene elimination" or "DISE."

20 Claims, 99 Drawing Sheets

Specification includes a Sequence Listing.

(56) References Cited

OTHER PUBLICATIONS

Ceppi P, Hadji A, Kohlhapp F, Pattanayak A, Hau A, Xia L, Liu H, Murmann AE, Peter ME. (2014). CD95 and CD95L promote and protect cancer stem cells. Nature Commun. 5:5238.
Cao W, Yang W, Fan R, Li H, Jiang J, Geng M, Jin Y, Wu Y. (2014). miR-34a regulates cisplatin-induce gastric cancer cell death by modulating PI3K/AKT/survivin pathway. Tumour Biol. 35:1287-95.
Chandradoss SD, Schirle NT, Szczepaniak M, MacRae IJ, Joo C. (2015). A Dynamic Search Process Undedies MicroRNA Targeting. Cell. 162:96-107.
Chang BD, Broude EV, Dokmanovic M, Zhu H, Ruth A, Xuan Y, Kandel ES, Lausch E, Christov K, Roninson IB. (1999). A senescence-like phenotype distinguishes tumor cells that undergo terminal proliferation arrest after exposure to anticancer agents. Cancer Res. 59:3761-7.
Concepcion CP, Bonetti C, Ventura A. (2012). The microRNA-17-92 family of microRNA clusters in development and disease. Cancer journal. 18:262-7.
Concepcion CP, Han YC, Mu P. Bonetti C, Yao E, D'Andrea A, Vidigal JA, Maughan WP, Ogrodowski P. Ventura A. (2012). Intact p53-dependent responses in miR-34-deficient mice. PLoS Genet. 8:e1002797.
Di Martino MT, Leone E, Amodio N, Foresta U, Lionetti M, Pitari MR, Cantafio ME, Gulla A, Conforti F, Morelli E, Tomaino V, Rossi M, Negrini M, Ferrarini M, Caraglia M, Shammas MA, Munshi NC, Anderson KC, Neri A, Tagliaferri P, Tassone P. (2012). Synthetic miR-34a mimics as a novel therapeutic agent for multiple myeloma: in vitro and in vivo evidence. Clin Cancer Res. 18:6260-70.
Elkayam E, Faehnle CR, Morales M, Sun J, Li H, Joshua-Tor L. (2017). Multivalent Recruitment of Human Argonaute by GW182. Mol Cell. 67:646-58 e3.
Eom YW, Kim MA, Park SS, Goo MJ, Kwon HJ, Sohn S, Kim WH, Yoon G, Choi KS. (2005). Two distinct modes of cell death induced by doxorubicin: apoptosis and cell death through mitotic catastrophe accompanied by senescence-like phenotype. Oncogene. 24:4765-77.
Esquela-Kerscher A, Slack FJ. (2006). Oncomirs—microRNAs with a role in cancer. Nat Rev Cancer. 6:259-69.
Eulalio A, Huntzinger E, Izaurralde E. (2008). GW182 interaction with Argonaute is essential for miRNA-mediated translational repression and mRNA decay. Nature structural & molecular biology. 15:346-53.
Fedorov Y, Anderson EM, Birmingham A, Reynolds A, Karpilow J, Robinson K, Leake D, Marshall WS, Khvorova A. (2006). Off-target effects by siRNA can induce toxic phenotype. RNA. 12:1188-96.
Friedman RC, Farh KK, Burge CB, Bartel DP. (2009). Most mammalian mRNAs are conserved targets of microRNAs. Genome Res. 19:92-105.
Grimson A, Farh KK, Johnston WK, Garrett-Engele P, Lim LP, Bartel DP. (2007). MicroRNA targeting specificity in mammals: determinants beyond seed pairing. Mol Cell. 27:91-105.
Gu S, Zhang Y, Jin L, Huang Y, Zhang F, Bassik MC, Kampmann M, Kay MA. (2014). Weak base pairing in both seed and 3' regions reduces RNAi off-targets and enhances si/shRNA designs. Nucleic Acids Res. 42:12169-76.
Hadji A, Ceppi P, Murmann AE, Brockway S, Pattanayak A, Bhinder B, Hau A, De Chant S, Parimi V, Kolesza P, Richards JS, Chandel N, Djaballah H, Peter ME. (2014). Death induced by CD95 or CD95 ligand elimination. Cell Reports. 10:208-22.
Han J, Lee Y, Yeom KH, Kim YK, Jin H, Kim VN. (2004). The Drosha-DGCR8 complex in primary microRNA processing. Genes Dev. 18:3016-27.
Hau A, Ceppi P, Peter ME. (2012). CD95 is part of a let-7/p53/miR-34 regulatory network. PLoS one. 7:e49636.
Hauptmann J, Schraivogel D, Bruckmann A, Manickavel S, Jakob L, Eichner N, Pfaff J, Urban M, Sprunck S, Hafner M, Tuschl T, Deutzmann R, Meister G. (2015). Biochemical isolation of Argonaute protein complexes by Ago-APP. Proc Natl Acad Sci U S A. 112:11841-5.
Hermeking H. (2010). The miR-34 family in cancer and apoptosis. Cell Death Differ. 17:193-9.
He X, He L, Hannon GJ. (2007). The guardian's little helper: microRNAs in the p53 tumor suppressor network. Cancer Res. 67:11099-101.
Hua YJ, Larsen N, Kalyana-Sundaram S, Kjems J, Chinnaiyan AM, Peter ME. (2013). miRConnect 2.0: Identification of antagonistic, oncogenic miRNA families in three human cancers. BMC Genomics. 14:179.
Hutvagner G, McLachlan J, Pasquinelli AE, Balint E, Tuschl T, Zamore PD. (2001). A cellular function for the RNA-interference enzyme Dicer in the maturation of the let-7 small temporal RNA Science (New York, NY). 293:834-8.
Jackson AL, Bartz SR, Schelter J, Kobayashi SV, Burchard J, Mao M, Li B, Cavet G, Linsley PS. (2003). Expression profiling reveals off-target gene regulation by RNAi. Nat Biotechnol. 21:635-7.
Karlas A, Berre S, Couderc T, Varjak M, Braun P, Meyer M, Gangneux N, Karo-Astover L, Weege F, Raftery M, Schonrich G, Klemm U, Wurzlbauer A, Bracher F, Merits A, Meyer TF, Lecuit M. (2016). A human genome-wide loss-of-function screen identifies effective chikungunya antiviral drugs. Nat Commun. 7:11320.
Kim YK, Kim B, Kim VN. (2016). Re-evaluation of the roles of DROSHA, Export in 5, and DICER in microRNA biogenesis. Proc Natl Acad Sci U S A. 113:E1881-9.
Louie E, Ott J, Majewski J. (2003). Nucleotide frequency variation across human genes. Genome Res. 13:2594-601.
Meijer HA, Smith EM, Bushell M. (2014). Regulation of miRNA strand selection: follow the leader? Biochem Soc Trans. 42:1135-40.
Mignone F, Gissi C, Liuni S, Pesole G. (2002). Untranslated regions of mRNAs. Genome Biol. 3:REVIEWS0004.
Mohr SE, Smith JA, Shamu CE, Neumuller RA, Perrimon N. (2014). RNAi screening comes of age: improved techniques and complementary approaches. Nat Rev Mol Cell Biol. 15:591-600.
Murmann AE, Gao QQ, Putzbach WT, Patel M, Bartom ET, Law CY, Bridgeman B, Chen S, McMahon KM, Thaxton CS, Peter ME. (2018). Small interfering RNAs based on huntingtin trinucleotide repeats are highly toxic to cancer cells. In revision.
Murmann AE, McMahon KM, Halluck-Kangas A, Ravindran N, Patel M, Law C, Brockway S, Wei JJ, Thaxton CS, Peter ME. (2017). Induction of DISE in ovarian cancer cells in vivo. Oncotarget. 8:84643-58.
Narendrula R, Mispel-Beyer K, Guo B, Parissenti AM, Pritzker LB, Pritzker K, Masilamani T, Wang X, Lanner C. (2016). RNA disruption is associated with response to multiple classes of chemotherapy drugs in tumor cell lines. BMC Cancer. 16:146.
Park SM, Gaur AB, Lengyel E, Peter ME. (2008). The miR-200 family determines the epithelial phenotype of cancer cells by targeting the E-cadherin repressors, ZEB1 and ZEB2. Genes Dev. 22:894-907.
Park SM, Shell S, Radjabi AR, Schickel R, Feig C, Boyerinas B, Dinulescu DM, Lengyel E, Peter ME. (2007). Let-7 Prevents Early Cancer Progression by Suppressing Expression of the Embryonic Gene HMGA2. Cell Cycle. 6:2585-90.
Patel M, Peter ME. (2017). Identification of DISE-inducing shRNAs by monitoring cellular responses. Cell Cycle, doi: 10.1080/15384101.2017.1383576.
Patel VD, Capra JA. (2017). Ancient human miRNAs are more likely to have broad functions and disease associations than young miRNAs. BMC Genomics. 18:672.
Peter ME. (2009). Let-7 and miR-200 microRNAs: guardians against pluripotency and cancer progression. Cell Cycle. 8:843-52.
Petri S, Meister G. (2013). siRNA design principles and off-target effects. Methods Mol Biol. 986:59-71.
Utzbach W, Gao QQ, Patel M, Haluck-Kangas A, Murmann AE, Peter ME. (2017). DISE—A Seed Dependent RNAi Off-Target Effect that Kills Cancer Cells. Trends in Cancer. In press.
Putzbach W, Gao QQ, Patel M, van Dongen S, Haluck-Kangas A, Sarshad AA, Bartom E, Kim KY, Scholtens DM, Halner M, Zhao JC, Murmann AE, Peter ME. (2017). Many si/shRNAs can kill cancer cells by targeting multiple survival genes through an off-target mechanism. eLife. 6: e29702.

(56) References Cited

OTHER PUBLICATIONS

Schickel R, Boyerinas B, Park SM, Peter ME. (2008). MicroRNAs: key players in the immune system, differentiation, tumorigenesis and cell death. Oncogene. 27:5959-74.

Schirle NT, MacRae IJ. (2012). The crystal structure of human Argonaute2. Science (New York, NY). 336:1037-40.

Selbach M, Schwanhausser B, Thierfelder N, Fang Z, Khanin R, Rajewsky N. (2008). Widespread changes in protein synthesis induced by microRNAs. Nature. 455:58-63.

Slabakova E, Culig Z, Remsik J, Soucek K. (2017). Alternative mechanisms of miR-34a regulation in cancer. Cell Death Dis. 8:e3100.

Stark A, Brennecke J, Bushati N, Russell RB, Cohen SM. (2005). Animal MicroRNAs confer robustness to gene expression and have a significant impact on 3'UTR evolution. Cell. 123:1133-46.

Ui-Tei K, Naito Y, Takahashi F, Haraguchi T, Ohki-Hamazaki H, Juni A, Ueda R, Saigo K. (2004). Guidelines for the selection of highly effective siRNA sequences for mammalian and chick RNA interference. Nucleic Acids Res. 32:936-48.

Wa;z AL, Ooms A, Gadd S, Gerhard DS, Smith MA, Guidry Auvil JM, Meerzaman D, Chen QR, Hsu CH, Yan C, Nguyen C, Hu Y, Bowlby R, Brooks D, Ma Y, Mungall AJ, Moore RA, Schein J, Marra MA, Huff V, Dome JS, Chi YY, Mullighan CG, Ma J, Wheeler DA, Hampton OA, Jafari N, Ross N, Gastier-Foster JM, Perlman EJ. (2015). Recurrent DGCR8, DROSHA, and SIX homeodomain mutations in favorable histology Wilms tumors. Cancer Cell. 27:286-97.

Wang D, Lippard SJ. (2005). Cellular processing of platinum anticancer drugs. Nat Rev Drug Discov. 4:307-20.

Wang Y, Sheng G, Juranek S, Tuschl T, Patel DJ. (2008). Structure of the guide-strand-containing argonaute silencing complex. Nature. 456:209-13.

Whitehurst AW, Bodemann BO, Cardenas J, Ferguson D, Girard L, Peyton M, Minna JD, Michnoff C, Hao W, Roth MG, Xie XJ, White MA. (2007). Synthetic lethal screen identification of chemosensitizer loci in cancer cells. Nature. 446:815-9.

Yang J, Chen D, He Y, Melendez A, Feng Z, Hong Q, Bai X, Li Q, Cai G, Wang J, Chen X. (2013). MiR-34 modulates Caenorhabditis elegans lifespan via repressing the autophagy gene atg9. Age. 35:11-22.

Yeung TK, Germond C, Chen X, Wang Z. (1999). The mode of action of taxol: apoptosis at low concentration and necrosis at high concentration. Biochem Biophys Res Commun. 263:398-404.

Yi R, Qin Y, Macara IG, Cullen BR. (2003). Exportin-5 mediates the nuclear export of pre-microRNAs and short hairpin RNAs. Genes Dev. 17:3011-6.

Yoo SH, Yoon YG, Lee JS, Song YS, Oh JS, Park BS, Kwon TK, Park C, Choi YH, Yoo YH. (2012). Etoposide induces a mixed type of programmed cell death and overcomes the resistance conferred by Bcl-2 in Hep3B hepatoma cells. Int J Oncol. 41:1443-54.

Zare H, Khodursky A, Sartorelli V. (2014). An evolutionarily biased distribution of miRNA sites toward regulatory genes with high promoter-driven intrinsic transcriptional noise. BMC Evol Biol. 14:74.

Kozomara A, Griffiths-Jones S. (2014). miRBase: annotating high confidence microRNAs using deep sequencing data. Nucleic acids research. 42:D68-73.

Kumar MS, Lu J, Mercer KL, Golub TR, Jacks T. (2007). Impaired microRNA processing enhances cellular tansformation and tumorigenesis. Nat Genet. 39:673-7.

Kwon HK, Shin HJ, Lee JH, Park SH, Kwon MC, Panneerselvam S, Lee CG, Kim SG, Kim JH, Choi S. (2015). Etoposide Induces Necrosis Through p53-Mediated Antiapoptosis in Human Kidney Proximal Tubule Cells. Toxicol Sci. 148:204-19.

Meredith AM, Dass CR. (2016). Increasing role of the cancer chemotherapeutic doxorubicin in cellular metabolism. J Pharm Pharmacol. 68:729-41.

Mutational heterogeneity in cancer and the search for new cancer-associated genes. Nature. 499:214-8.

Navarro F, Lieberman J. (2015). miR-34 and p53: New Insights into a Complex Functional Relationship. PLoS One. 10:e0132767.

Lee Y, Kim M, Han J, Yeom KH, Lee S, Baek SH, Kim VN. (2004). MicroRNA genes are transcribed by RNA polymerase II. EMBO J. 23:4051-60.

Lenkala D, LaCroix B, Gamazon ER, Geeleher P, Im HK, Huang RS. (2014). The impact of microRNA expression on cellular proliferation. Human genetics. 133:931-8.

Leuschner PJ, Ameres SL, Kueng S, Martinez J. (2006). Cleavage of the siRNA passenger strand during RISC assembly in human cells. EMBO reports. 7:314-20.

Lewis BP, Burge CB, Bartel DP. (2005). Conserved seed pairing, often flanked by adenosines, indicates that thousands of human genes are microRNA targets. Cell. 120:15-20.

* cited by examiner

FIG. 19

| The TS-D genes | Full name | TSG for Cancer | Kd lethal for # of cell lines | AVG H score |
|---|---|---|---|---|
| PAFAH1B1/LIS1 | Platelet-activating factor acetylhydrolase 1b, regulatory subunit 1 (45kDa) | HCC [1] | | |
| NGFR | Nerve growth factor receptor | HCC [2], retinoblastoma [3], prostate cancer [4], bladder cancer [5] | | |
| ITGAV/CD51 | Integrin Alpha V | Ovarian cancer [6], SCC [7] | | 76 |
| DPP4/CD26 | Dipeptidyl-peptidase 4 | NSCLC [8] | 10 | |
| EFNA5 | Ephrin-A5 | Glioma [9] | 10 | |
| TMEFF1 | Transmembrane protein with EGF-like and two follistatin-like domains 1 | Brain cancers [10] | 10 | |
| CHEK1 | Checkpoint kinase 1 | BrCa [11], Multiple cancers [12] | 10 | 55 |
| PTCH2 | Patched 2 | Basal cell carcinoma [13] | 9 | |
| ARMC10/SVH | Armadillo repeat containing 10 | Osteosarcoma [14], Leukemia [15] | 9 | |
| BECN1/ATG6 | Beclin 1 | Breast cancer [16, 17, 18] | 9 | |
| FASLG | Fas ligand | Multiple cancers [19] | 9 | |
| DDX3X/DBX | DEAD (Asp-Glu-Ala-Asp) box helicase 3, X-linked | HCC [20, 21], cutaneous squamous cell carcinoma [21] | 9 | |
| THY1/CD90 | Thy-1 cell surface antigen | Nasopharyngeal carcinoma [22], ovarian cancer [23, 24] | 9 | |
| PHB | Prohibitin | Prostate cancer [25], liver cancer [26] | 9 | |
| SOCS3 | Suppressor of cytokine signaling 3 | Breast cancer [27] | 9 | |
| ZNF366/DC-SCRIPT | Zinc finger protein 366 | Breast cancer [28] | 9 | |
| MAPKAPK5/MK5/PRAK | Mitogen-activated protein kinase-activated protein kinase 5 | Colon cancer [29], skin cancer [30] | 9 | 68 |
| TGFBR2 | Transforming growth factor, beta receptor II (70/80kDa) | HCC [31], breast cancer [32, 33] | 9 | 58 |

| Treatment group: Mouse ID: | Units | siScr 870 | siScr 887 | siL2 912 | siL2 877 | siL3 865 | siL3 894 |
|---|---|---|---|---|---|---|---|
| Assay | | | | | | | |
| CHOL | mg/dL | 85 | 85 | 90 | 86 | 89 | 101 |
| TRIG | mg/dL | 76 | | 46 | 42 | 60 | 38 |
| ALT | U/L | 366 | 12 | 8 | 15 | 15 | 17 |
| AST | U/L | | 130 | 77 | 84 | 100* | 116 |
| GGT | U/L | | | 3* | 3* | 3* | 3* |
| ALK | U/L | 27 | 18 | 24 | 27 | 33 | 25 |
| GLU | mg/dL | 129 | 95 | 114 | 144 | 120 | 123 |
| PHOS | mg/dL | | | | | 8.2 | |
| Ca | mg/dL | | | 8.6 | 8.9 | 9.1 | |
| TBIL | mg/dL | 0.65 | 0.25 | 0.35 | 0.31 | 0.26 | 0.27 |
| TP | g/dL | 4.6* | 4.4* | 4.5 | 4.5 | 4.6 | 4.6 |
| ALB | g/dL | 2.0* | 1.9* | 2.2 | 2.3 | 2.4 | 2.2 |
| GLOB | g/dL | | | 2.3 | 2.2 | 2.2 | 2.4 |
| A/G | | | | 1.0* | 1.00* | 1.1 | 0.9 |
| BUN | mg/dL | 19 | 13 | 14 | 16 | 19 | 16 |
| CREAT | mg/dL | | | 0.2* | 0.2* | 0.2* | 0.2* |
| B/C | | | | | | | |
| Na | mEq/L | | | | | 148 | |
| K | mEq/L | | | | | 6.5 | |
| Cl | mEq/L | | | | | 117 | |
| Na/K | - | | | | | 22.77 | |

Ranked

| GO Term | Description | P-value | FDR q-value | Enrichment |
|---|---|---|---|---|
| GO:0032502 | developmental process | 1.66E-14 | 2.52E-10 | 1.40 |
| GO:0006357 | regulation of transcription by RNA polymerase II | 2.86E-14 | 2.17E-10 | 1.57 |
| GO:0080090 | regulation of primary metabolic process | 3.80E-13 | 1.92E-09 | 1.25 |
| GO:0031325 | positive regulation of cellular metabolic process | 6.39E-13 | 2.42E-09 | 1.39 |
| GO:0048856 | anatomical structure development | 6.87E-13 | 2.08E-09 | 1.50 |
| GO:0048522 | positive regulation of cellular process | 7.06E-13 | 1.78E-09 | 1.31 |
| GO:0050794 | regulation of cellular process | 8.92E-13 | 1.93E-09 | 1.16 |
| GO:0051173 | positive regulation of nitrogen compound metabolic process | 9.24E-13 | 1.75E-09 | 1.40 |
| GO:0065007 | biological regulation | 9.67E-13 | 1.63E-09 | 1.13 |
| GO:0010604 | positive regulation of macromolecule metabolic process | 1.72E-12 | 2.60E-09 | 1.39 |
| GO:0031323 | regulation of cellular metabolic process | 2.21E-12 | 3.05E-09 | 1.24 |
| GO:0050793 | regulation of developmental process | 3.16E-12 | 3.99E-09 | 1.44 |
| GO:0048523 | negative regulation of cellular process | 3.63E-12 | 4.23E-09 | 1.30 |
| GO:0051171 | regulation of nitrogen compound metabolic process | 6.14E-12 | 6.64E-09 | 1.24 |
| GO:0009893 | positive regulation of metabolic process | 6.18E-12 | 6.24E-09 | 1.36 |
| GO:0050789 | regulation of biological process | 6.23E-12 | 5.90E-09 | 1.14 |
| GO:0048518 | positive regulation of biological process | 7.15E-12 | 6.37E-09 | 1.25 |
| GO:0051254 | positive regulation of RNA metabolic process | 9.66E-12 | 8.13E-09 | 1.57 |

Reverse ranked

| GO Term | Description | P-value | FDR q-value | Enrichment |
|---|---|---|---|---|
| GO:0050907 | detection of chemical stimulus involved in sensory perception | 1.22E-105 | 1.85E-101 | 7.82 |
| GO:0050911 | detection of chemical stimulus involved in sensory perception of smell | 1.18E-100 | 8.98E-97 | 8.42 |
| GO:0009593 | detection of chemical stimulus | 1.11E-95 | 5.60E-92 | 6.9 |
| GO:0050906 | detection of stimulus involved in sensory perception | 7.82E-90 | 2.96E-86 | 6.49 |
| GO:0051606 | detection of stimulus | 2.07E-68 | 6.28E-65 | 5.23 |
| GO:0007186 | G-protein coupled receptor signaling pathway | 7.50E-49 | 1.89E-45 | 4.49 |
| GO:0007608 | sensory perception of smell | 3.19E-22 | 6.91E-19 | 127 |
| GO:0007606 | sensory perception of chemical stimulus | 1.10E-17 | 2.09E-14 | 7.08 |
| GO:0006959 | humoral immune response | 4.51E-15 | 7.59E-12 | 3.2 |
| GO:0042742 | defense response to bacterium | 1.07E-14 | 1.62E-11 | 2.99 |
| GO:0009617 | response to bacterium | 9.50E-14 | 1.32E-10 | 2.61 |

| | | | HCT116 wt | | | | HCT116 wt | | |
|---|---|---|---|---|---|---|---|---|---|
| Ranking | Fold up | miRNA | Most upregulated 5' end | Percent of all | Seed viability | Most abundant 5' end | Percent of all | Seed viability |
| 1 | 6.5x | hsa-miR-148a-3p | TCAGTGCACTACAGAACTT | 1.1% | 73.9% | TCAGTGCACTACAGAACTT | 1.1% | 73.9% |
| 2 | 5.1x | hsa-miR-143-3p | TGAGATGAAGCACTGTAGC | 0.6% | 78.1% | TGAGATGAAGCACTGTAGC | 0.6% | 78.1% |
| 3 | 3.9x | hsa-miR-21-5p | GAGCTTATCAGACTGATGT | 8.0% | 84.2% | GAGCTTATCAGACTGATGT | 8.0% | 84.2% |
| 47 | 1.8x | hsa-miR-320a-3p | AAAAGCTGGGTTGAGAGGCG | 0.4% | 3.2% | AAAAGCTGGGTTGAGAGGG | 2.2% | 47.3% |

| | | | HCT116 Drosha−/− | | | | | | |
|---|---|---|---|---|---|---|---|---|---|
| 1 | 1.5x | hsa-miR-320a-3p | AAAAGCTGGGTTGAGAGGGCG | 2.6% | 3.2% | AAAAGCTGGGTTGAGAGGG | 77.1% | 47.3% |

US 11,613,754 B2

TOXIC RNAI ACTIVE SEED SEQUENCES FOR KILLING CANCER CELLS

CROSS-REFERENCE TO RELATED PATENT APPLICATIONS

This application claims the benefit of priority under 35 U.S.C. § 119(e) to U.S. Provisional Application No. 62/596,457, filed on Dec. 8, 2017, to U.S. Provisional Application No. 62/531,991, filed on Jul. 13, 2017, and to U.S. Provisional Application No. 62/461,042, filed on Feb. 20, 2017, the contents of which are incorporated herein by reference in their entireties.

STATEMENT REGARDING FEDERALLY SPONSORED RESEARCH OR DEVELOPMENT

This invention was made with government support under R35 CA197450 awarded by the National Institutes of Health. The government has certain rights in the invention.

BACKGROUND

The field of the invention relates to RNA interference (RNAi) and the use of RNAi active sequences for treating diseases and disorders. In particular, the field of the invention relates to the use of toxic RNAi active seed sequences for killing cancer cells.

SUMMARY

Disclosed are polynucleotides, compositions, and methods related to RNA interference (RNAi). The disclosed polynucleotides, compositions, and methods may be utilized for treating diseases and disorders through RNAi. Particular disclosed are toxic RNAi active seed sequences and methods of using toxic RNAi active seed sequences for killing cancer cells.

The disclosed toxic RNAi active seed sequences preferentially target and inhibit the expression of multiple essential genes for cell survival and/or growth through a process called "death-induced by survival gene elimination" or "DISE." The disclosed toxic RNAi active seed may be presented or administered in siRNAs, shRNAs, and/or vectors that express siRNAs and/or shRNAs.

TAAAACCGTTTGCTGGGGCTGG; (SEQ ID NO: 151)

TATCCCCAGATCTACTGGGTGG; (SEQ ID NO: 152)

CCTTGTGATCAATGAAACTGGG; (SEQ ID NO: 153)

CCCGGGTCAATCTTGCAACAAC; (SEQ ID NO: 154)

CCGGACCCAGAATACCAAGTGC; (SEQ ID NO: 155)

TGTTTGCTCATTTAAACACTGG. (SEQ ID NO: 156))

Figure 3:
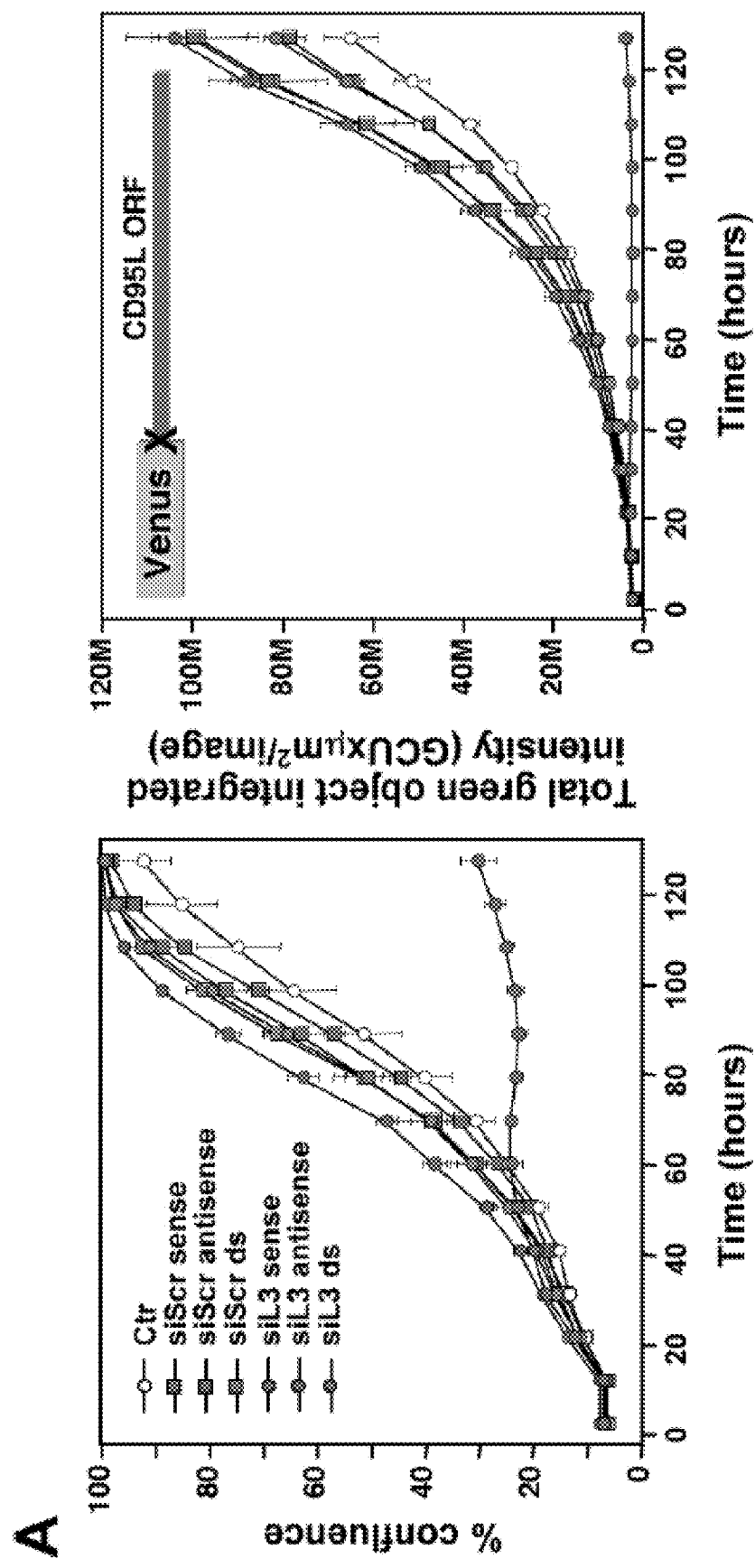
Figure 3:
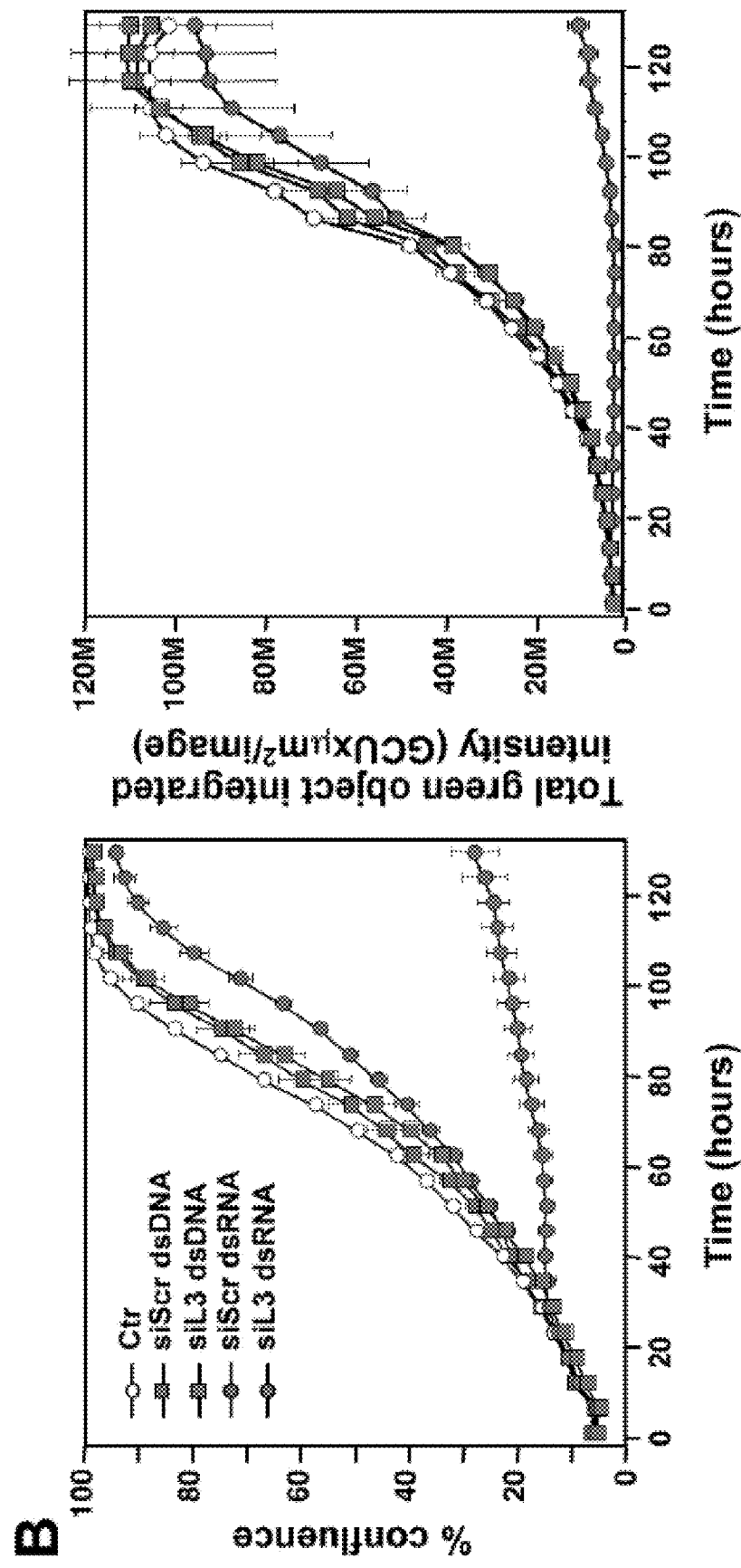
Figure 3:
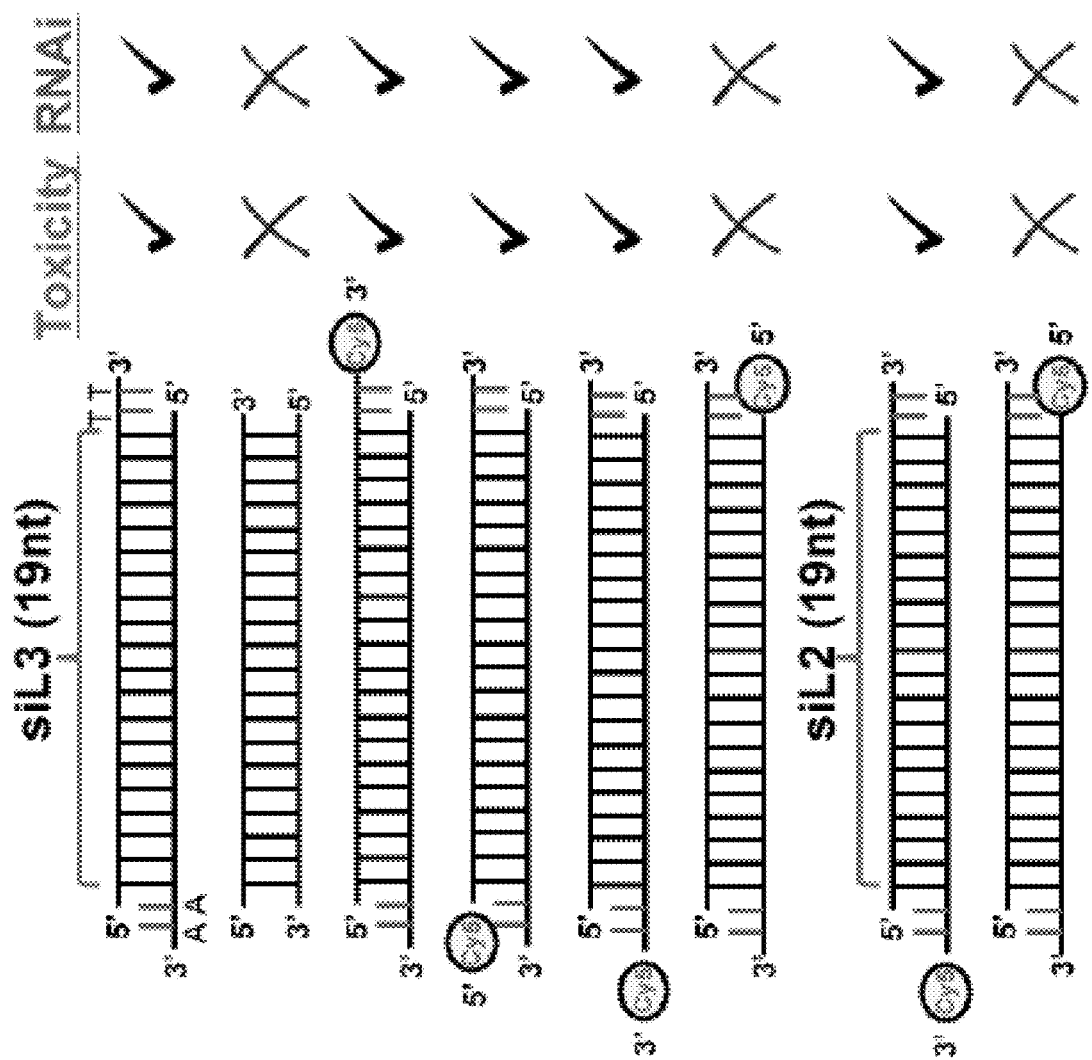
Figure 3:
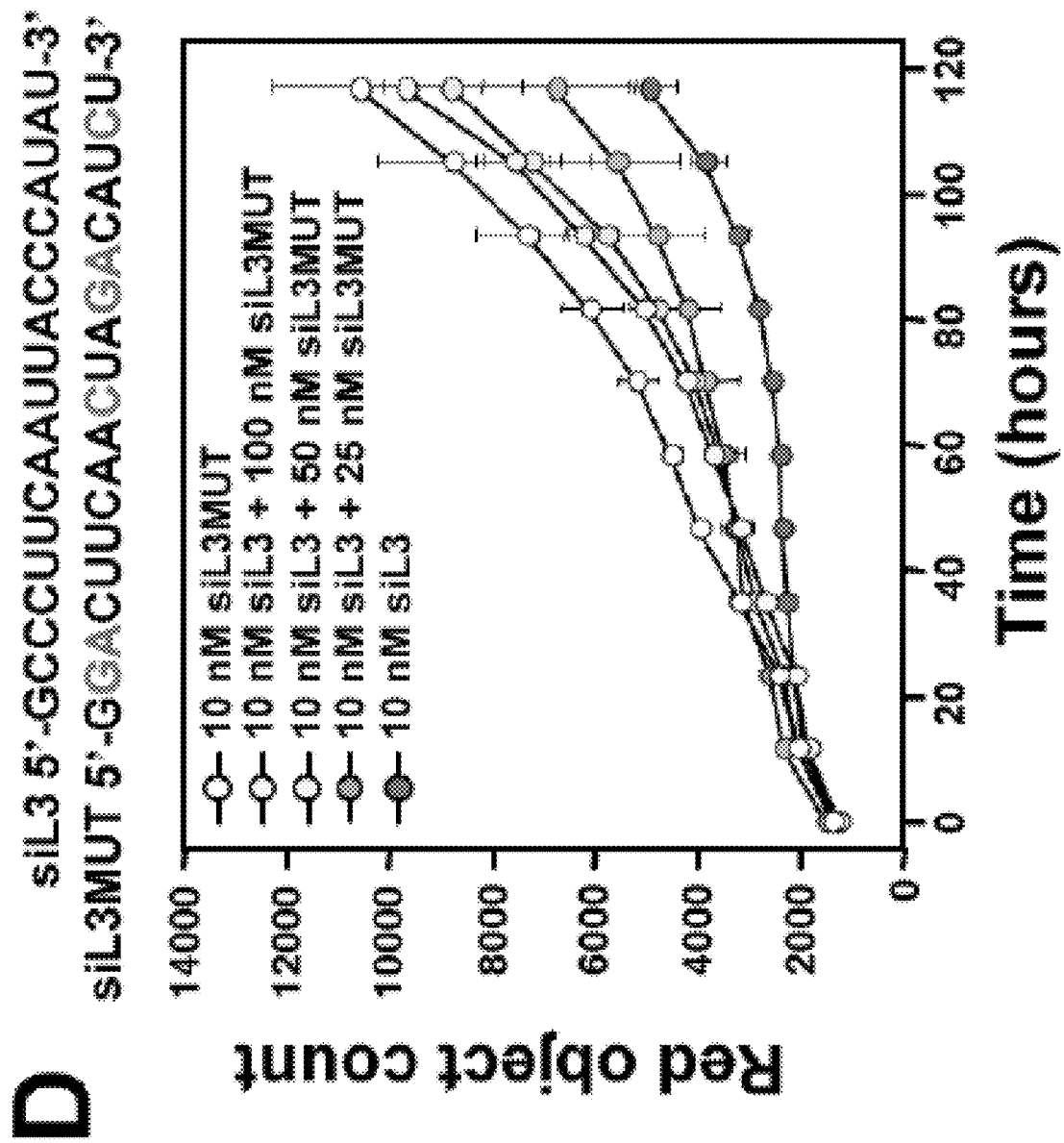
Figure 3:
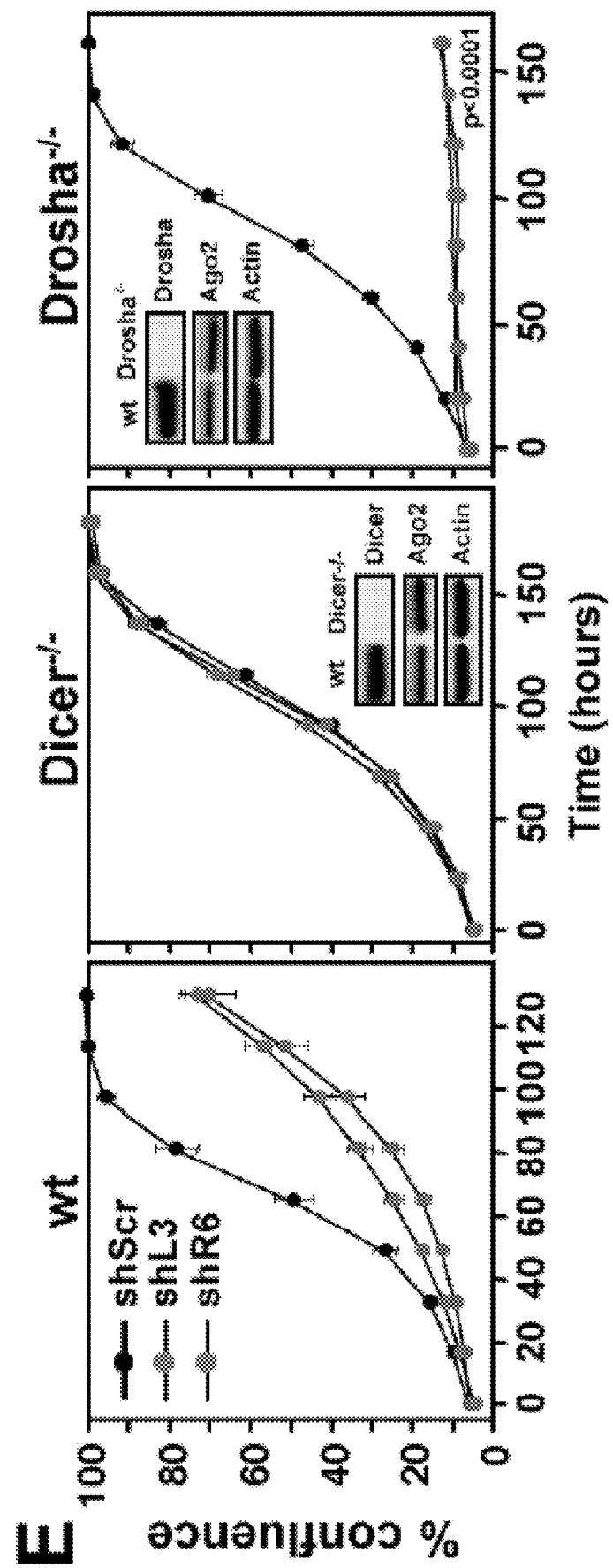
Figure 3:
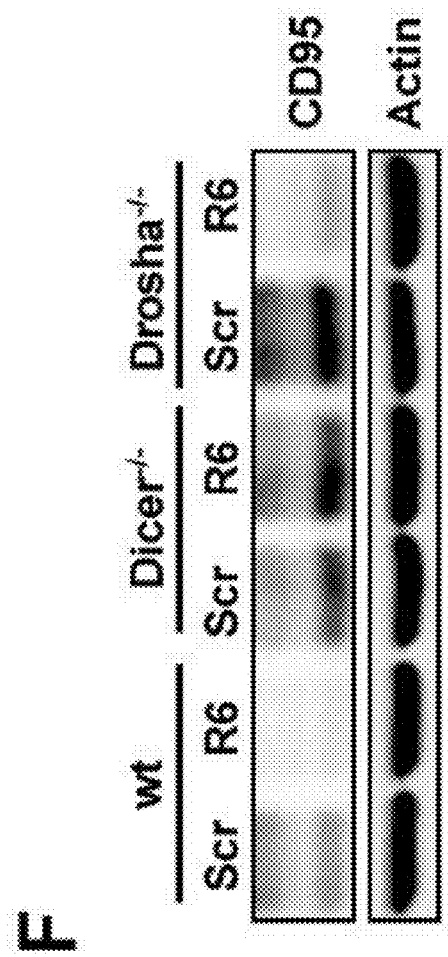
Figure 3:
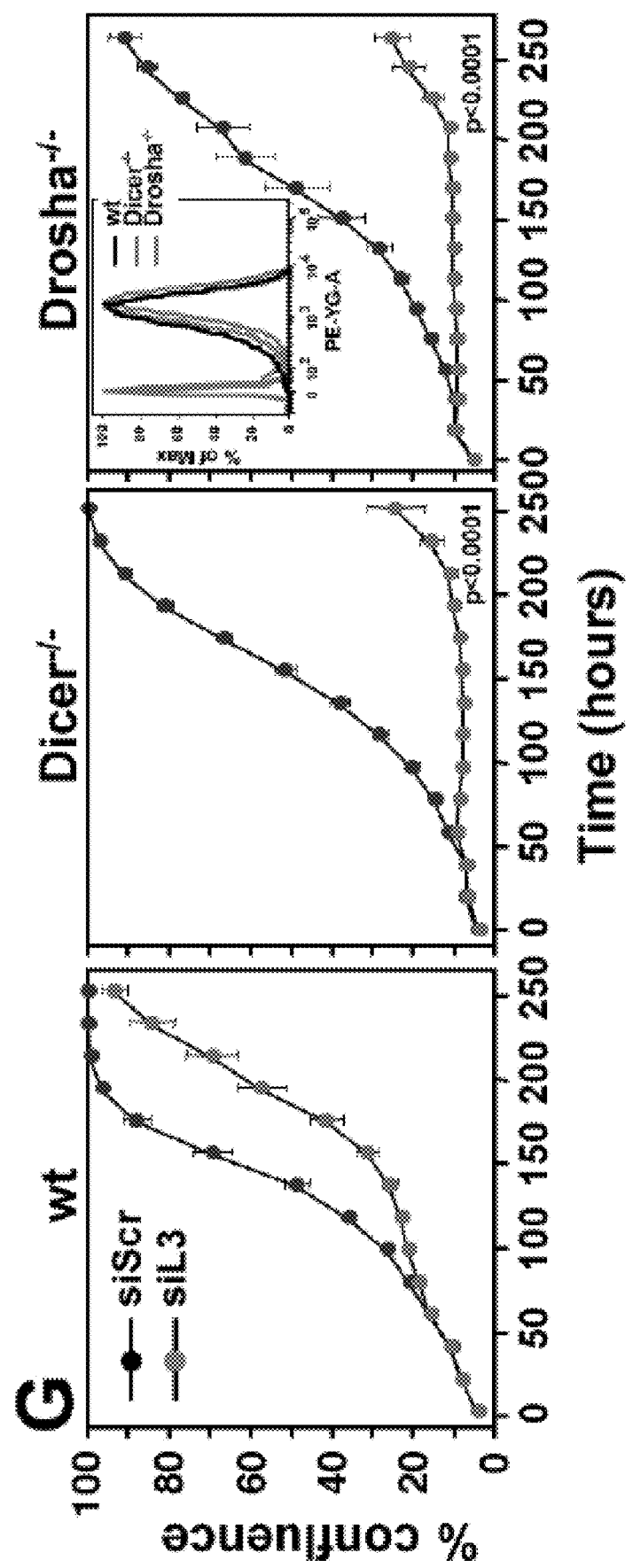
Figure 3:
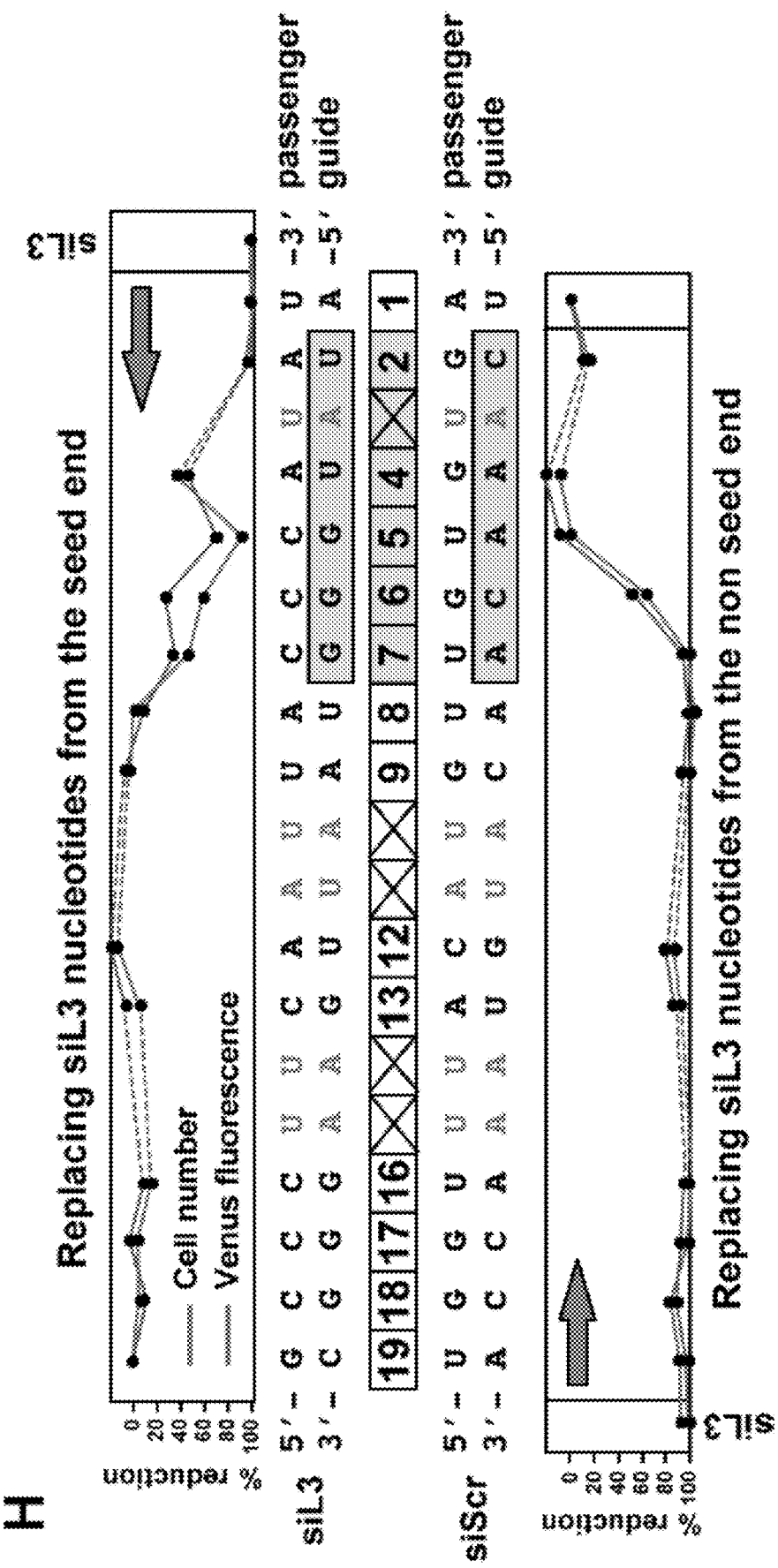

FIGS. 3. (A, B, C, D, E, F, G, and H) Toxicity of CD95L derived siRNAs involves canonical RNAi activity. (A) Percent cell confluence (left) and total green object integrated intensity (right) over time of a HeyA8 CD95 knockout clone (ΔR6 cl #2) expressing the Venus-CD95L sensor either untreated (Ctr) or after transfection with 25 nM of single-stranded sense, single-stranded antisense, or double-stranded (ds) siScr or siL3 siRNAs. The CD95L sensor is schematically shown and comprises the Venus ORF fused to the CD95L ORF lacking the A of the ATG start codon (X). Data are representative of two independent experiments. Each data point represents mean±SE of three replicates. (B) Percent cell confluence (left) and total green object integrated intensity (right) over time of the HeyA8 CD95L sensor cell used in FIG. 3A after transfection with 5 nM siScr or siL3 double-stranded RNA (dsRNA) or double-stranded DNA (dsDNA). Data are representative of two independent experiments. Each data point represents mean±SE of three replicates. (C) Summary of experiments to test whether siL3 and siL2 siRNAs modified as indicated (left) were active (check mark) or not (X) in reducing green fluorescence or cell growth (both >70% reduction at end point) when transfected at 25 nM (except for blunt end oligonucleotides which were used at 5 nM and compared to 5 nM of siL3) into HeyA8 CD95L sensor cells used in FIG. 3A. Endpoints were 164 hours for blunt end siRNA transfection, 180 hrs for modified siL3 and 144 hrs for modified siL2 siRNA transfections. Every data row is based on cell growth and green fluorescence quantification data executed as shown in A. Each analysis was done in triplicate and based on two independent repeats. (D) Red object count over time of HeyA8 cells (expressing NucRed) after transfection with different ratios of siL3 and mutant siL3 (siL3MUT). Data are representative of two independent experiments. Each data point represents mean±SE of three replicates. (Sequence Listing: GCCCUUCAAUUACCCAUAU (SEQ ID NO:40); GGACUUCAACUAGACAUCU (SEQ ID NO:42)). (E) Percent cell confluence over time of HCT116 parental (left) or Dicer$^{-/-}$ (clone #43, another Dicer$^{-/-}$ clone, #45, gave a similar result, data not shown), or Drosha$^{-/-}$ (right) cells after infection with either shScr, shL3 or shR6 pLKO viruses. Inserts show the level of protein expression levels of Drosha/Dicer and AGO2 levels in the tested cells. Data are representative of three independent experiments. Each data point represents mean±SE of four replicates. Drosha$^{-/-}$ cells were more sensitive to toxic shRNAs than wt cells (p<0.0001, according to a polynomial fitting model). (F) Western blot analysis of HCT116 wt, Dicer$^{-/-}$ or Drosha$^{-/-}$ cells 4 days after infection with either pLKO-shScr or pLKO-shR6. (G) Percent cell confluence over time of HCT116 wt, Dicer$^{-/-}$ (clone #43) and Drosha$^{-/-}$ cells after transfection with 25 nM siScr or siL3. Data are representative of four independent experiments (Dicer$^{-/-}$ clone #45, gave a similar result, data not shown). Each data point represents the mean±SE of four replicates. Data in insert confirm similar uptake of transfected siRNA (25 nM of siGLO Red) into wild-type, Dicer$^{-/-}$ and Drosha$^{-/-}$ cells. Dicer$^{-/-}$ and Drosha$^{-/-}$ cells were more sensitive to siL3 than wt cells (p<0.0001, according to a polynomial fitting model). (H) Percent reduction in Venus expression and in cell number over time of HeyA8 cells expressing the Venus-CD95L sensor and red nuclei after transfection with 5 nM of different chimeric siRNAs generated by substituting nucleotides in the toxic siL3 with the scrambled siRNA sequence beginning at either the seed match end (top) or the opposite end (bottom) of siL3 after 188 hours. The schematic in the middle shows the sequence of siL3 and the siScr siRNA (both sense and antisense strands). The 6mer seed sequence region of siL3 (positions 2 to 7) is highlighted. Nucleotides shared by siScr and siL3 are shown in grey font. Data are representative of two independent experiments. Each data point represents mean of three replicates. In another independent experiment cells were transfected with 25 nM with a very similar result (data not shown).

Figure 4:
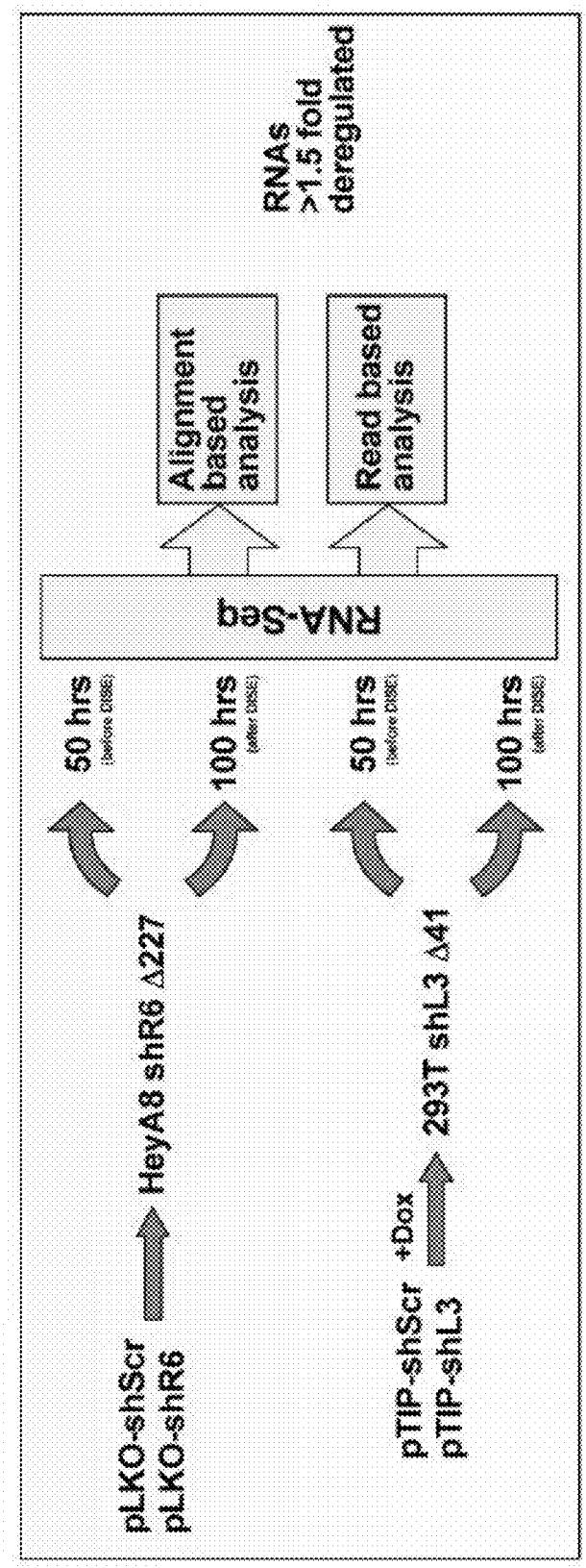
Figure 4:
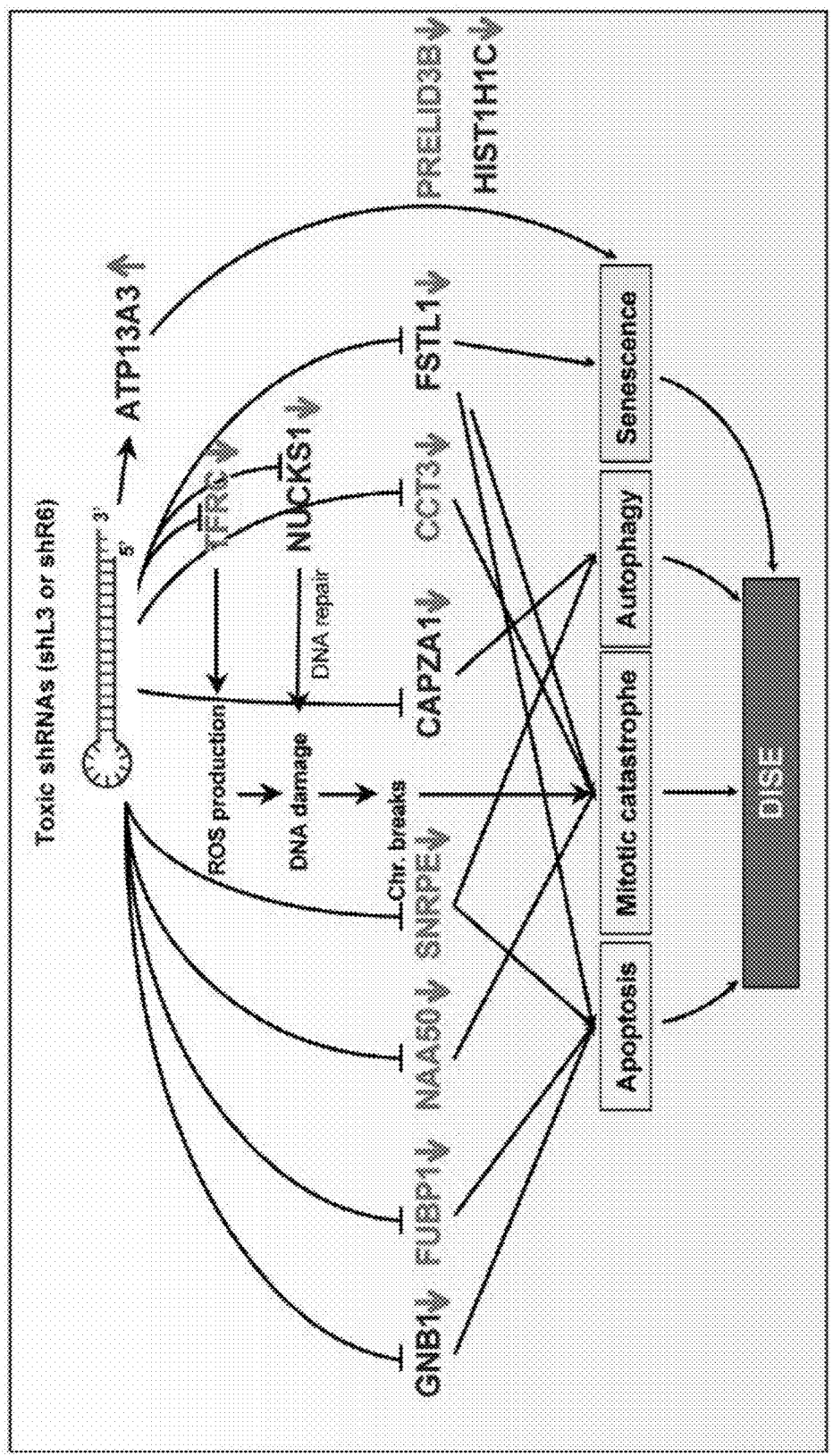
Figure 4:
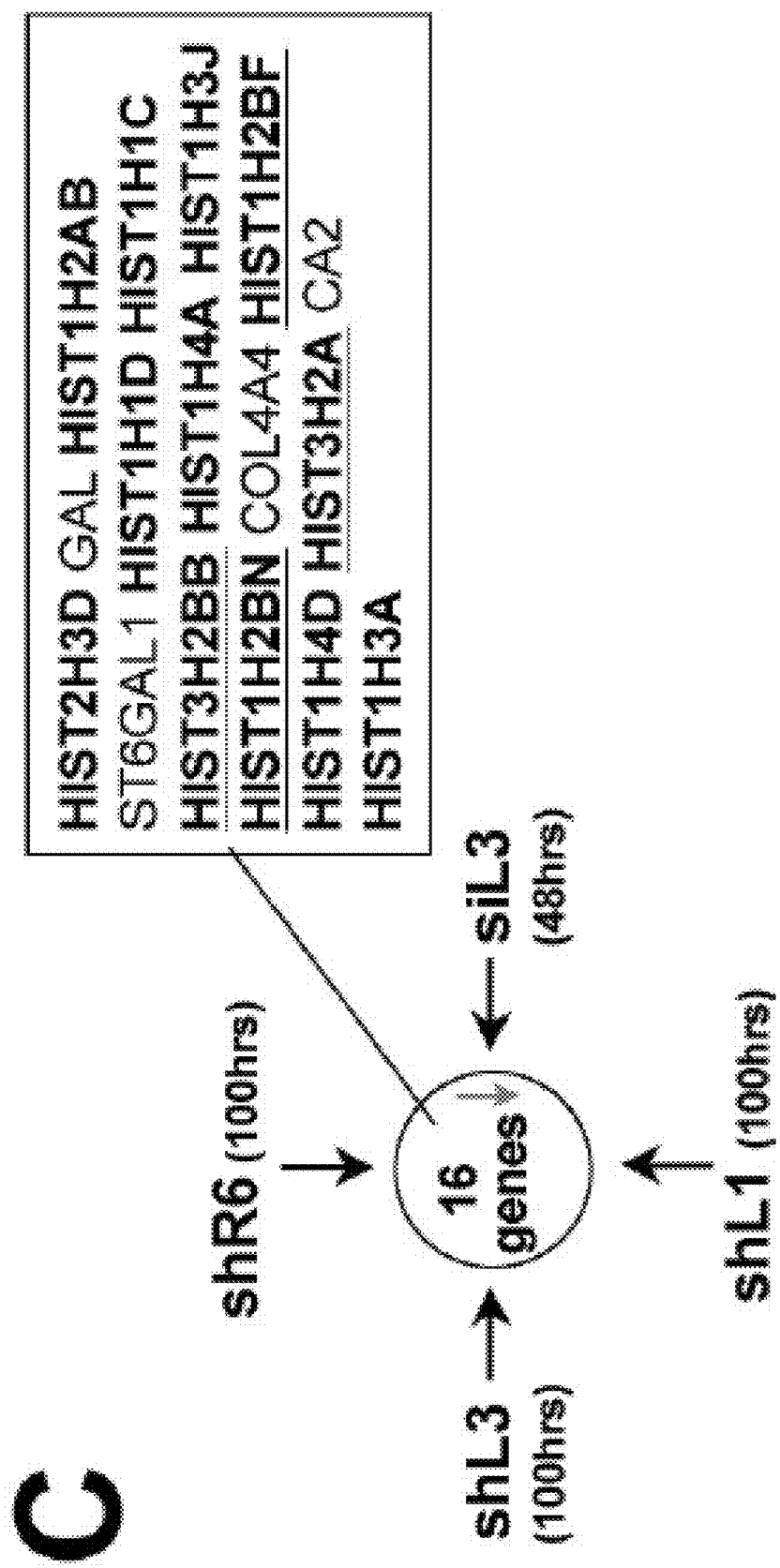

FIGS. 4. (A, B, and C). Toxic shRNAs derived from CD95 and CD95L cause downregulation of critical survival genes. (A) Schematic of RNA-Seq work flow for total RNA sample prepared both before (50 hrs) and during (100 hrs) DISE after expressing either shR6 or shL3 from different vector systems (i.e. pLKO-shR6 and pTIP-shL3) in different cells (HeyA8 shR6 Δ227 cells and 293T shL3 Δ41 cells). (B) One mRNA was up and 11 mRNAs were downregulated in the cells treated with toxic shL3 and shR6 as shown in FIG. 4A. Illustrated mRNAs were found to be essential cancer survival genes in two genome-wide lethality screens. The number of essential genes was enriched from 6.6% of the tested genes (Blomen et al., 2015; Wang et al., 2015) to 54.5% in our study (p=3×10$^{-6}$ according to binomial distribution). (C) Schematics showing all RNAs at least 1.5 fold downregulated (adj p-value <0.05) in cells treated as in FIG. 4A. Histones that are underlined contain a 3'UTR.

Figure 5:
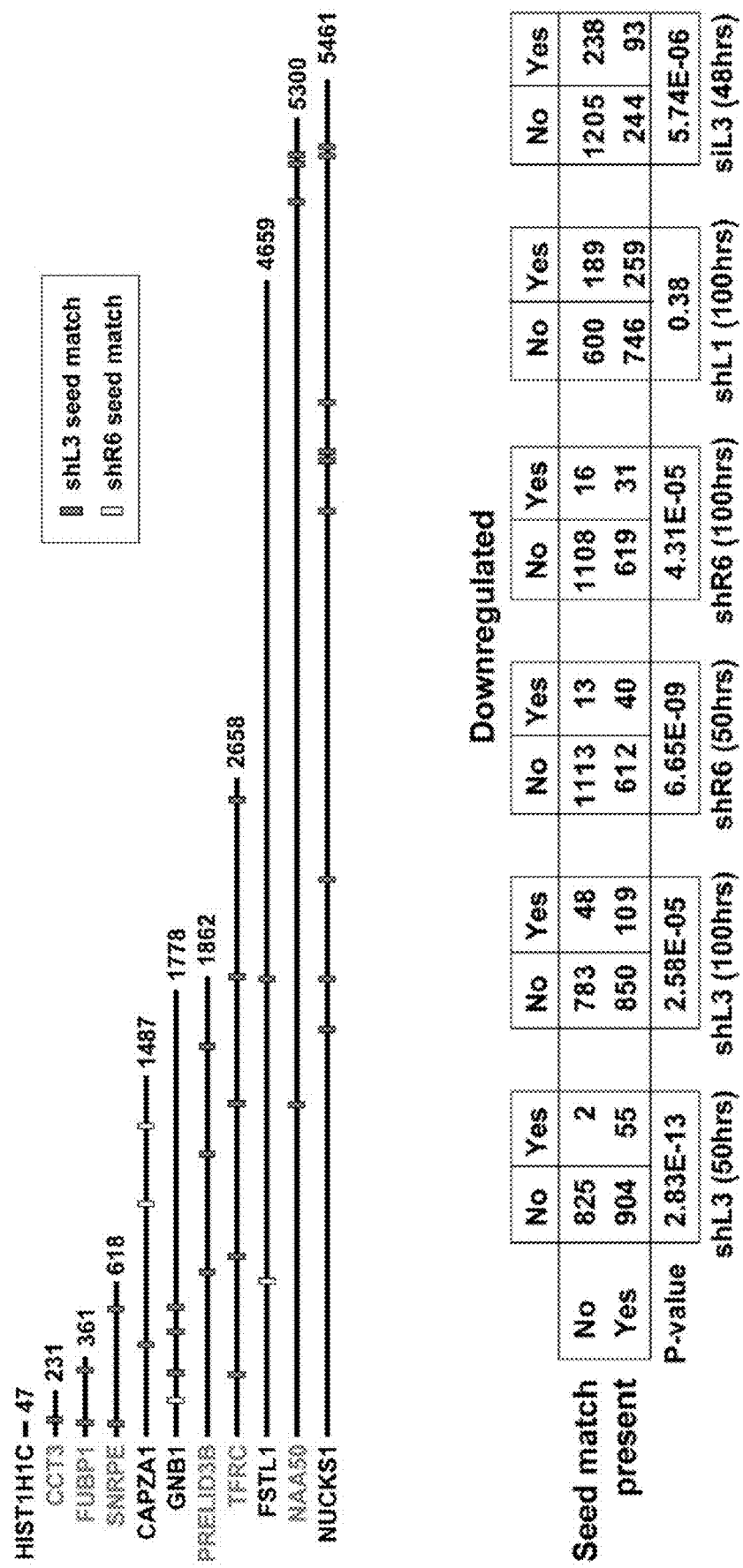

FIG. 5. DISE inducing si/shRNAs target critical survival genes through RNAi. (Top panel) Location of the 6mer seed matches of either shL3 or shR6 in the 3'UTRs of the 11 genes (shown at scale) identified in the RNA-Seq experiment described in FIG. 4A. Illustrated critical survival genes include CCT3, FUBP1, SNRPE, PRELID3B, TFRC, and NAA50. (Bottom panel) A series of six 2×2 contingency tables comparing whether or not a critical survival gene is downregulated after treatment with the indicated siRNA or shRNA to whether or not its 3'UTR contains at least 1 seed match for the introduced sh/siRNA. p-values were calculated using Fisher's Exact Test to determine any significant relationship between gene downregulation and presence of seed matches in 3'UTR.

Figure 6:
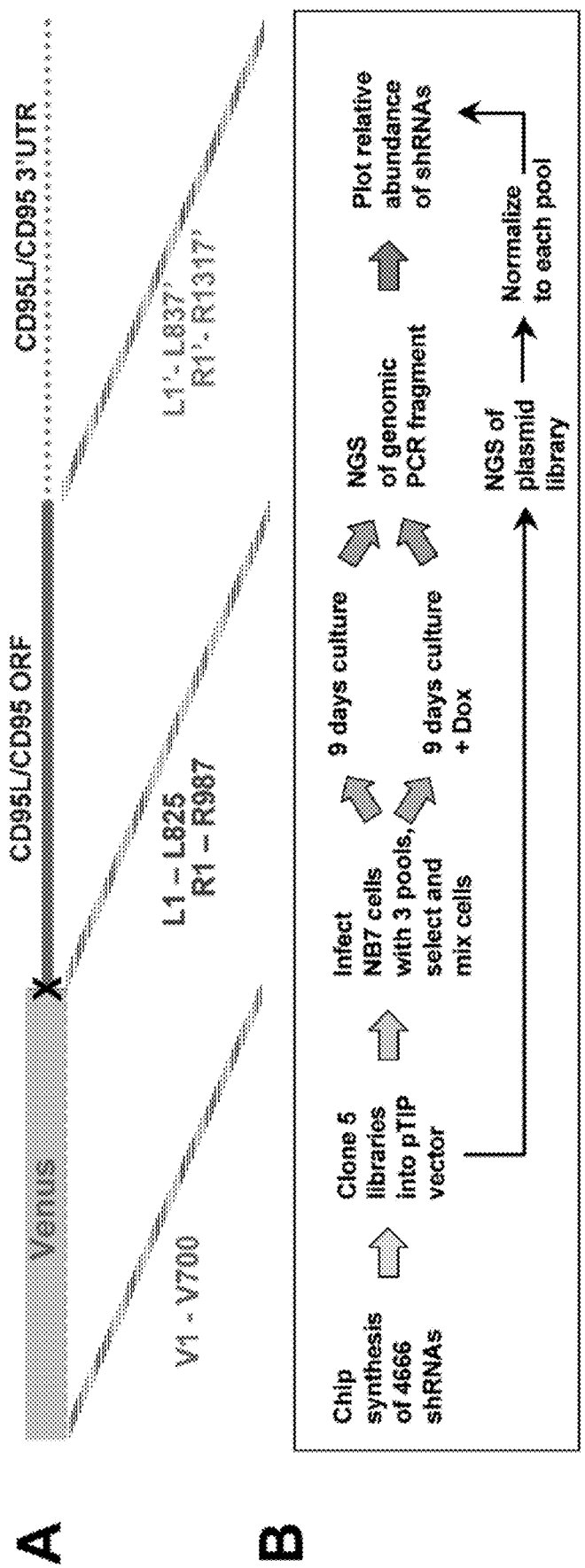

FIGS. 6. (A and B) Identifying all toxic shRNAs derived from CD95L and CD95. (A) Schematic showing the cloned shRNAs covering the ORF of Venus and the ORFs and 3'UTRs of CD95L and CD95. The 3'UTR is displayed as a dashed line because it was not included in the full-length Venus-CD95L/CD95 sensors. (B) Work-flow of pTIP-shRNA library synthesis, shRNA screen and data analysis.

Figure 6C:
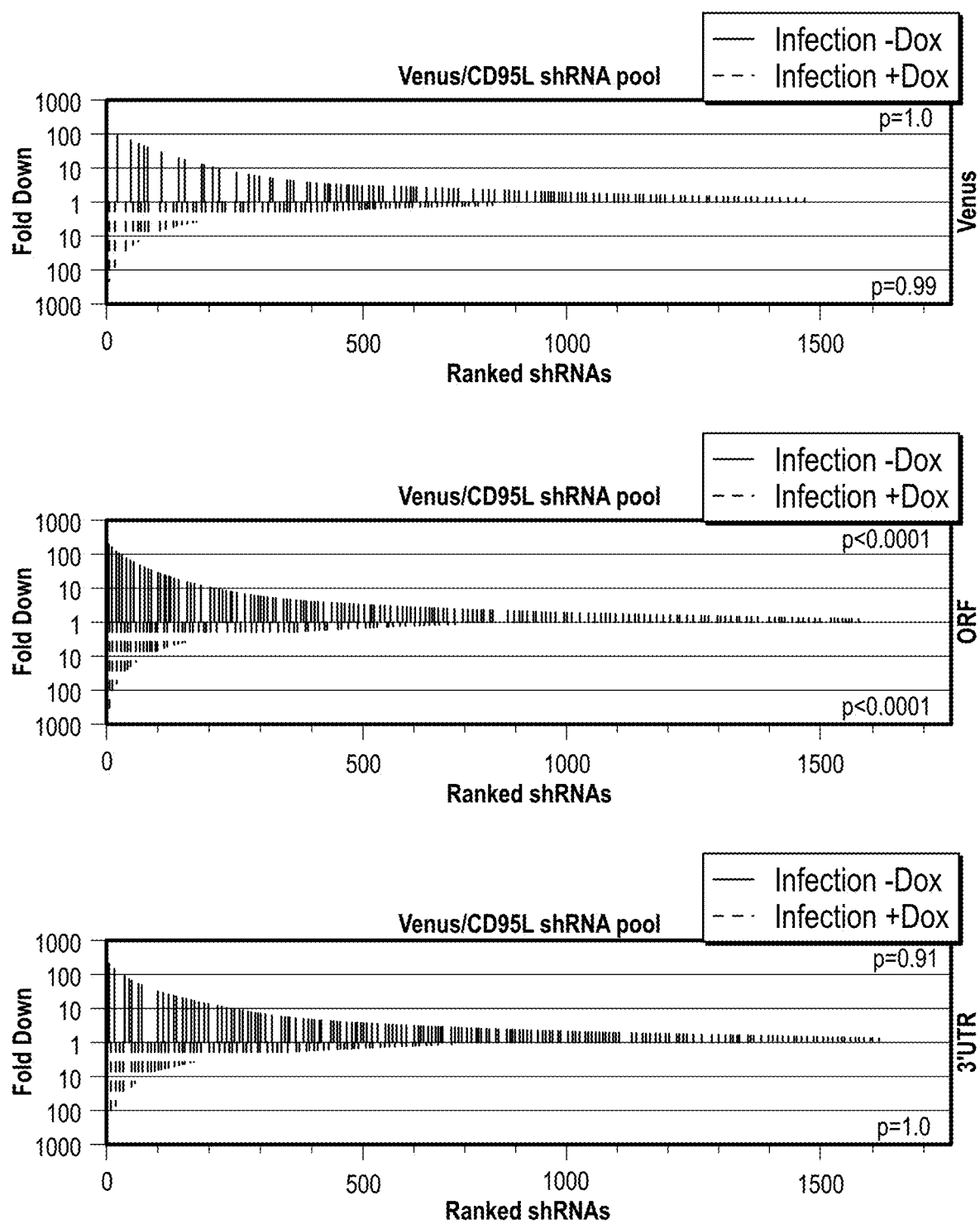
Figure 6C:
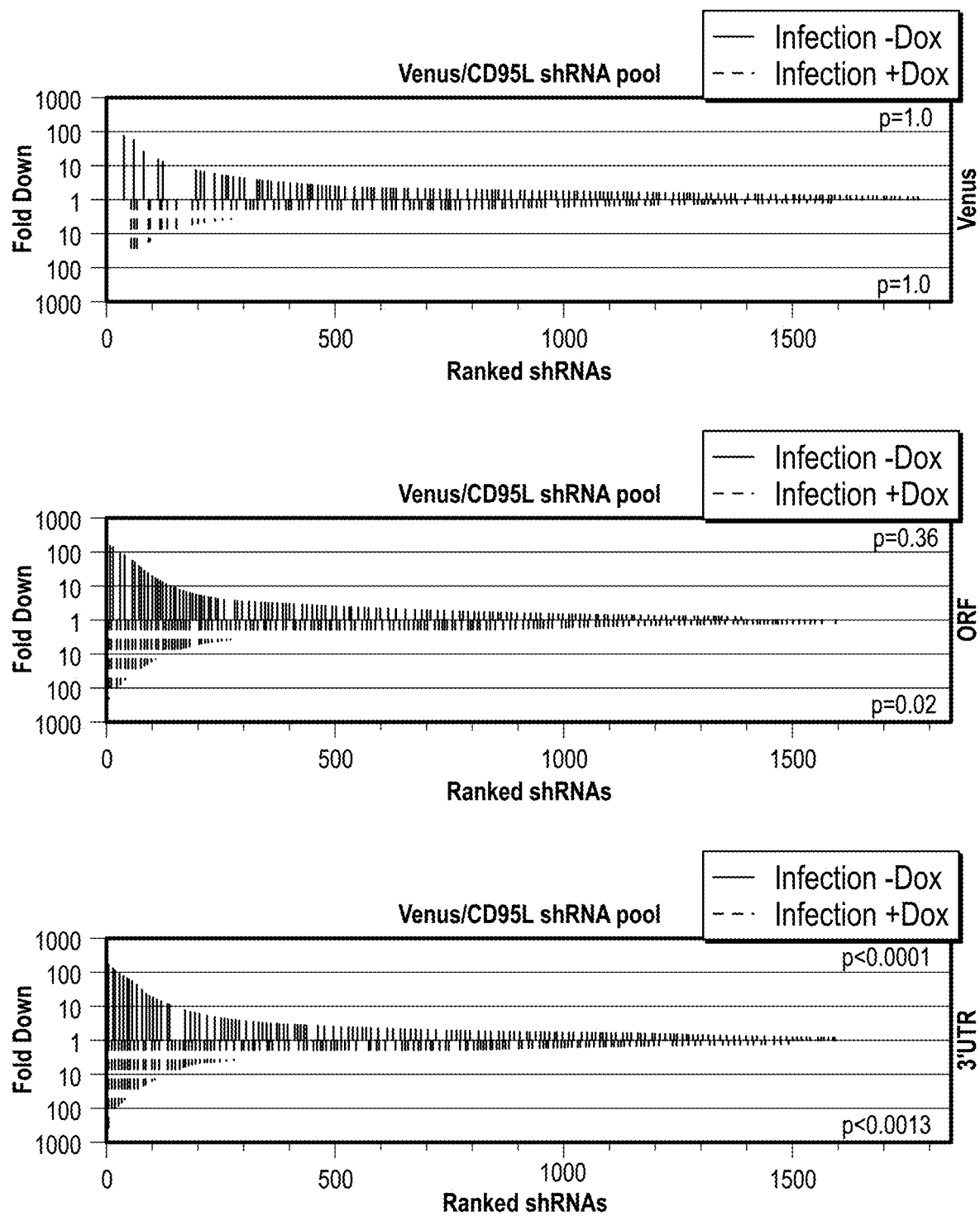

FIG. 6C. Ranked fold reduction of shRNAs spanning Venus and CD95L (ORF and 3'UTR) (left 3 panels) and Venus and CD95 (ORF and 3'UTR) (right 3 panels). The ranked lists were separated into the shRNAs derived from Venus (top), the ORFs (center) and the 3'UTRs (bottom). The p-value of enrichment for each ranked set of shRNAs is given. Only the parts of the ranked lists are shown with the downregulated shRNAs. For all 6 panels, the top section of each panel (boxed) contains the data on shRNAs downregulated after infection of cells and cultured for 9 days without Dox when compared to the composition of the shRNA plasmid library and the bottom half (boxed) contains the data on shRNAs downregulated after culture with Dox for 9 days when compared to the culture without Dox. P-values were calculated using Mann Whitney U tests with a one-sided alternative that the rank was lower.

Figure 6D:
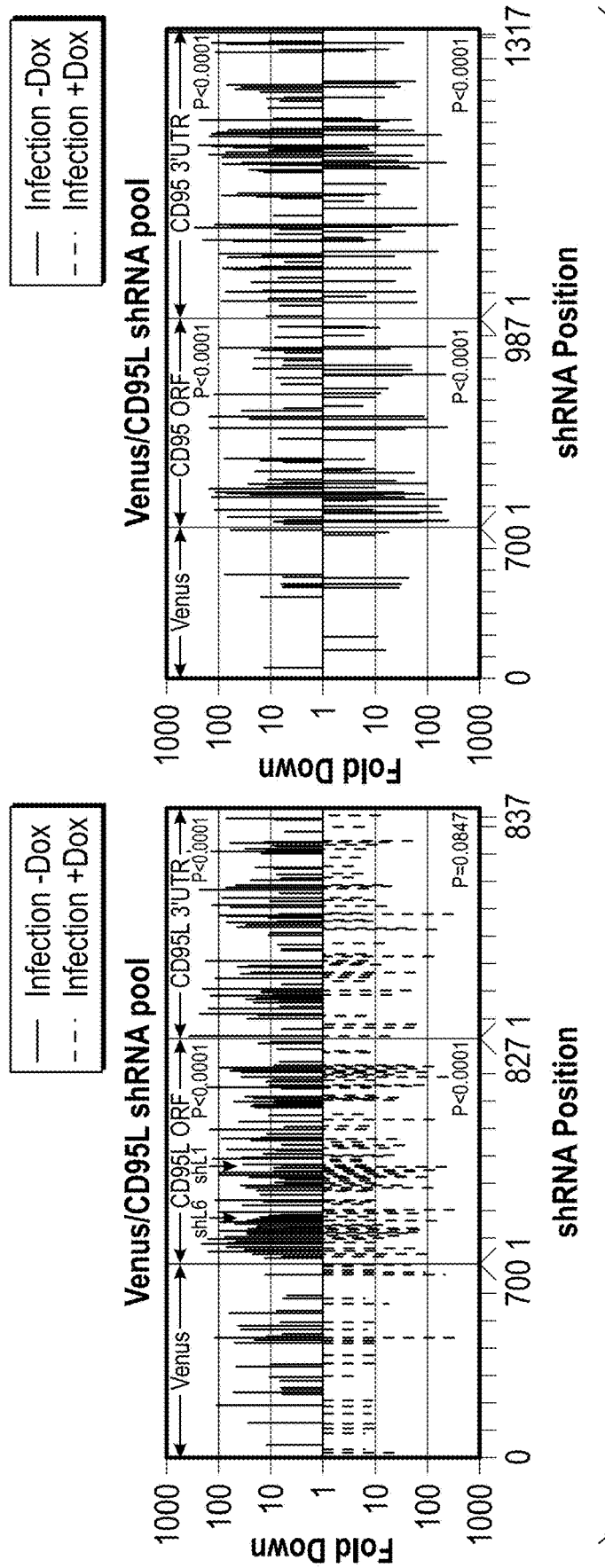

FIG. 6D. The location of all shRNAs significantly downregulated at least 5 fold along the sequences of Venus, CD95L ORF, CD95L 3'UTR (left panel) and Venus, CD95 ORF, and CD95 3'UTR (right panel). The top half of each sub panel (ticks) shows the shRNAs downregulated after infection and the bottom half (ticks) contains the data on shRNAs downregulated after culture with Dox for 9 days. Significance of enrichment in the different subpanels is shown. p-values were calculated according to statistical tests of two proportions. Each data set was compared to the corresponding Venus distribution. The illustrated line is the sequence that corresponds to the intracellular domain of CD95L.

Figure 7:
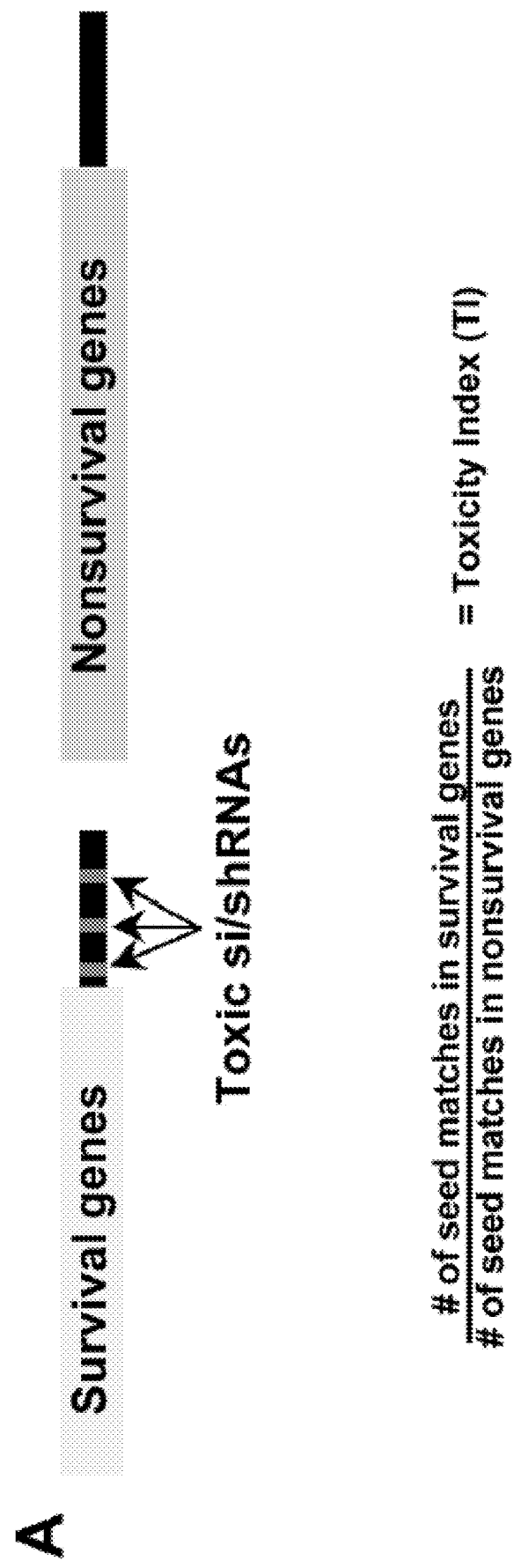

FIG. 7. (A) In silico prediction of DISE activity tracks with experimental determined toxicity of shRNAs. Top: Schematic showing the preferential targeting of seed matches present in the 3'UTRs (illustrated marks) of survival genes by toxic si/shRNAs. Bottom: The toxicity index (TI) is the normalized ratio of the number of 6mer or 8mer seed matches present in a list of survival genes versus a list of nonsurvival genes.

Figure 7B:
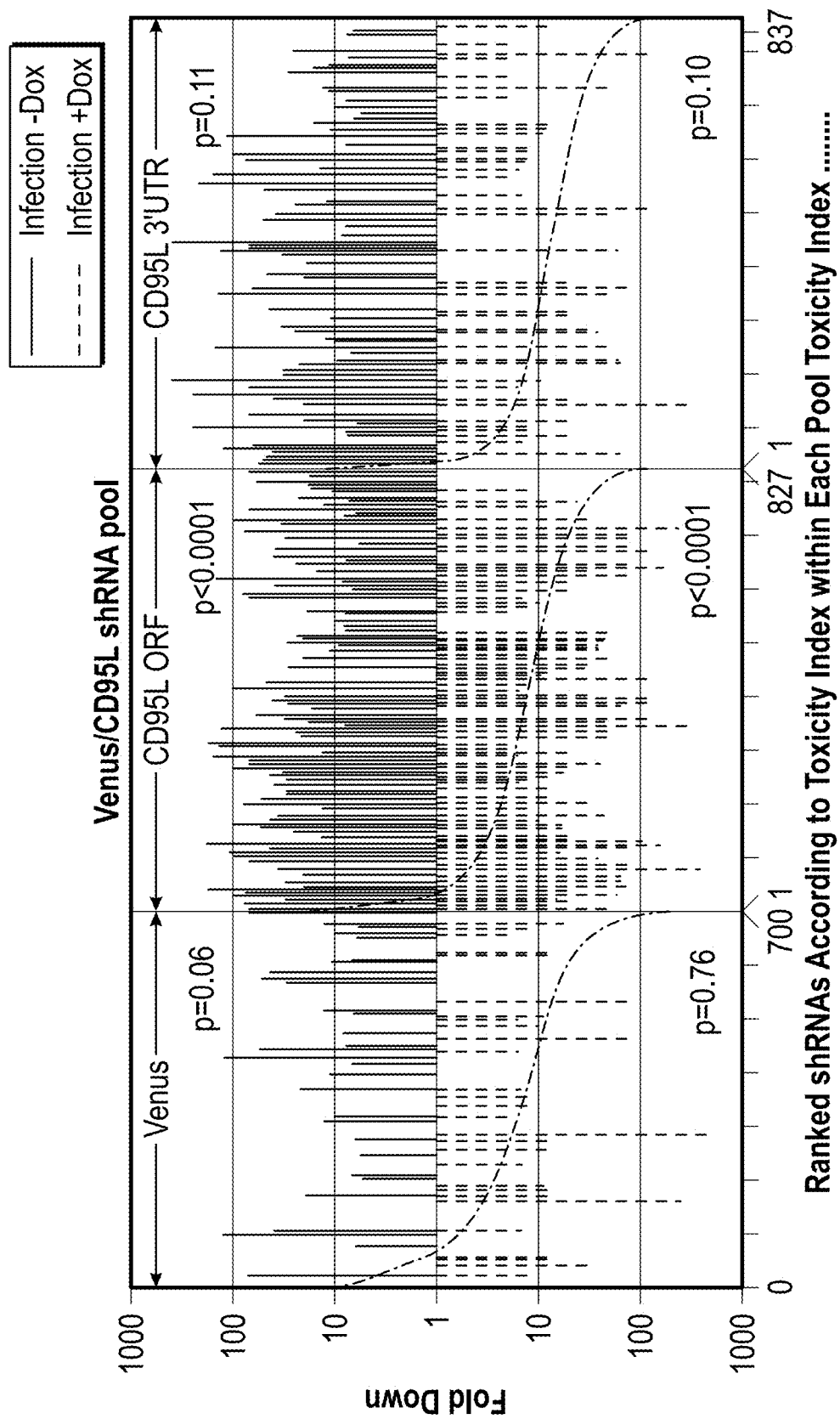
Figure 7B:
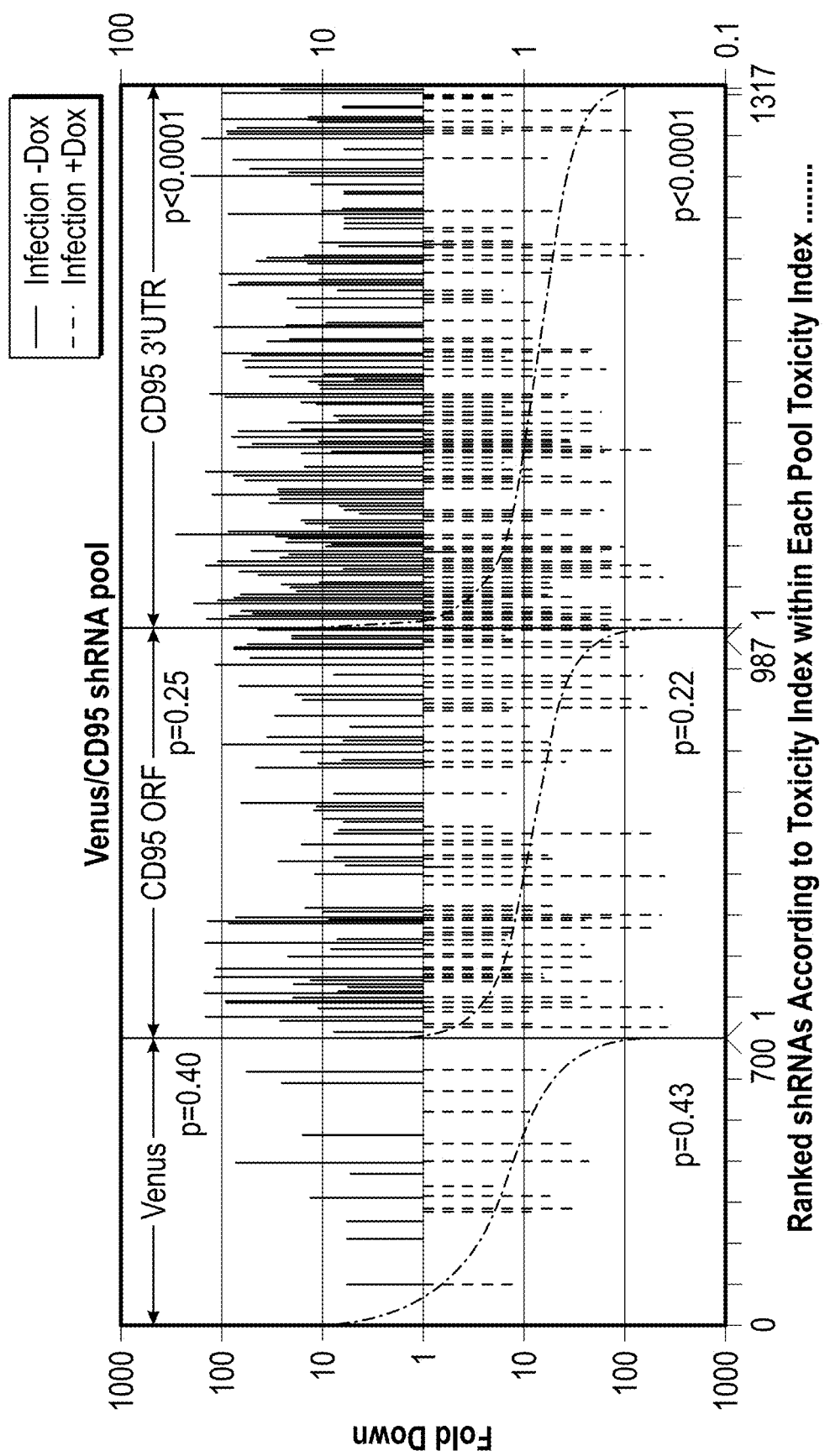

FIG. 7B. Fold downregulation versus ranked (8mer seed matched based) Toxicity Index for shRNAs of the Venus/CD95L pool (left three panels) and the Venus/CD95 pool (right three panels). Tick marks indicate the same as in FIG. 6D. To test if higher TI is enriched in shRNAs that were highly downregulated, p-values were calculated based on permutated datasets using Mann-Whitney U tests. The ranking of TI was randomly shuffled 10,000 times and the W statistic from our dataset was compared to the distribution of the W statistic of the permutated datasets.

Figure 7C:
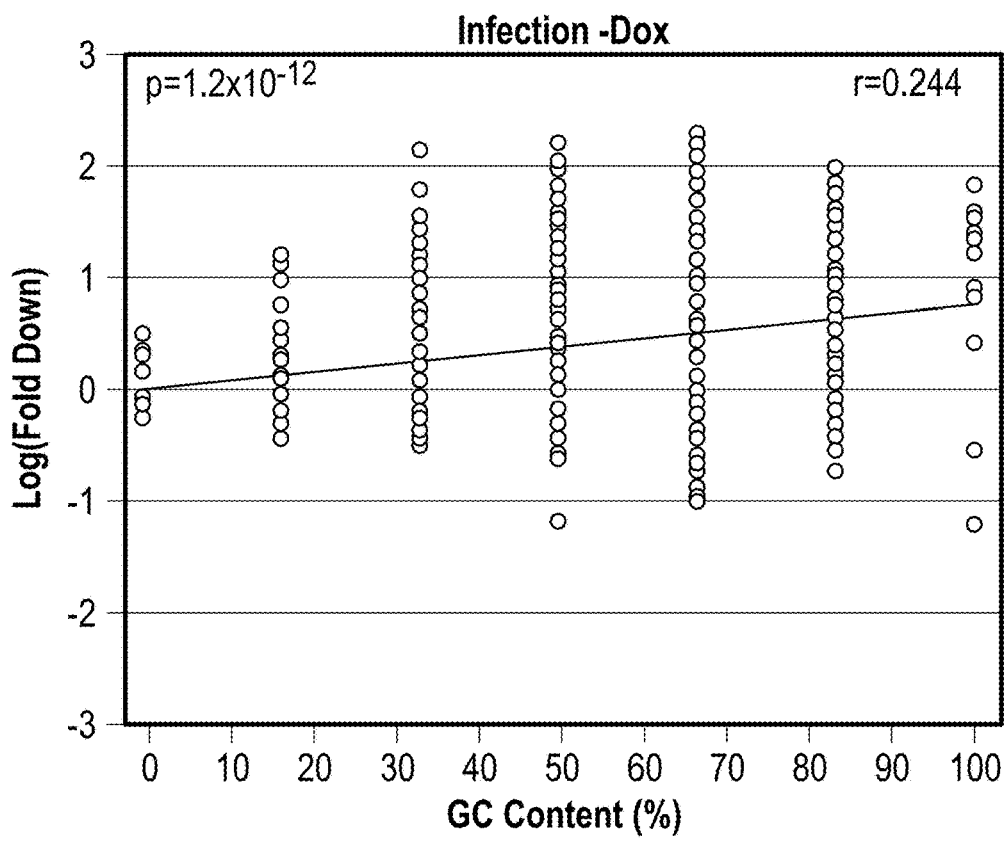

FIG. 7C. Plot of fold downregulation of toxic shRNAs derived from CD95L ORF of the toxicity screens –Dox (left) or +Dox (center) versus GC content the 6mer seed in each shRNA.

Figure 7D:
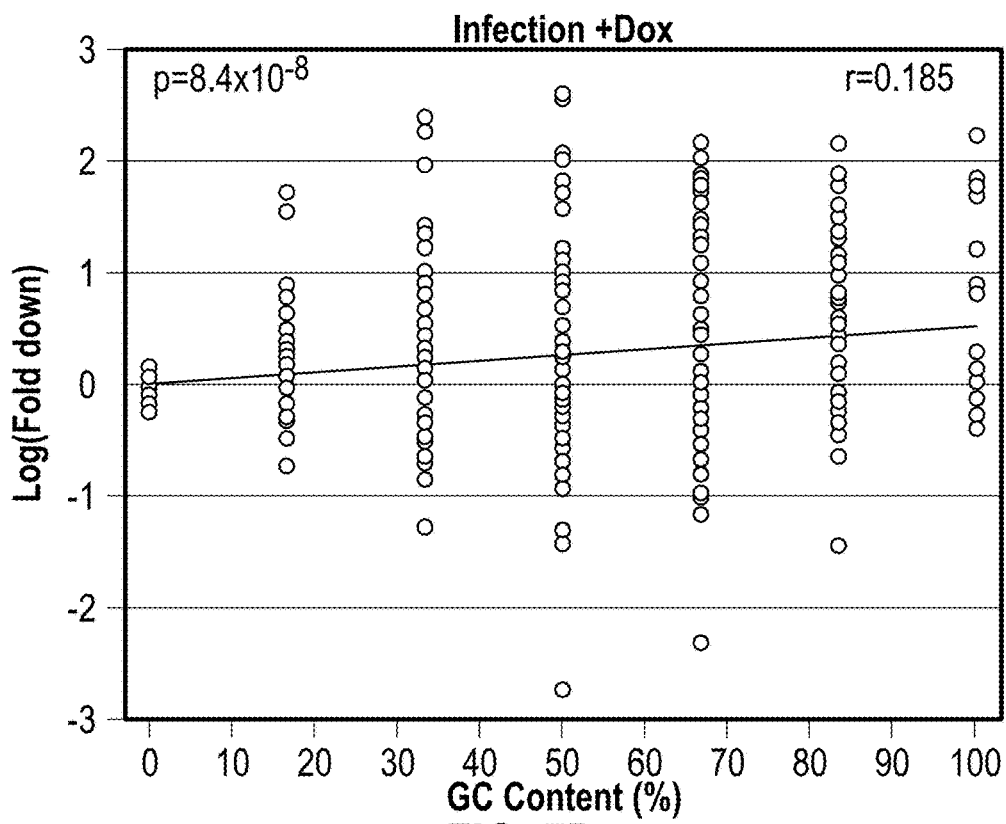

FIG. 7D. Plot of fold downregulation of toxic shRNAs derived from CD95L ORF of the toxicity screens –Dox (left) or +Dox (center) versus GC content the 6mer seed in each shRNA.

Figure 7E:
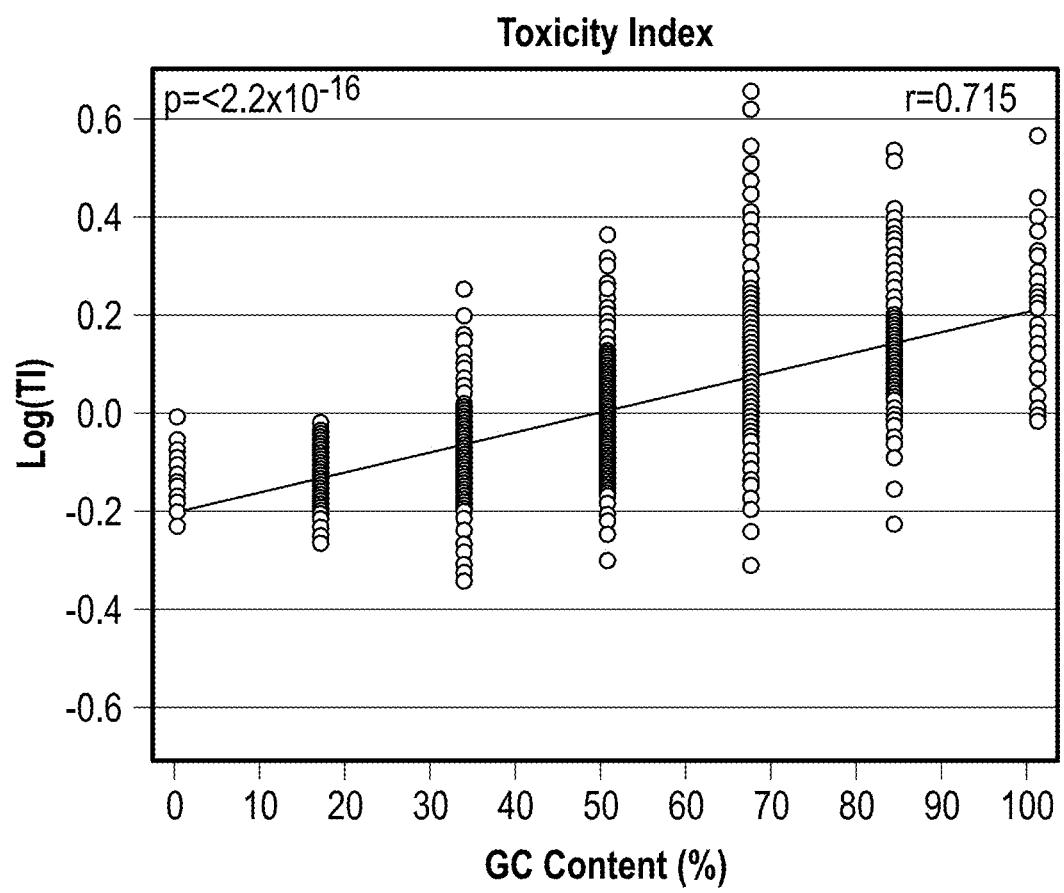

FIG. 7E. Plot of the log(TI) of all 4092 possible 6mers versus GC content of the seeds. Pearson correlation coefficient and significance (p values) are given.

Figure 8:
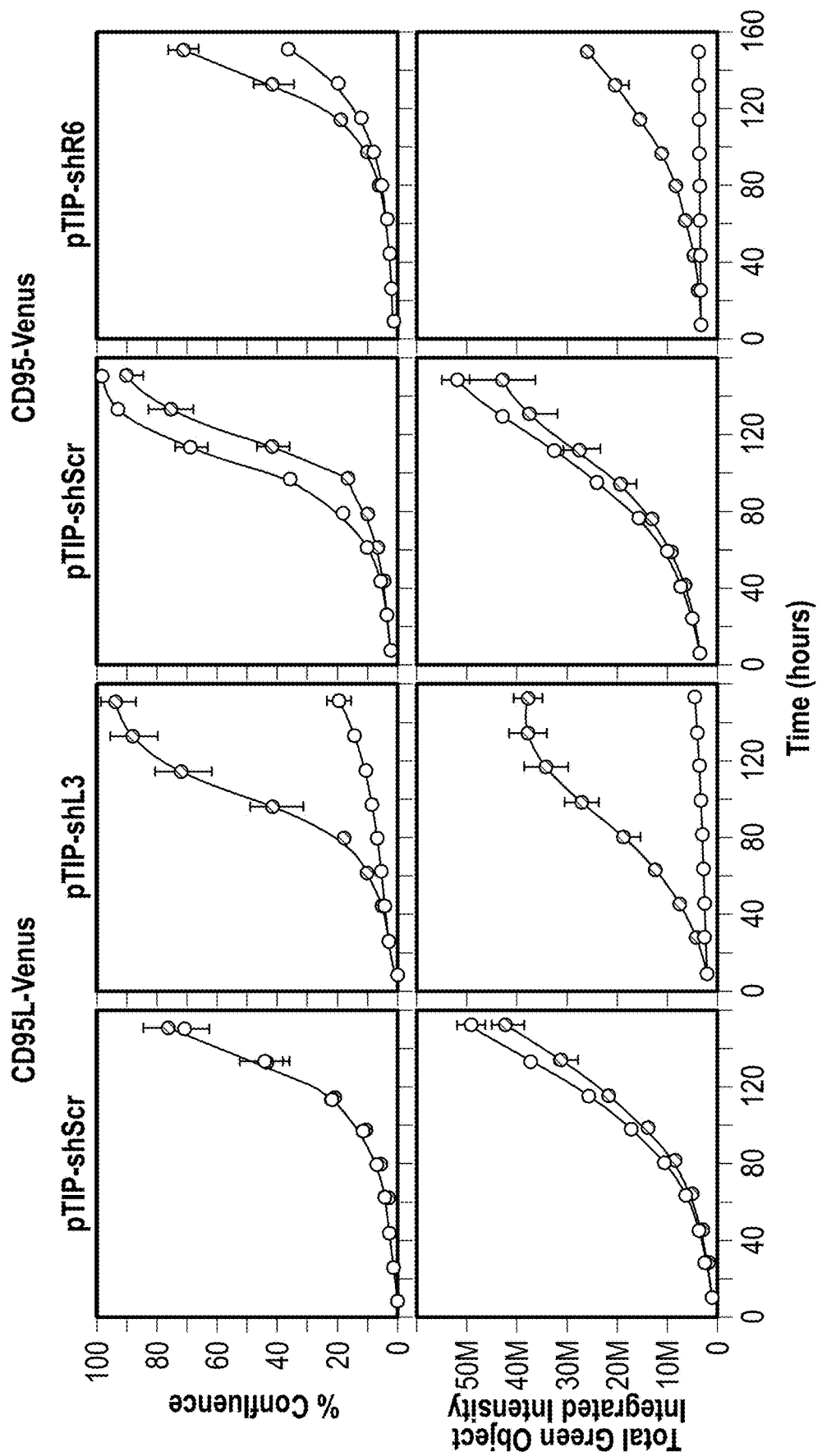

FIG. 8. Toxicity of si/shRNAs is dose dependent. Confluence (top) and total green fluorescence (bottom) over time of NB7-Venus-CD95L (left) or NB7-Venus CD95 (right) cells infected with the pTIP vector minus/plus Dox to induce expression of the indicated shRNAs.

Figure 9:
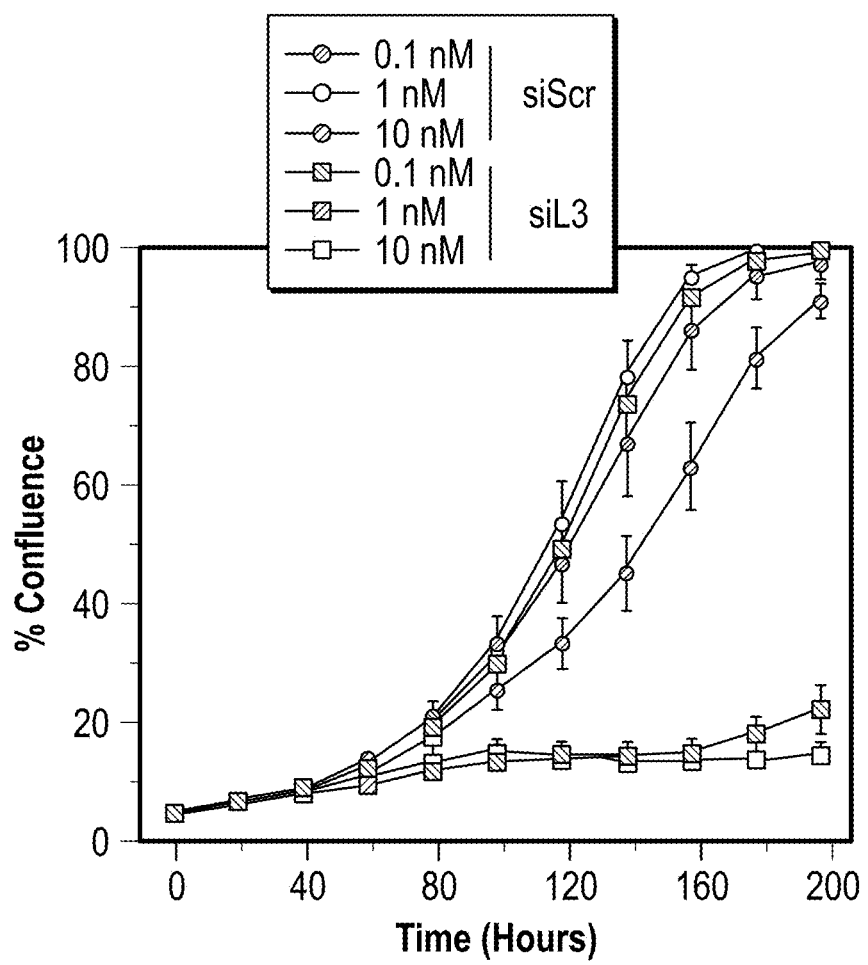

FIG. 9. Toxicity of si/shRNAs is dose dependent. Confluence over time of HeyA8 cells transfected with the indicated concentration of either siScr or siL3. Each data point represents mean±SE of six replicates. The experiment was repeated three times.

Figure 10:
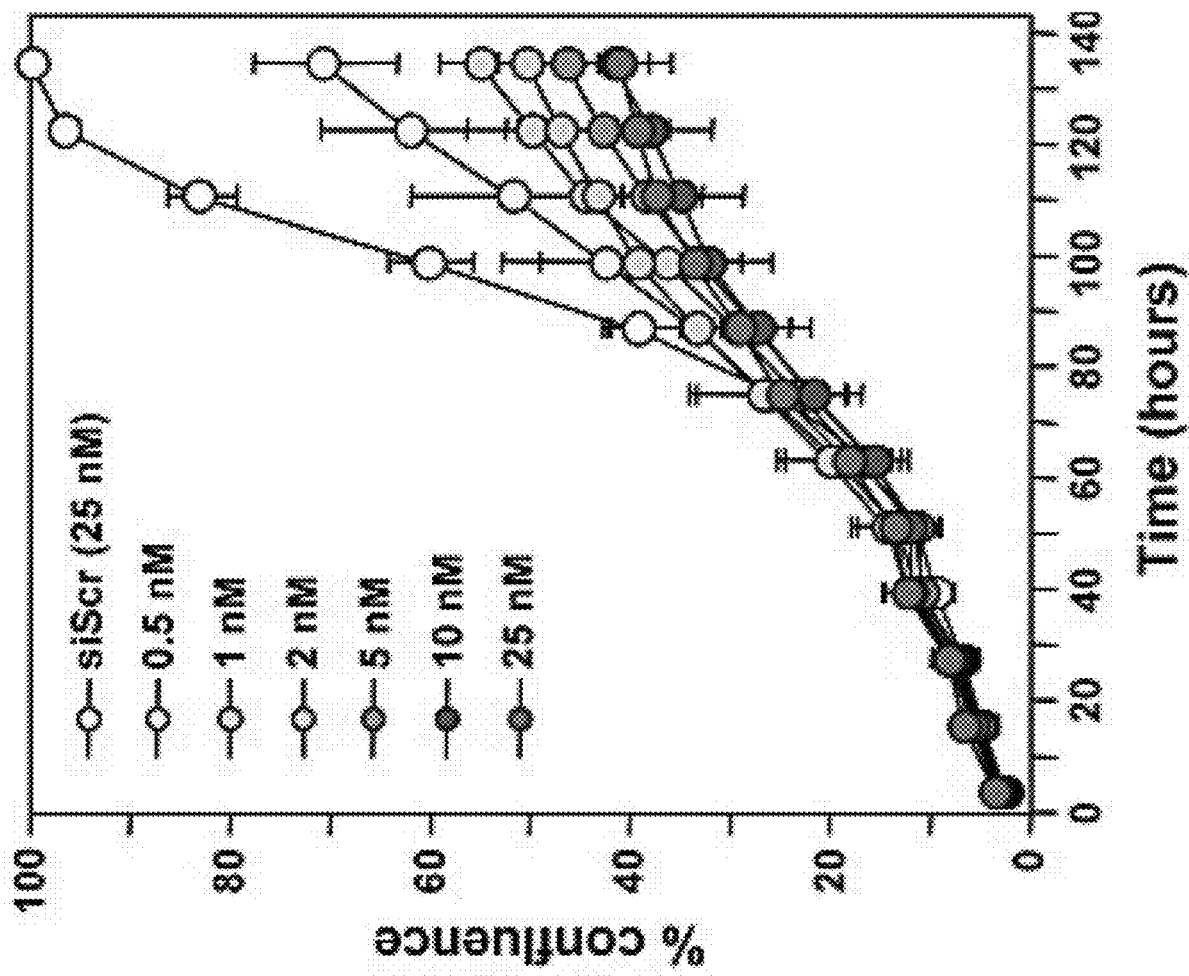

FIG. 10. Characterization of the six genes downregulated in shL3 and shR6 treated cells and found to be critical survival genes in lethality screens. Percent confluence over time of HeyA8 cells transfected with increasing concentrations of a pool of siRNAs (28 different siRNAs) targeting 7 different genes: CCT3, TFRC, NAA50, FUBP1, PRELID3B, GNB1 and FSTL1. Each siRNA SmartPool was comprised of 4 individual siRNAs. Data are representative of two independent experiments. Values were calculated from samples done in quadruplicates shown as mean±SE.

Figure 11:
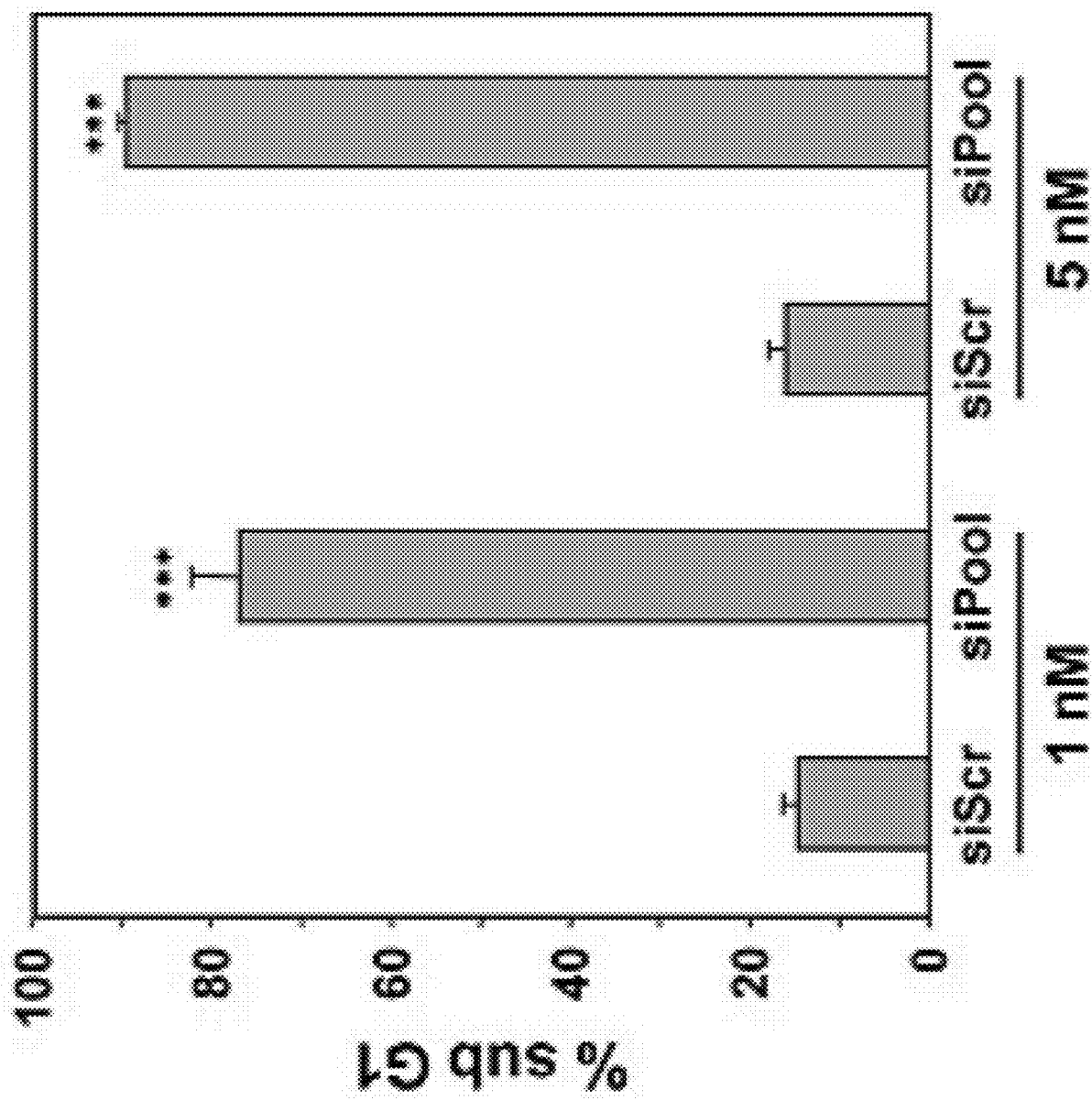

FIG. 11. PI staining used to quantify percent subG1 for cells 4 days after transfection with 1 nM and 5 nM of combined siRNA pools targeting the 7 different survival genes as in FIG. 10. Data are representative of two independent experiments. Values were calculated from samples done in quadruplicates shown as mean±SD. *** p<0.0001, unpaired t-test.

Figure 12:
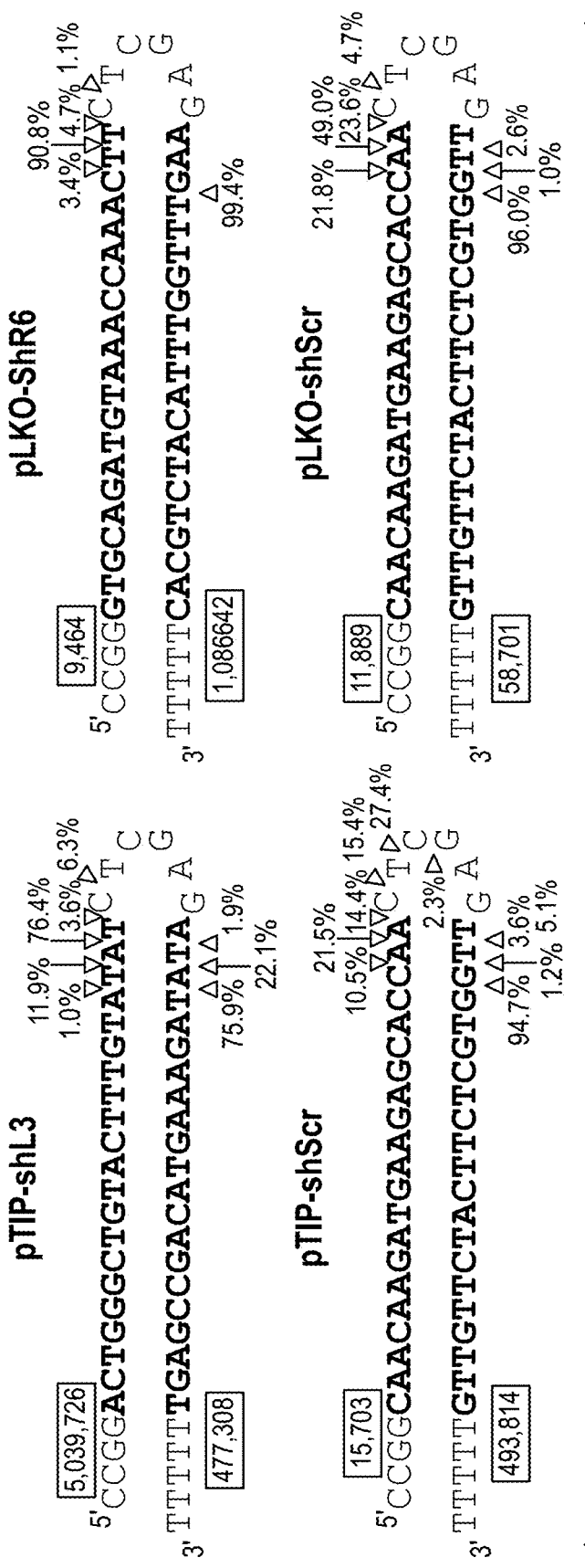

FIG. 12. Quantification of the mature shRNA forms. Graphical representation of the percentage of the different Dicer cut sites to produce the mature passenger (top) and guide (bottom) strands of 3 shRNAs expressed from two vectors. All analyses were performed with cells 50 hrs after either Dox addition (in pTIP expressing cells) or infection with the pLKO virus. Vector sequences and passenger and guide strands of shRNAs are shown; Arrow heads label the most highly cleaved residues; the darker the arrow head the more highly cleaved. Numbers in box represent total number of reads detected for passenger and guide strands. (Sequence Listing:

```
                                          (SEQ ID NO: 159)
CCGGACTGGGCTGTACTTTGTATATCTCGAGATATACAAAGTACAGCCCA

GTTTTTT;

(SEQ ID NO: 160)
CCGGGTGCAGATGTAAACCAAACTTCTCGAGAAGTTTGGTTTACATCTGC

ACTTTTTG;

(SEQ ID NO: 130))
CCGGCAACAAGATGAAGAGCACCAACTCGAGTTGGTGCTCTTCATCTTGT

TGTTTTT.
```

Figure 13:
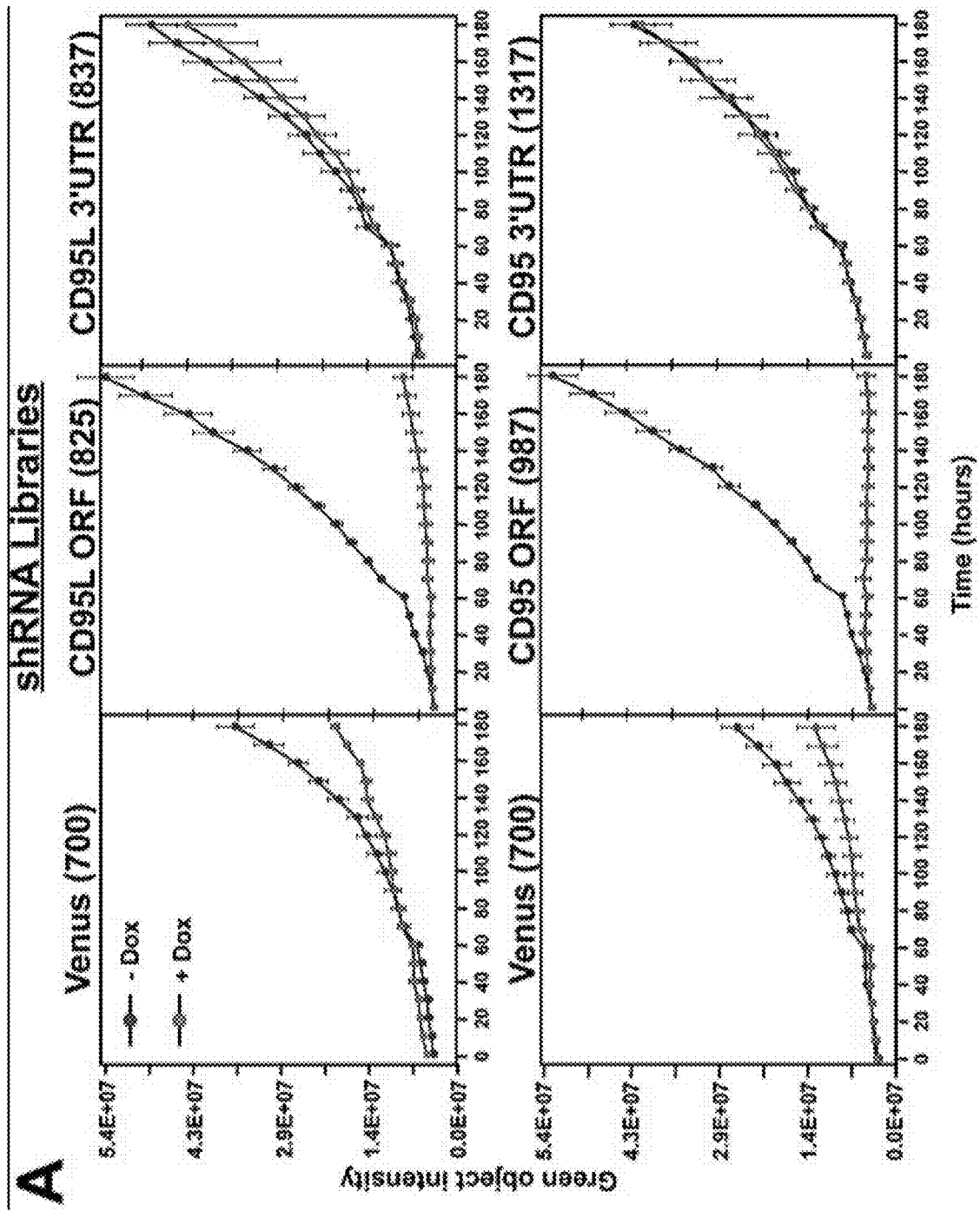
Figure 13:
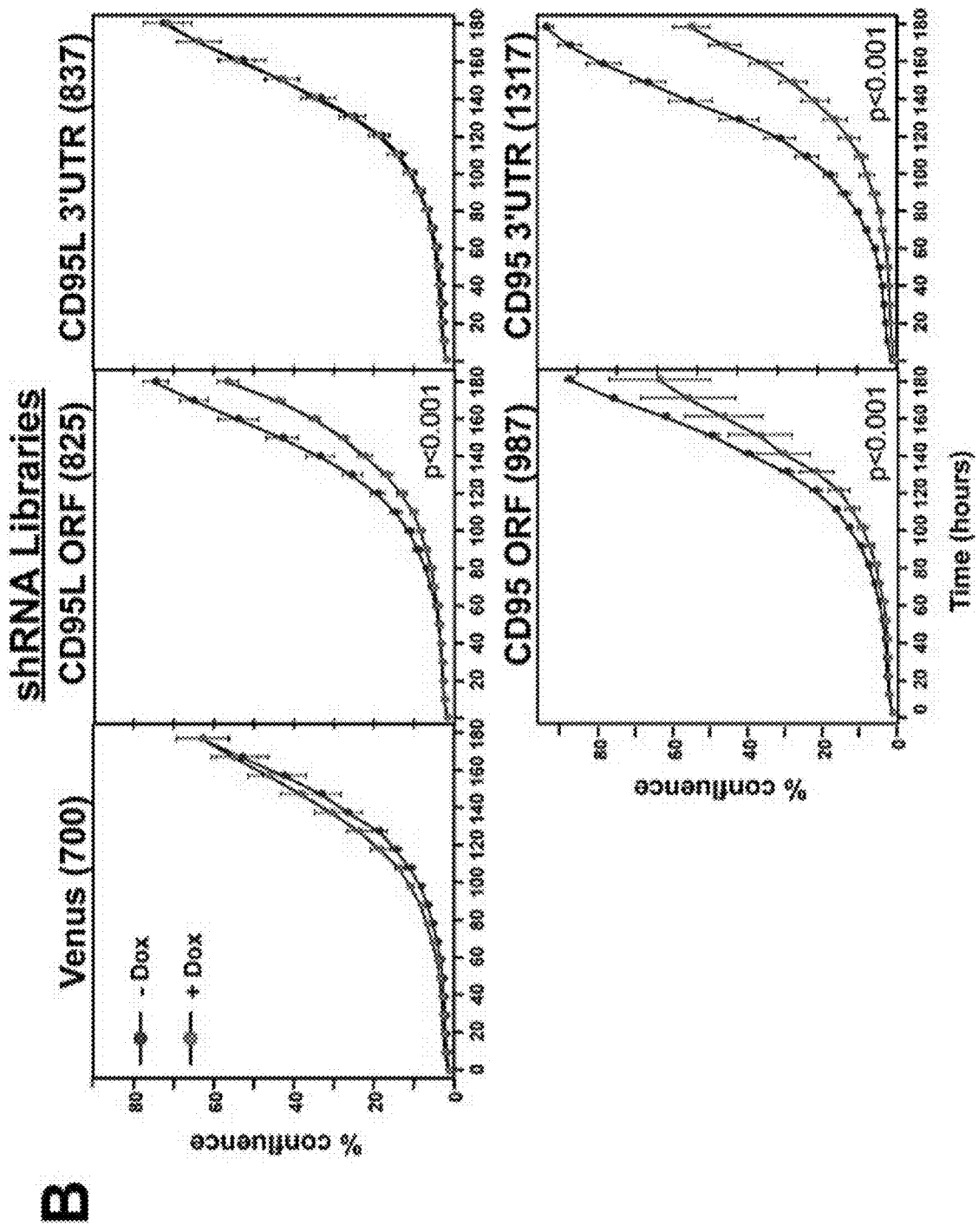

FIGS. 13. (A, and B). Toxicity and RNAi of individual shRNA pools. (A) Top panels: Green object intensity over time of NB7 Venus-CD95L sensor cells infected with the pTIP-Venus shRNA pool (left panel), pTIP-CD95L ORF shRNA pool (center panel), or pTIP-CD95L 3'UTR shRNA pool (right panel) with or without Dox treatment. Bottom panels: Green object intensity over time of NB7 Venus-CD95 sensor cells infected with the pTIP-Venus shRNA pool (left panel), pTIP-CD95 ORF shRNA pool (center panel), or pTIP-CD95 3'UTR shRNA pool (right panel) with or without Dox treatment. Values were calculated from samples done in quadruplicates shown as mean±SE. (B) Percent confluence over time of parental NB7 cells infected with the pTIP-Venus shRNA pool (top left panel), pTIP-CD95L ORF shRNA pool (top center panel), pTIP-CD95L 3'UTR shRNA pool (top right panel), pTIP-CD95 ORF-shRNA pool (bottom center panel), and pTIP-CD95 3'UTR shRNA pool (bottom right panel) with or without Dox treatment. Values were calculated from samples done in triplicate shown as mean±SE. P-values were calculated using two-way ANOVA with a factor for Dox treatment and a factor for time. Similar data were obtained when either HCT116 or 293T cells were treated with each of the five shRNA pools (data not shown).

Figure 14A:
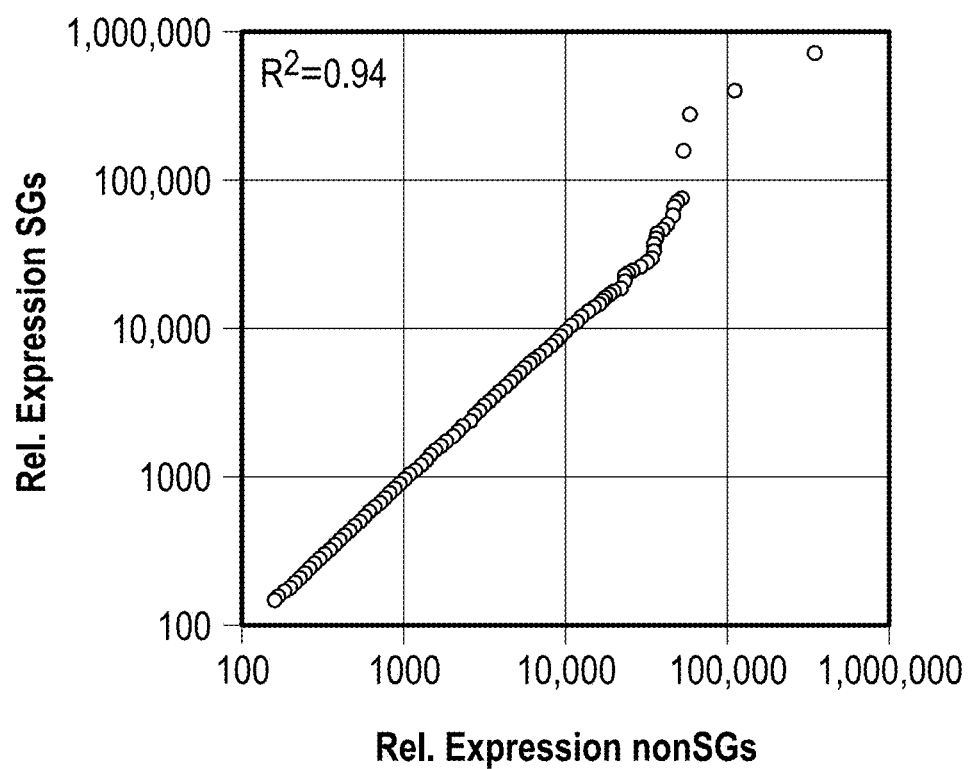

FIG. 14A. DISE does not just target all highly expressed genes. Correlation between 850 survival genes (genes identified as critical survival genes in two genome-wide lethality screens (Blomen et al., 2015; Wang et al., 2015) and expressed at least at 100 reads in all of the 16 control RNA Seq samples in this study) and 850 expression matched nonsurvival genes (genes not identified as critical survival genes in two genome-wide lethality screens (Blomen et al., 2015; Wang et al., 2015) and expressed at least at 100 reads in all of the 16 control RNA Seq samples in this study).

Figure 14B:
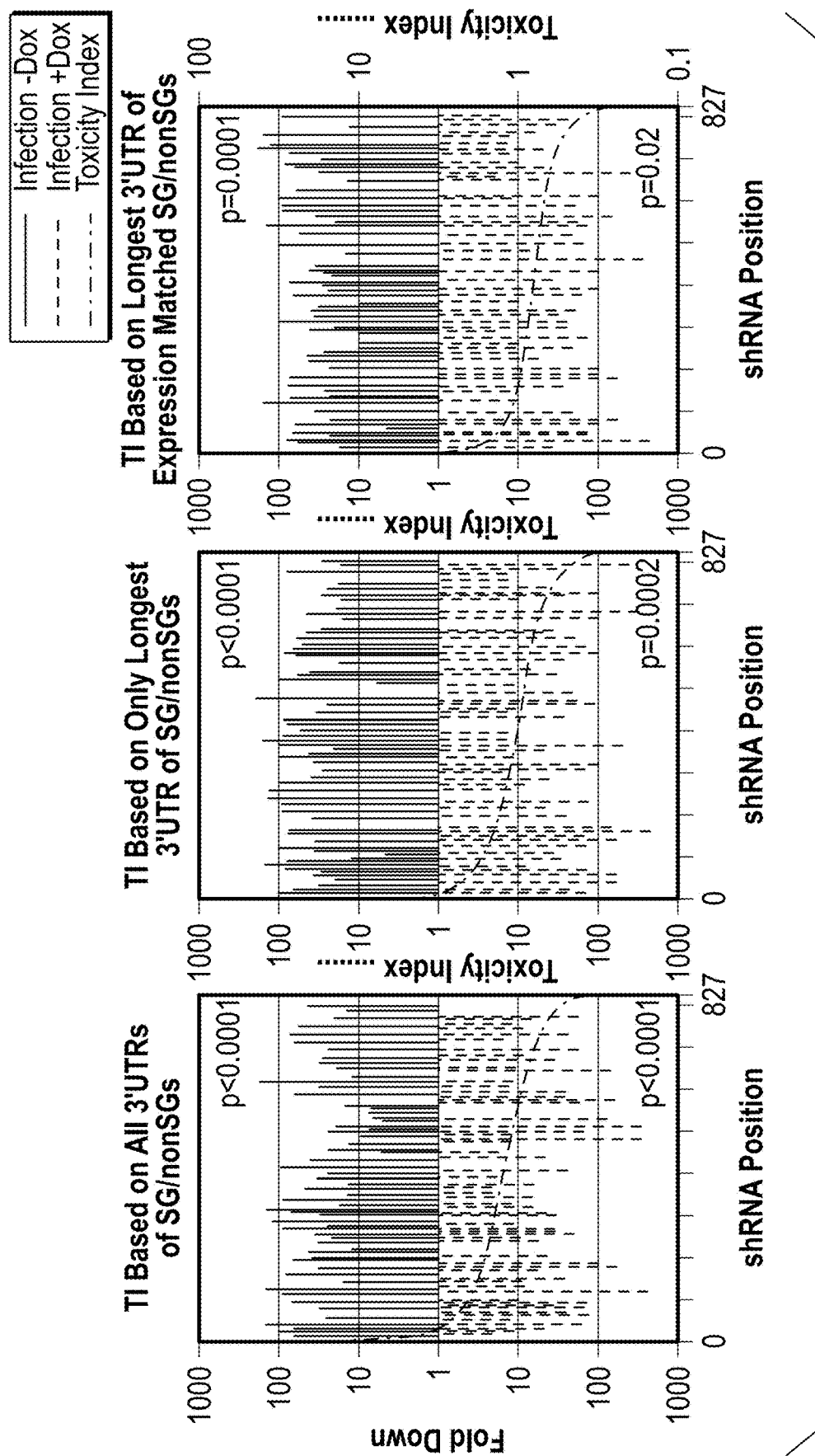

FIG. 14B. Reanalysis of the CD95L ORF data in FIG. 7B using two alternative ways to calculate the toxicity index (TI). Left: the analysis shown in FIG. 7B with the data ranked using the original TI (using all known 3'UTRs for each gene group). Center: analysis with the data ranked using the original TI but based on only the longest 3'UTR for each gene. Right: analysis with the data ranked using the new TI based on expression matched SGs and nonSGs identified in A and using the longest 3'UTR for each gene. To test if higher TI is enriched in shRNAs that were highly downregulated, p-values were calculated based on permutated datasets using Mann-Whitney U tests.

Figure 15:
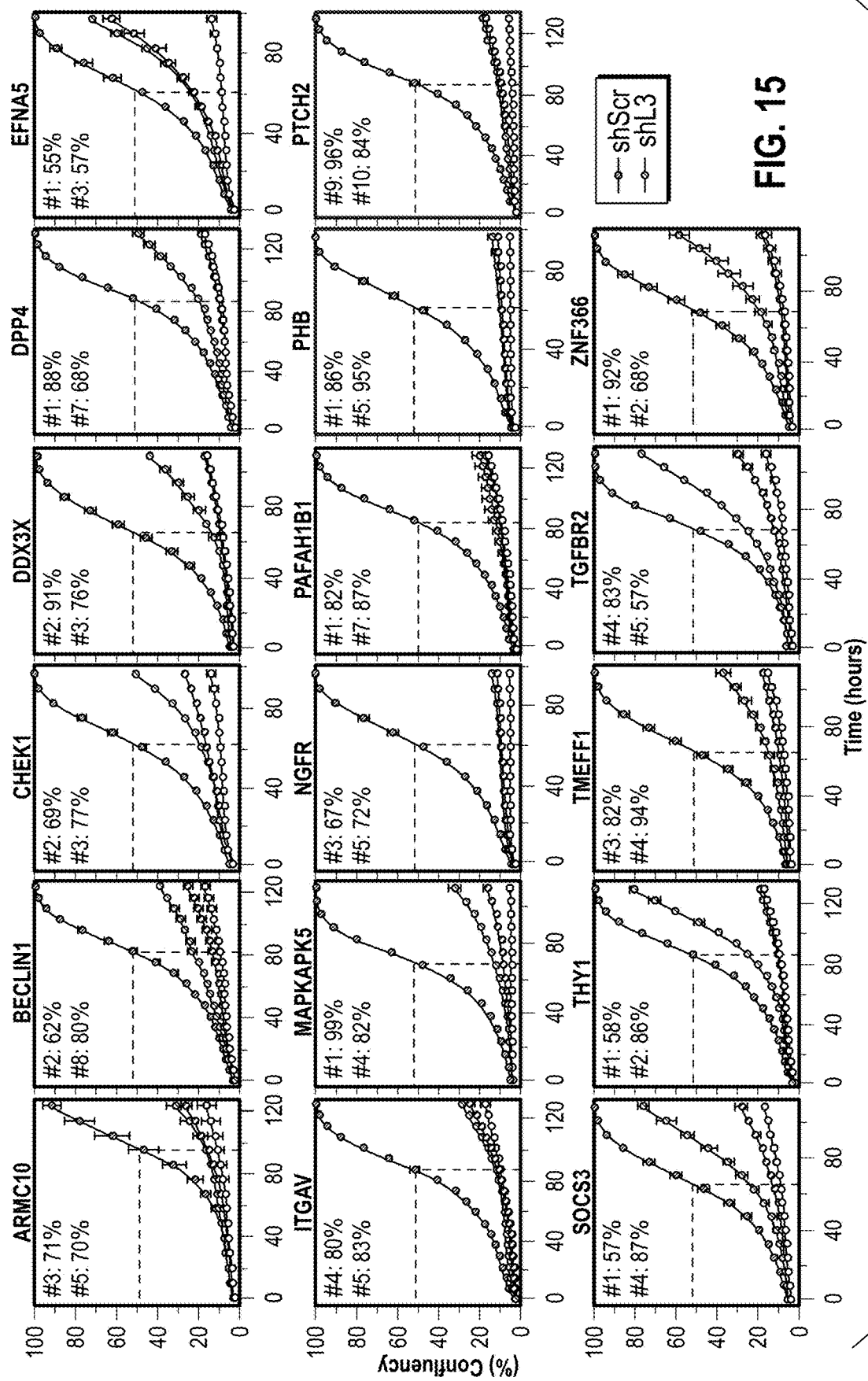

FIG. 15. shRNAs derived from 17 tumor suppressive (TS) genes cause growth reduction in HeyA8 cells. Percent cell confluence over time of HeyA8 cells after infection with shScr, shL3 and two shRNAs for each of the 17 TS genes. The curves for cells infected with two independent shRNAs for each TS gene and their specific ID number and respective growth reduction caused by each shRNA are shown. Percent growth reduction values were calculated using STATA1C software when cells infected with shScr reached half maximal confluency as indicated by the dotted line.

Figure 16:
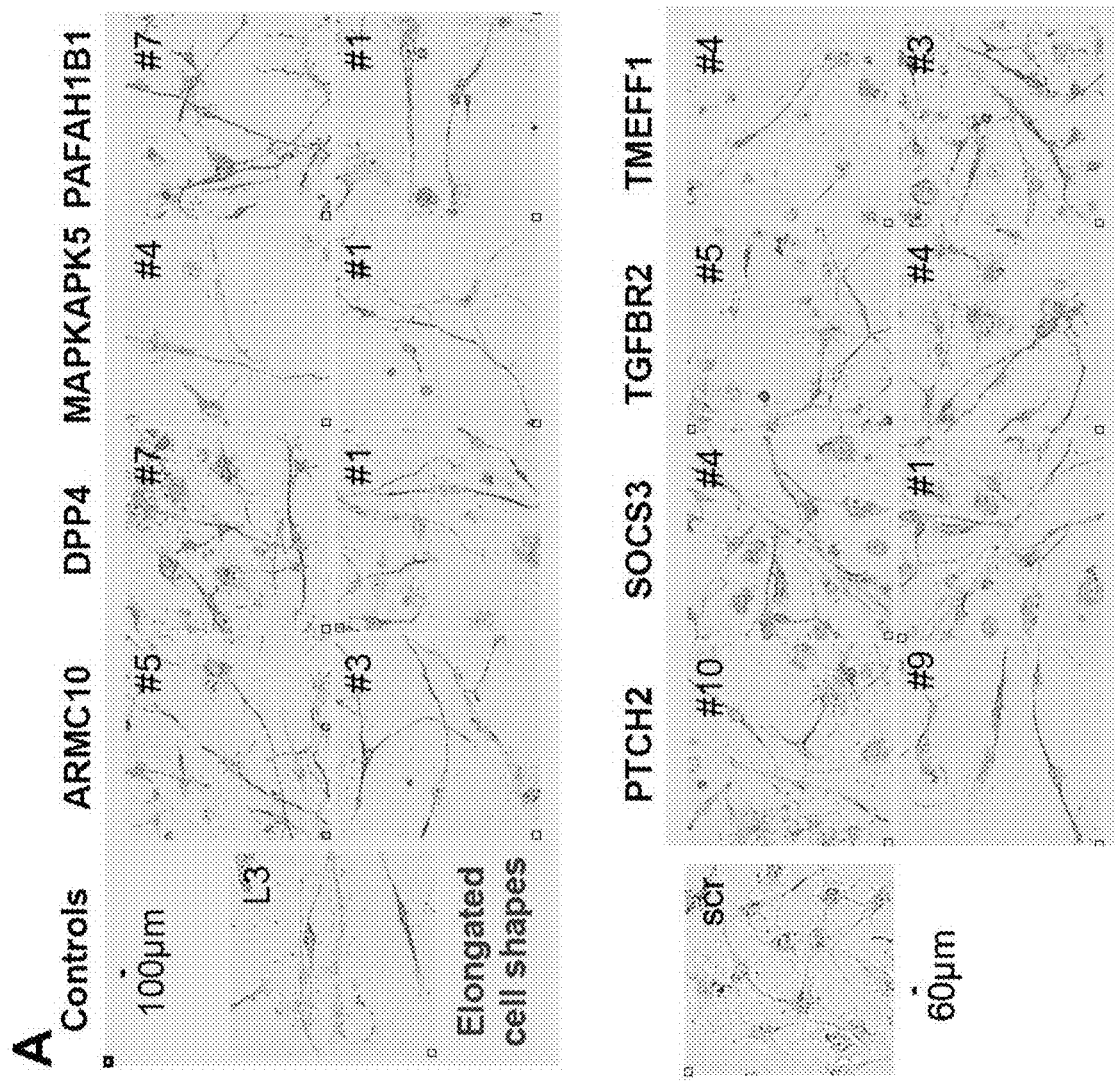
Figure 16:
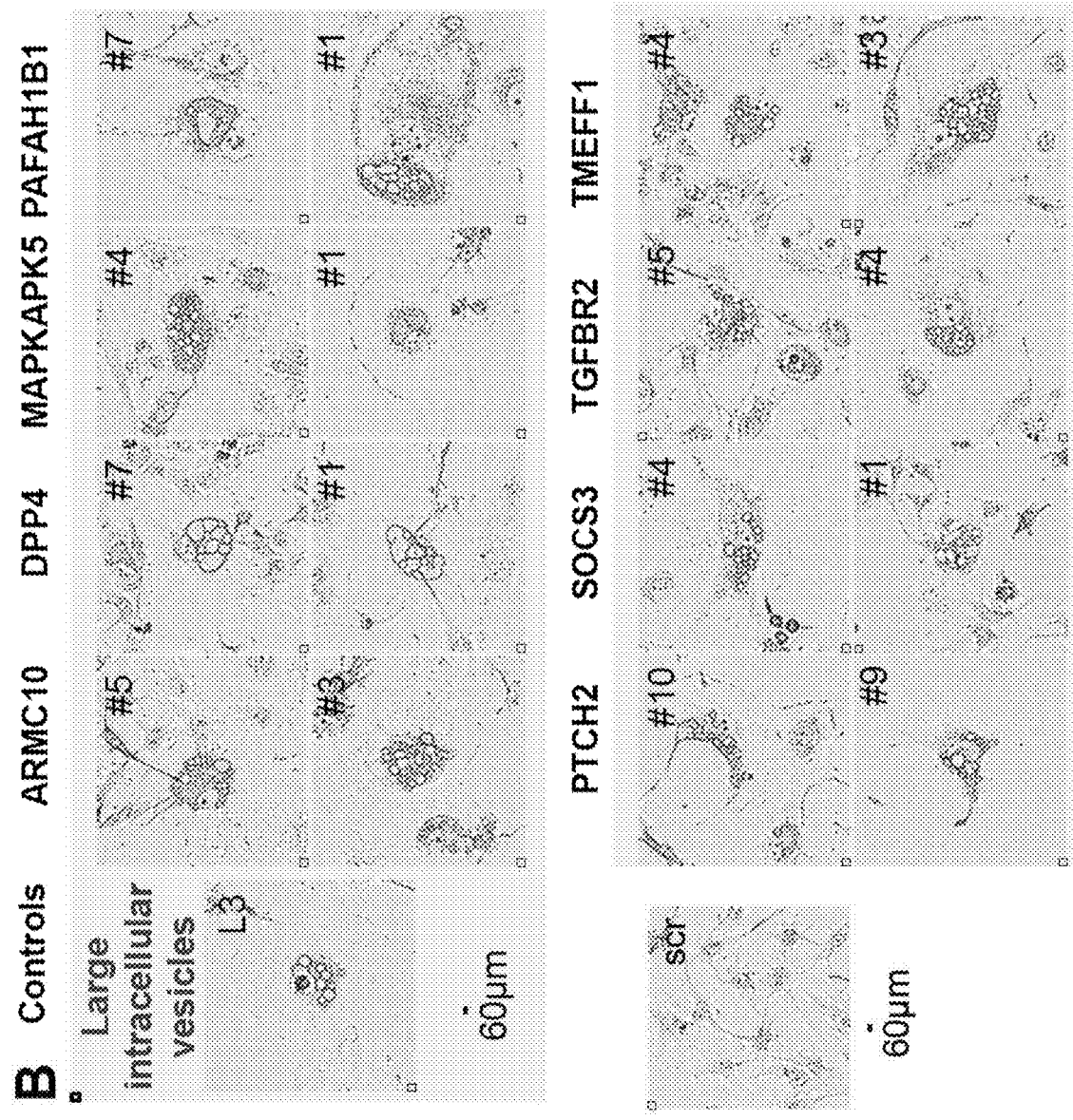

FIG. 16. (A, B). Toxic shRNAs derived from eight TS genes induce DISE-like morphological changes in HeyA8 cells. Representative phase-contrast images showing elongated cell shapes (A); enlarged, flattened cells and presence of intracellular granules in HeyA8 cells infected with shRNAs against eight of the 17 TS and shL3 (B). shScr treated cells are shown as control.

Figure 17:
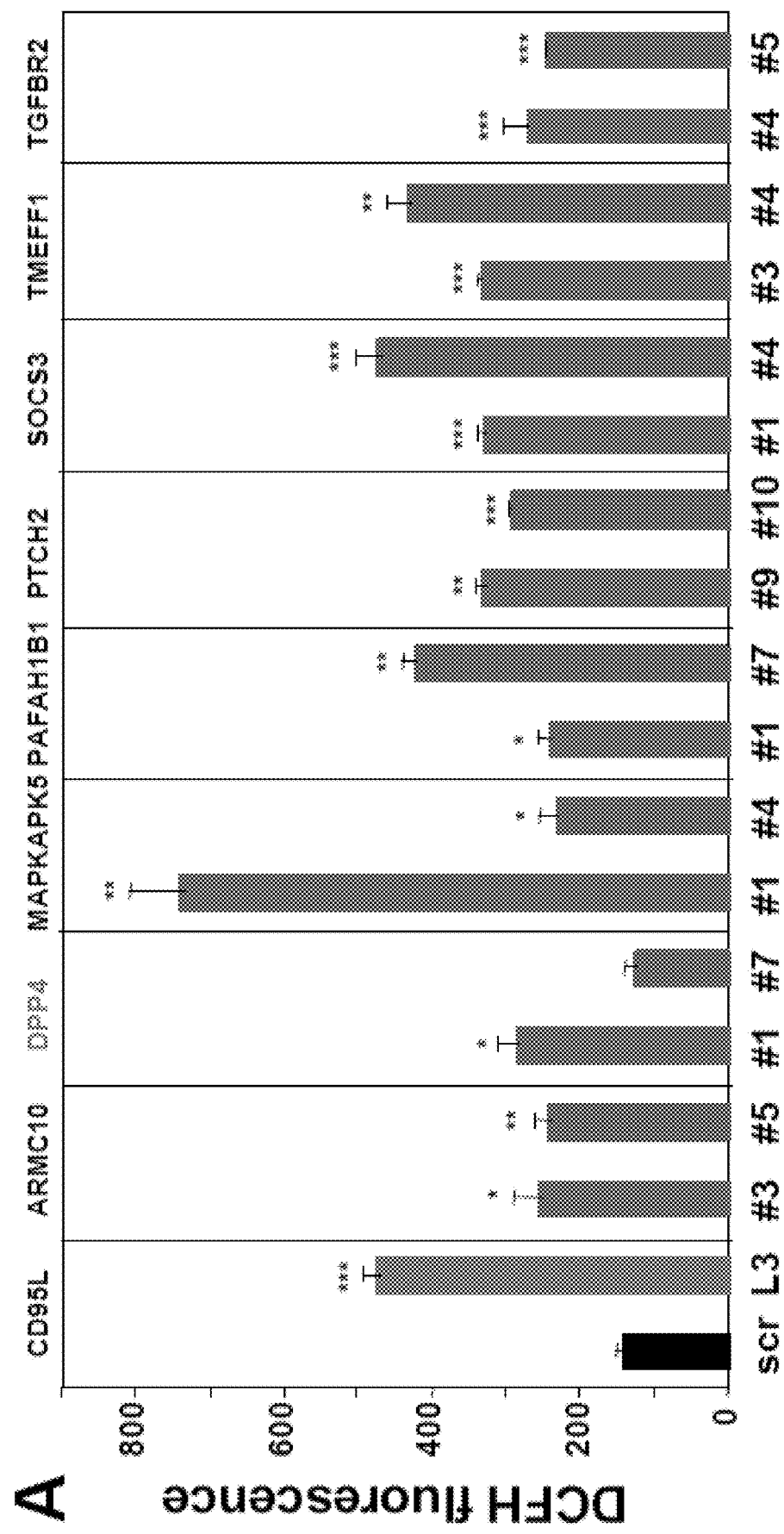
Figure 17:
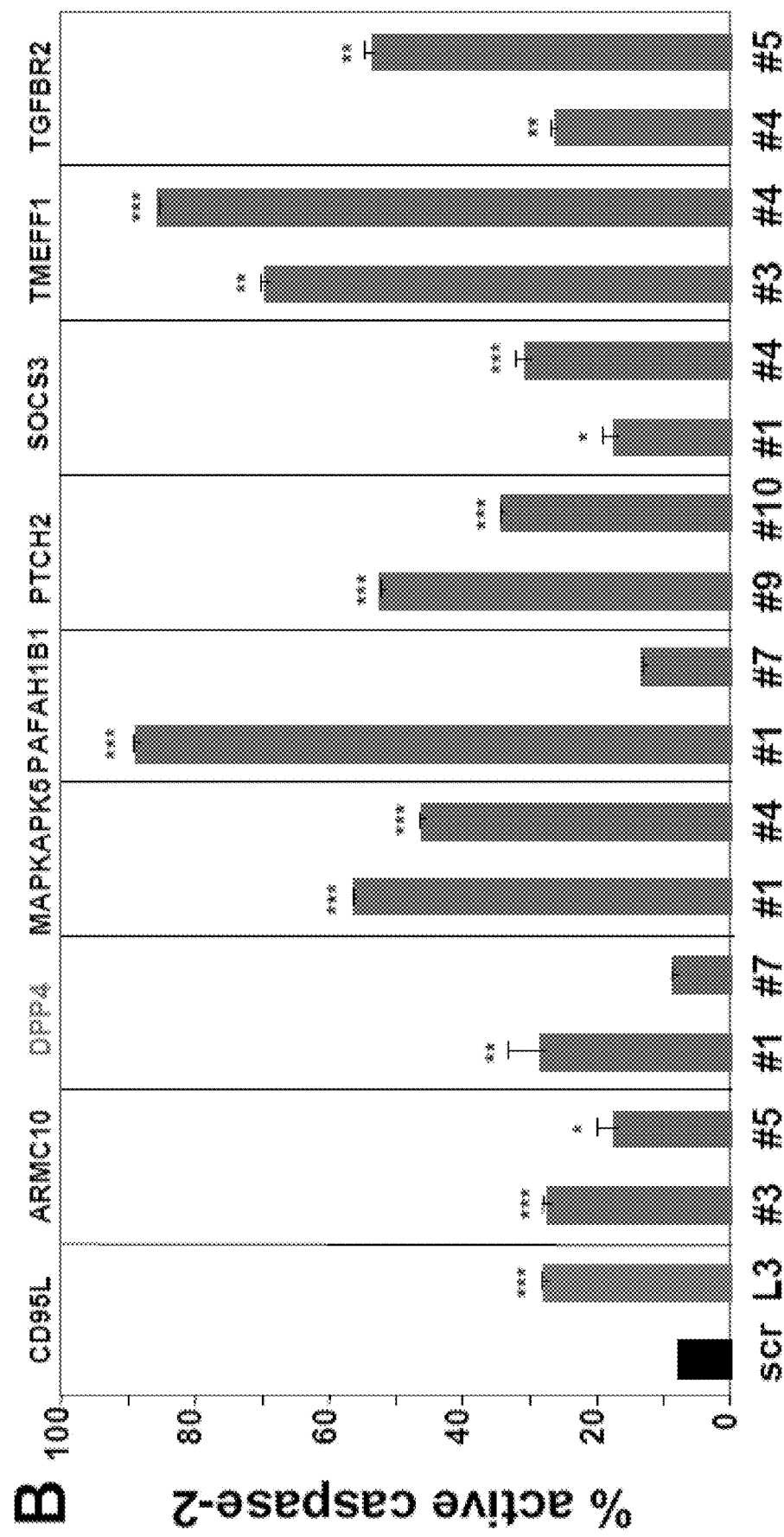
Figure 17:
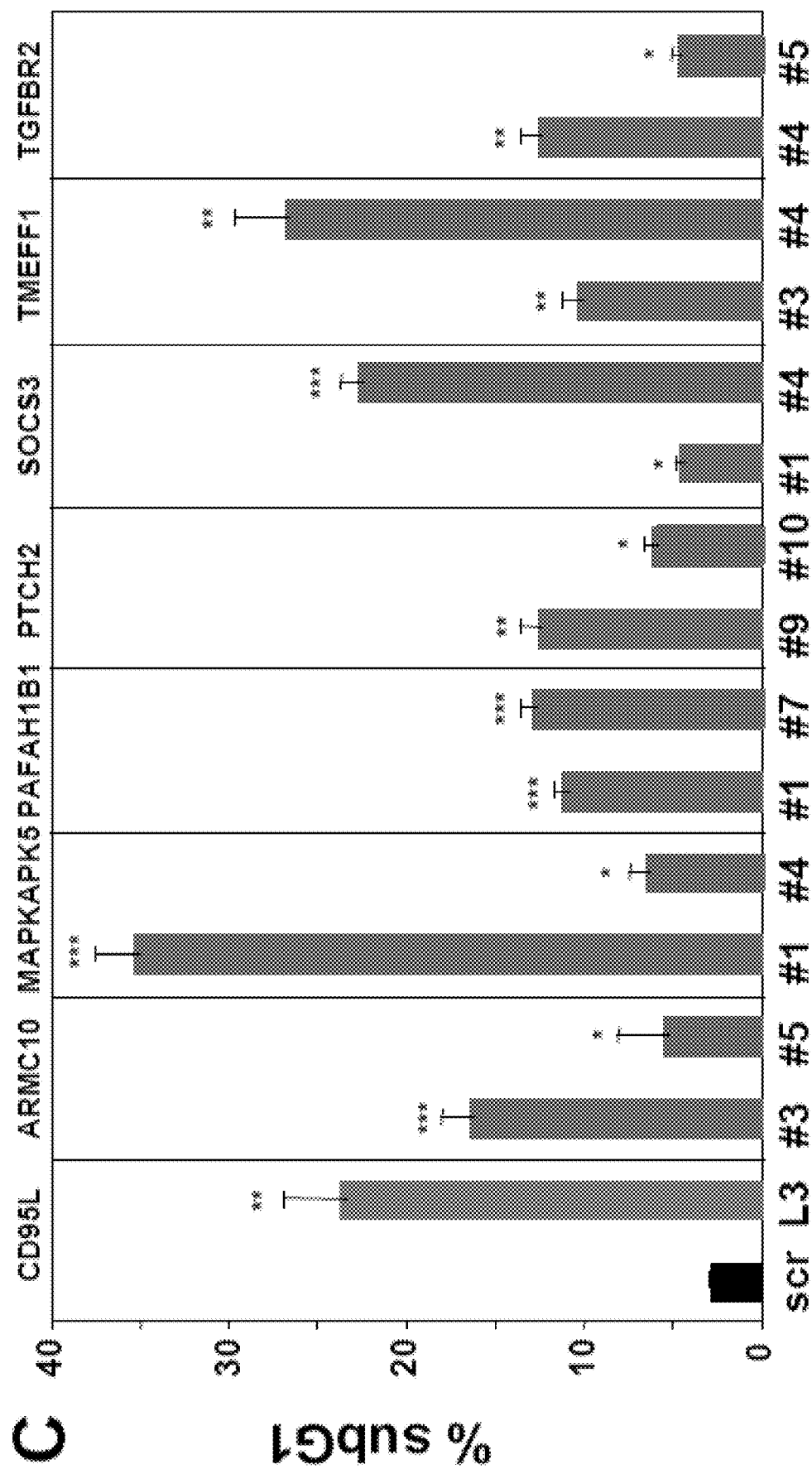

FIGS. 17. (A, B, and C). Toxic shRNAs derived from seven TS genes induce death that is biochemically similar to DISE. Quantification of ROS production by dichlorofluorescin (DCFH) fluorescence (A), caspase-2 activity (B) and quantification of cell death with PI staining (C) in HeyA8 cells 8 days after infection with shScr, shL3, and shRNAs derived from eight of the TS genes. ID numbers are shown in Table 1. p-values were calculated using students t-test. *p<0.01, p<0.001, *p<0.0001. For genes in black, both shRNAs were functionally active whereas genes shown in grey, only one the two shRNAs had a significant effect.

Figure 18:
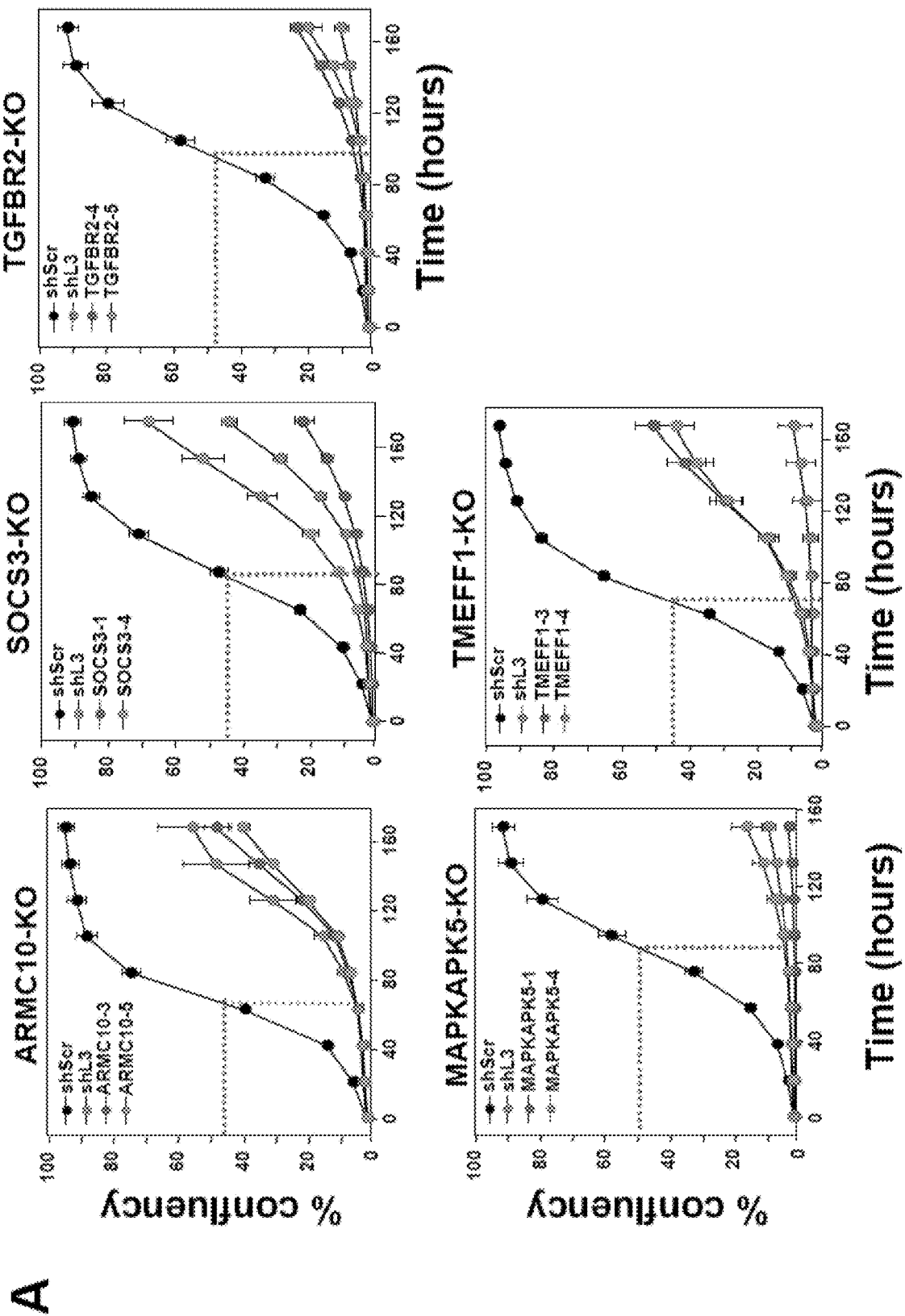

FIG. 18. shRNAs derived from four TS genes kill cells in the absence of the transcript and/or protein produced from the targeted gene. Percent cell confluence over time of HAP1 parental cells, or HAP1 knock-out cells, after infection with shScr, shL3, or one of two shRNAs each targeting the respective TS. Percent growth reduction values were calculated using STATA1C software when cells infected with shScr reached half maximal confluency as indicated by the dotted line. p-values were calculated using a t-test.

FIG. 19. List of the 17 genes that are putative tumor suppressors and were identified in our lethality screen. The genes are ranked first according to the number of lethality screens in which these genes were found to be survival genes, and second according to the average H score. Higher counts are indicated by darker colors. HCC, hepatocellular carcinoma. FASLG is also shown for comparison. [1], [32]; [2], [33]; [3], [34]; [4], [35]; [5], [36]; [6], [37]; [7], [38]; [8], [39]; [9], [40]; [10], [41]; [11], [42]; [12], [43]; [13], [44]; [14], [45]; [15], [46]; [16], [47]; [17], [48]; [18], [49]; [19], [50]; [20], [51]; [21], [52]; [22], [53]; [23], [54]; [24], [55]; [25], [56]; [26], [57]; [27], [58]; [28], [59]; [29], [60]; [30], [61]; [31], [62]; [32], [63]; [33], [64]. http://bioinfo.mc.vanderbilt.edu/TSGene[65].

Figure 20:
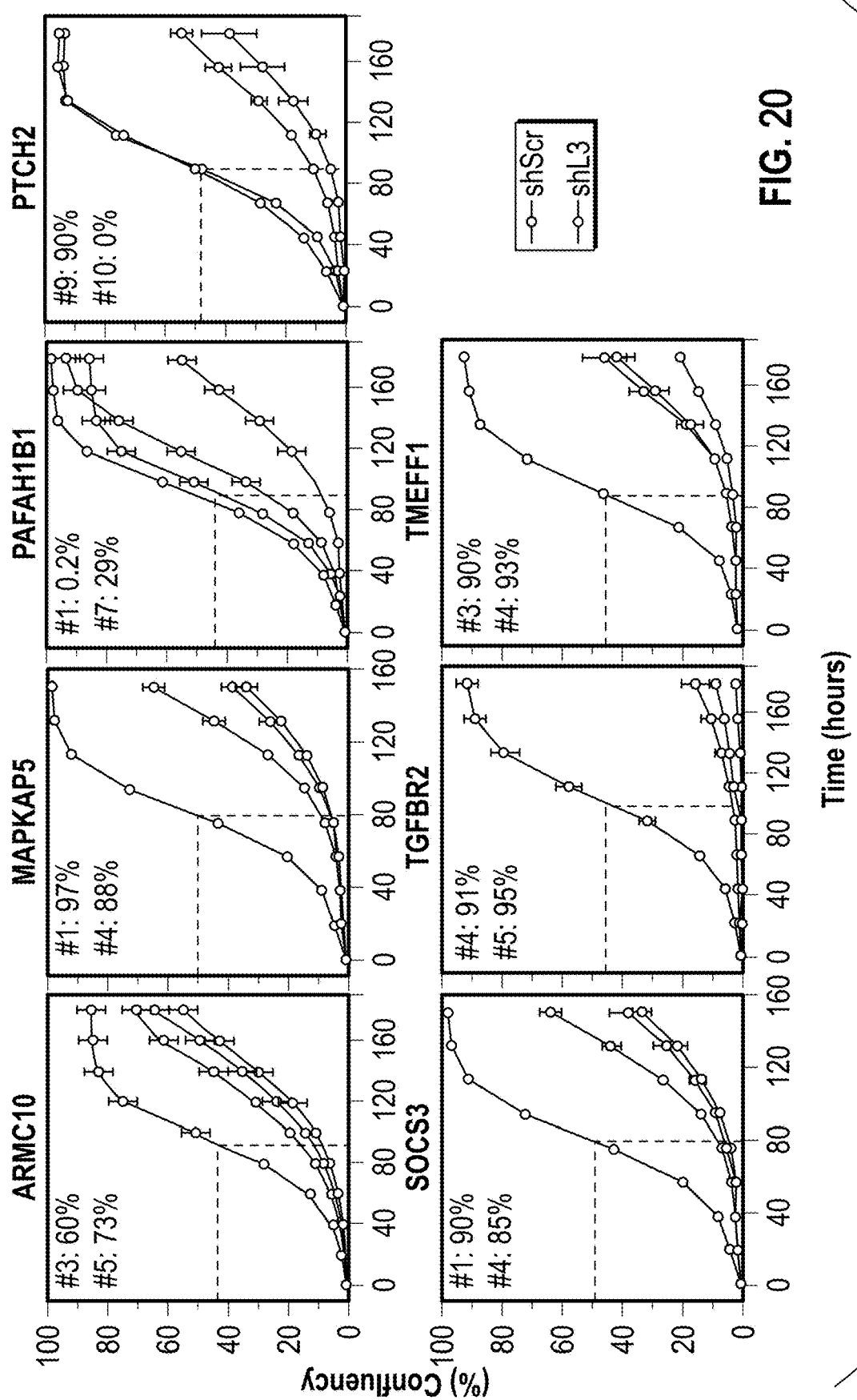

FIG. 20. Toxic shRNAs cause growth reduction in Hap1 cells. Percent cell confluency over time of Hap1 cells infected with shScr, shL3, and two shRNAs derived from each listed TS gene. The curves for cells infected with two independent shRNA for each TS gene and their specific ID number and respective growth reduction caused by each shRNA are shown. Percent growth reduction values were calculated using STATA1C software when cells infected with shScr reached half maximal confluency as indicated by the dotted line. Names of genes for which only one of the two shRNAs reduced growth more than 50% are shown in grey.

Figure 21:
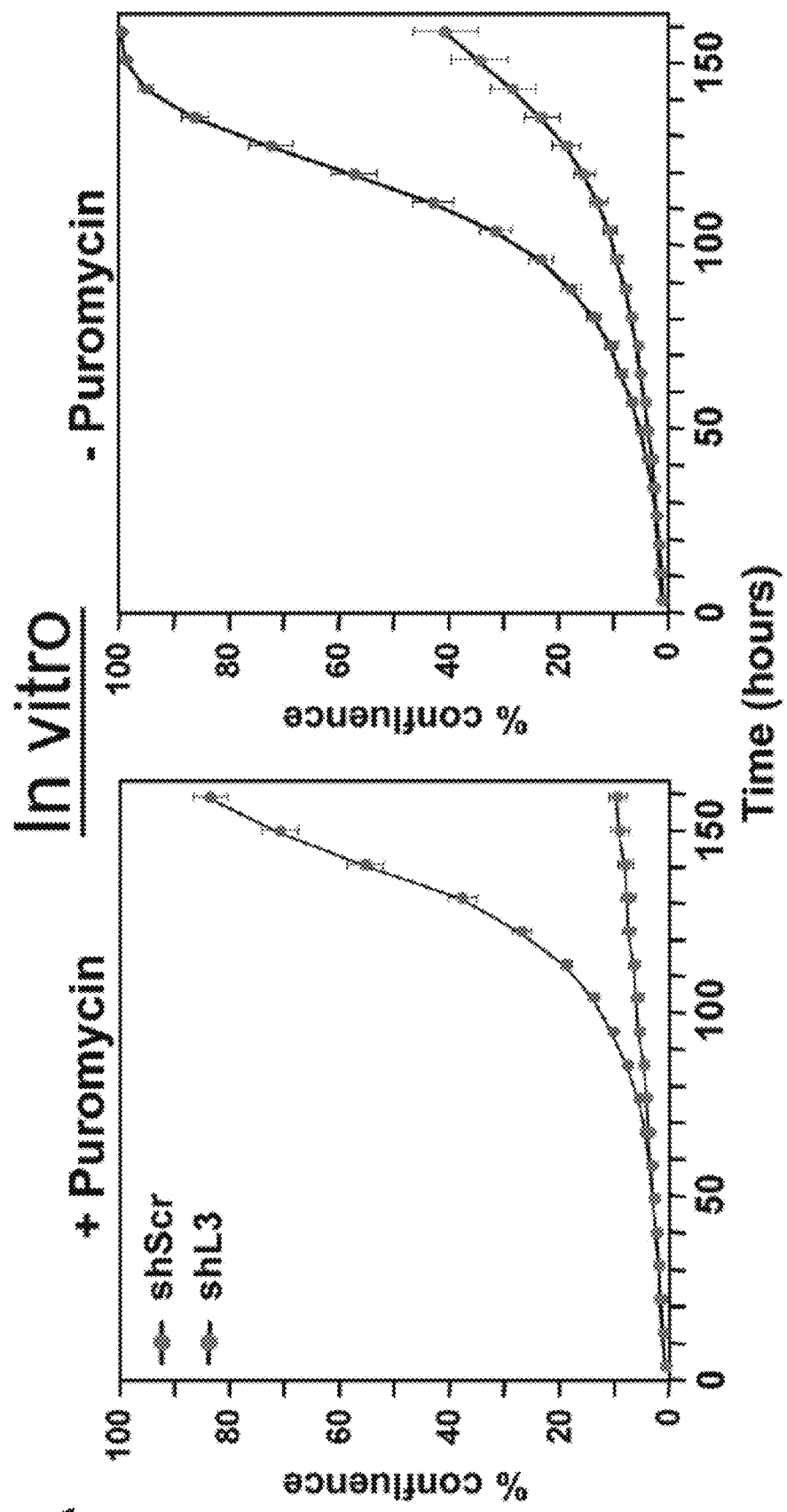
Figure 21:
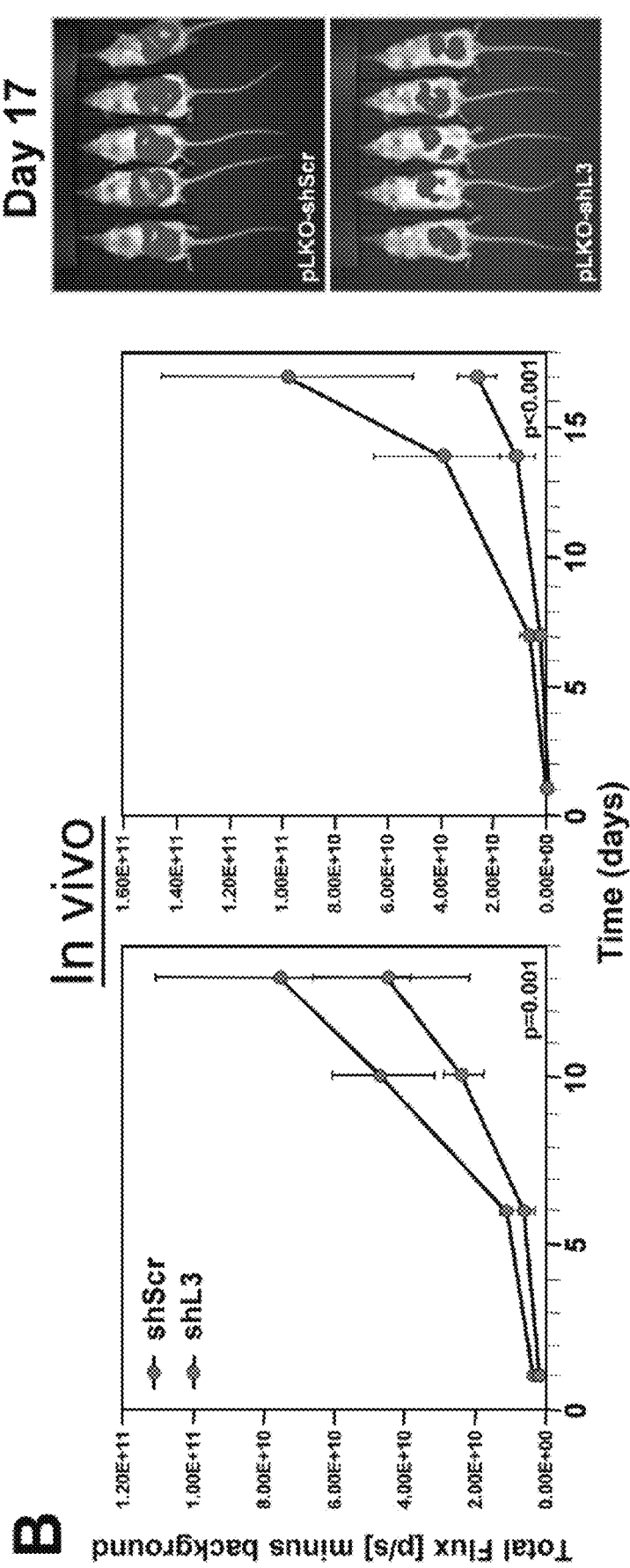
Figure 21:
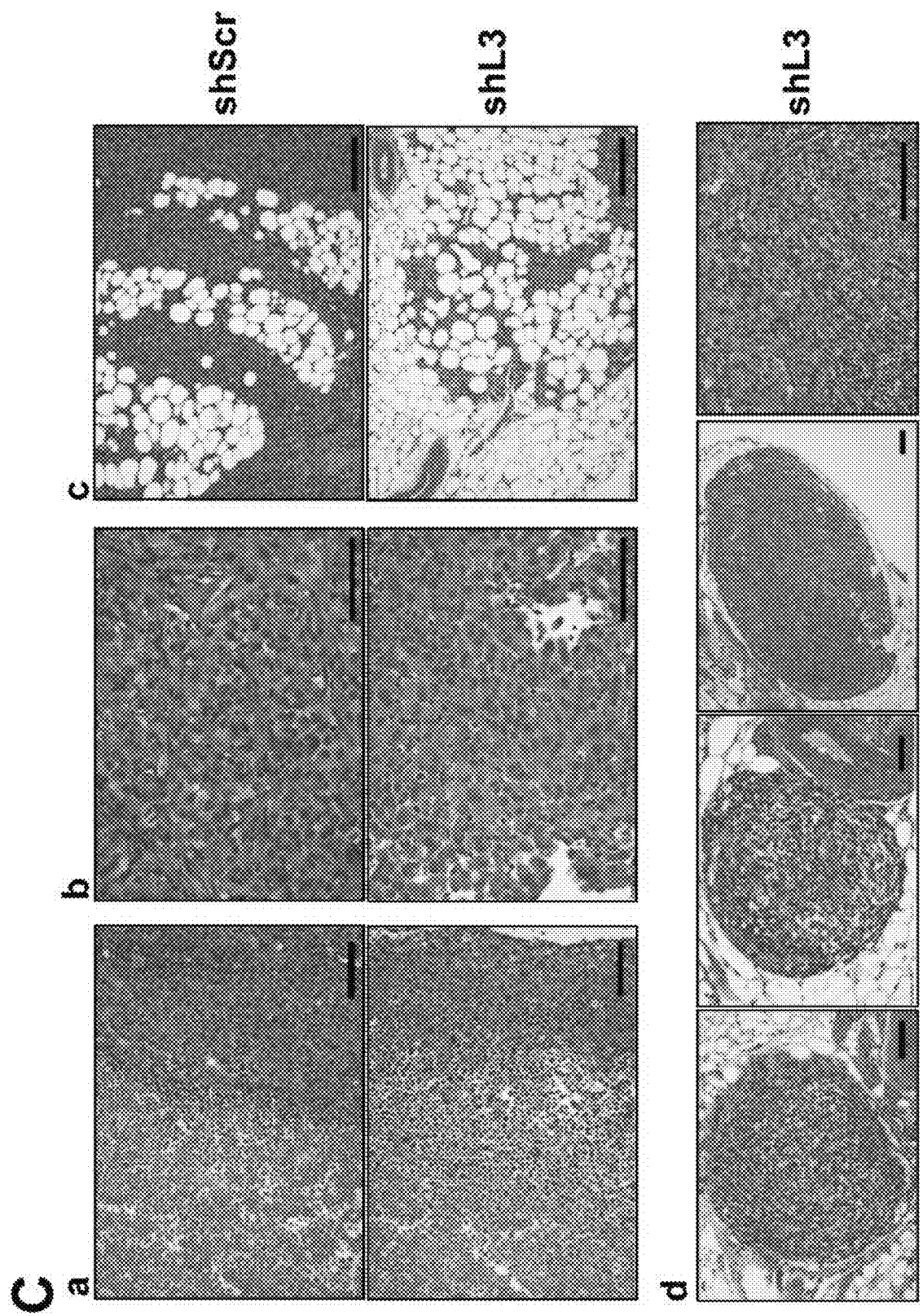

FIGS. 21. (A, B, and C). Expression of a CD95L derived shRNA causes induction of DISE in vitro and in vivo. A: Percent growth change over time of HeyA8 Venus-siL3-pfuL2T cells infected with either shScr or shL3 pLKO lentiviruses (MOI=5) (with and without puromycin selection) at 250 cells/well. B: Small animal imaging of HeyA8 pfuL2T cells infected with either shScr or shL3 pLKO lentiviruses (MOI=5) after i.p. injection into NSG mice (10 mice per group, $10^6$ cells/mouse). Left: mice injected with cells infected with virus without puromycin selection; Center: Mice injected with HeyA8 cells infected with shRNAs and selected with puromycin for 24 hours. Right: Bioluminescence image of 5 mice 17 days after i.p. injection with HeyA8 cells infected with either shScr or shL3 virus. Two-way ANOVA was performed for pairwise comparisons of total flux over time between shScr and shL3 expressing cells. C: H&E staining of representative tumors isolated from mice carrying HeyA8-shScr (a, b, c, top row) and HeyA8-shL3 tumors (a, b, c, bottom row and d). a, in shScr treated tumors, tumor mass showed two zones of viable (right) and necrotic (left) tumor regions with sharply demarked boundary. The viable tumor cells were cohesive with dense basophilic and pale cytoplasm. In shL3 treated tumor, a zone of dying tumor cells sites were seen in between viable and necrotic zones. This zone had tumor cells that were loosely cohesive with mixed dying, dead and viable cells. b, Close view of tumor cells revealed the different cytologic features. In shScr treated tumors, cells were more cohesive with a solid growth pattern with centrally located large and high grade nuclei. In shL3 treated tumors, cells were loosely cohesive with eccentrically located nuclei and eosinophilic and hyaline cytoplasm. These findings suggest early degenerative or regressing changes. c, Tumor infiltrating into fat had minimal or no tumor cell necrosis. In shScr treated tumors, tumor mass in fat had large and high tumor volume (top panel). In shL3, infiltrating tumor cells were much smaller in size and volume and areas of regression change were seen (bottom panel). d, Tumor regression could be frequently seen in shL3 treated tumors, characterized by well demarked tumor nodules (left three images) with peripheral rim of viable tumor cells (right panel) and central regression of tumor bed which was replaced by histiocytes, lymphocytes and fibrotic stromal cells.

Figure 22:
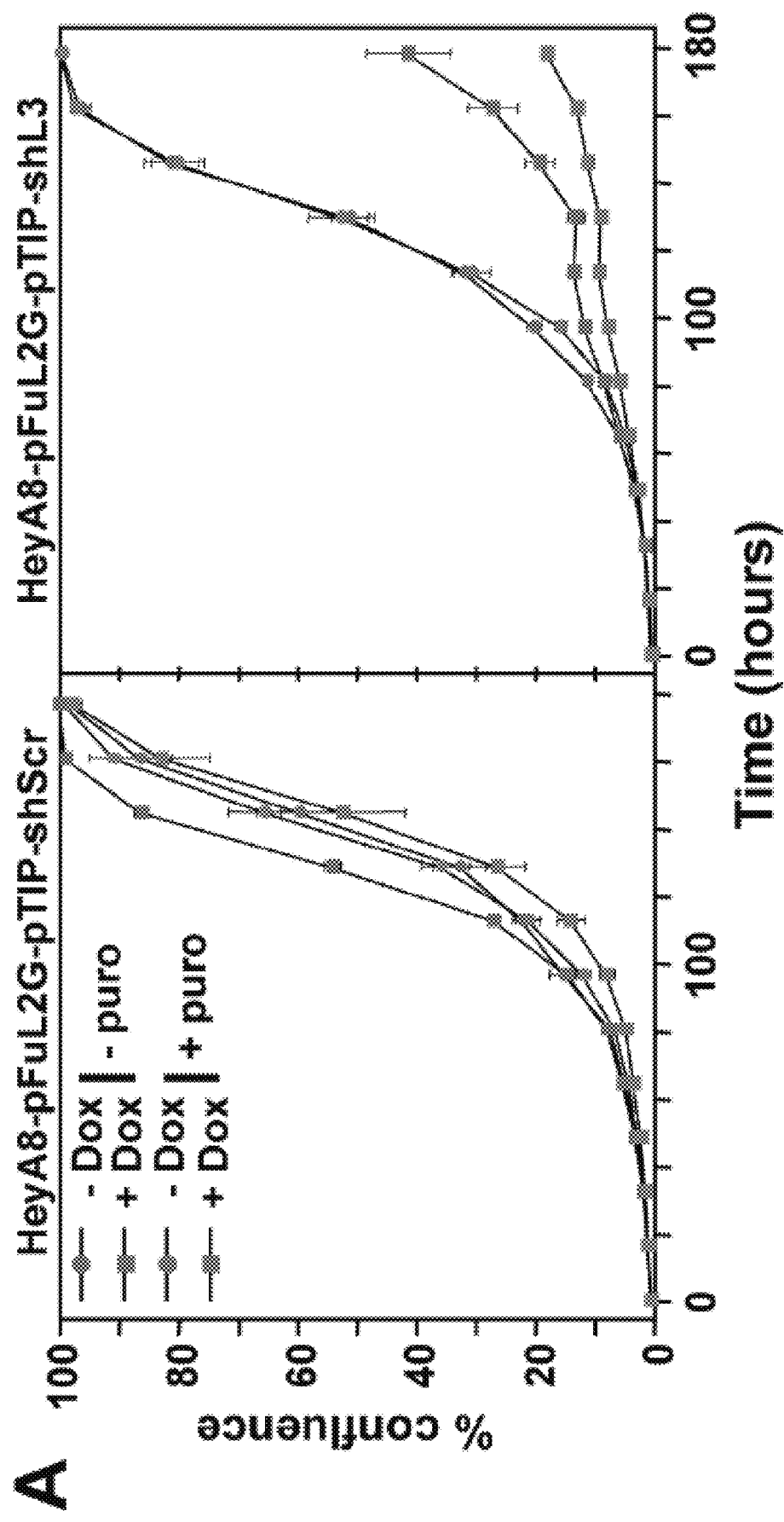
Figure 22:
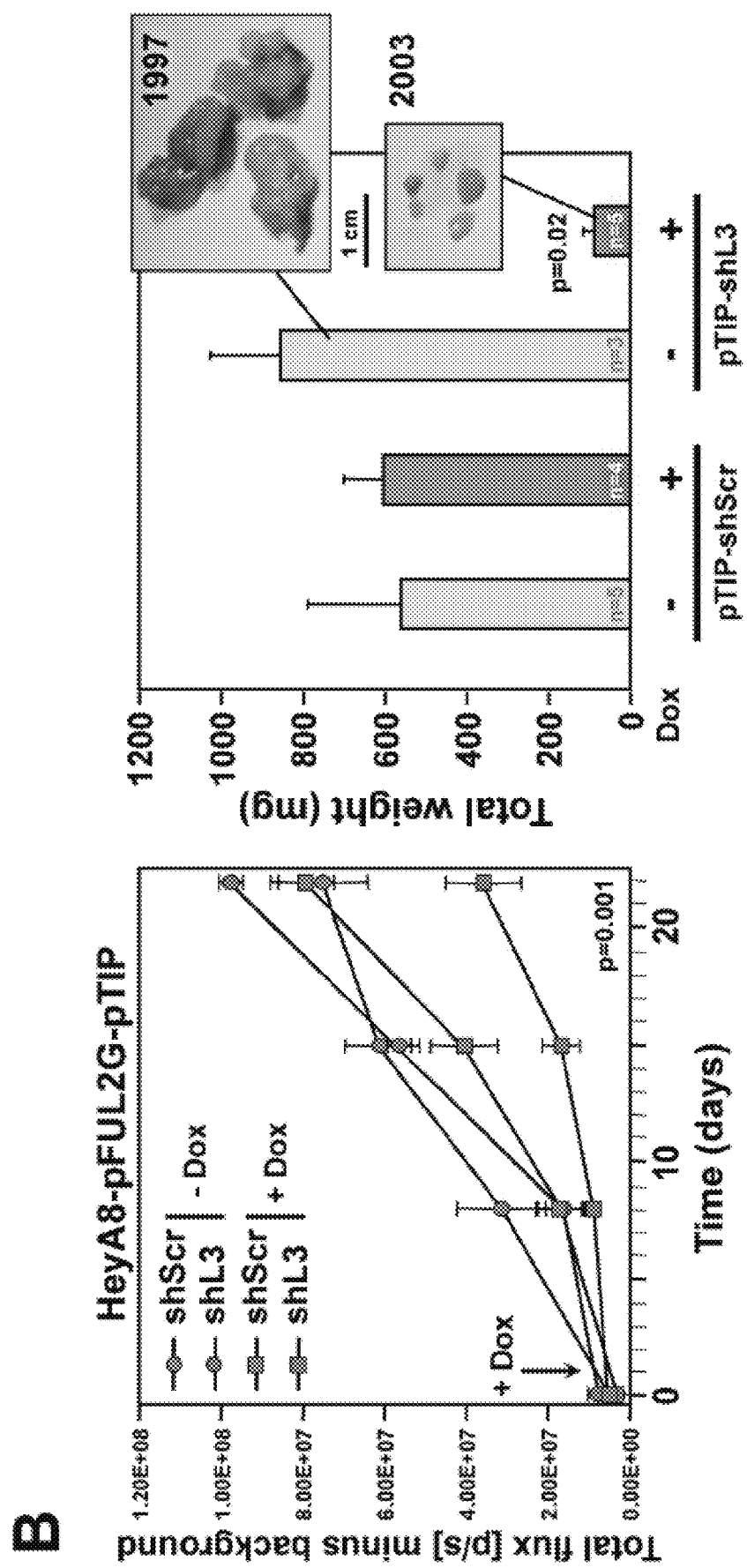
Figure 22:
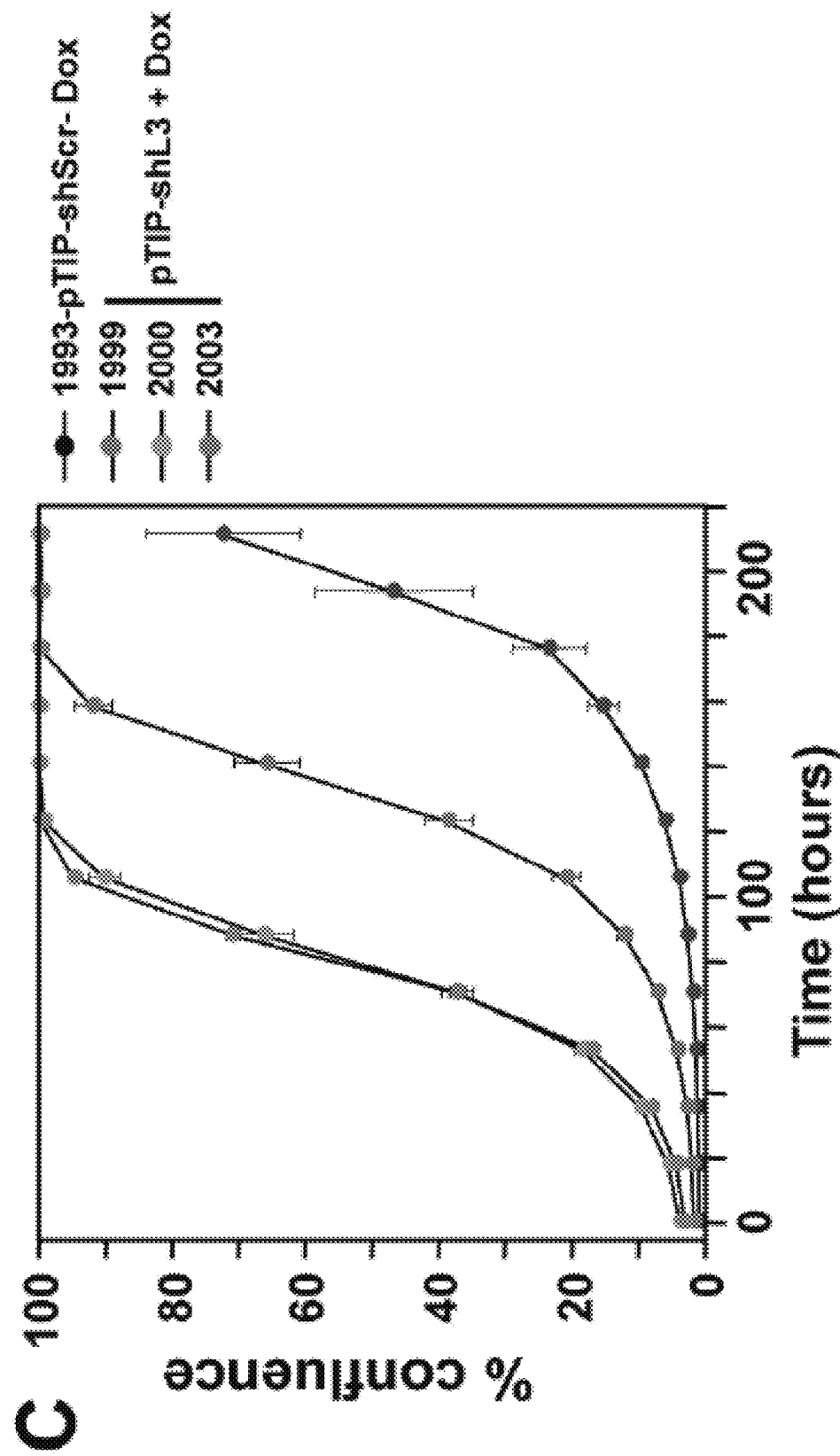
Figure 22:
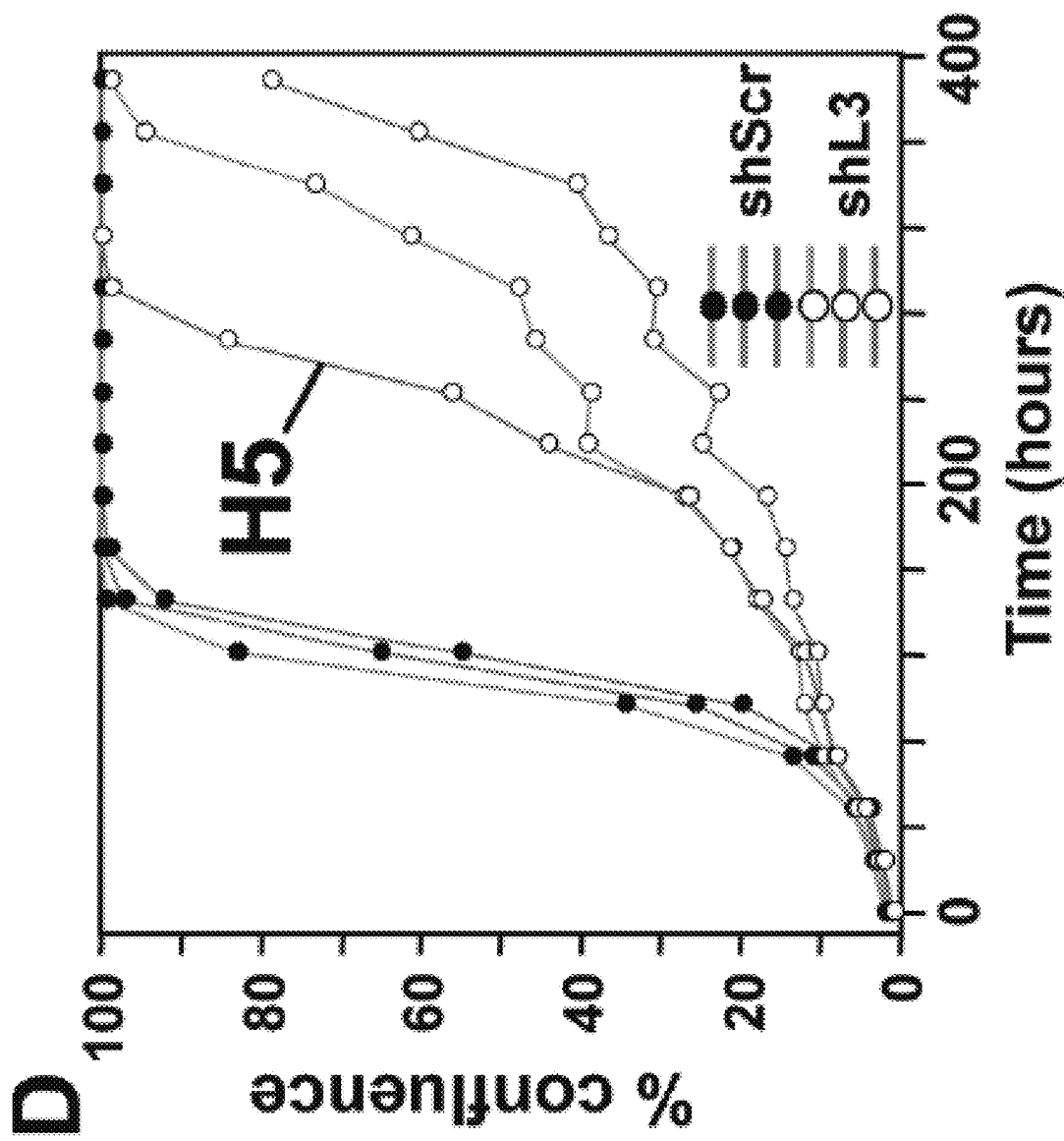
Figure 22:
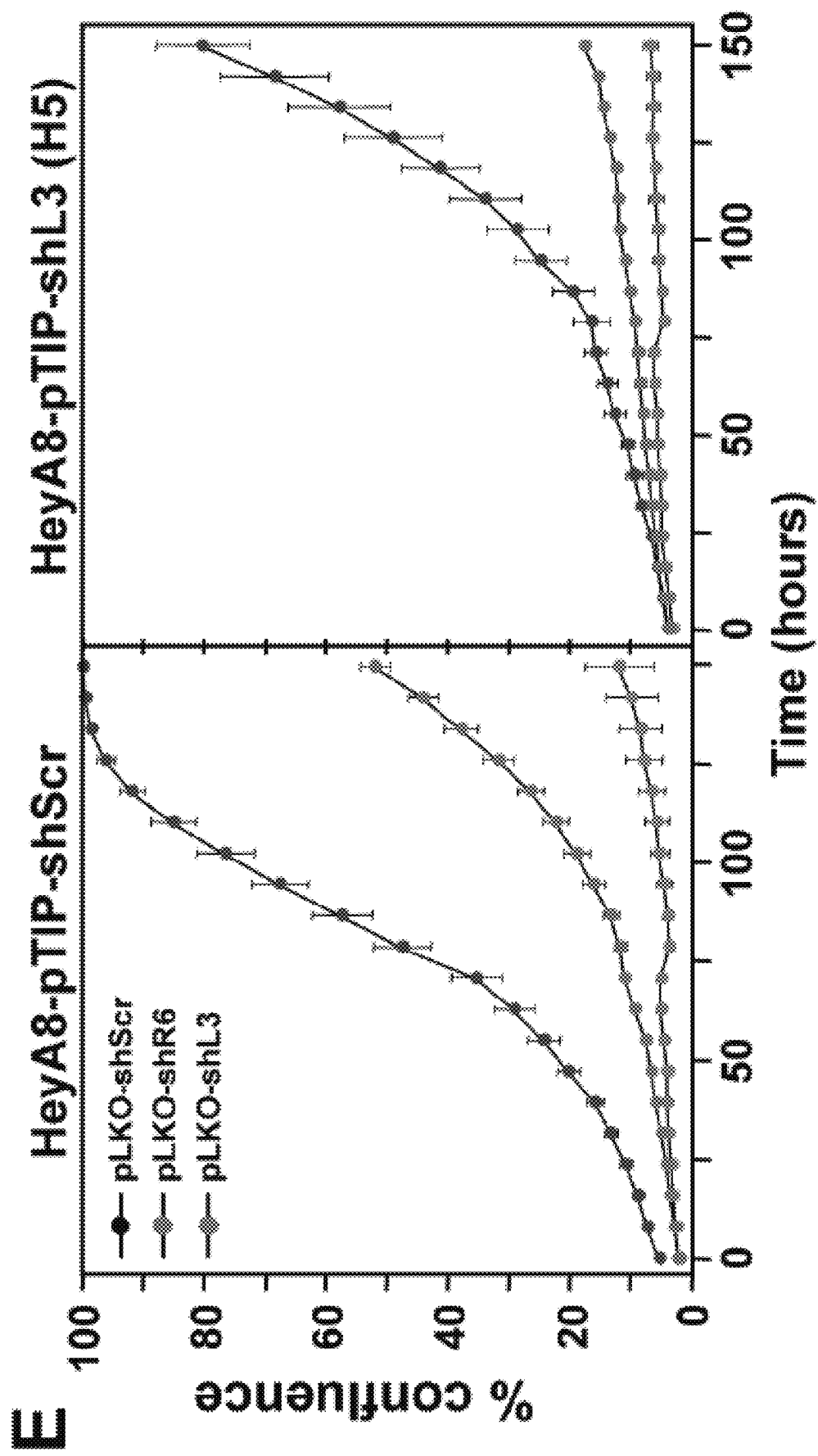
Figure 22:
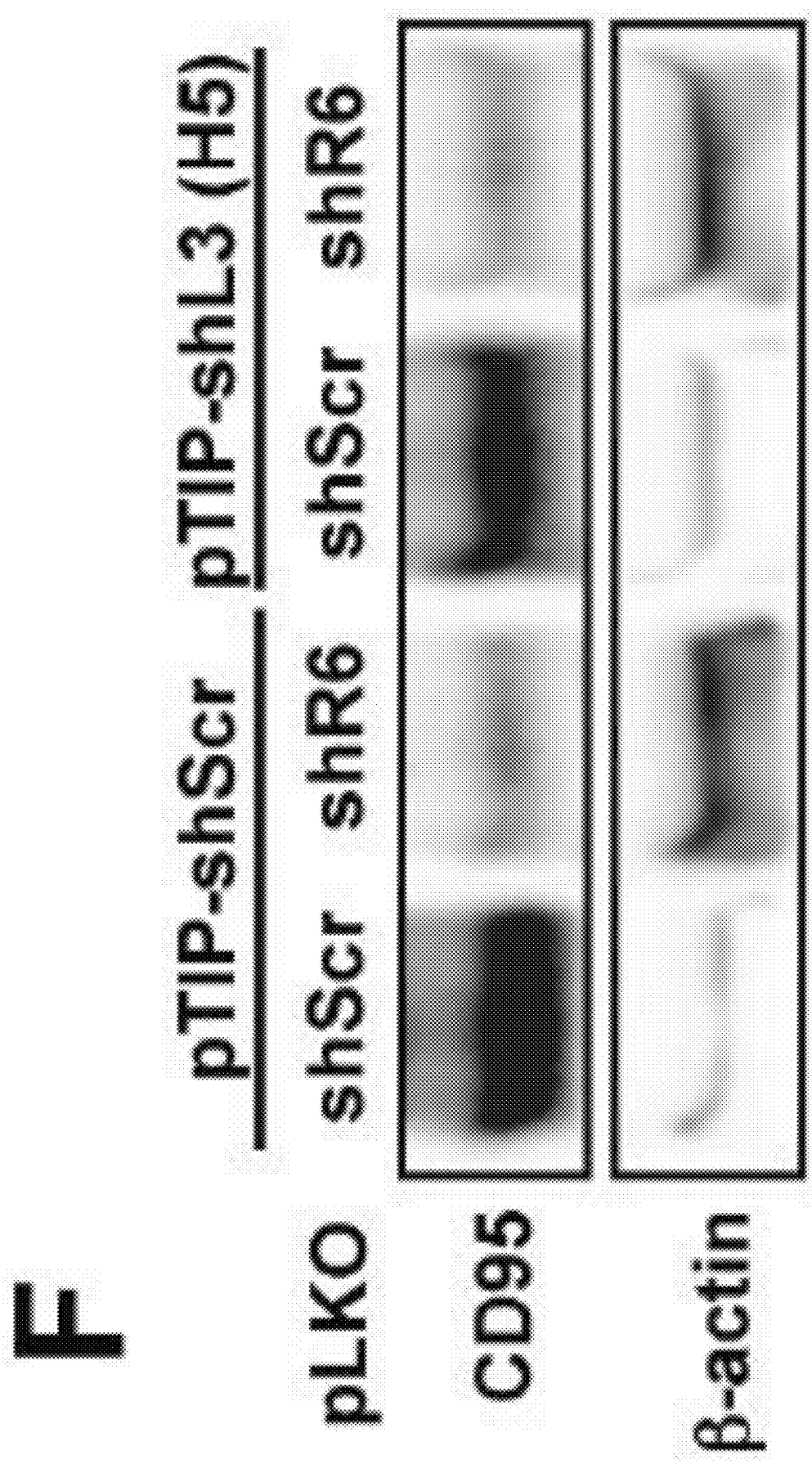

FIGS. 22. (A, B, C, D, E, and F). HeyA8 cells regress in vivo after inducible expression of shL3 and become resistant to the inducible vector but not to DISE induction. A: Percent growth change over time of HeyA8-pFul2G cells (plated at 250 cells per 96 well) expressing either pTIP-shScr or pTIP-shL3 cultured with or without Dox. B: Small animal imaging of HeyA8-pFul2G cells expressing either pTIP-shScr or pTIP-shL3 after i.p. injection into NSG mice ($10^6$ cells/mouse). Left: Tumor growth over time. The day the mice were given Dox containing drinking water is labeled with an arrow. ANOVA was performed for pairwise comparisons of total flux over time between shScr and shL3 expressing cells. Right: Tumor weight in each treatment group 22 days after tumor cell injection (pictures of the tumors of two representative mice are shown). P-value was calculated using Student's ttest. C: Change in confluence over time of four tumors isolated from 4 mice in B treated as indicated all in the presence of Dox. D: Change in confluency of HeyA8 cells expressing either pTIP-shScr or pTIP-shL3 in the presence of Dox. Confluency of three wells each is shown. The Dox resistant clone H5 was chosen for further analysis. E: Change in confluency of Hey8-pFul2G cells or the H5 clone over time in the presence of Dox after infection with either pLKO-shScr, pLKO-shL3 or pLKO-shR6 (MOI=6). F: Western blot analysis for CD95 of the cells in E infected with either pLKO-shScr or pLKO-shL3.

Figure 23:
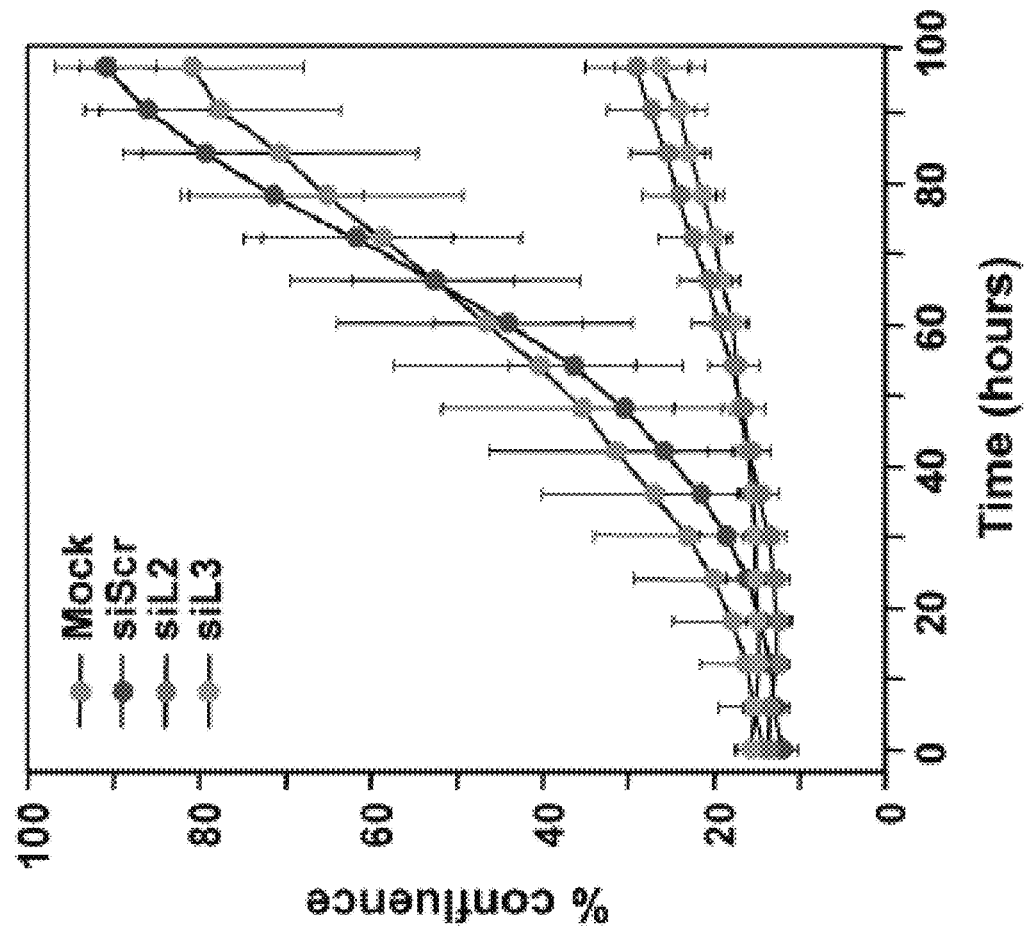
Figure 23:
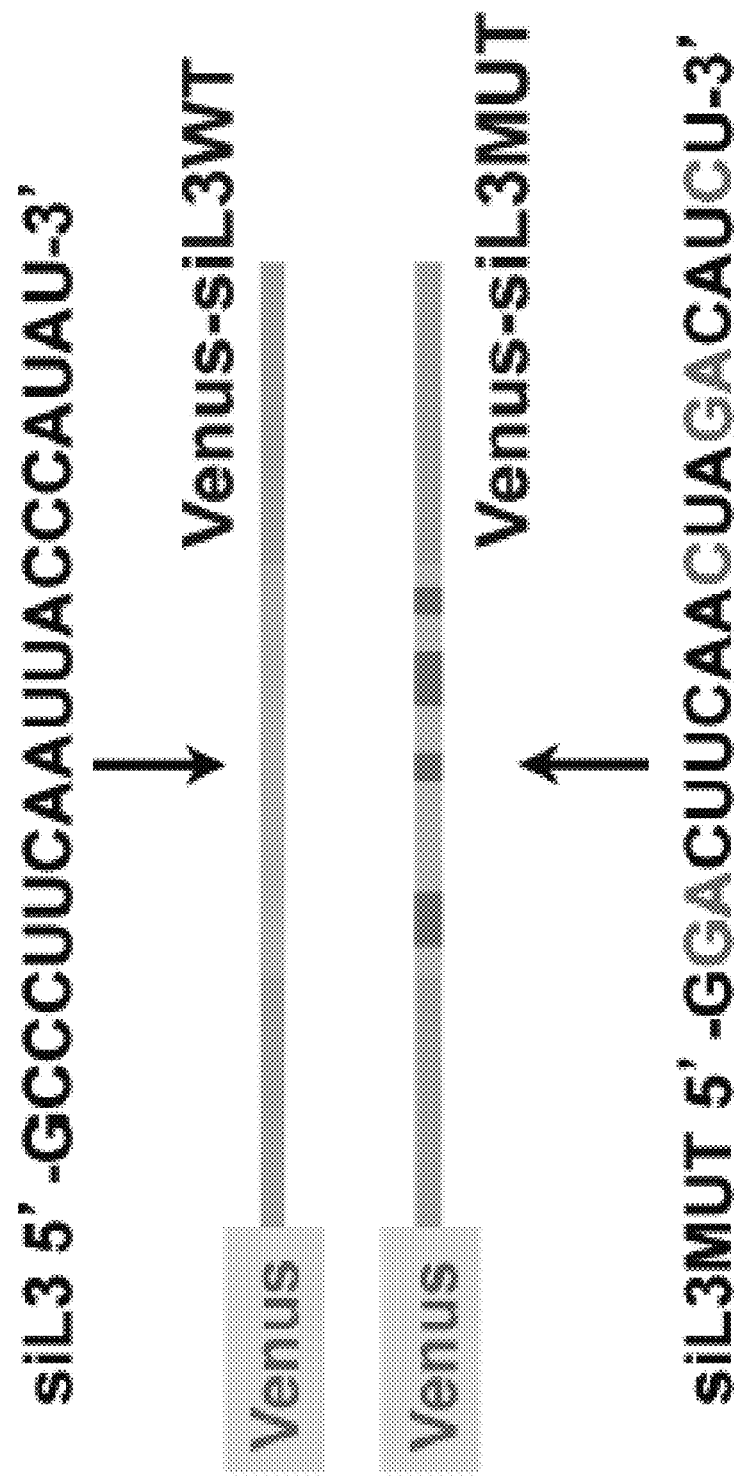
Figure 23:
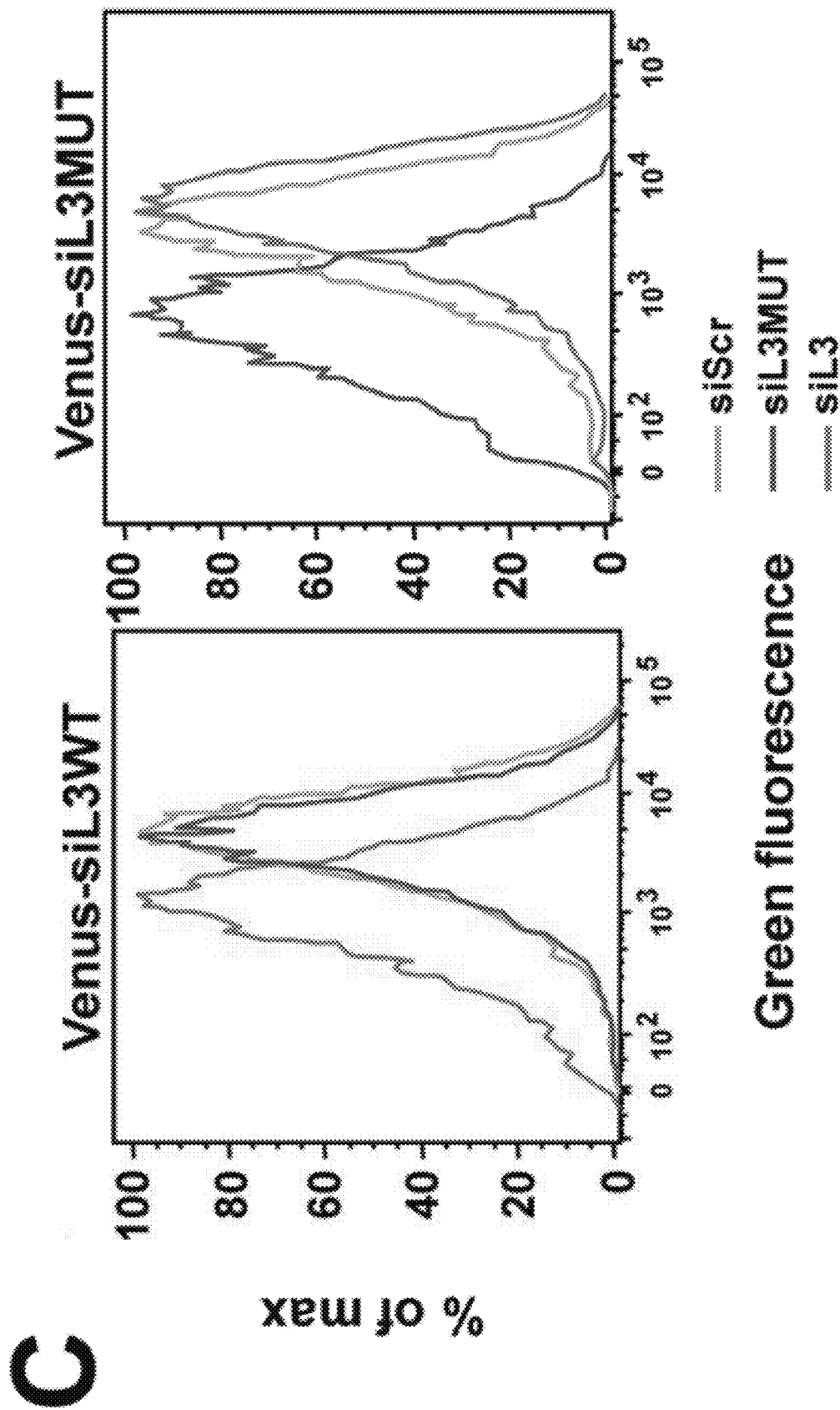
Figure 23:
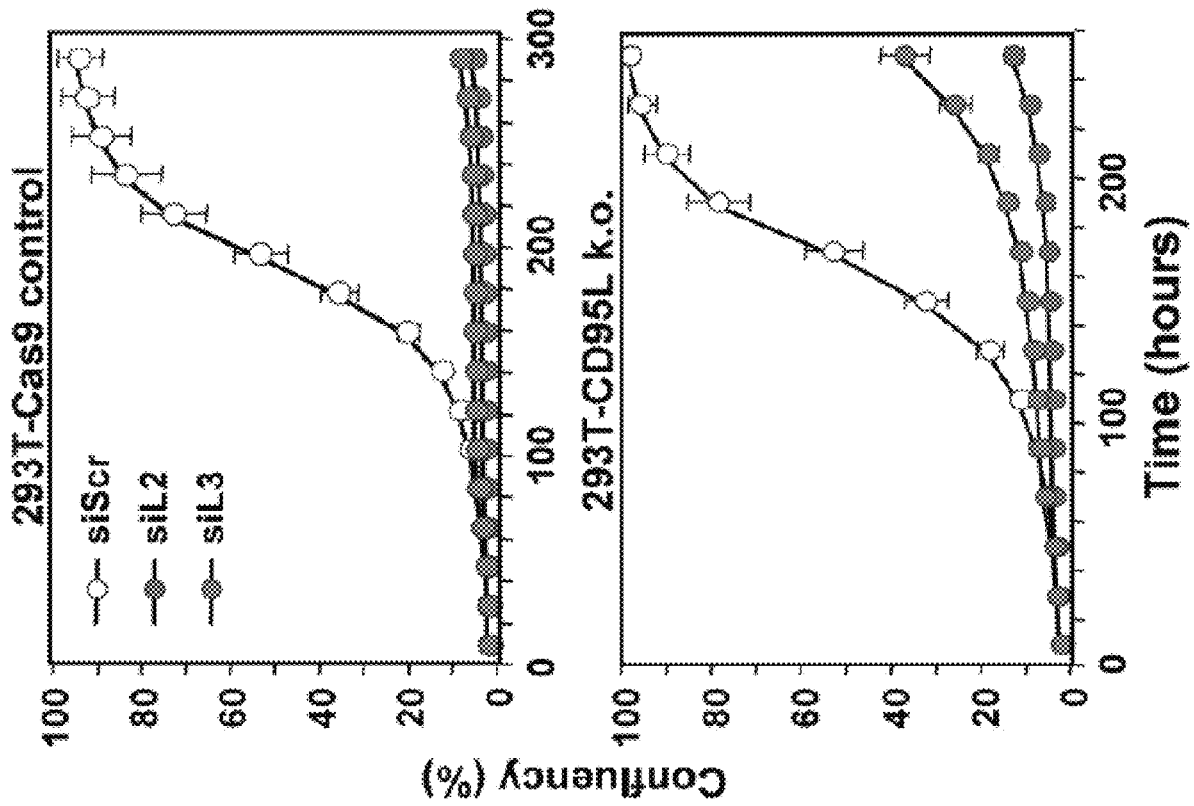

FIGS. 23. (A, B, D, and D). CD95L derived siL2 and siL3 knockdown CD95L and induce DISE by targeting critical survival genes. A: Specific targeting of a minisensor containing Venus fused to a CD95L minigene comprised of the 50 nt surrounding the siL3 target site in CD95L. Cells were either mock transfected (Lipofectamine only) or transfected with either 5 nM siScr, siL2 or siL3. Shown is change in percent confluency over time when cells were plated at 3000 cells per well in a 48-well plate 24 hours after transfection. B: Schematic showing the design of the wt Venus-siL3 sensor and a sensor carrying a mutated siL3 targeted site. Sequences of targeting siRNAs are given. C: FACS analysis of HeyA8 cells stably expressing either the wt or the mutant Venus-siL3 sensor (see B) 24 after transfection with 10 nM of either siScr, siL3WT or siL3MUT. D: Change in confluency over time of a mix of three 293T-Cas9 clones compared to a mix of two complete 293T CD95L deletion clones after transfection with 25 nM siScr, siL2 or siL3 (all from Dharmacon, IDT oligonucleotides gave very similar results (data not shown)). (Sequence Listing:

(SEQ ID NO: 143)
GCCCUUCAAUUACCCAUAU;

(SEQ ID NO: 42))
GGACUUCAACUAGACAUCU.

Figure 24:
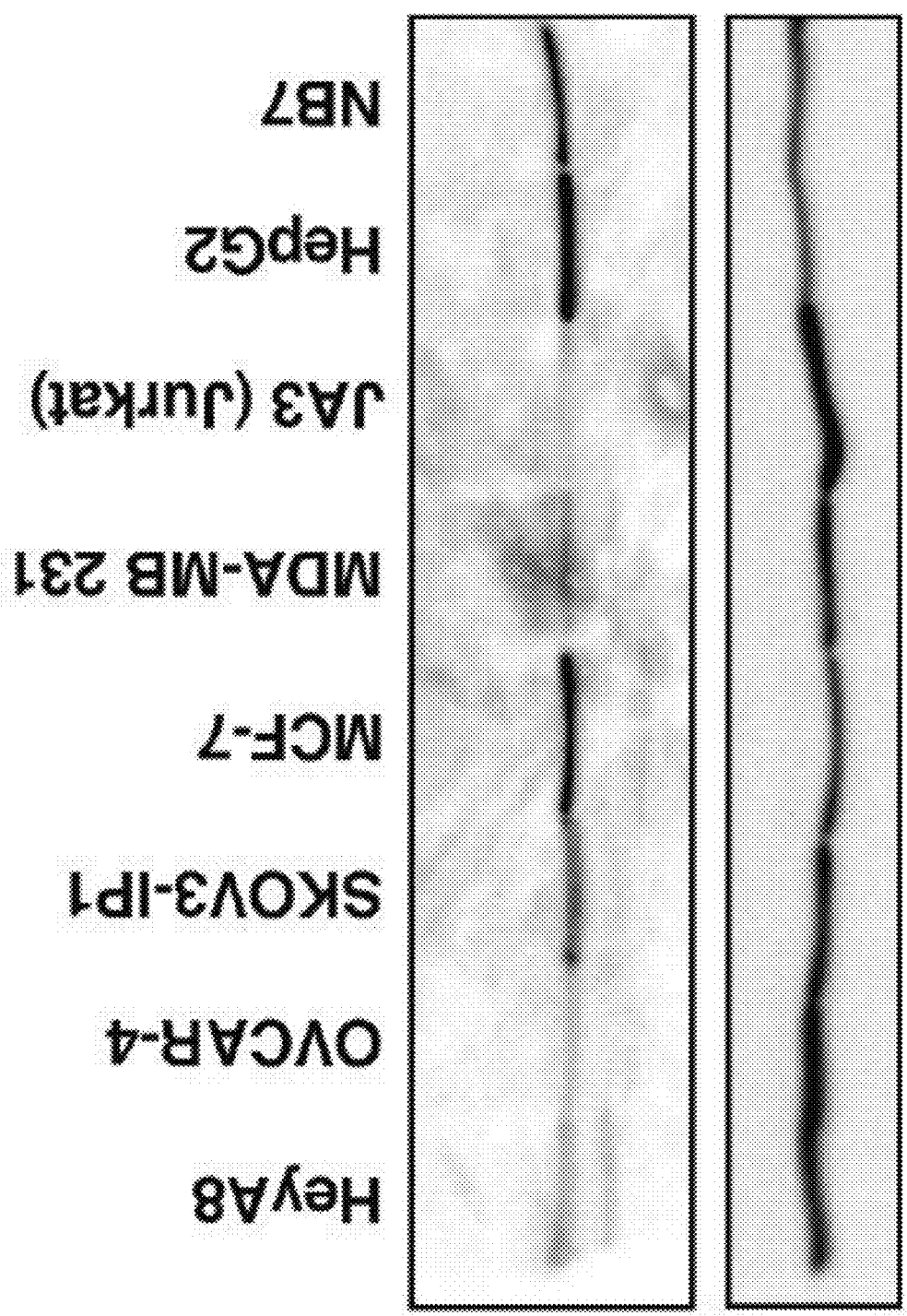
Figure 24:
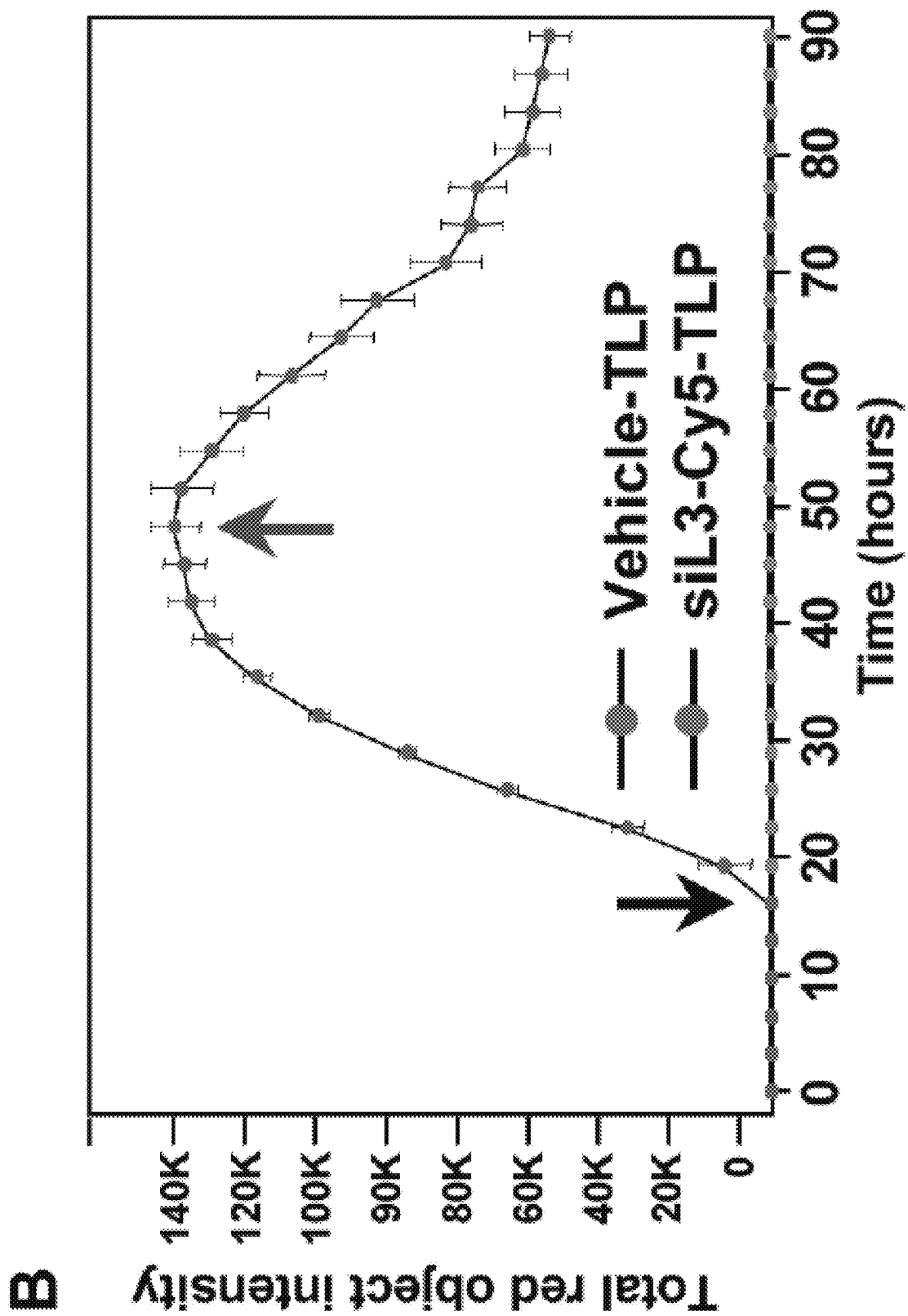
Figure 24:
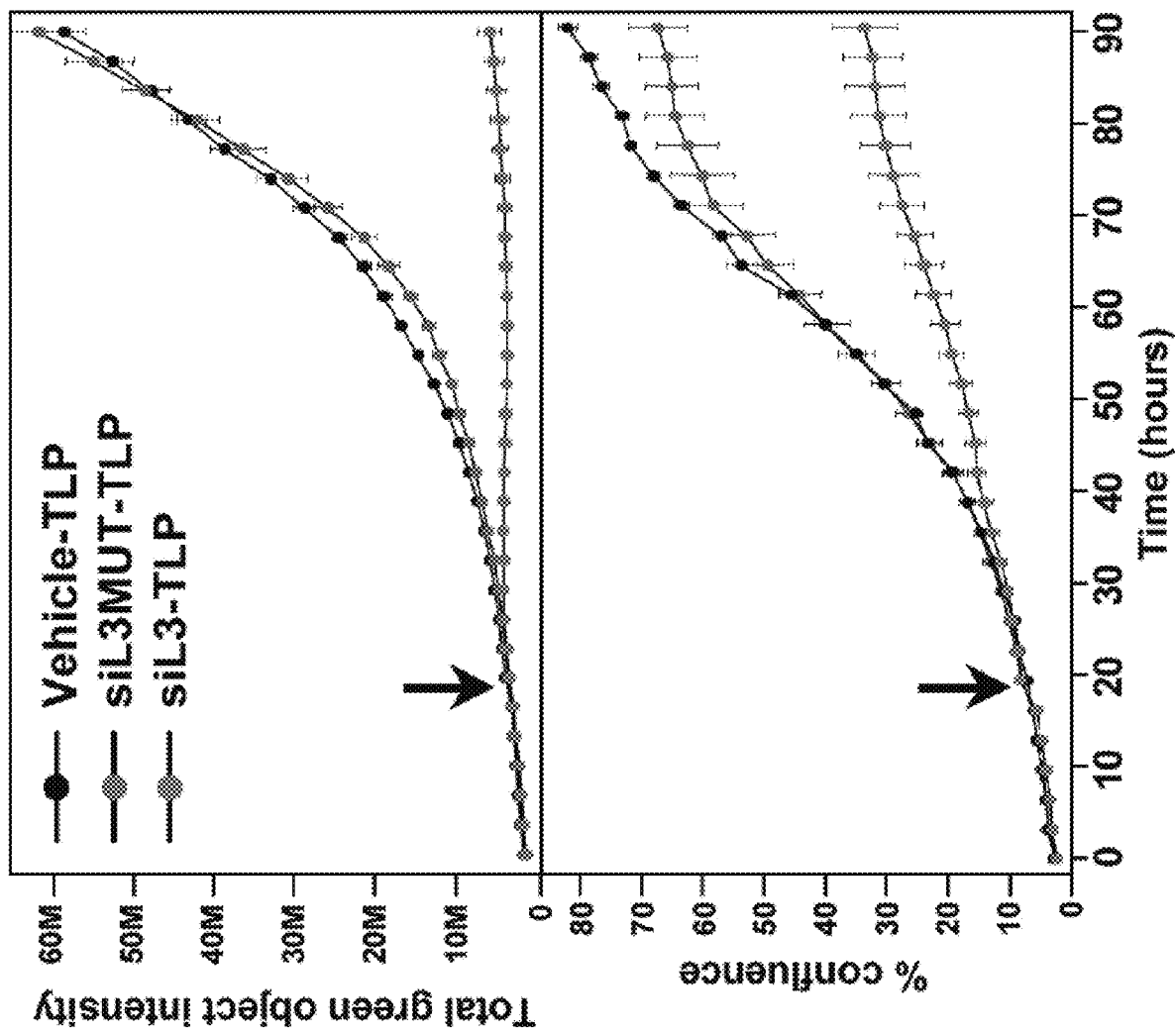

FIGS. 24. (A, B, and C). siL3-TLP uptake and DISE induction. A: Western blot analysis for SR-B 1 in different cancer cell lines. B: Change of red (Cy5) fluorescence (red object count) over time of HeyA8 cells treated with TLPs. Black arrow, particles were added; Arrow, cells were washed and particles removed. C: HeyA8 cells expressing the Venus-siL3 sensor were incubated for 90 hours with 8 nM (RNA concentration) siL3-TLP, siL3MUT-TLP, or Vehicle-TLPs. Cells were analyzed in an IncuCyte Zoom. Top: Total (Venus) green fluorescence. Bottom: Confluency.

Figure 25:
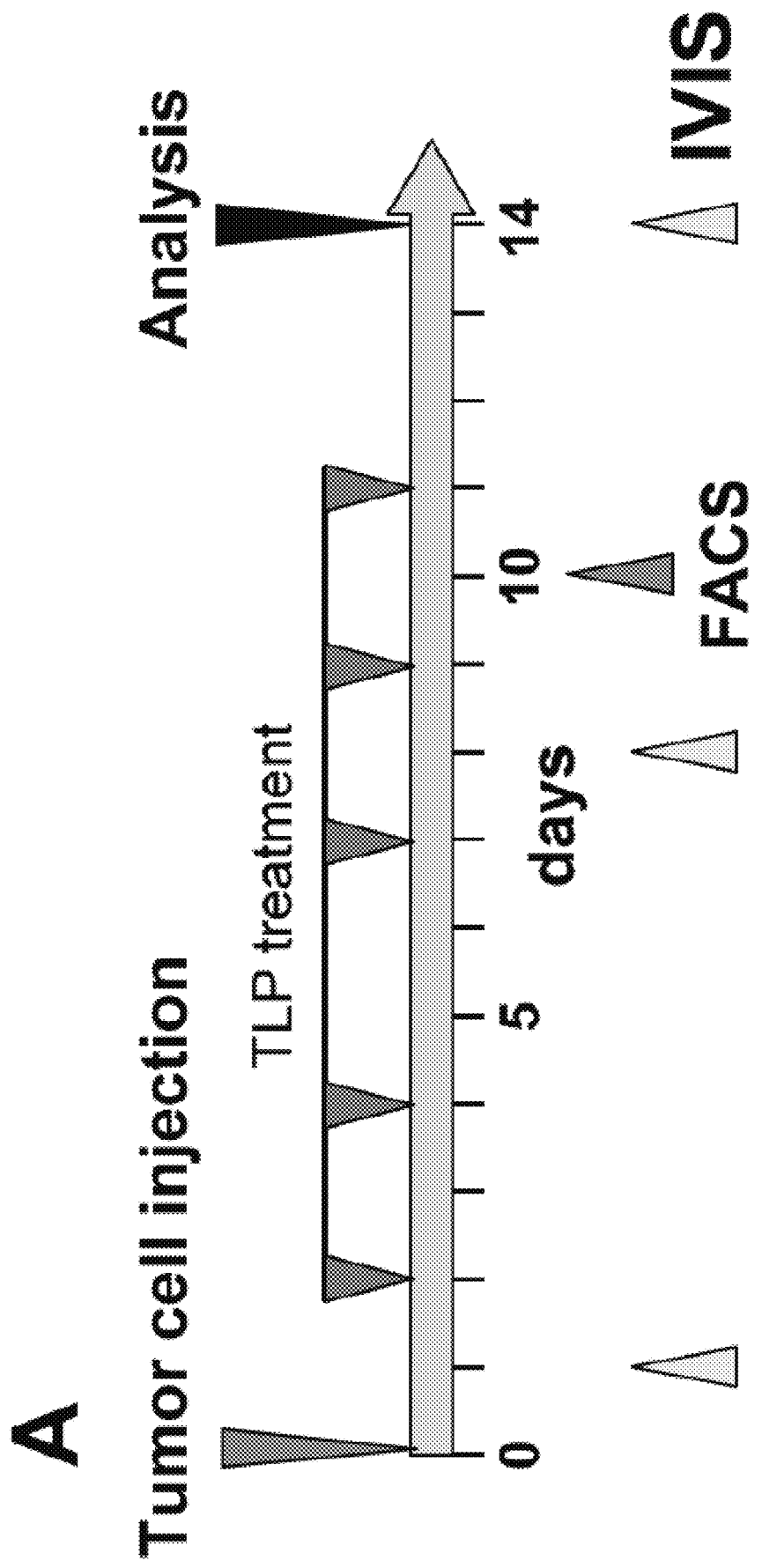
Figure 25:
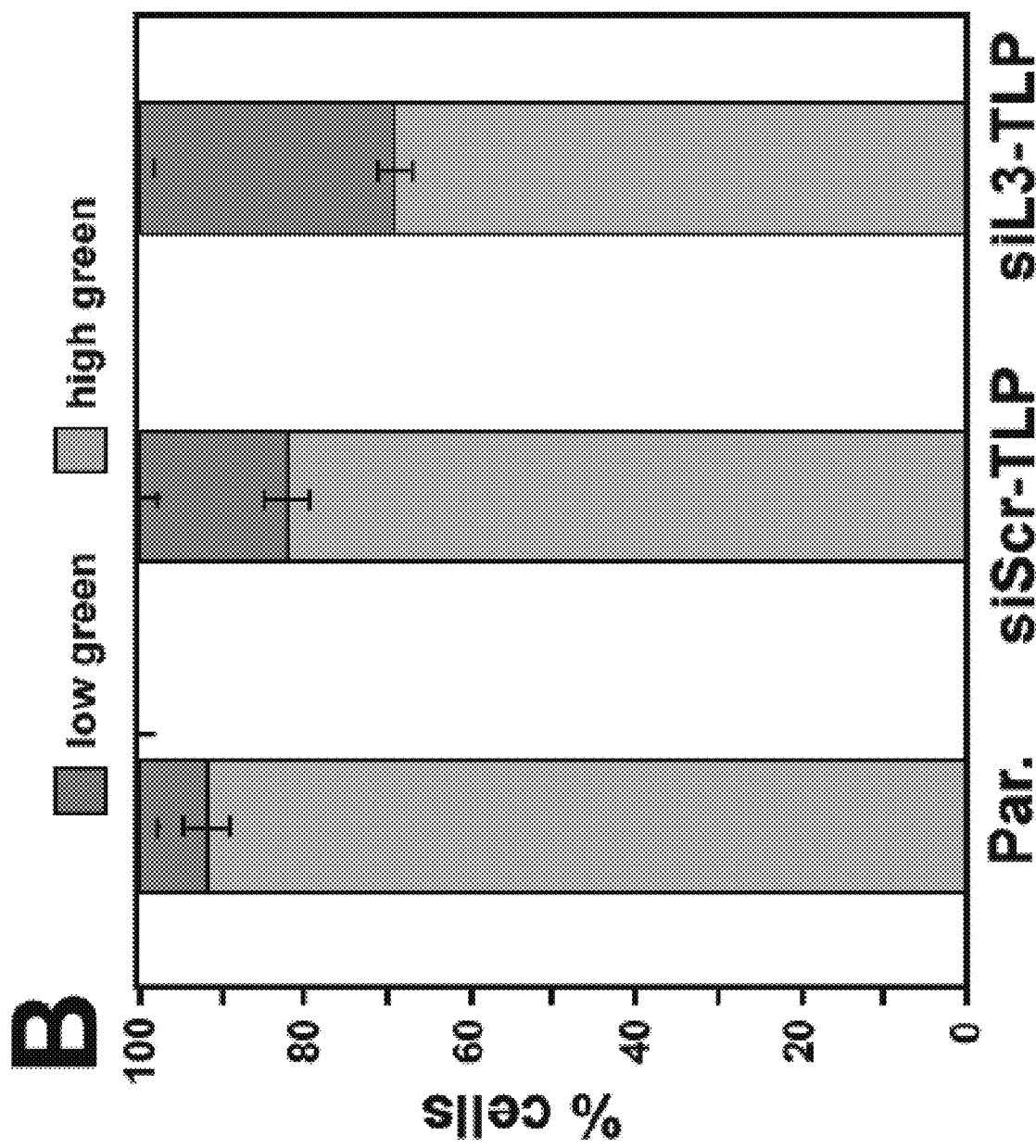
Figure 25:
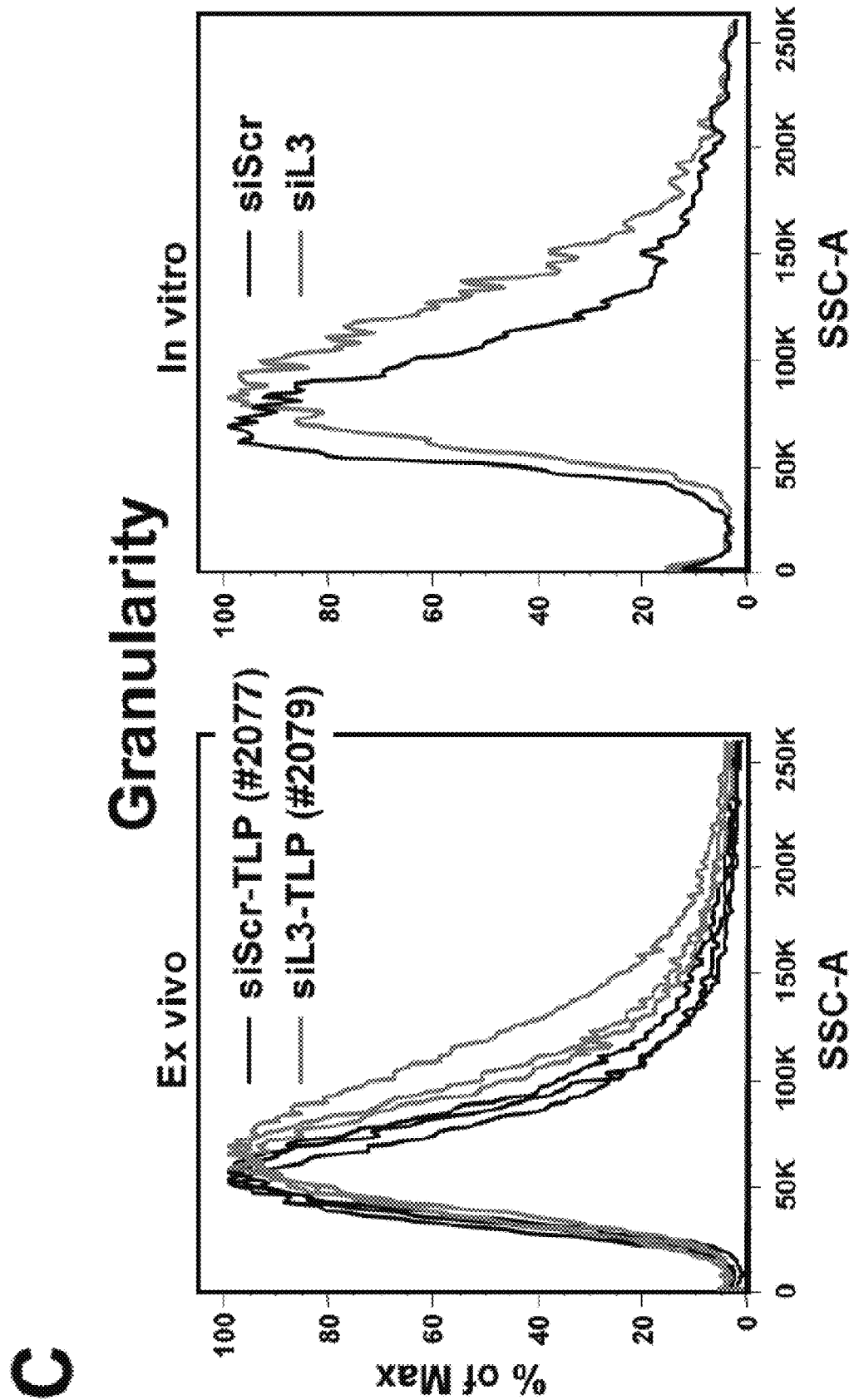
Figure 25:
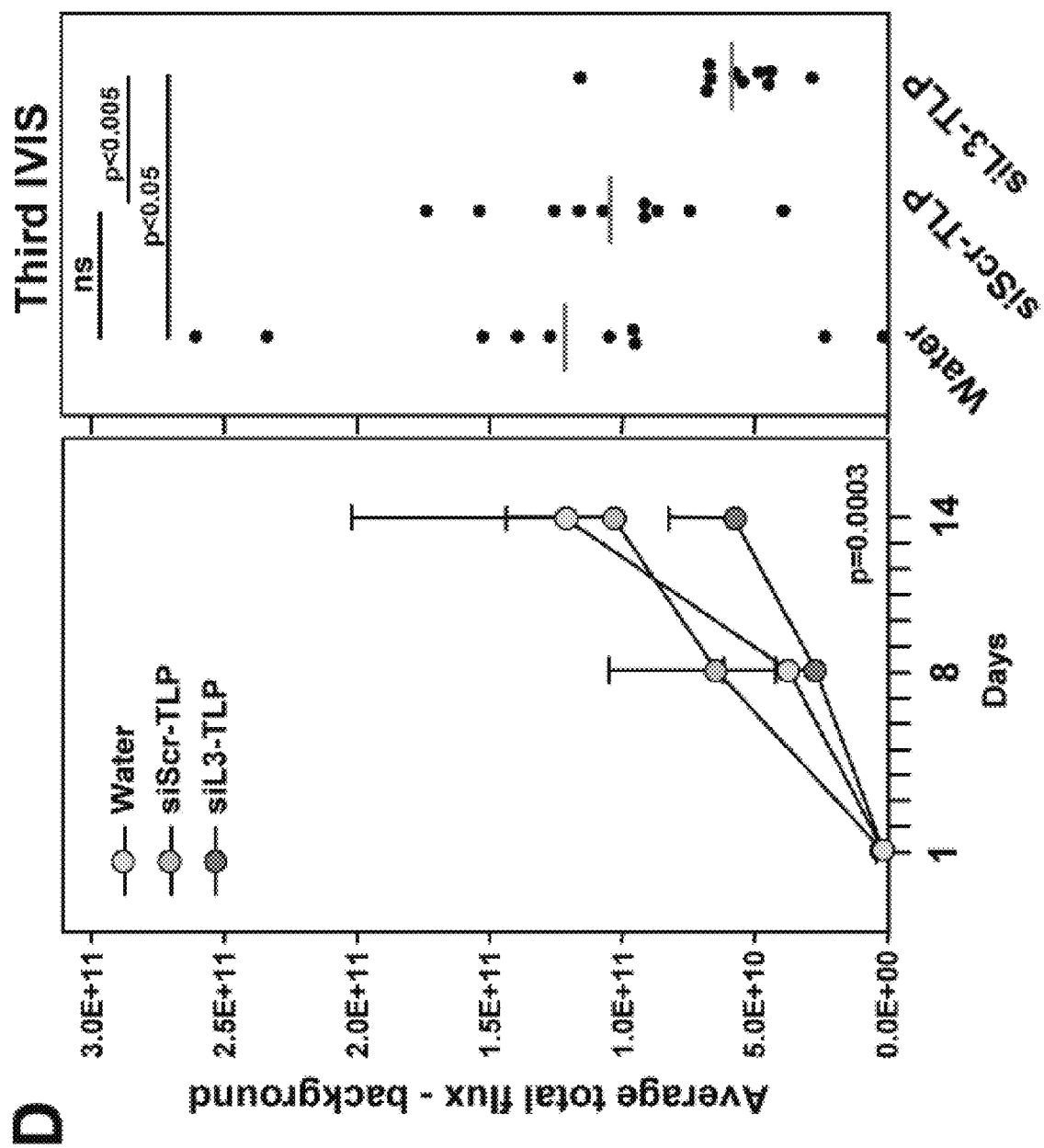

FIGS. 25. (A, B, C, and D). Induction of DISE in vivo. A: Treatment scheme. B: Red/green ratio of tumor cells isolated from three mice each treated with either siScr-TLP and siL3-TLP compared to parental HeyA8-Venus-siL3-pFul2T cells. C: Left: Change in sideward scatter (granularity) of cells isolated from three tumors from two mice treated with either siScr-TLP or siL3-TLP. Right: Change in granularity in HeyA8 cells in which DISE was induced by transfection of siL3 (2'O-methylated, Dharmacon) compared to matching siScr. D: Small animal imaging of $5\times10^5$ HeyA8-pFul2G cells injected i.p. into NGS mice treated with either water, siScr-TLPs or siL3-TLPs. Left: Tumor growth over time. ANOVA was performed for pairwise comparisons of average flux over time between siScr and siL3 treated cells. Right: Bioluminescence signal in individual mice at the third IVIS (14 days after tumor injection) treated as indicated following the treatment protocol outlined in A. P-values were calculated using Student's ttest.

Figure 26:
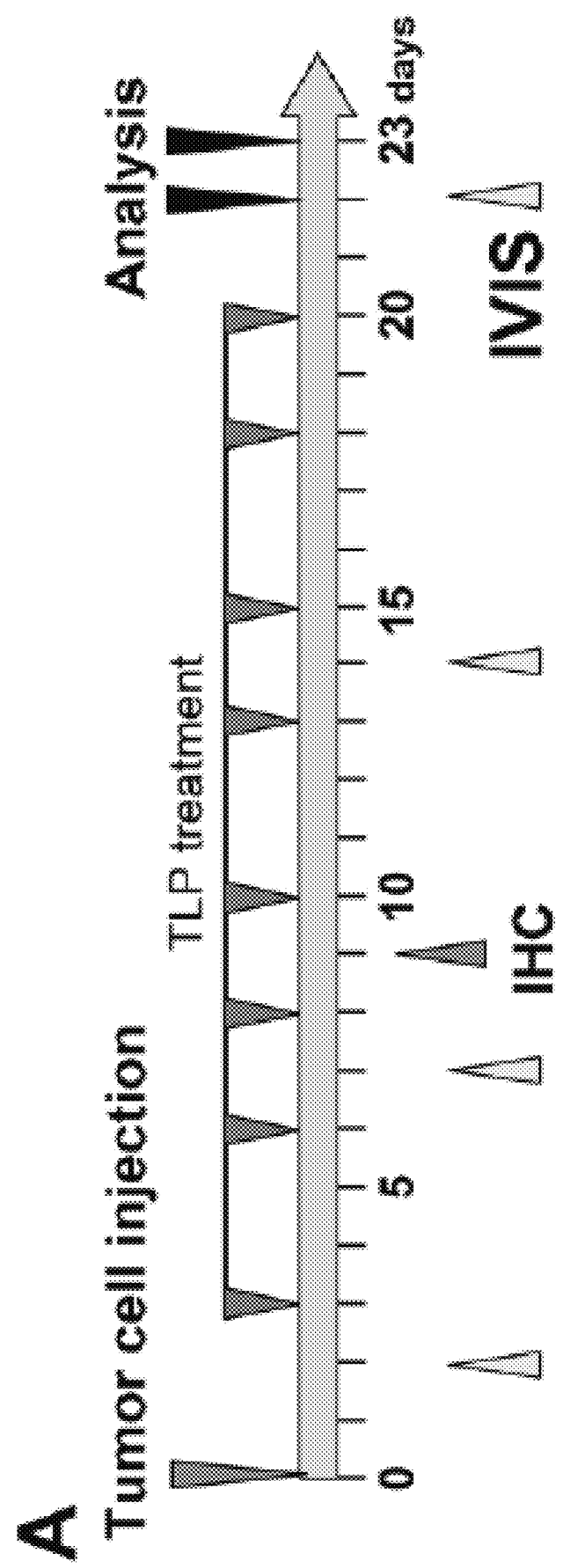
Figure 26:
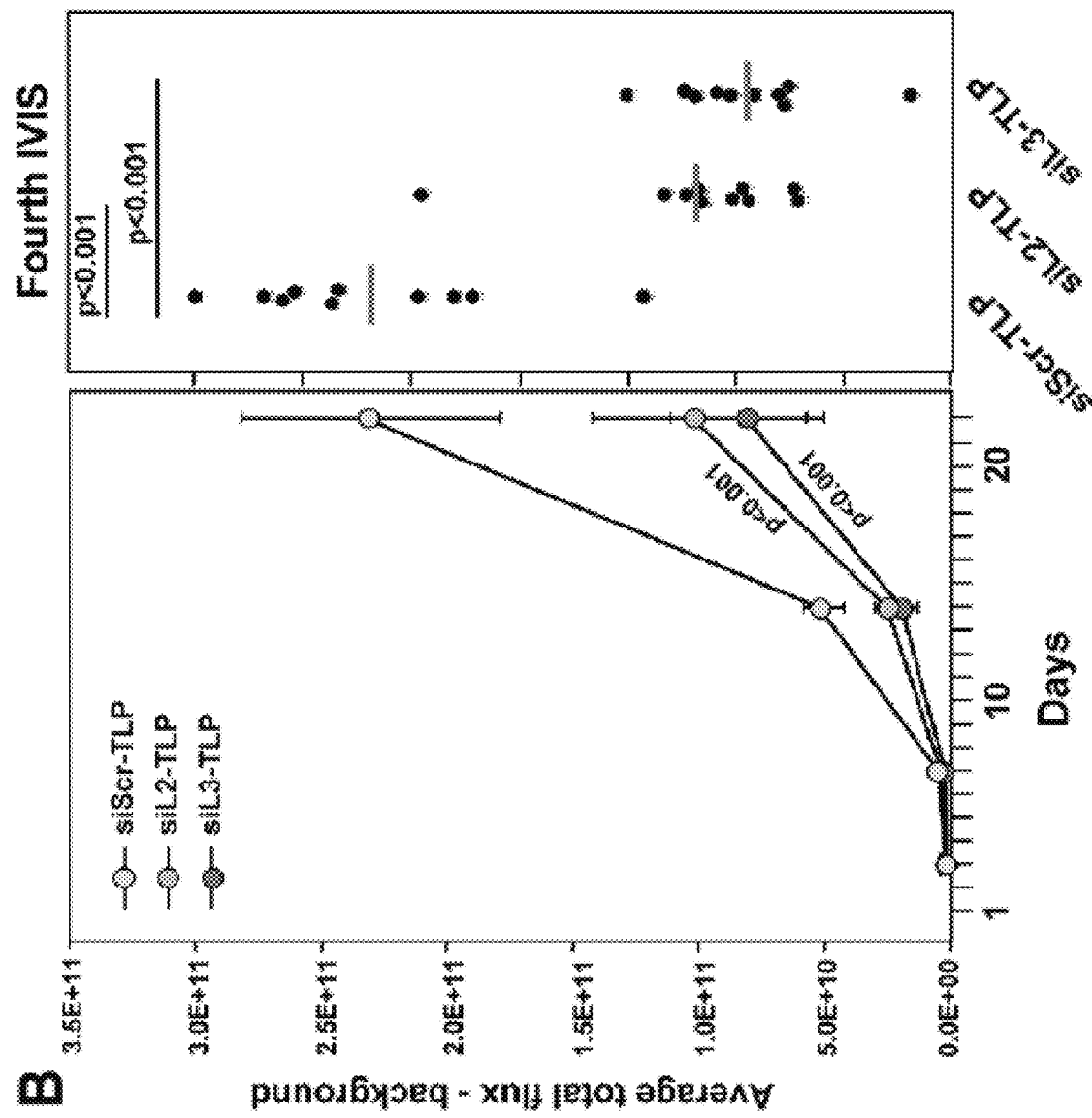

FIGS. 26. (A and B) Tumors do not fully regress in response to siL3-TLP and siL2-TLP treatment but retain sensitivity to DISE. A: Treatment scheme. B: Small animal imaging of 100,000 HeyA8-Nuc-red-Luc-neo-Venus-CD95L cells injected i.p. into NGS mice treated with either siScr-TLPs, siL2-TLPs, or siL3-TLPs. Left: Tumor growth over time. Right: Bioluminescence signal in individual mice at the fourth IVIS (22 days after tumor injection) treated as indicated following the treatment protocol outlined in A. ANOVAs were performed for pairwise comparisons of average flux over time between siScr and siL3 treated and siScr and siL3 mice, respectively.

Figure 26C:
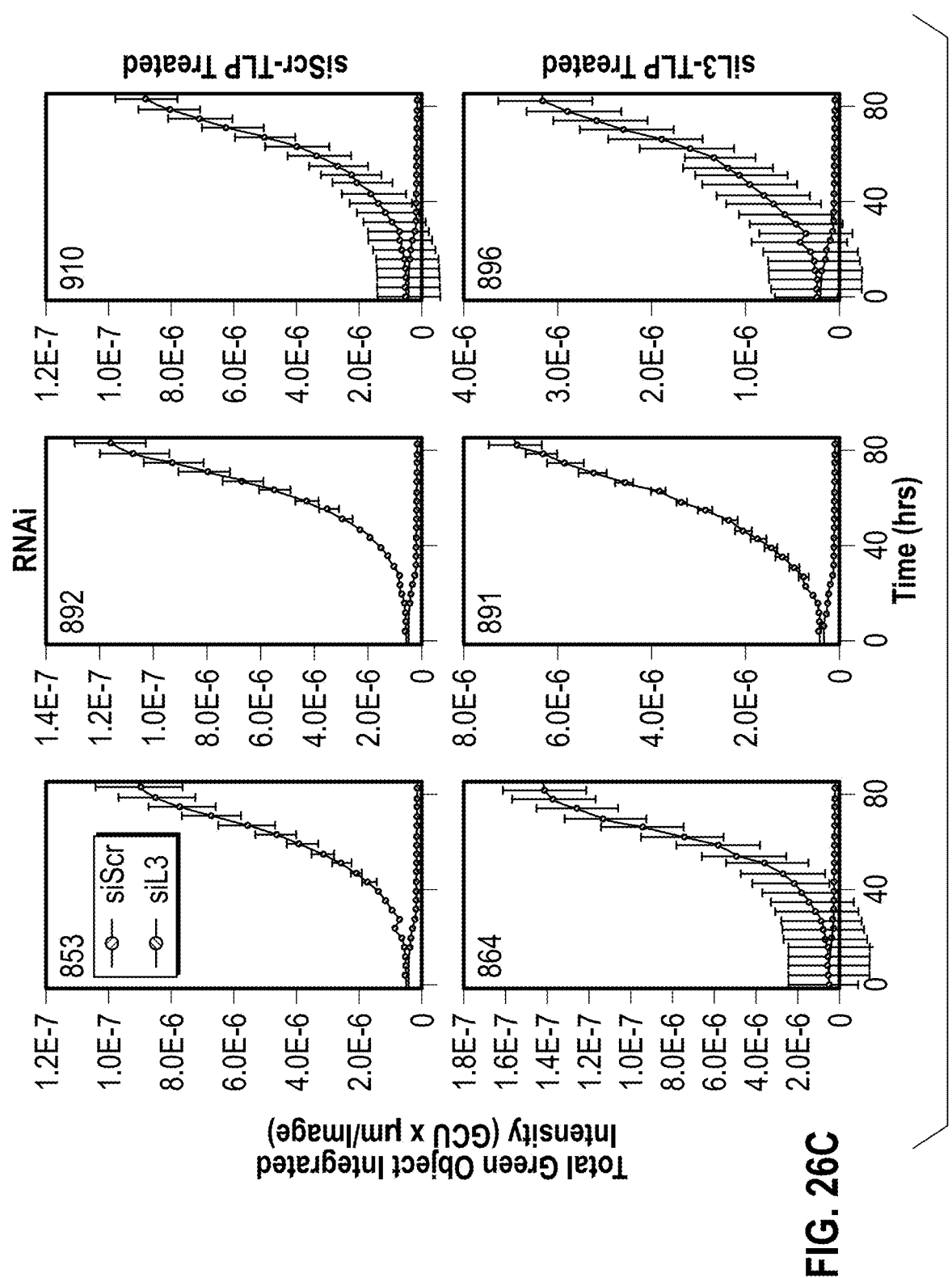

FIG. 26C Change in green fluorescence (RNAi) and change in red object count of tumor cells from 3 mice per siScr-TLP and siL3-TLP treatment group after transfection with either siScr or siL3. 1000 cells per well were plated (mouse numbers indicated in top left).

Figure 26D:
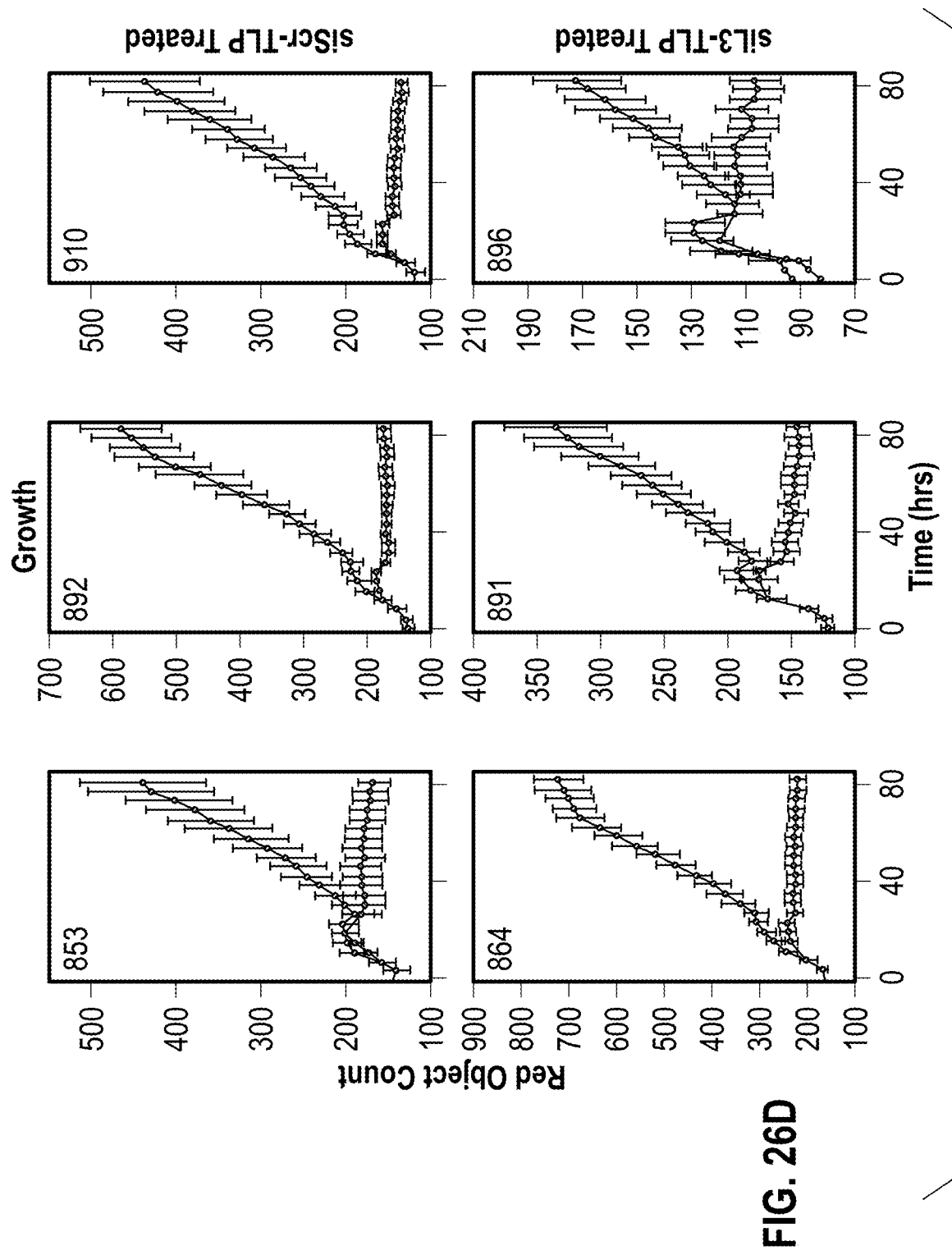

FIG. 26D Change in green fluorescence and change in red object count (growth) of tumor cells from 3 mice per siScr-TLP and siL3-TLP treatment group after transfection with either siScr or siL3. 1000 cells per well were plated (mouse numbers indicated in top left).

Figure 27:
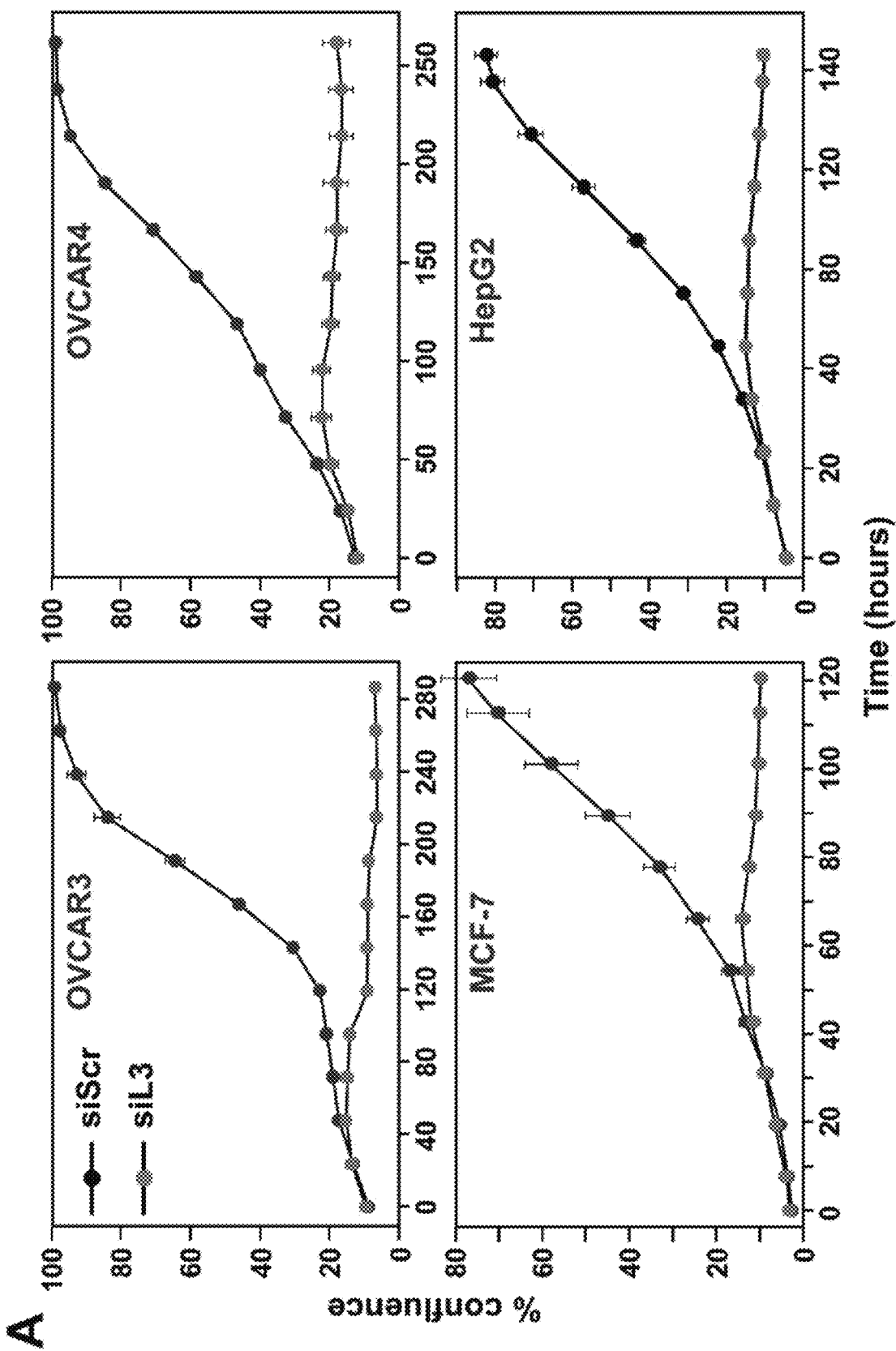
Figure 27:
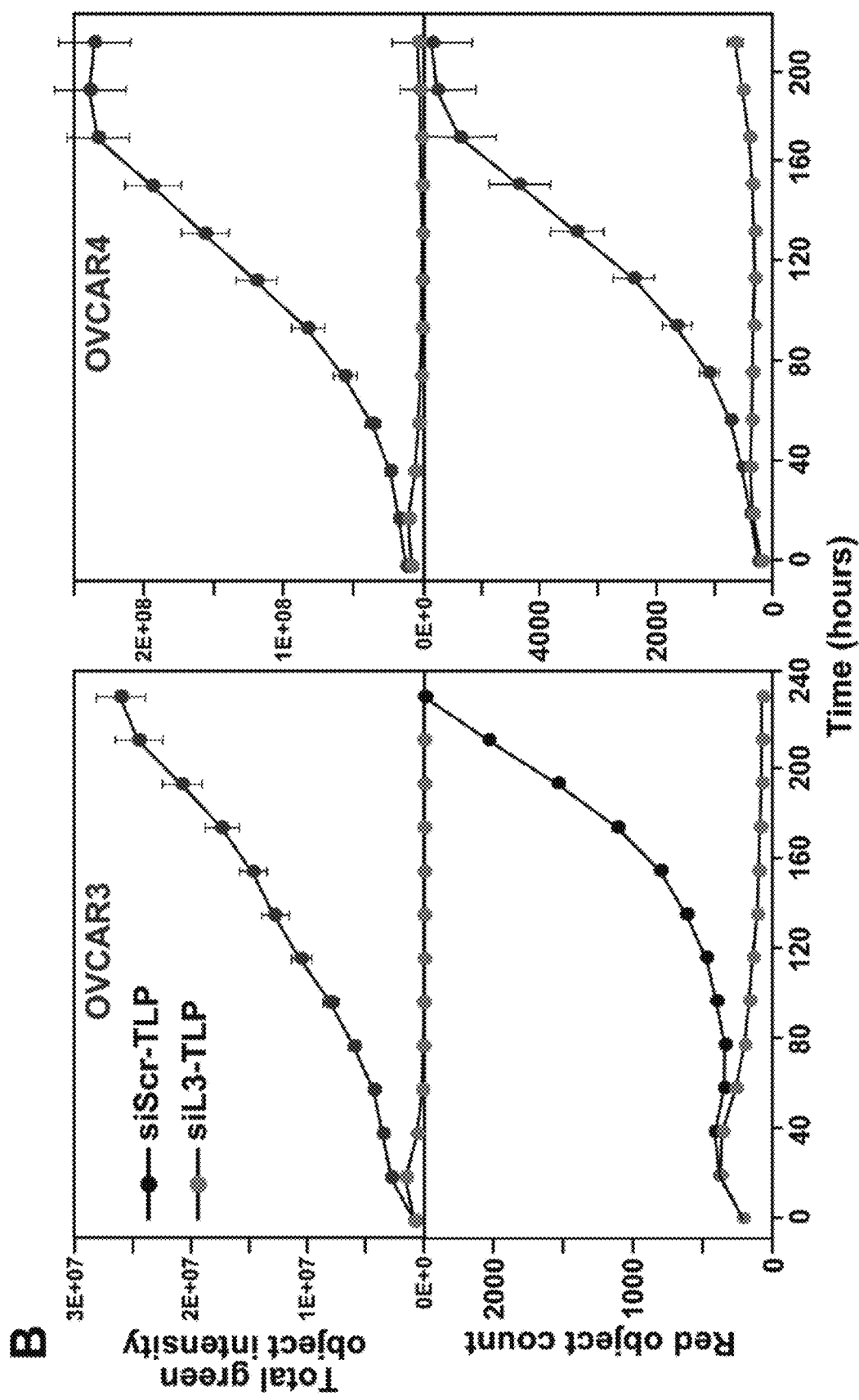

FIGS. 27. (A and B). Induction of DISE by siL3 in different cancer cell lines. A: Confluency over time of four cancer cell lines transfected with 10 nM (OVCAR3, OVCAR4 or HepG2) or 25 nM (MCF-7) siScr or siL3. B: Top: Total green intensity or bottom: confluency over time of OVCAR3 Venus siL3 or OVCAR4 Venus siL3 cells treated with 30 nM of either siScr-TLP or siL3-TLP.

Figure 28:
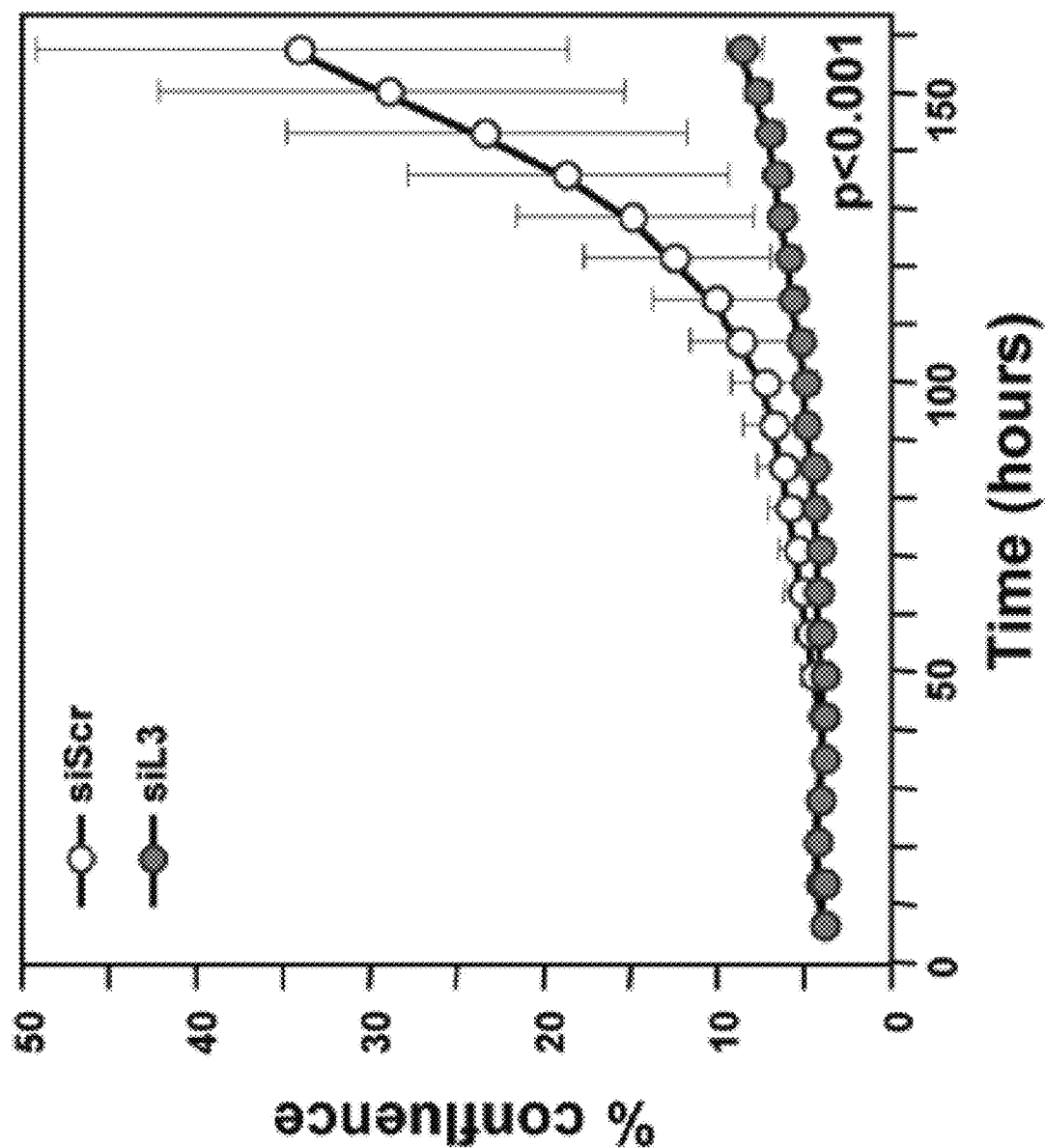

FIGS. 28. (A and B). No toxicity of siL3-TLP in NGS mice. A: Serum analysis of two mice per treatment group. 1=Sample assay value is less than the dynamic range. For most assays, the dynamic range low limit is reported. 2=Sample was diluted for testing. Assay value for sample was below dynamic range, but results have been corrected for dilution. 3=Assay is a calculated value. Either or both assay values used in the calculation were below the dynamic range of the assay, therefore no result is reported. B: Induction of DISE in ID8-Venus-mFLg cells after transfection with 25 nM siL3. As a control cells were transfected with siScr. ANOVA was performed for pairwise comparison of change in confluence over time between siScr and siL3 treated cells.

Figure 29:
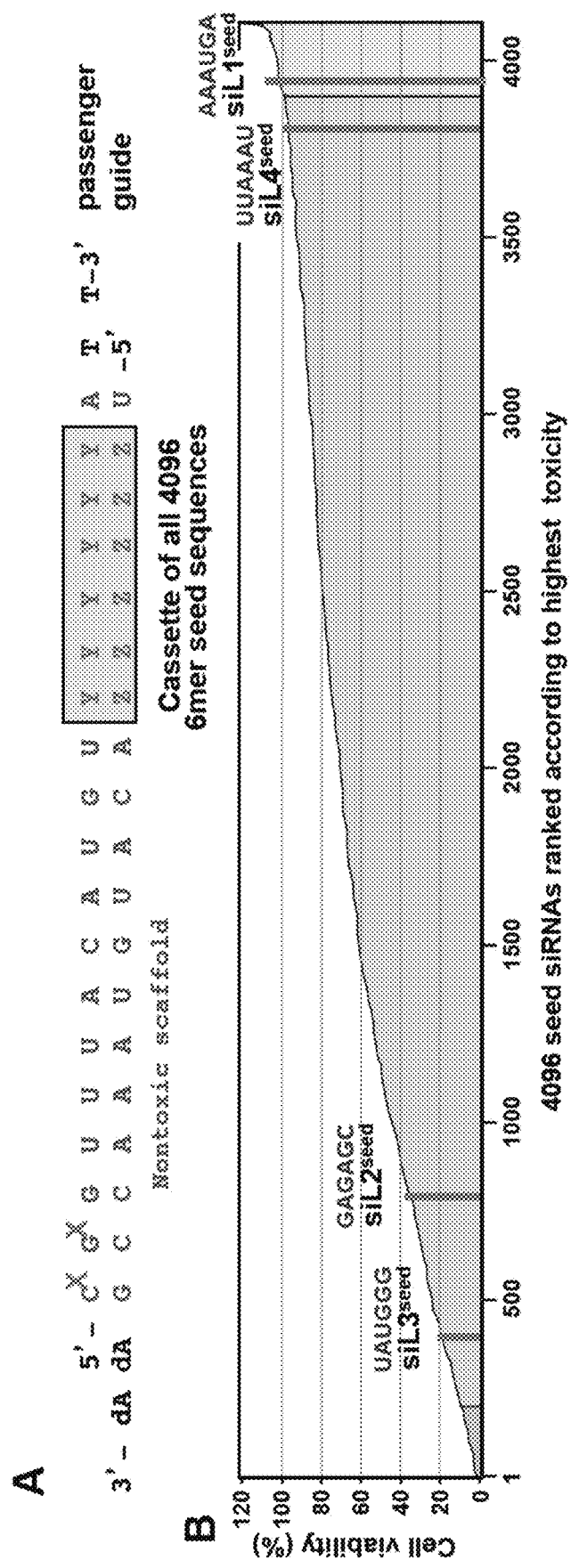
Figure 29:
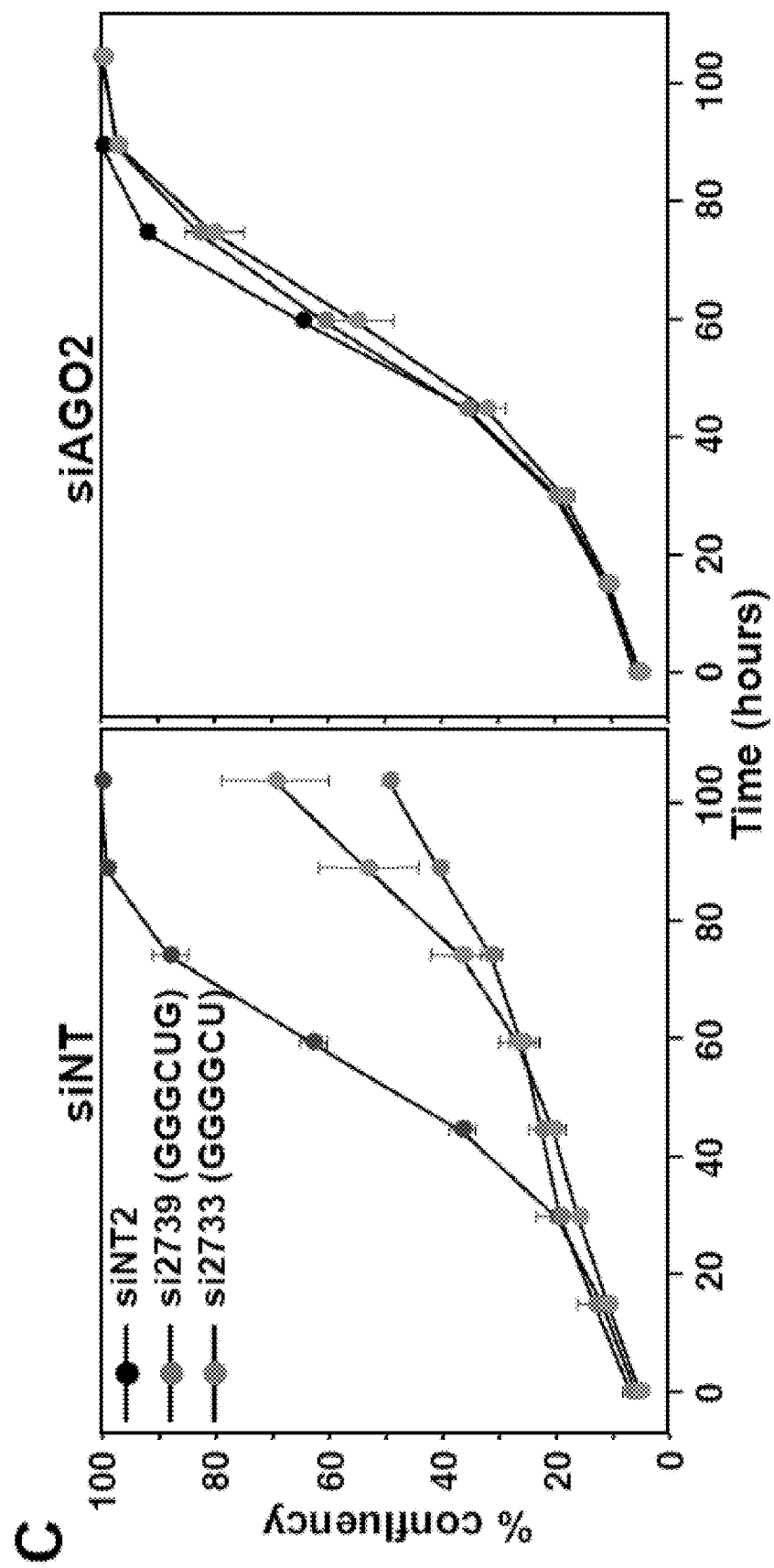
Figure 29:
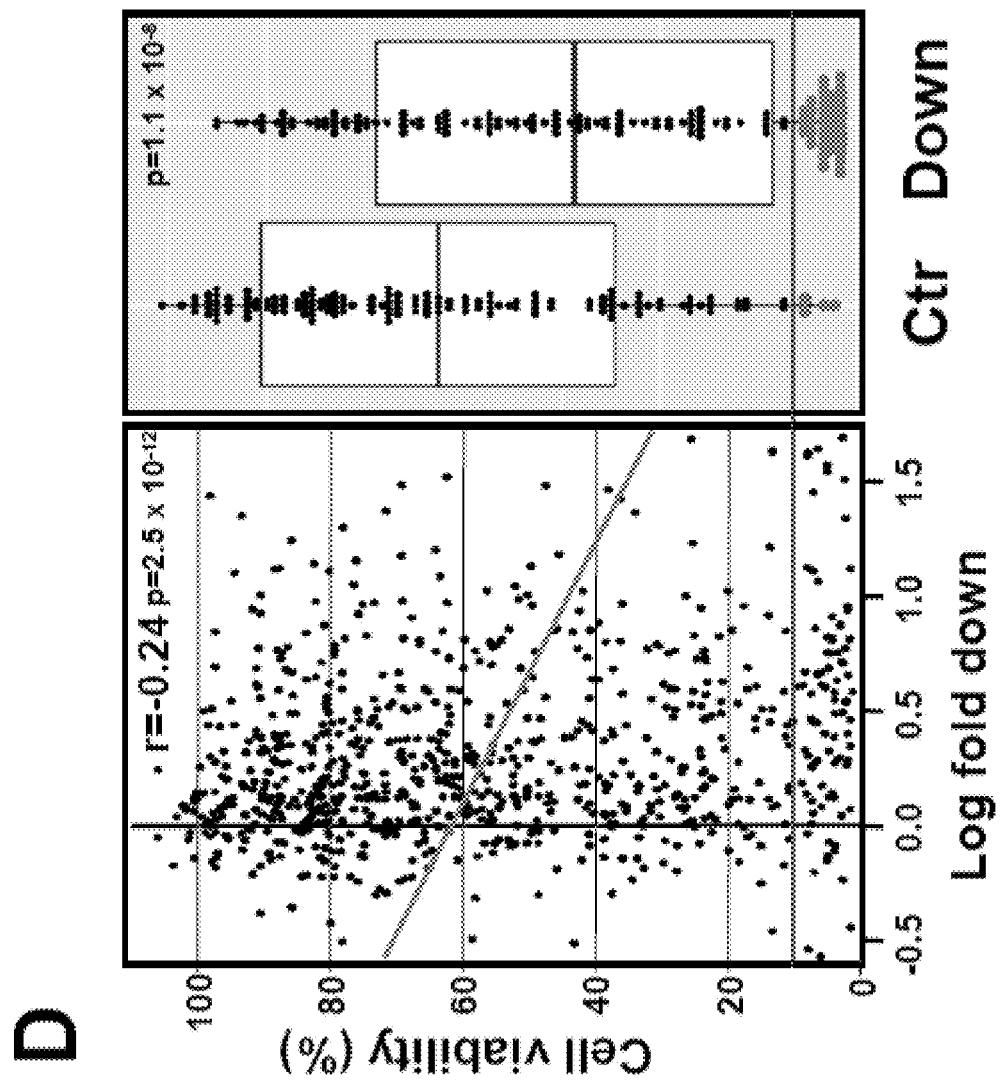
Figure 29:
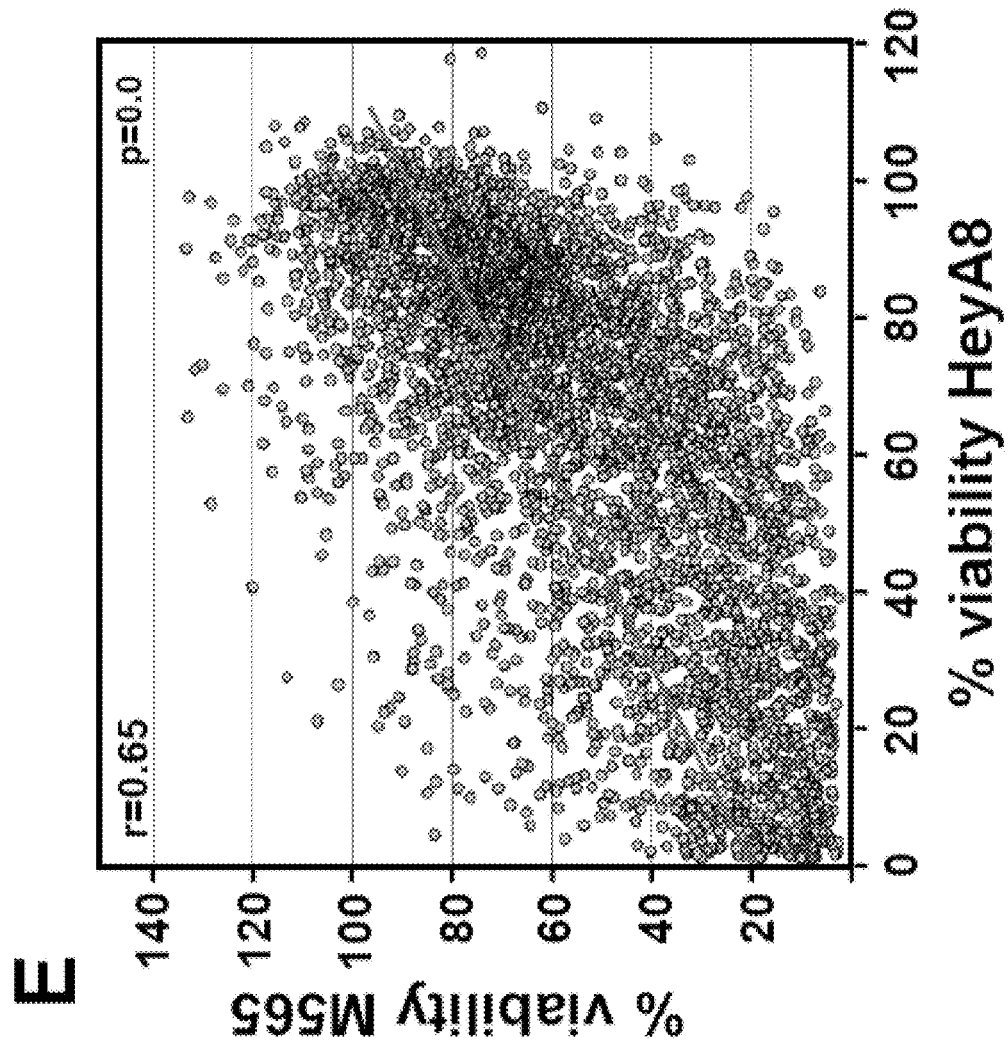

FIGS. 29. (A, B, C, D, and E). A comprehensive screen to identify the most toxic DISE-inducing 6mer seeds. (A) Schematic of the siRNA backbone used in the screen. 2'-O-methylation modifications at position 1 and 2 of the passenger strand were added to prevent passenger strand loading (marked by the red crosses) (26). The nucleotides that remained constant in the scaffold are indicated. The variable 6mer seed sequence is illustrated and boxed. (Sequence Listing: GGUUUACAUGUNNNNNNATT (SEQ ID NO:161); UNNNNNNACAUGUAAACCGAA (SEQ ID NO:162)). (B) Result of the 4096 6mer seed screen in HeyA8 cells. The cell viability of each 6mer seed was determined by an ATP quantification assay. All 4096 6mer seeds are ranked by their effects on cell viability from the lowest (most toxic) (left) to the highest (least toxic) (right). Positions of the 6mer seeds of four previously characterized CD95L derived siRNAs (siL1, siL2, siL3, and siL4) are highlighted in red. The top 200 toxic seeds (cell viability <10%) and the bottom 200 least toxic seeds (cell viability >100%) are highlighted. (C) Percent cell confluence over time of HeyA8 parental cells transfected with either nontargeting control (siNT2) or the two most toxic siRNA duplexes (si2739 and si2733) at 10 nM. Cells were pretreated with either nontargeting SMARTpool siRNAs (left) or AGO2 SMARTpool siRNAs for 24 hours at 25 nM (right). Insert shows Western blot to document AGO2 knockdown efficiency. (D) Comparison of the toxicity of CD95L derived shRNAs recently identified (22) with the matching 6mer seed toxicity. Regression analysis showing that the log fold downregulation of CD95L derived shRNAs in that screen correlates with the effects on cell viability caused by the matching 6mer seed siRNAs (left panel). Boxplot comparing the average cell viability of the matching 6mer seeds of 139 shRNAs that were downregulated at least 5 fold and a control set of 139 shRNAs that were not downregulated (right panel). shRNAs carrying seed sequences found to be super toxic in the seed screen (>90% reduction in cell viability) are marked in both sets. (E) Regression analysis showing the correlation between the 6mer seed toxicity observed in the mouse liver cancer cell line M565 (y axis) and the matching 6mer toxicity observed in the human ovarian cancer cell line HeyA8 (x axis).

Figure 29F:
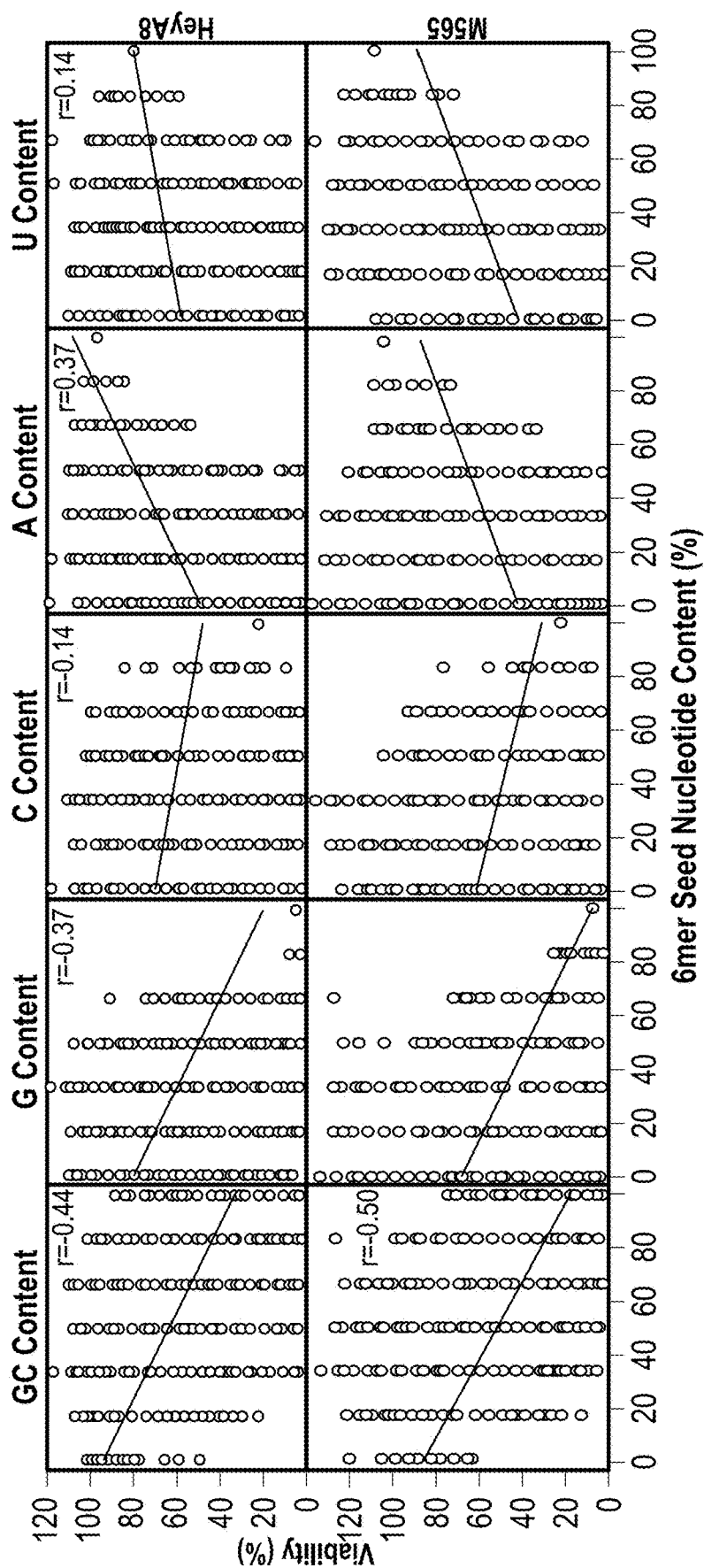

FIG. 29F. Regression analysis of cell viability of 6mer seeds in HeyA8 cells (top panel) or M565 cells (bottom panel) versus GC content or individual nucleotide content (G, C, A, U) of the seeds. All p-values of the Pearson correlation coefficients were 0.0.

Figure 30A:
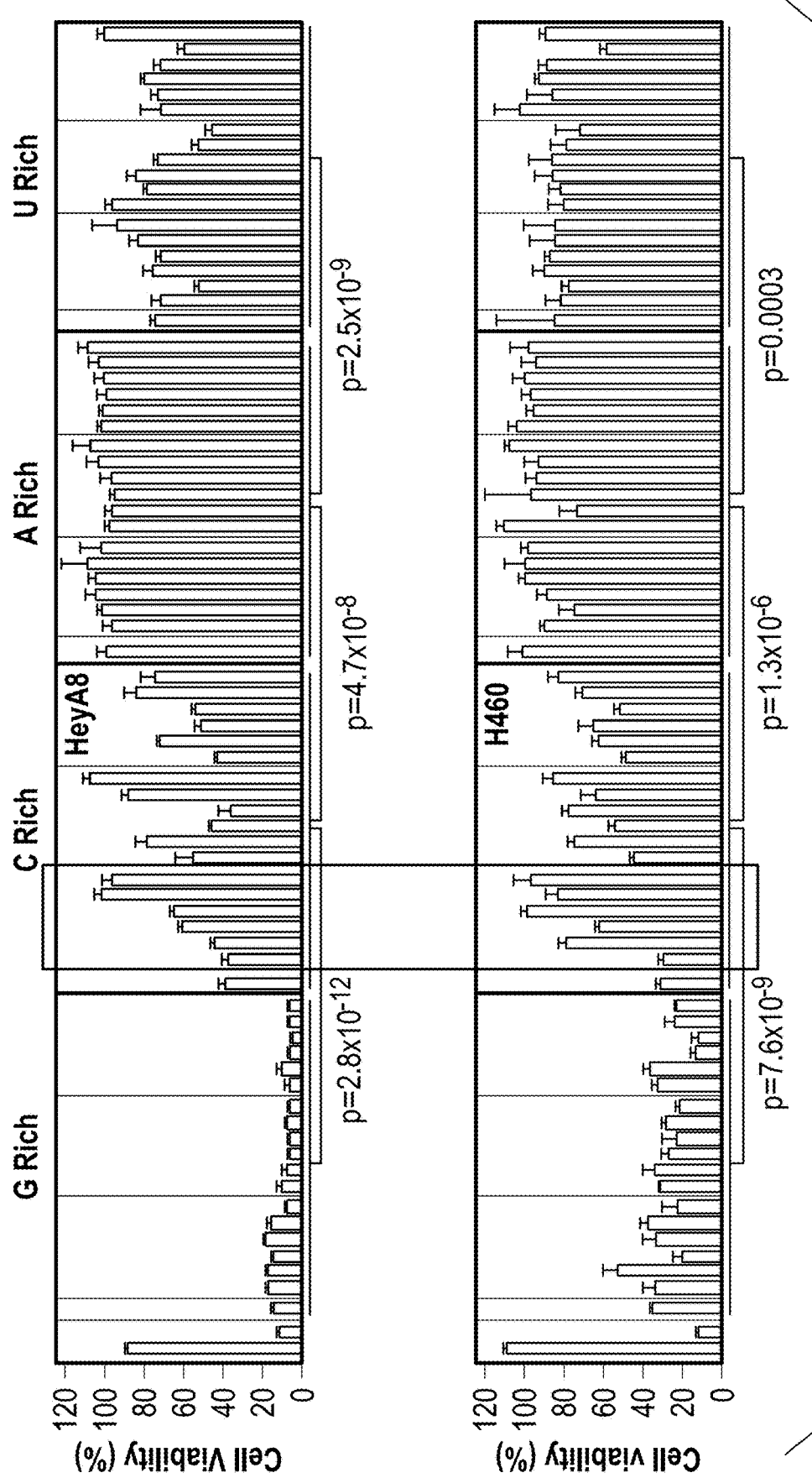
Figure 30A:
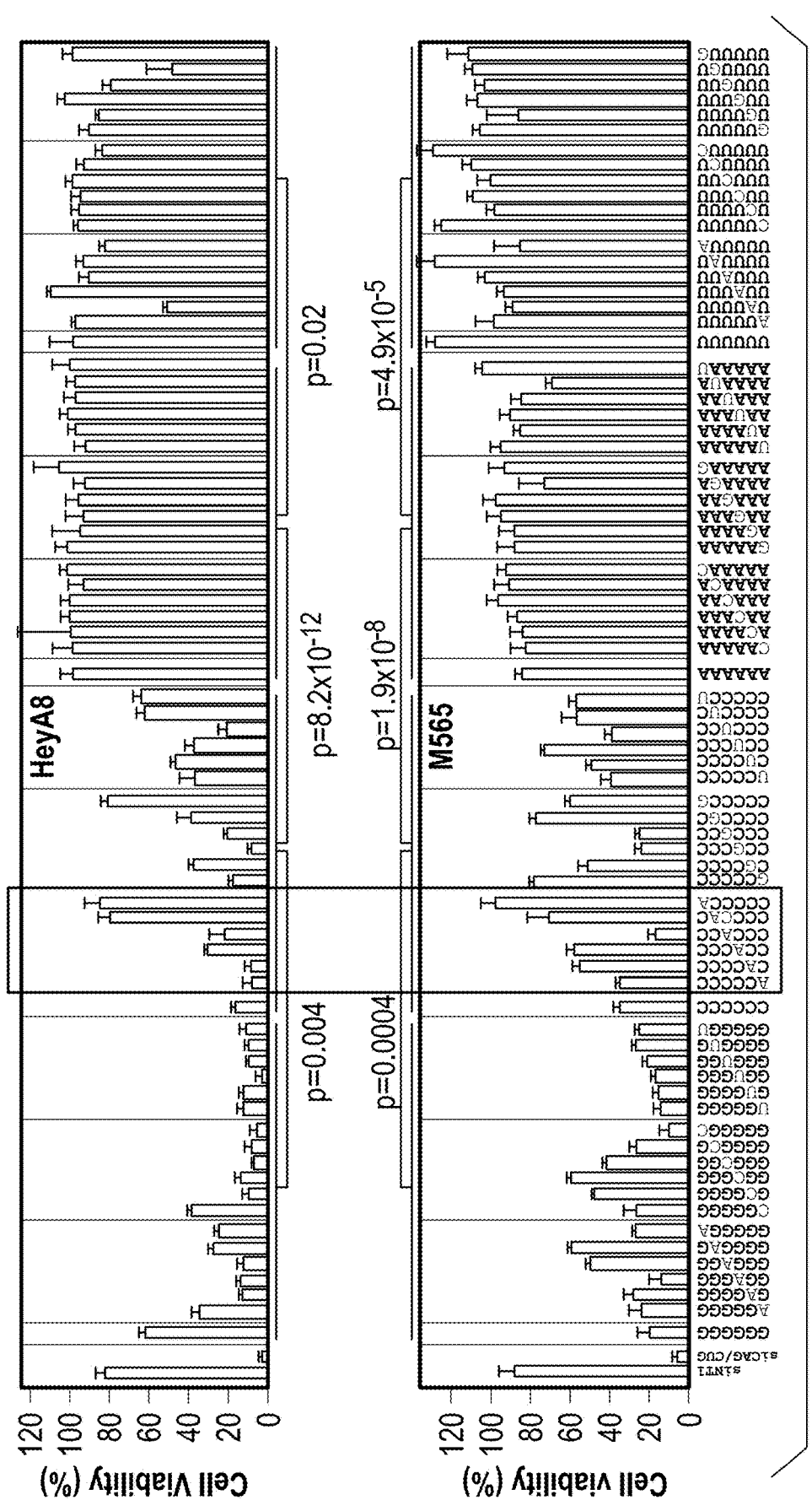
Figure 30:
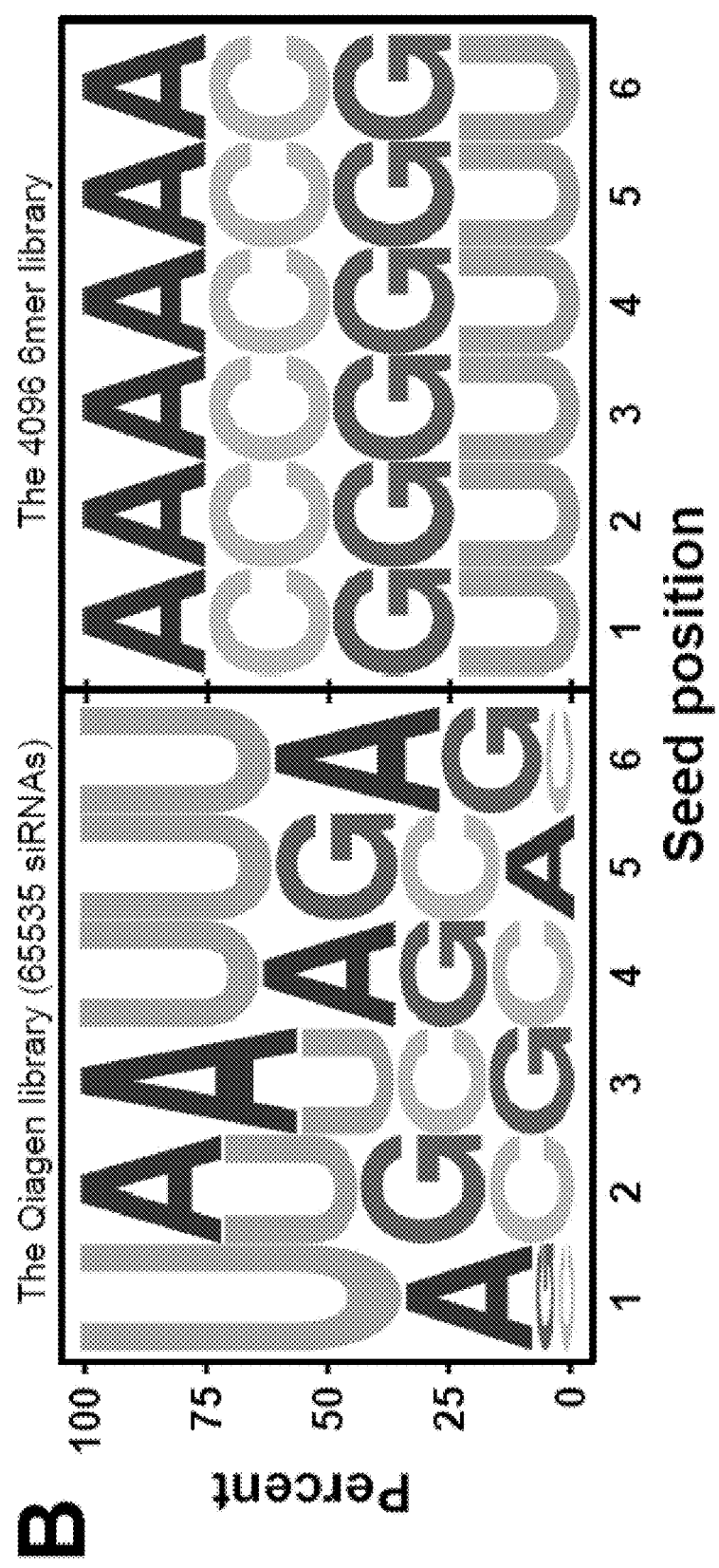
Figure 30:
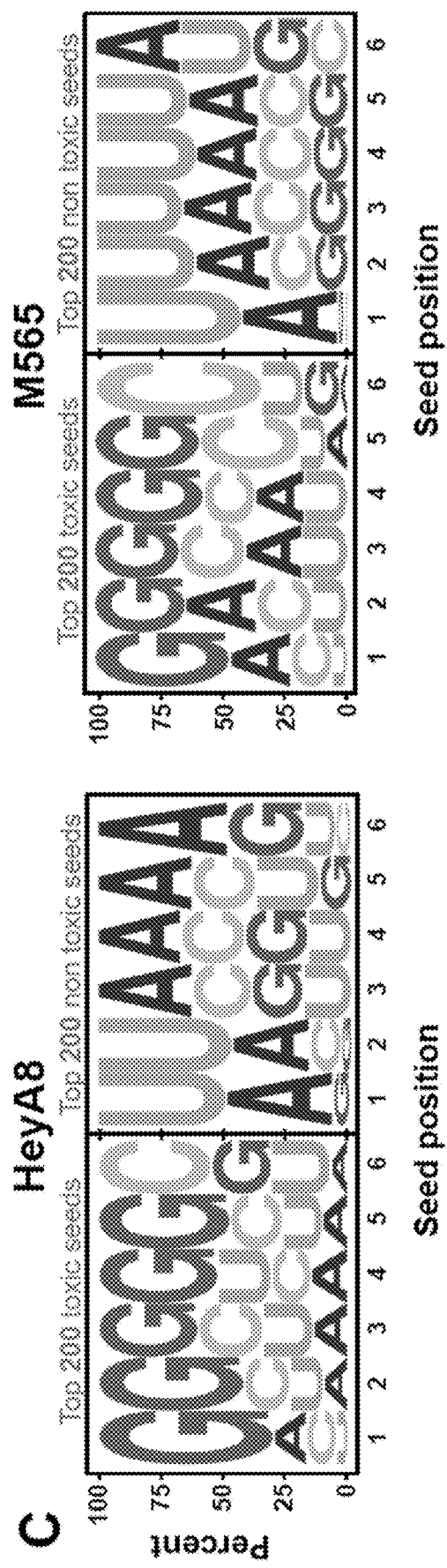

FIG. 30A. DISE-inducing toxic seeds prefer G rich nucleotide composition. (A) Cell viability of the 19 seed duplexes with the highest content (>80%) in the 6mer seed region for each nucleotide group in two human and two mouse cell lines: HeyA8 (first row), H460 (second row), 3LL (third row), and M565 (last row). The G rich seeds, the C rich seeds, the A rich seeds, and the U rich seeds are indicated. The box highlights an example of reduced toxicity in all four cell lines (grey stippled line) caused by moving an A from the 5' to the 3' end of the 6mer seed.

FIG. 30B. Nucleotide composition at each of the 6 seed positions in a commercial human genomic siRNA library (left panel) or our balanced 6mer seed duplexes library (right panel).

FIG. 30C. Nucleotide composition at each of the 6 seed positions in the top 200 most toxic (left) or the top 200 least toxic (right) seed duplexes in either HeyA8 cells (left panels) or M565 cells (right panels).

Figure 31:
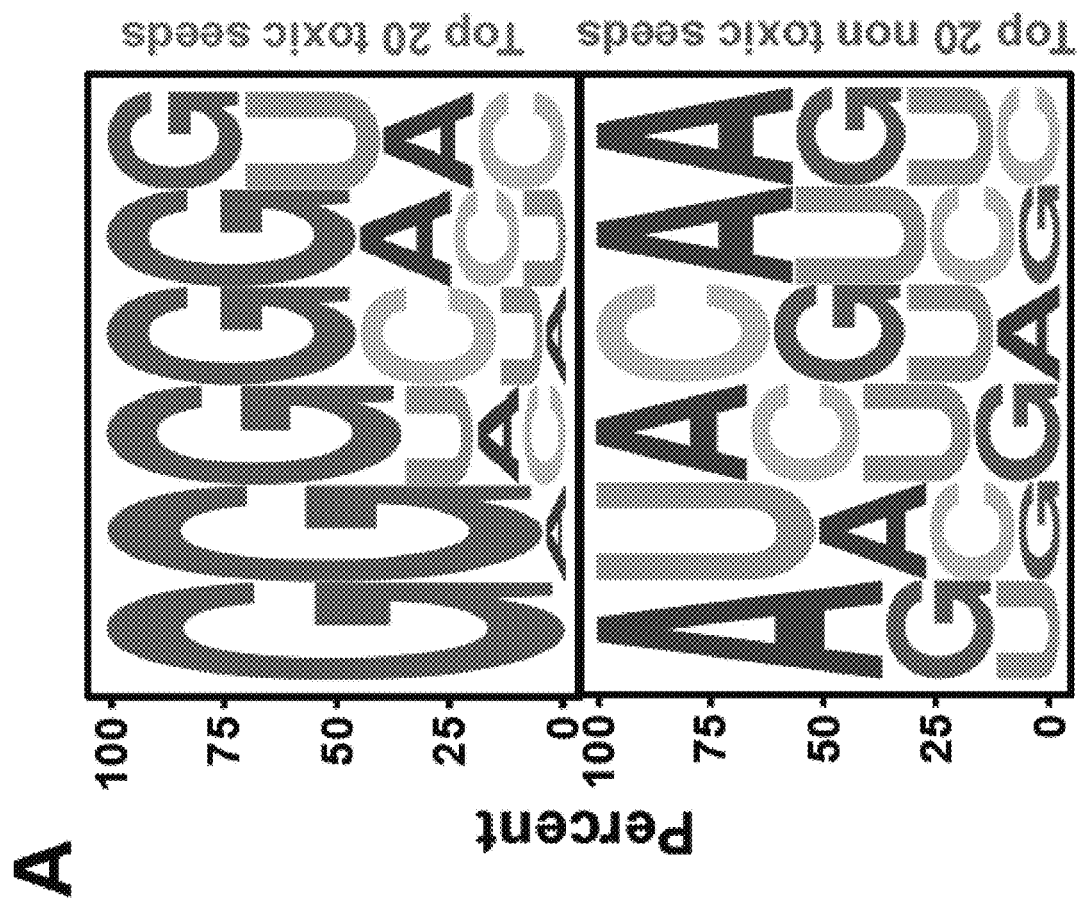
Figure 31:
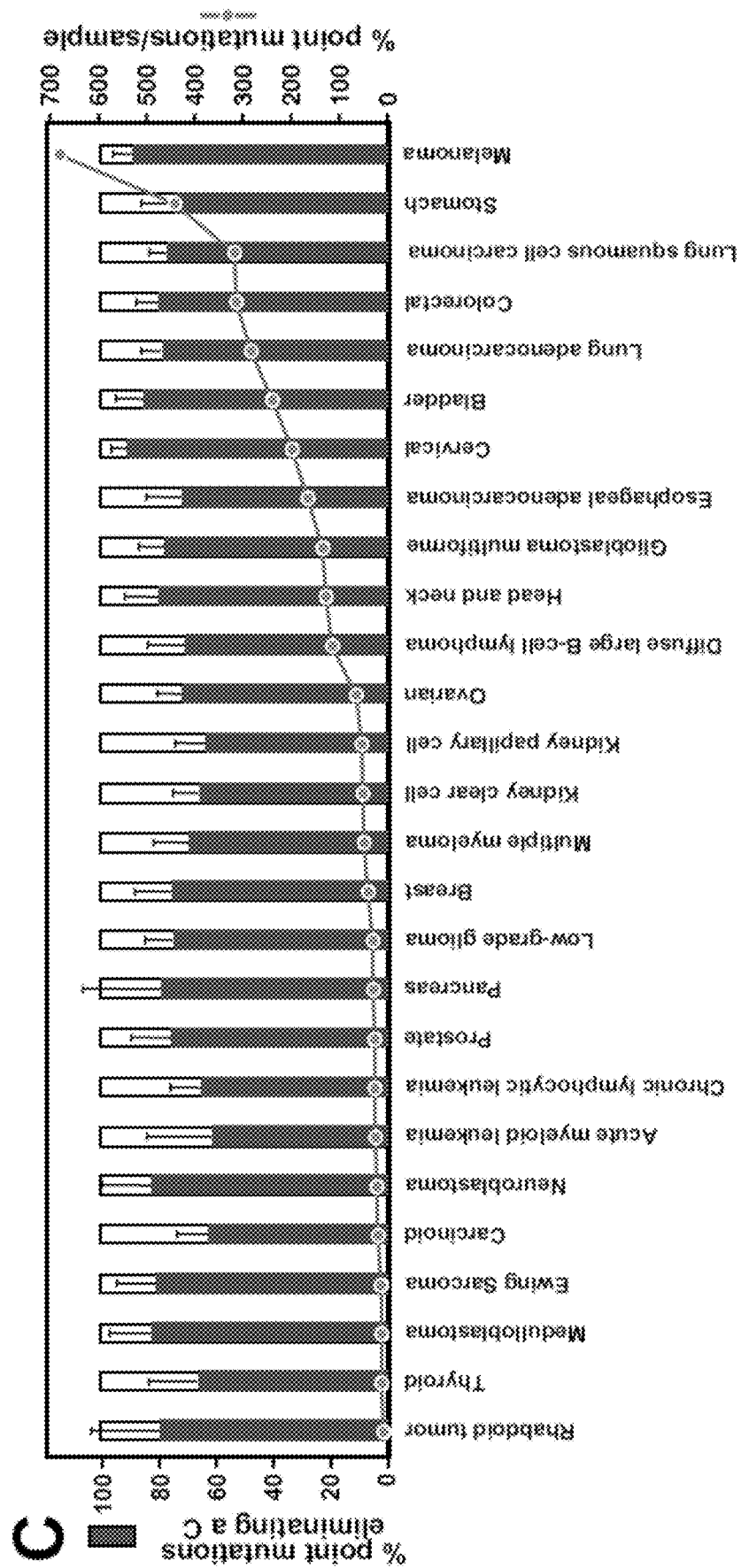

FIGS. 31. (A, B, and C). The most toxic G rich seed containing duplexes preferentially target house keeping genes enriched in Cs close to the 3' UTR start. (A) Nucleotide composition of the top 20 most toxic and the top least toxic seeds. The reverse complement of toxic matrix was used as the input for the PWM Scan analysis to search for potential targets of the toxic seeds. (B) Results of a GOrilla gene ontology analysis using a gene list ranked by the PWM matrix match score with the toxic matrix in their 3'UTRs ranked either from the highest to the lowest (top panel) or from the lowest to the highest score (bottom panel). Only GO clusters are shown that had a significance of enrichment of at least $10^{-11}$. (C) Contribution of synonymous single nucleotide mutations that result in a los of Cs (indicated column) to all documented point mutations (indicated column) across 27 human cancer ranked according to their mutational load.

Figure 32A:
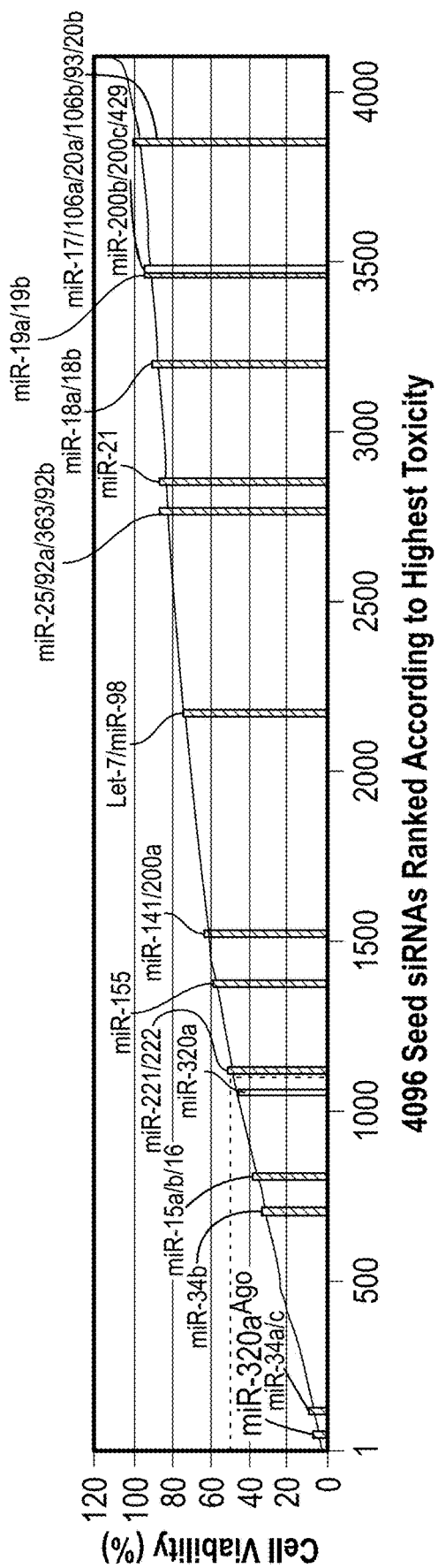

FIG. 32A. Tumor suppressive miRNAs inhibit cancer cell growth via DISE-inducing 6mer seeds. All 4096 6mer seeds ranked from the lowest to the highest by their effects on cell viability in HeyA8 cells. Locations of 6mer seeds present in known tumor suppressive or tumor promoting miRNAs are highlighted as individual bars.

Figure 32:
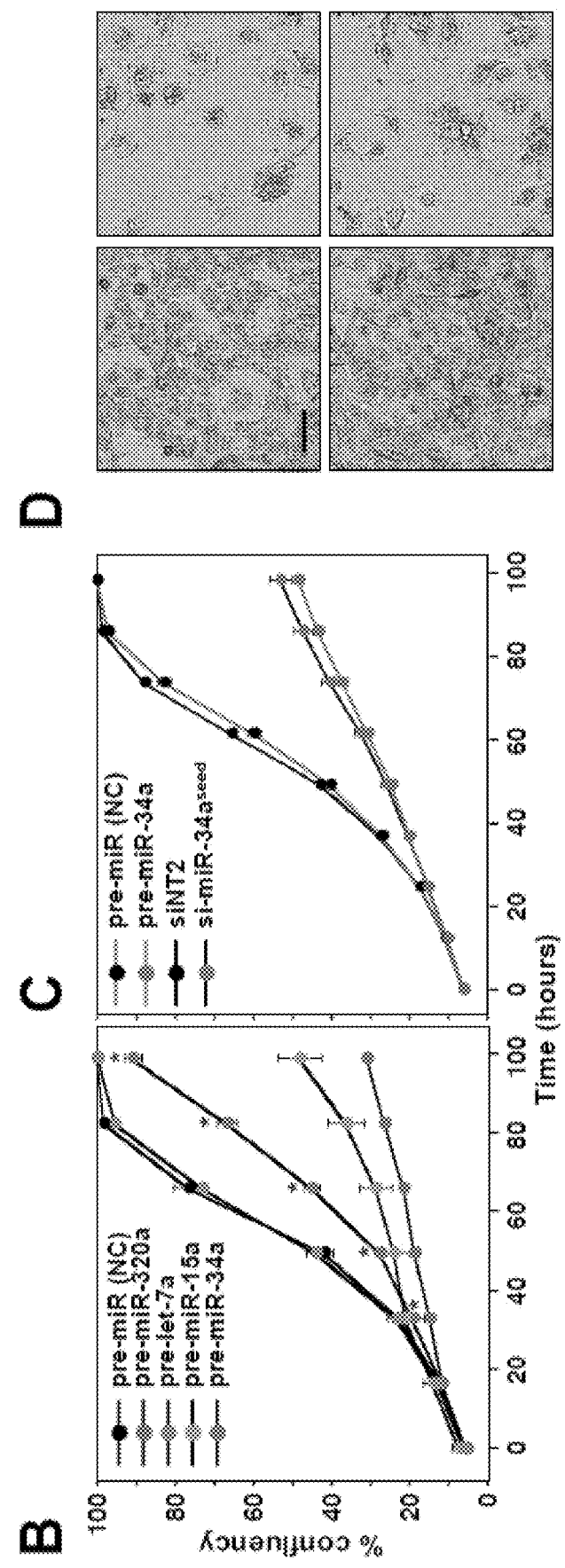

FIGS. 32 (B, C, and D) Percent cell confluence over time of HeyA8 cells transfected with 5 nM of either tumor suppressive miRNA precursors including pre-miR-320a, pre-miR-let-7a, pre-miR-15a, and pre-miR-34a or a miRNA precursor nontargeting control. * ANOVA p-value between cells treated with pre-miR-(NC) and pre-let-7=0.0. (C) Percent cell confluence over time of HeyA8 parental cells transfected with either pre-miR-34a or si-miR-34a$^{seed}$ and compared to their respective controls (pre-miR (NC) for pre-miR-34a and siNT2 for si-miR-34a$^{seed}$) at 10 nM. (D) DISE-like morphology observed in HeyA8 cells transfected with either pre-miR-34a or si-miR-34a$^{seed}$ compared to their respective controls at 10 nM three days after transfection.

Figure 33:
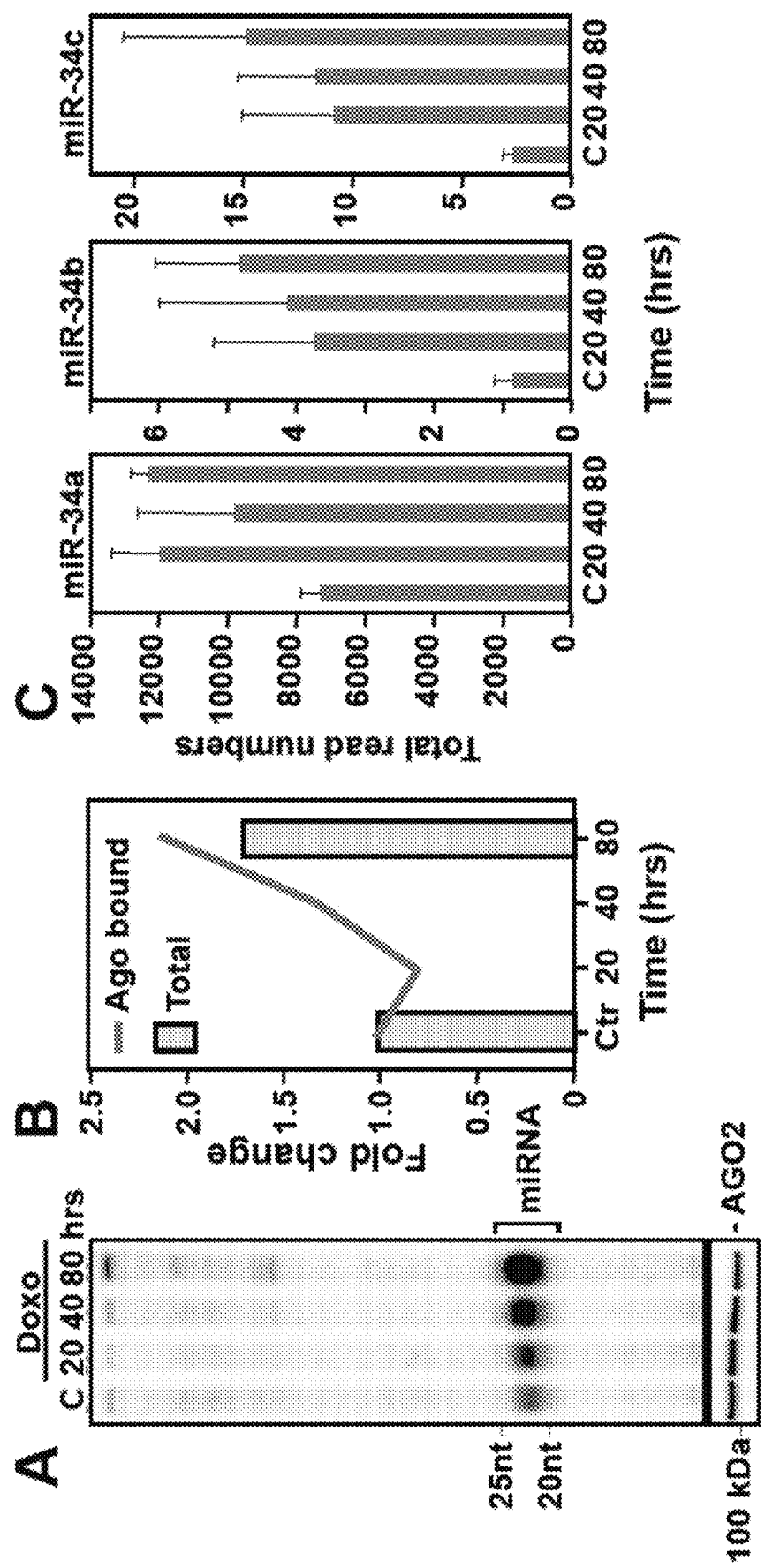
Figure 33:
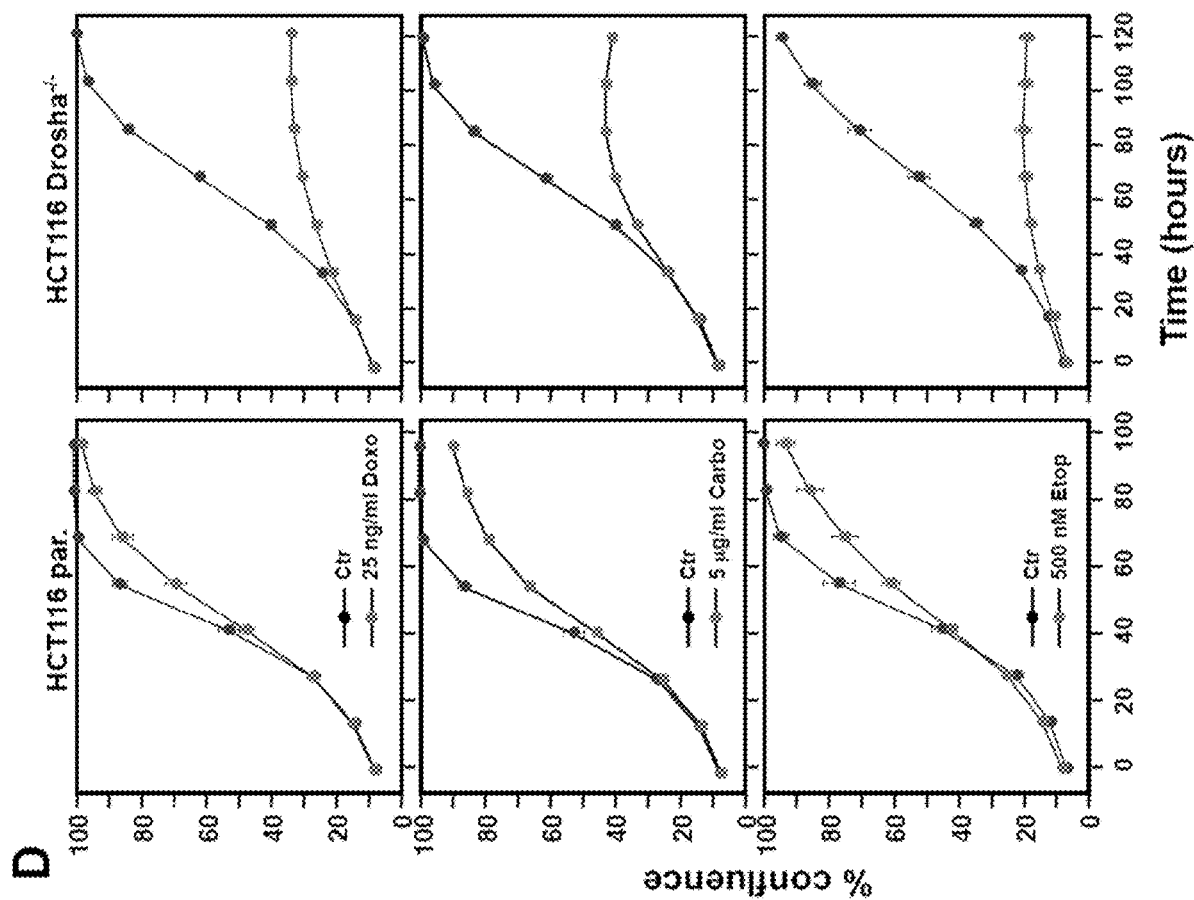
Figure 33:
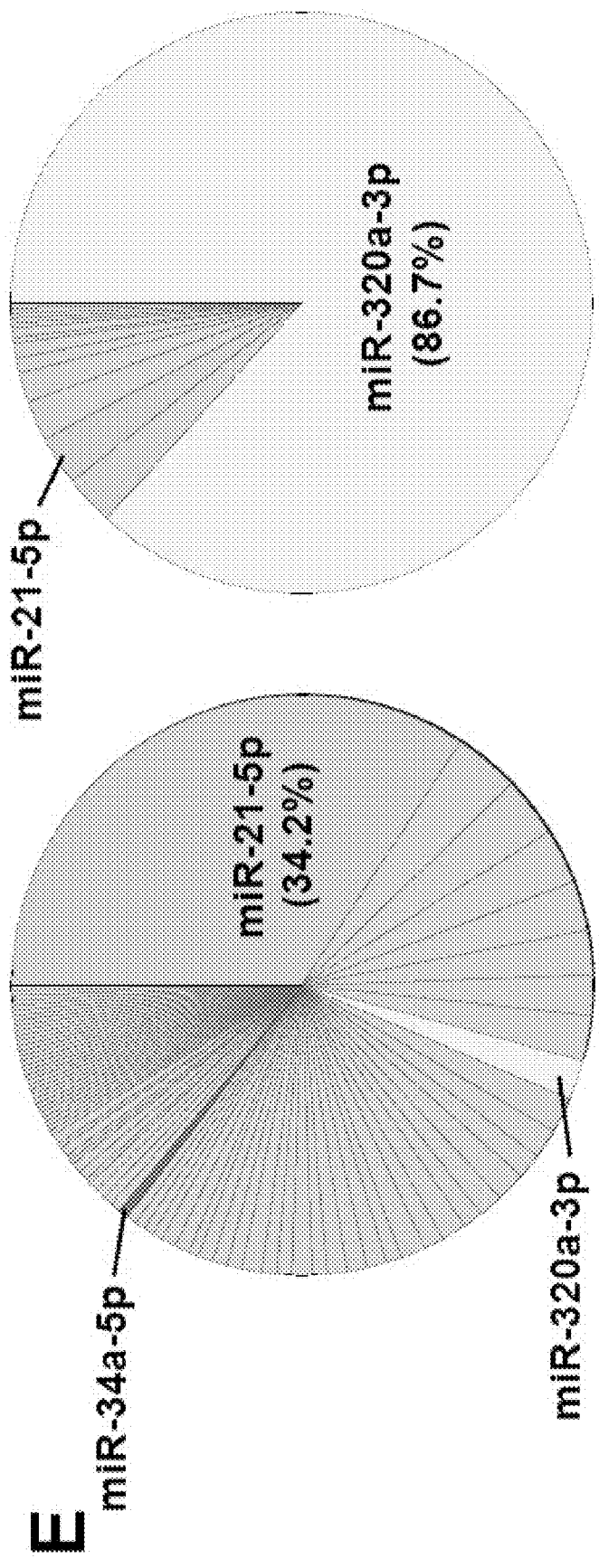
Figure 33:
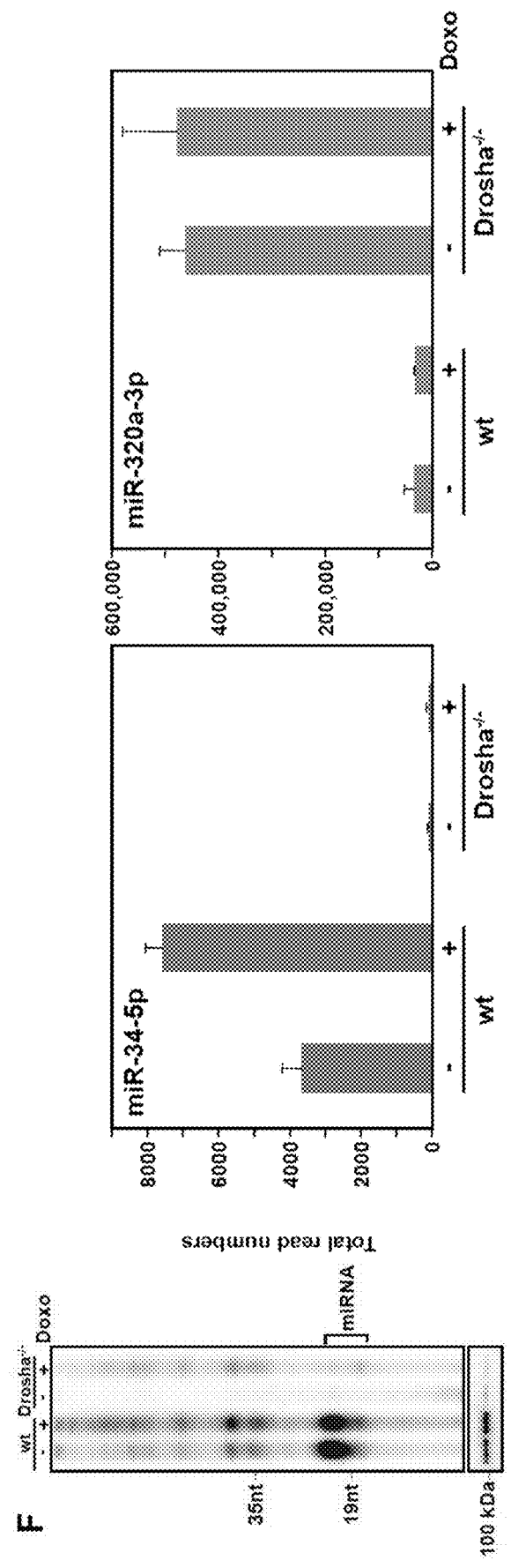

FIGS. 33. (A, B, C, D, E, and F). Genotoxic drugs cause upregulation of small RNAs. (A) Top: Plot of radiolabeled RNAs pulled down with the Ago proteins (Ago-IP) from HeyA8 cells treated with doxorubicin (Doxo) for 20, 40, and 80 hours. The amount of miRNA-sized small RNAs pulled down with AGO proteins increased over time after Doxo treatment compared to the control treated cells. Bottom: Western blot for the pulled down AGO2 of the same samples shown above. (B) Fold change of the total reads of Ago bound small RNAs after 20, 40, or 80 hours of Doxo treatment compared to the control sample from Ago-IP sequencing data (Ago bound). Fold change of the total reads of cytosolic small RNAs in HeyA8 cells treated with Doxo for 80 hours compared to the control sample from small RNA-Seq data is given (Total). (C) Total read numbers of Ago bound miR-34a (left panel), miR-34b (middle panel), and miR-34C (right panel) in control treated cells or after 20, 40, or 80 hours of Doxo treatment. (D) Percent cell confluence over time of HCT116 parental or Drosha$^{-/-}$ cells treated with three genotoxic drugs. (E) Pie charts showing the composition of miRNAs bound to Ago proteins after 80 hrs Doxo treatment in HCT116 wild-type (left) or Drosha$^{-/-}$ cells (right). (F) Ago-IP pull down was performed for the HCT116 wild-type and Drosha$^{-/-}$ cells treated with Doxo (left). Comparison of read numbers of pre-miR-34a-5p (middle panel) or miR-320a-3p (right panel) bound to Ago proteins between control and Doxo treated samples in either wild-type (wt) or Drosha$^{-/-}$ cells.

Figure 34:
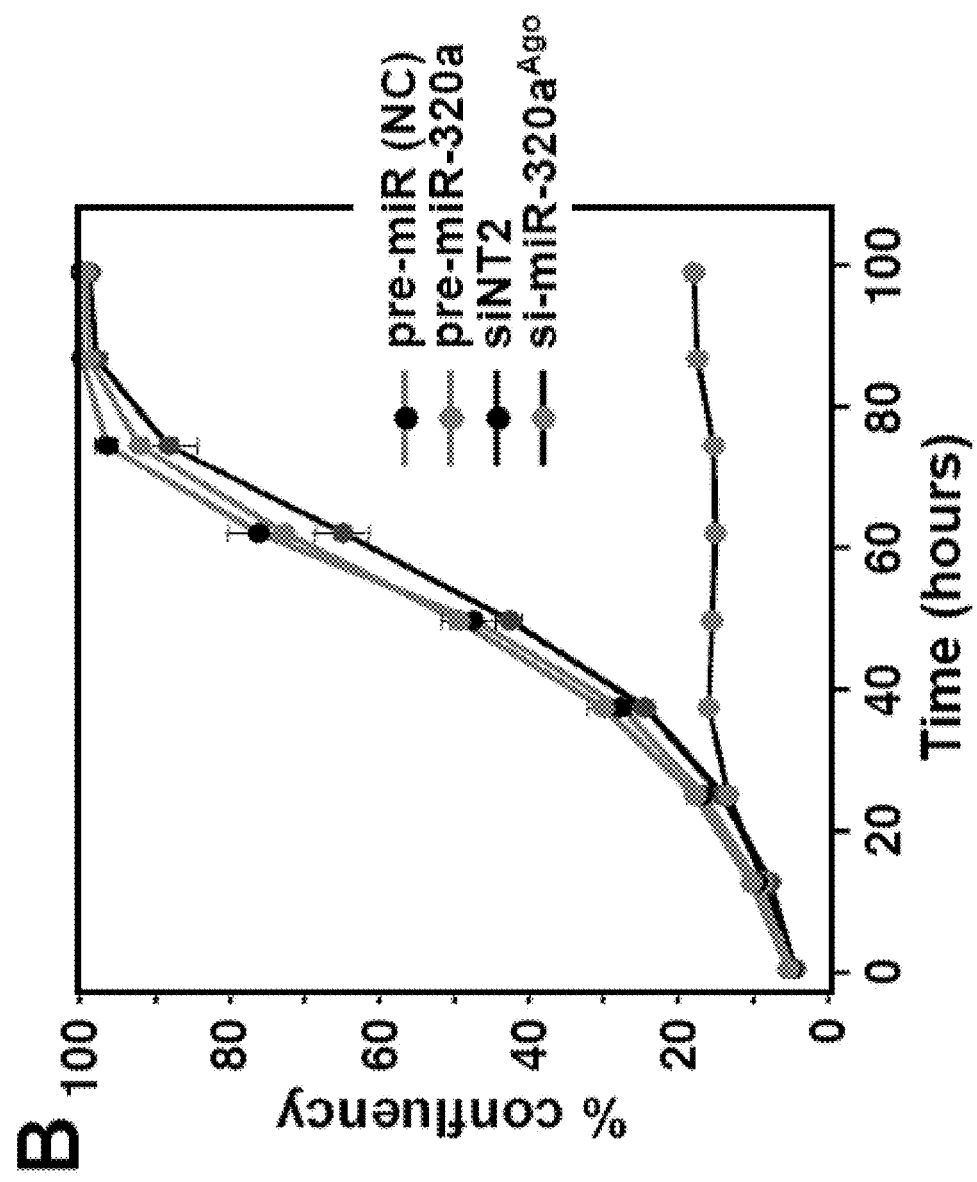
Figure 34:
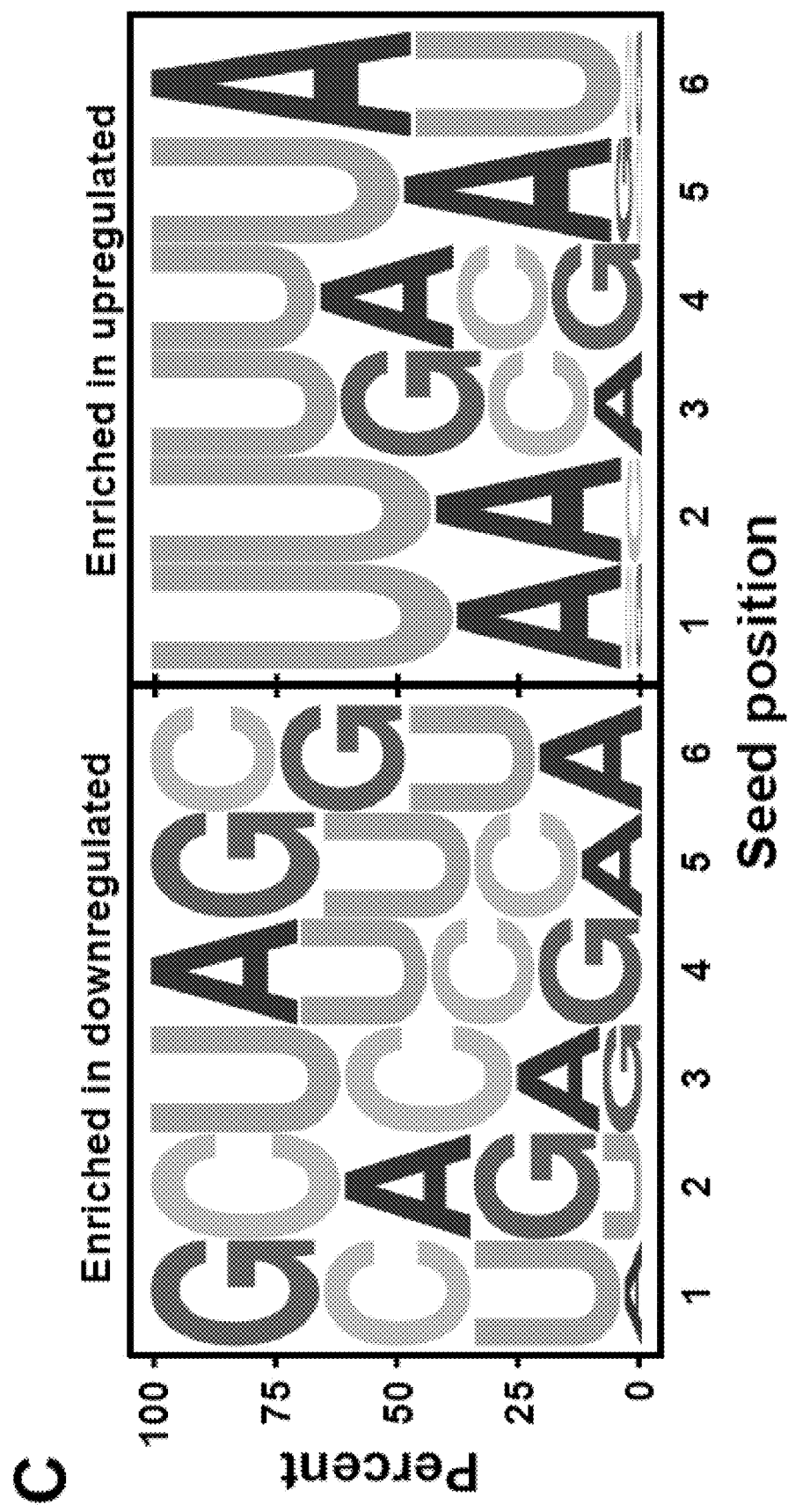
Figure 34:
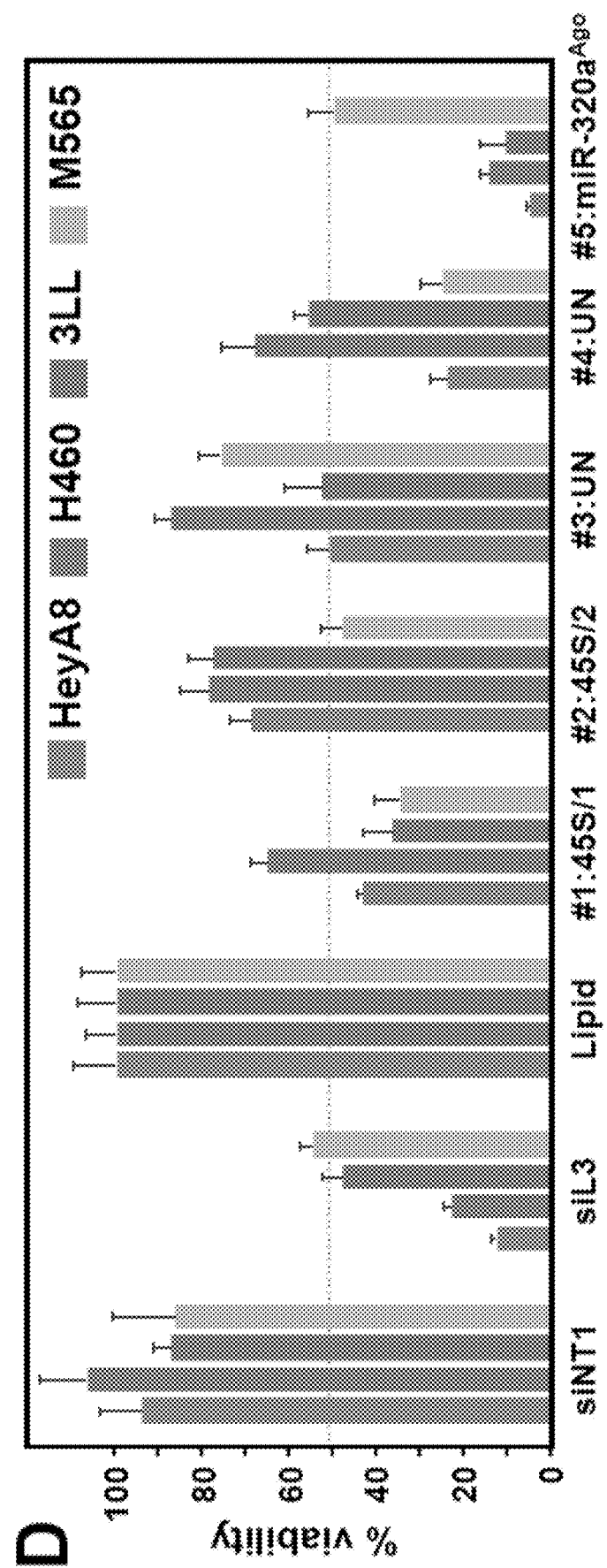

FIGS. 34. (A, B, C, and D). Small toxic RNA duplexes are upregulated in cells in response to genotoxic cell death. (A) Comparison of the sequence and the predicted toxicity of the most highly expressed and most highly upregulated Ago bound miRNAs in HCT116 wt and Drosha$^{-/-}$ cells. (Sequence Listing: TCAGTGCACTACAGAACTT (SEQ ID NO:163); TCAGTGCACTACAGAACTT (SEQ ID NO:164); TGAGATGAAGCACTGTAGC (SEQ ID NO:165); TGAGATGAAGCACTGTAGC (SEQ ID NO:166); GAGCTTATCAGACTGATGT (SEQ ID NO:167); GAGCTTATCAGACTGATGT (SEQ ID NO:168); AAGCTGGGTTGAGAGGGCG (SEQ ID NO:169); AAAAGCTGGGTTGAGAGGG (SEQ ID NO:170); AAGCTGGGTTGAGAGGGCG (SEQ ID NO:171); AAAAGCTGGGTTGAGAGGG (SEQ ID NO:172)). (B) Percent cell confluence over time of HeyA8 cells transfected with 5 nM of controls, pre-miR-320a or an siRNA duplex that corresponds to the shortened form of miR-320a (si-miR-320a$^{Ago}$) that was found to be up regulated and bound to Ago proteins upon Doxo treatment. (C) Nucleotide compositions of the 6mer sequences enriched (left) or depleted (right) in the most highly downregulated genes in HeyA8 cells treated with Doxo, Carbo, or Eto, as determined in a Sylamer analysis. (D) Five siRNA duplexes corresponding to the only five small RNAs upregulated in HeyA8 cells, HCT116 wild-type, and HCT116 Drosha$^{-/-}$ cells after Doxo treatment tested for their effects on cell viability (at 10 nM) in four cell lines.

Figure 35:
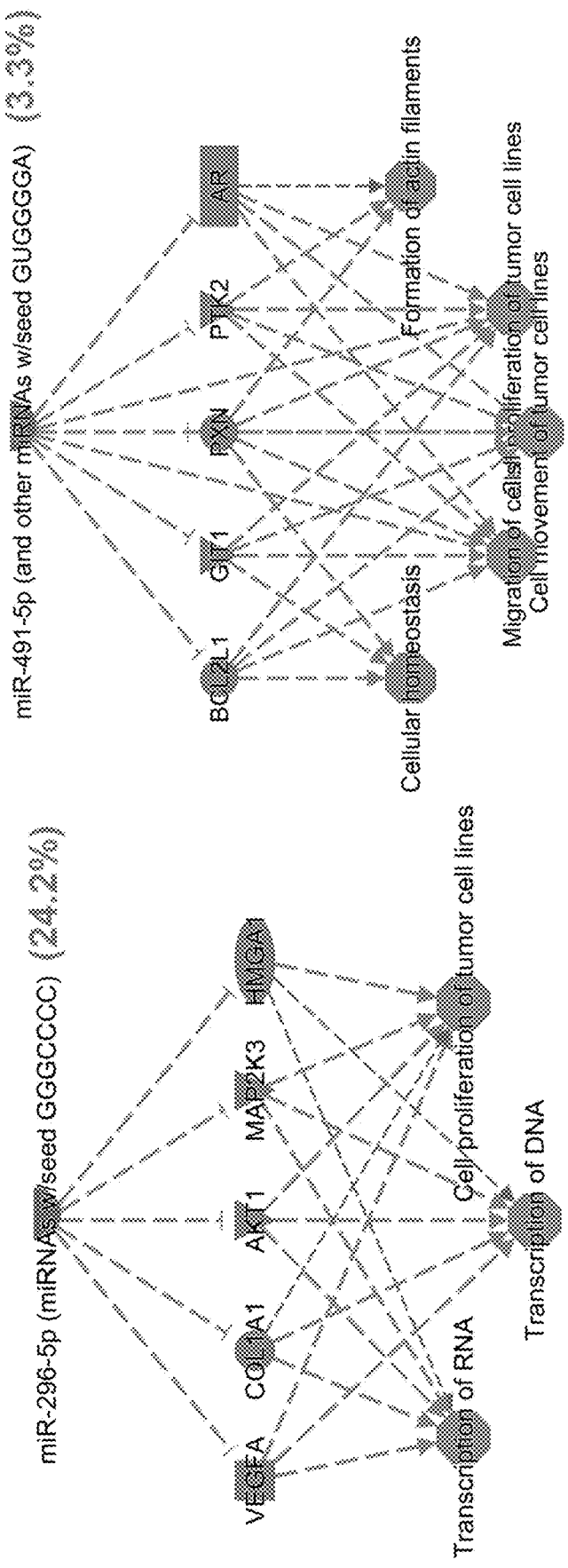

FIG. 35. Ingenuity pathway analysis identifies miRNAs with G rich seeds to target survival genes. Top Two Top Regulator Effect Networks identified by IPA regulated by miRNAs with G rich seeds. The top 4288 genes with the highest PWM score (>400) were analyzed. The 6mer seed toxicities of the miRNA seeds as determined by the 6mer seed screen (see FIG. 29A) are illustrated.

Figure 36:
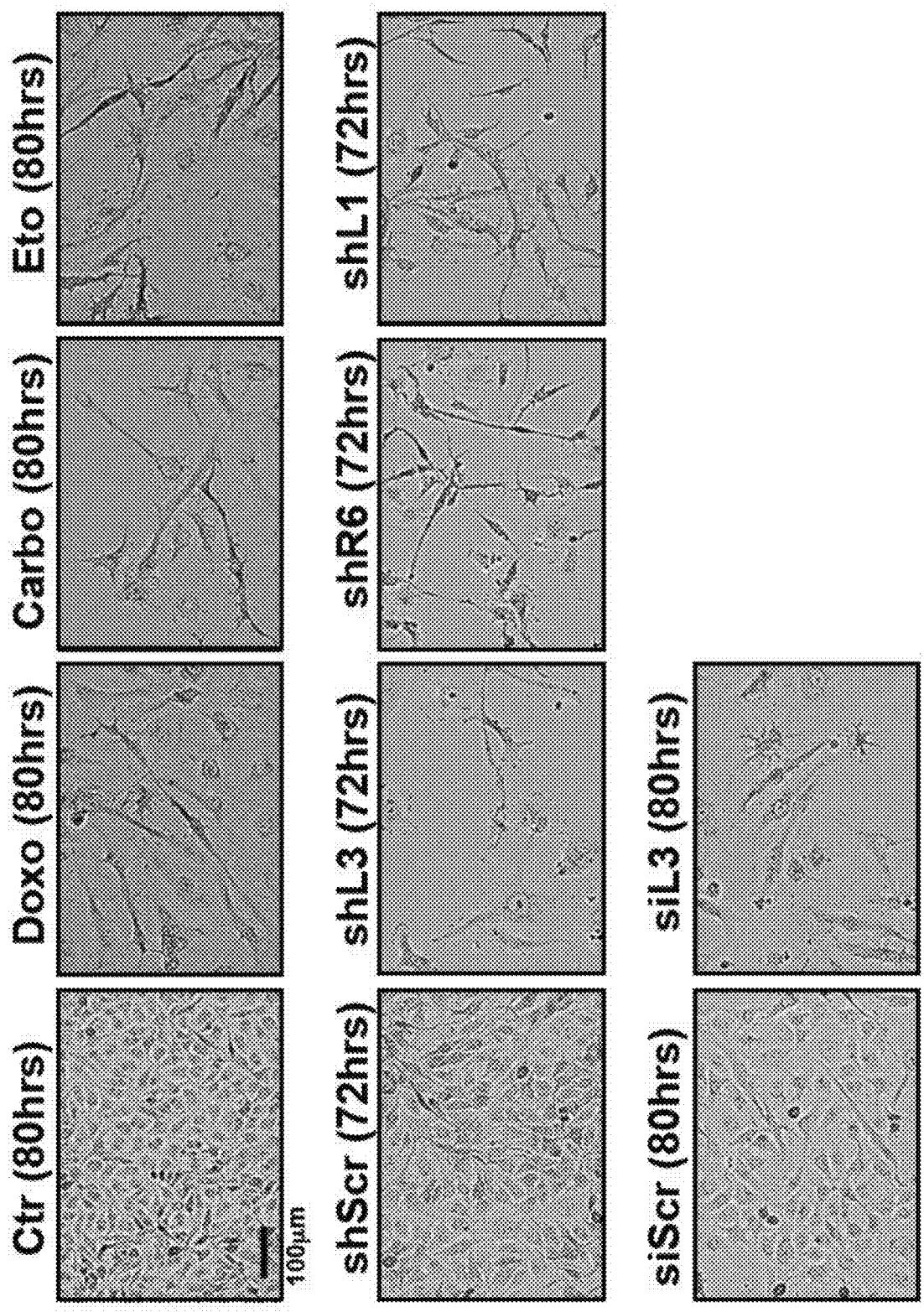

FIG. 36. Cells treated with genotoxic chemotherapeutic drugs have features of cells undergoing DISE. Morphological features of HeyA8 cells treated with three genotoxic drugs or control, with the 3 indicated shRNAs (and shScr), or with 10 nM siL3 and siScr for the indicated time.

Figure 37:
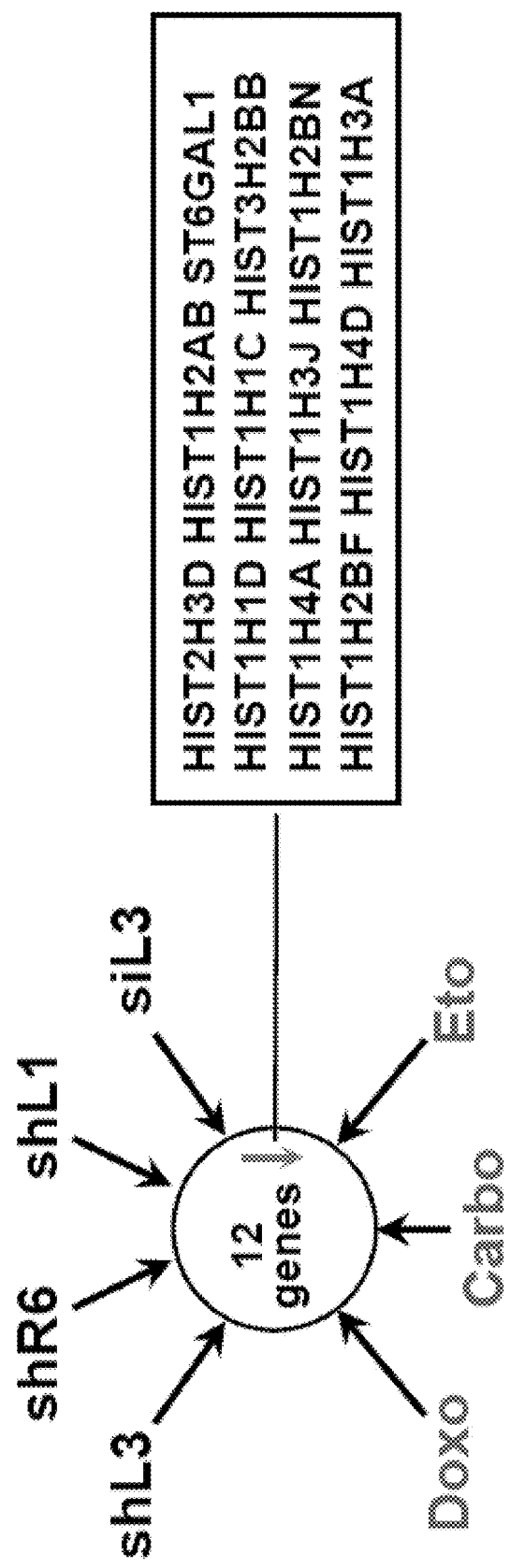

FIG. 37. Similarities between genes downregulated after DISE induction with CD95L and CD95 derived si/shRNAs and cell death induced by genotoxic drugs. (A) 11 of the 12 genes downregulated in cells treated with all four CD95 or CD95L derived DISE-inducing shRNAs and all three genotoxic stress inducing drugs in RNA-Seq data are histones.

Figure 38:
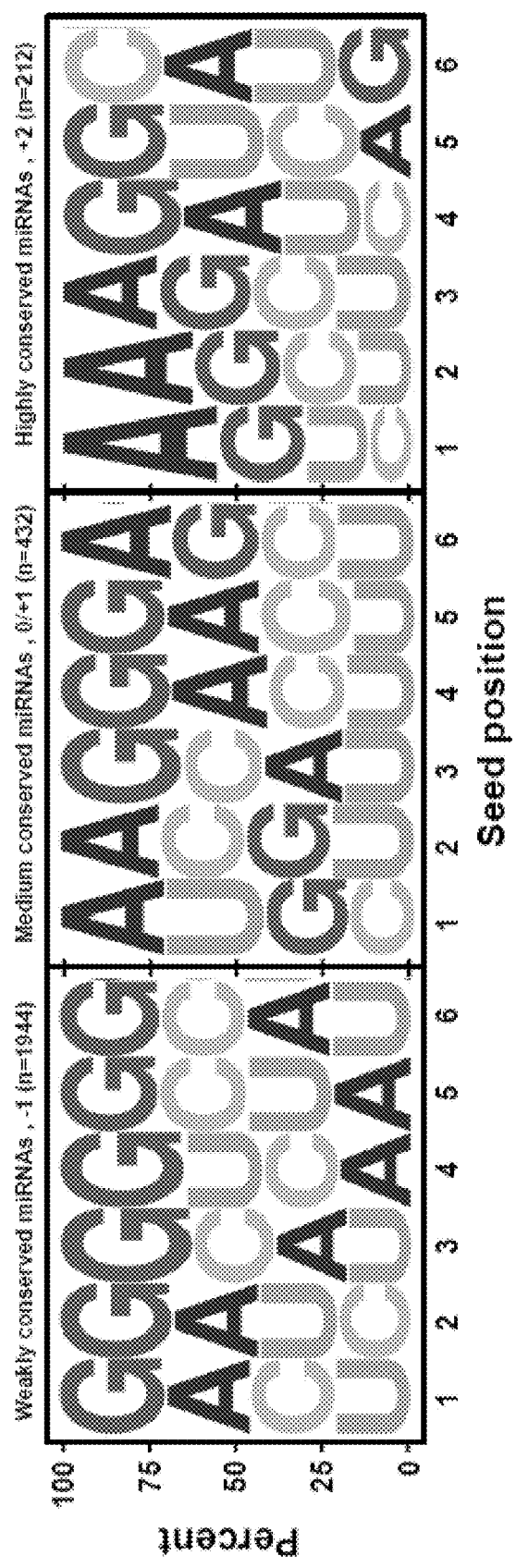

FIG. 38. Loss of Gs with increasing conservation of miRNAs. Nucleotide composition of each of the 6 seed positions in either poorly conserved (left), moderately conserved (center), highly conserved miRNAs (right). Note: The most toxic CD95L derived siRNAs we tested (siL3 (UAUGGG) and siL2 (GAGAGC)) and the two toxic miRNAs miR-34a (GGCAGU) and Ago bound miR-320a (AGCUGG) all contain three Gs in their 6mer seed.

DETAILED DESCRIPTION

The present invention is described herein using several definitions, as set forth below and throughout the application.

Unless defined otherwise, all technical and scientific terms used herein have the same meaning as commonly understood by one of skill in the art to which the invention pertains. All definitions, as defined and used herein, should be understood to control over dictionary definitions, definitions in documents incorporated by reference, and/or ordinary meanings of the defined terms.

Unless otherwise specified or indicated by context, the terms "a", "an", and "the" should be interpreted to mean "one or more." For example, "an shRNA" or "an siRNA" should be interpreted to mean "one or more shRNA's" and "one or more siRNA's," respectively As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" should be interpreted to mean plus or minus ≤10% of the particular term and "substantially" and "significantly" should be interpreted to mean plus or minus >10% of the particular term.

As used herein, the terms "include" and "including" should be interpreted to have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

A range includes each individual member. Thus, for example, a group having 1-3 members refers to groups having 1, 2, or 3 members.

It should also be understood that, unless clearly indicated to the contrary, in any methods claimed herein that include more than one step or act, the order of the steps or acts of the method is not necessarily limited to the order in which the steps or acts of the method are recited.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, a "subject" may be interchangeable with "patient" or "individual" and means an animal, which may be a human or non-human animal, in need of treatment.

A "subject in need of treatment" may include a subject having a disease, disorder, or condition that can be treated by administering to the subject one or more therapeutic RNAs as disclosed herein. A subject in need thereof may include a subject having or at risk for developing a cell proliferative disease or disorder such as cancer. A subject in need thereof may include, but is not limited to, a subject having or at risk for developing any of adenocarcinoma, leukemia, lymphoma, melanoma, myeloma, sarcoma, and teratocarcinoma, (including cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus). As such, methods of treating cancers are contemplated herein, including methods of treating cancers selected from, but not limited to any of adenocarcinoma, leukemia, lymphoma, melanoma, myeloma, sarcoma, and teratocarcinoma, (including cancers of the adrenal gland, bladder, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus).

The disclosed technology relates to nucleic acid and the use of nucleic acid for treated diseases and disorders. The terms "nucleic acid" and "oligonucleotide," as used herein, refer to polydeoxyribonucleotides (containing 2-deoxy-ribose), polyribonucleotides (containing ribose), and to any other type of polynucleotide that is an N glycoside of a purine or pyrimidine base. As used herein, the terms "A," "T," "C", "G" and "U" refer to adenine, thymine, cytosine, guanine, uracil as a nucleotide base, respectively. There is no intended distinction in length between the terms "nucleic acid," "oligonucleotide," and "polynucleotide," and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

The disclosed polynucleotides may include a fragment of a reference polynucleotide. As used herein, a "fragment" of a polynucleotide is a portion of a polynucleotide sequence which is identical in sequence to but shorter in length than a reference sequence. A fragment may comprise up to the entire length of the reference sequence, minus at least one nucleotide. For example, a fragment may comprise from 5 to 1000 contiguous nucleotides of a reference polynucleotide. In some embodiments, a fragment may comprise at least 5, 10, 15, 20, 25, 30, 40, 50, 60, 70, 80, 90, 100, 150, 250, or 500 contiguous nucleotides of a reference polynucleotide; in other embodiments a fragment may comprise no more than 5, 10, 15, 20, 25, 30, 40, 50, 60, 70, 80, 90, 100, 150, 250, or 500 contiguous nucleotides of a reference polynucleotide; in further embodiments a fragment may comprise a range of contiguous nucleotides of a reference polynucleotide bounded by any of the foregoing values (e.g. a fragment comprising 20-50 contiguous nucleotides of a reference polynucleotide). Fragments may be preferentially selected from certain regions of a molecule. The term "at least a fragment" encompasses the full length polynucleotide. A "variant," "mutant," or "derivative" of a reference polynucleotide sequence may include a fragment of the reference polynucleotide sequence.

The disclosed polynucleotides may include a deletion relative to a reference polynucleotide. As used herein, a "deletion" refers to a change in a reference nucleotide sequence that results in the absence of one or more nucleotide residues. For example, a deletion may remove at least 1, 2, 3, 4, 5, 10, 20, 50, 100, or 200 nucleotide residues or a range of nucleotide residues bounded by any of these values (e.g., a deletion of 5-10 nucleotides). A deletion may include an internal deletion or a terminal deletion (e.g., an 5'-terminal truncation or a 3'-terminal truncation of a reference polynucleotide). A "variant" of a reference nucleotide sequence may include a deletion relative to the reference polynucleotide sequence.

The disclosed polynucleotides may include an insertion or an addition relative to a reference polynucleotide. As used herein, "insertion" and "addition" refer to changes in an nucleotide sequence resulting in the addition of one or more nucleotide residues. An insertion or addition may refer to 1, 2, 3, 4, 5, 10, 20, 30, 40, 50, 60, 70, 80, 90, 100, 150, or 200 nucleotide residues or a range of nucleotide residues bounded by any of these values (e.g., an insertion or addition of 5-10 nucleotides). A "variant" of a reference polynucleotide sequence may include an insertion or addition relative to the reference polynucleotide sequence.

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 20%, at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Letters 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "promoter" as used herein refers to a cis-acting DNA sequence that directs RNA polymerase and other trans-acting transcription factors to initiate RNA transcription from the DNA template that includes the cis-acting DNA sequence.

As used herein, the term "complementary" in reference to a first polynucleotide sequence and a second polynucleotide sequence means that the first polynucleotide sequence will base-pair exactly with the second polynucleotide sequence throughout a stretch of nucleotides without mismatch. The term "cognate" may in reference to a first polynucleotide sequence and a second polynucleotide sequence means that the first polynucleotide sequence will base-pair with the second polynucleotide sequence throughout a stretch of nucleotides but may include one or more mismatches within the stretch of nucleotides. As used herein, the term "complementary" may refer to the ability of a first polynucleotide to hybridize with a second polynucleotide due to base-pair interactions between the nucleotide pairs of the first polynucleotide and the second polynucleotide (e.g., A:T, A:U, C:G, G:C, G:U, T:A, U:A, and U:G).

As used herein, the term "complementarity" may refer to a sequence region on an anti-sense strand that is substantially complementary to a target sequence but not fully complementary to a target sequence. Where the anti-sense strand is not fully complementary to the target sequence, mismatches may be optionally present in the terminal regions of the anti-sense strand or elsewhere in the anti-sense strand. If mismatches are present, optionally the mismatches may be present in terminal region or regions of the anti-sense strand (e.g., within 6, 5, 4, 3, or 2 nucleotides of the 5' and/or 3' terminus of the anti-sense strand).

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions." Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning-A Laboratory Manual, Cold Spring Harbor Laboratory, Cold Spring Harbor, N.Y.; Wetmur, 1991, Critical Review in Biochem. and Mol. Biol. 26(3/4):227-259; and Owczarzy et al., 2008, Biochemistry, 47: 5336-5353, which are incorporated herein by reference).

As used herein, the term "double-stranded RNA" ("dsRNA") refers to a complex of ribonucleic acid molecules having a duplex structure comprising two anti-parallel and substantially complementary nucleic acid strands.

As used herein, the term "nucleotide overhang" refers to an unpaired nucleotide or nucleotides that extend from the 5'-end or 3'-end of a duplex structure of a dsRNA when a 5'-end of one strand of the dsRNA extends beyond the 3'-end of the other strand, or when a 3'-end of one strand of the dsRNA extends beyond the 5'-end of the other strand.

As used herein, the term "blunt" refers to a dsRNA in which there are no unpaired nucleotides at the 5'-end and/or the 3'-end of the dsRNA (i.e., no nucleotide overhang at the 5'-end or the 3'-end). A "blunt ended" dsRNA is a dsRNA that has no nucleotide overhang at the 5'-end or the 3'-end of the dsRNA molecule.

As used herein, the term "anti-sense strand" refers to a strand of a dsRNA which includes a region that is substantially complementary to a target sequence (i.e., where the target sequence has a sequence corresponding to the sense strand).

As used herein, the term "sense strand," refers to the strand of a dsRNA that includes a region that is substantially complementary to a region of the anti-sense strand and that includes a region that substantially corresponds to a region of the target sequence.

As used herein, RNAi active sequences may include "siRNA" and "shRNA" and dsRNA that is processed by nucleases to provide siRNA and/or shRNA. The term "siRNA" refers to a "small interfering RNA" and the term "shRNA" refers to "short hairpin RNA." RNA interference (RNAi) refers to the process of sequence-specific post-transcriptional gene silencing in a cell or an animal mediated by siRNA and/or shRNA.

As used herein, the term "siRNA targeted against mRNA" refers to siRNA specifically promote degradation of the targeted mRNA via sequence-specific complementary multiple base pairings (e.g., at least 6 contiguous base-pairs between the siRNA and the target mRNA at optionally at least 7, 8, 9, 10, 11, 12, 13, 14, 15, 16, 17, 18, 19, 20, 21, 22, or 23 contiguous base-pairs between the siRNA and the target mRNA).

The terms "target, "target sequence", "target region", and "target nucleic acid," as used herein, are synonymous and refer to a region or sequence of a nucleic acid which may be selected as a sequence to which the anti-sense strand of siRNA or shRNA is substantially complementary to and hybridizes to as discussed herein. A target sequence may refer to a contiguous portion of a nucleotide sequence of an mRNA molecule of a particular gene, including but not limited to, genes that are essential for survival and/or growth of cells and in particular cancer cells. The target sequence of a siRNA refers to a mRNA sequence of a gene that is targeted by the siRNA due to complementarity between the anti-sense strand of the siRNA and the mRNA sequence and to which the anti-sense strand of the siRNA hybridizes when brought into contact with the mRNA sequence.

As used herein, the term "transfecting" means "introducing into a cell" a molecule, which may include a polynucleotide molecule such as dsRNA. When referring to a dsRNA, transfecting means facilitating uptake or absorption into the cell, as is understood by the skilled person. Absorption or uptake of dsRNA can occur or may be facilitated through passive diffusive or active cellular processes, or through the use of auxiliary agents or devices. Transfection into a cell includes methods known in the art such as electroporation and lipofection. However, the meaning of the term "transfection" is not limited to introducing molecules into cells in vitro. As contemplated herein, a dsRNA also may be "introduced into a cell," where the cell is part of a living organism. For example, for in vivo delivery, a dsRNA may be injected into a tissue site or may be administered systemically.

As used herein, the terms "silencing" and "inhibiting the expression of" refer to at least partial suppression of the expression of a target gene, for example, as manifested by a reduction of mRNA associated with the target gene.

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

As used herein, the term "pharmaceutical composition" may include be defined as a composition that includes a pharmacologically effective amount of a dsRNA and a pharmaceutically acceptable carrier for delivering the dsRNA to target cells or target tissue. As used herein, the term "pharmaceutically acceptable carrier" refers to a carrier for administration of a therapeutic agent which facilitates the delivery of the therapeutic agent (e.g., dsRNA) to target cells or target tissue. As used herein, the term "therapeutically effective amount" refers to that amount of a therapeutic agent that provides a therapeutic benefit in the treatment, prevention, or management of a disease or disorder (e.g., a cell proliferation disease or disorder such as cancer).

In one aspect, the present inventors disclose an isolated double stranded short interfering ribonucleic acid (siRNA) molecule that silences expression of one or more mRNA's of essential genes that are required for survival and growth of cells such as cancer cells. Preferably, the disclosed siRNA molecules silence the expression of multiple mRNA's of essential genes that are required for survival and growth of cells such as cancer cells through a process called "death-induced by survival gene elimination" or "DISE."

The mechanism of action of siRNA is understood by the skilled person. Interfering RNA (RNAi) generally refers to a single-stranded RNA (ssRNA) or double-stranded RNA (dsRNA). The dsRNA is capable of targeting specific messenger RNA (mRNA) and silencing (i.e., inhibiting) the expression of a target gene. During this process, dsRNA (which may include shRNA) is enzymatically processed into short-interfering RNA (siRNA) duplexes of ~21-23 nucleotides in length. The anti-sense strand of the siRNA duplex is then incorporated into a cytoplasmic complex of proteins (RNA-induced silencing complex or RISC). The RISC complex containing the anti-sense siRNA strand also binds mRNA which has a sequence complementary to the anti-sense strand-allowing complementary base-pairing between the anti-sense siRNA strand and the sense mRNA molecule. The mRNA molecule is then specifically cleaved by an enzyme (RNase) associated with RISC resulting in specific gene silencing. For gene silencing or knock down (i.e., mRNA cleavage) to occur, anti-sense RNA (i.e., siRNA) has to become incorporated into the RISC. This represents an efficient process that occurs in nucleated cells during regulation of gene expression. When an anti-sense DNA molecule is introduced into a cell, it targets specific mRNA through base-pairing of the anti-sense DNA molecule to its RNA target.

As such, siRNA-mediated RNA interference may be considered to involve two-steps: (i) an initiation step, and (ii) an effector step. In the first step, input siRNA is processed into small fragments, such as ~21-23-nucleotide 'guide sequences.' The guide RNAs can be incorporated into the protein-RNA RISC complex which is capable of degrading mRNA. As such, the RISC complex acts in the second effector step to destroy mRNAs that are recognized by the guide RNAs through base-pairing interactions. RNA interference via use of siRNA may be considered to involve the introduction by any means of double stranded RNA into a cell which triggers events that cause the degradation of a target RNA, and as such siRNA may be considered to be a form of post-transcriptional gene silencing. The skilled person understands how to prepare and utilize siRNA molecules. (See, e.g., Hammond et al., Nature Rev Gen 2: 110-119 (2001); and Sharp, Genes Dev 15: 485-490 (2001), the contents of which are incorporate herein by reference in their entireties).

For purposes of this application, the anti-sense strand of the siRNA may comprise a contiguous nucleotide sequence, where the base sequence of the anti-sense strand has substantial or complete sequence complementarity to the base sequence of a contiguous nucleotide sequence of corresponding length contained in an mRNA sequence of the targeted mRNA (e.g., in a non-coding 3'-end of an mRNA sequence). Substantial complementary permits some nucleotide mismatches (i.e., non-pairing nucleotides) and as such, the anti-sense strand of the siRNA need not have full complementarity.

In some embodiments, at least a portion of an anti-sense strand of an siRNA molecule comprises or consists of a sequence that is 100% complementary to a target sequence or a portion thereof. In another embodiment, at least a portion of an anti-sense strand of an siRNA molecule comprises or consists of a sequence that is at least about 90%, 95%, or 99% complementary to a target sequence or a portion thereof. For purposes of this application, the anti-sense strand of the siRNA molecule preferably comprises or consists of a sequence that specifically hybridizes to a target sequence or a portion thereof so as to inhibit expression of the target mRNA. The portion of the anti-sense strand of an siRNA molecule that comprises or consists of a sequence that is 100% complementary to a target sequence or a portion thereof may be a 6-nucleotide sequence referred to as a "seed sequence" which may be complementary to a corresponding 6-nucleotide sequence in a 3' UTR of a mRNA of a survival gene. The complementarity in this 6-nucleotide seed sequence may be sufficient to induce "death-induced by survival gene elimination" or "DISE" as disclosed herein.

Methods for preparing and isolating siRNA also are known in the art. (See, e.g., Sambrook et al., Molecular Cloning, A Laboratory Manual (2.sup.nd Ed., 1989), the content of which is incorporated herein by reference in its entirety). The disclosed siRNA may be chemically synthesized, using any of a variety of techniques known in the art. The disclosed siRNA may include modifications, for example, modifications that stabilize the siRNA and/or protect the siRNA from degradation via endonucleases and/or exonucleases. In some embodiments, the disclosed siRNA may include nucleic acid protecting and coupling groups, such as dimethoxytrityl at the 5'-end and/or phosphoramidites at the 3'-end.

In one embodiment, the disclosed RNAs comprise a double stranded region of about 15 to about 30 nucleotides in length. Preferably, the disclosed RNAs are about 20-25 nucleotides in length. The disclosed RNAs of the present invention are capable of silencing the expression of a target sequence in vitro and in vivo.

In one embodiment, the dsRNA disclosed herein comprises a hairpin loop structure and may be referred to as shRNA which may be processed to a siRNA. In another embodiment, the dsRNA or siRNA has an overhang on its 3' or 5' ends relative to the target RNA which is to be cleaved. The overhang may be 2-10 nucleotides long. In one embodiment, the dsRNA or siRNA does not have an overhang (i.e., the dsRNA or siRNA has blunt ends).

In another embodiment, the disclosed RNA molecules (e.g., siRNA molecules) may contain one or more modified nucleotides, including one or more modified nucleotides at the 5' and/or 3' terminus of the RNA molecules. In yet another embodiment, the disclosed RNA molecules may comprise one, two, three four or more modified nucleotides in the double-stranded region. Exemplary modified nucleotides may include but are not limited to, modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and the like. The preparation of modified siRNA is known by one skilled in the art. In some embodiments, the disclosed dsRNA molecules include one or more modified nucleotides at the 5'-terminus of the passenger strand of the dsRNA that prevent incorporation of the passenger strand into RISC.

(See, e.g., Walton et al., Minireview: "Designing highly active siRNAs for therapeutic applications," the FEBS Journal, 277 (2010) 4806-4813).

In some embodiments, the disclosed siRNA molecules are capable of silencing one or more target mRNAs and may reduce expression of the one or more target mRNAs by at least about 20%, 30%, 40%, 50%, 60%, 70%, 80%, 90%, or 100% relative to a control siRNA molecule (e.g., a molecule not exhibiting substantial complementarity with the target mRNA). As such, in some embodiments, the presently disclosed siRNA molecules targeting the mRNA of essential genes may be used to down-regulate or inhibit the expression of essential genes (e.g., by at least about 20%, 30%, 40%, 50%, 60%, 70%, 80%, 90%, or 100% relative to a control siRNA molecule).

The disclosed RNA molecules may conveniently be delivered to a target cell or a target tissue through a number of delivery systems. For example, RNA may be delivered via electroporation, lipofection, calcium phosphate precipitation, plasmids, viral vectors that express the RNA, viral nucleic acids, phage nucleic acids, phages, cosmids, nanoparticles, or via transfer of genetic material in cells or carriers such as cationic liposomes. In one embodiment, transfection of RNA may employ viral vectors, chemical transfectants, or physico-mechanical methods such as electroporation and direct diffusion of DNA.

Also disclosed herein are pharmaceutical compositions (e.g., pharmaceutical compositions comprising therapeutic siRNA) and methods of administering pharmaceutical compositions for treating diseases and disorders (e.g., cell proliferative diseases and disorders such as cancer). The pharmaceutical composition may comprise one or more siRNAs as therapeutic agents for inhibiting the gene activity of one or more essential genes and a pharmaceutical acceptable carrier. Pharmaceutically acceptable carriers include, but are not limited to, excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Pharmaceutical compositions containing siRNA may be administered to a mammal in vivo to treat cancer. In one embodiment, the pharmaceutical formulation includes a dosage suitable for oral administration. In another embodiment, the pharmaceutical formulation is designed to suit various means for siRNA administration. Exemplary means include uptake of naked siRNA, liposome fusion, intramuscular injection via a gene gun, endocytosis and the like.

Toxic RNAi Active Seed Sequence for Killing Cancer Cells

Chemotherapeutic treatment of cancer eventually fails because tumor cells develop resistance and metastasize. This resistance happens because tumor cells have an elevated rate of mutagenesis and eventually acquire new mutations that prevent chemotherapies from working. We have discovered a category of genes we coined Donor (D) genes whose mRNA transcripts give rise to naturally-occurring short interfering (si)RNAs that target a network of survival genes in cancer cells. However, we can artificially target this survival network by introducing synthetic siRNAs designed from the sequences of these D genes, resulting in activation of multiple death pathways that robustly kill transformed and cancer stem cells across multiple solid tumor types. Since we target a network of survival genes, cancer cells would have to develop multiple concurring genetic alterations to short-circuit the multiple forms of cell death activated by interrupting numerous survival pathways. Our method of killing cancer cells would be superior to current treatment with small molecules or any targeted therapy, which are designed to target a single specific gene, which can easily be circumvented by the enhanced rate of mutation that cancer cells experience.

Applications and Advantages

Applications for the disclosed technology include cancer therapy in which siRNAs and/or shRNAs are designed to target specific cancer cells. The disclosed technology is advantageous in that the disclosed siRNAs and/or shRNAs preferentially kill transformed and cancer stem cells. The disclosed siRNAs and/or shRNAs kill a very broad variety of cancer types, including cancers that are resistant to chemotherapy.

No one has been able to kill cancer cells in vivo without selecting for cancer cells that acquire resistance and metastasize. The discovery of these D genes will allow the development of siRNAs that target a network of survival genes and thereby overcome the obstacle of resistance to small molecule drugs or targeted therapy using biologicals. There is a major discrepancy between genes identified as being critical to cell survival when using either RNAi to knockdown the gene of interest versus knocking out a gene using genome-editing techniques such as CRISPR. This discovery provides a biological basis as to why this occurs and will be of interest to any scientists trying to identify genes critical for cancer cell survival.

This invention provides an entirely new way of killing cancer cells through a process that does not allow cancer cells to acquire resistance. The economic and non-economic value of effectively treating cancer is obvious. Furthermore, scientists can consult our list of D genes as a valuable resource to conduct research that use siRNAs. Since most biological research labs use siRNAs, our list would be extremely valuable to the scientific community.

Technical Field

The invention describes a new method of killing cancer cells by using naturally occurring toxic siRNA active seed sequences embedded in certain genes in the human genome (the donor or D genes) that target a global network of survival genes through targeting of 6-mer nucleotide sequence enriched in the mRNA of survival genes (such as in the 3' UTR of mRNA of survival genes), which causes simultaneous induction of multiple cell death pathways that specifically target transformed and cancer stem cells. Cancer cells have a hard time acquiring resistance to this novel mechanism.

Disclosed herein are toxic RNAi active seed sequences that may be utilized in therapeutic methods of killing cancer cells in a subject in need thereof. Particular disclosed are toxic RNAi active seed sequences such as siRNA and shRNA and methods of using toxic RNAi active sequence for killing cancer cells. The disclosed toxic RNAi active seed sequences preferentially target and inhibit the expression of multiple essential genes for cell survival and/or growth through a process called "death-induced by survival gene elimination" or "DISE."

In some embodiments, the disclosed toxic RNAis are polynucleotides that may be defined as polynucleotide comprising a dsRNA sequence defined as follows:

```
5'-P01 P02 P03 P04 P05 P06 P07 P08 P09 P10 P11 P12 P13 P14 P15 P16 P17 P18 P19
    *   *   *   *   *   *   *   *   *   *   *   *   |   |   |   |   |   |   *
3'-G19 G18 G17 G16 G15 G14 G13 G12 G11 G10 G09 G08 G07 G06 G05 G04 G03 G02 G01
``` wherein:

G01 through G19 and P01 through P19 are any ribonucleotide selected from A, U/T, G, and C, provided that:

G01 is A or U/T;

G0, G2, G03, G04, G05, G06, and G07 are complementary to P18, P17, P16, P15, P14, and P13, respectively;

the percentage GC content of the region from G02 to G07 is 70-100%;

the percentage GC content of the region from G08 to G16 is 0-30%;

the percentage GC content of the region from G17 to G19 is 31-100%.

The disclosed polynucleotides may include siRNA. For example, in some embodiments the disclosed siRNA may be defined as follows:

```
5'-        P01 P02 P03 P04 P05 P06 P07 P08 P09 P10 P11 P12 P13 P14 P15 P16 P17 P18 P19 P20 P21-3'
            *   *   *   *   *   *   *   *   *   *   *   *   |   |   |   |   |   |   *
3'-G21 G20 G19 G18 G17 G16 G15 G14 G13 G12 G11 G10 G09 G08 G07 G06 G05 G04 G03 G02 G01            -5'Phos
``` wherein:
G20, G21, P20, and P21 are any ribonucleotide.

In some embodiments, the disclosed siRNA including overhangs which comprise one or more deoxyribonucleotides (e.g., where in the definition above G20, G21, P20, and P21 are deoxyribonucleotides).

The disclosed polynucleotides may include shRNA. For example, in some embodiments the disclosed siRNA may be defined as follows:

```
5'-P01 P02 P03 P04 P05 P06 P07 P08 P09 P10 P11 P12 P13 P14 P15 P16 P17 P18 P19-Lo
    *   *   *   *   *   *   *   *   *   *   *   *   |   |   |   |   |   |   *   )
3'-G19 G18 G17 G16 G15 G14 G13 G12 G11 G10 G09 G08 G07 G06 G05 G04 G03 G02 G01-po
``` wherein $$\left. \begin{array}{c} Lo \\ po \end{array} \right)$$

comprises a polynucleotide loop sequence.

In the disclosed polynucleotides and the definitions provided above, G02, G03, G04, G05, G06, and G07 comprise the sequence NNNNNN, where N is any nucleotide. The contiguous sequence of G02, G03, G04, G05, G06, and G07 or NNNNNN may be referred to herein otherwise as a "seed sequence" which preferentially targets survival genes (e.g., survival genes in cancer cells). The present inventors have endeavored to screen a library of polynucleotides comprising all possible combinations of NNNNNN (i.e. "seed sequences), where the library will include $6^4$=4096 different members, for polynucleotides that exhibit toxicity to cancer cells and preferably target multiple essential genes that are required for survival and/or growth of the cancer cells.

In some embodiments of the disclosed polynucleotides, the seed sequence is selected from a group consisting of GGGCAG, GGGGCU, GGGCUG, GGGCGA, GGGGGC, GGGGGU, GGGCGG, GGGUGG, GGUGGG, GGCUGG, GGGGCA, GGGGUC, GGCAGC, GAAGAU, GGUGGU, GGUGGA, GGGCAA, GGGCAU, GGAGGU, GGGGCC, GGGGCG, GUCUUC, GGAGCU, GGGGAGA, GGGCGU, GGCGGU, GCAGGG, GGGAGU, CGGGGC, CUGGGC, GCAGGC, GGGCGC, GCUAAC, GGCGGG, GGGUGU, GGGUGC, GGGGGA, GAGGGU, GCGGGC, GUGGGC, GGGGUG, GGGAUC, GUAGUC, GACAGC, GCCUGU, GGUGCU, GGAGGA, GGGCCU, GCGGGG, GAGGGC, GGAUGC, GGGUGA, GCGGGU, UCUGGG, AGCUGG, GUGGGG, GGGCCG, GGAGGC, GGCUAU, CGUUGC, AGGGCC, GUUGCC, GAUGCU, GAGGGG, GUAGGC, GCUGGG, GUCUCC, AGUGGG, GGCUCU, GAAGUC, GUGGGU, GGCAGG, GGUGGC, GGCUAC, GCUAAU, GAUACC, GAUGCC, CCUGGG, GGGAGC, GAUGGC, CGGGUC, CGGGGG, UGGGGG, GUAGGU, GGGUAG, AGCGGC, GCGGCG, CGGGCC, CGCGGC, GUUUCC, GGCAUU, GGGGGG, GCUAGC, GCAGGU, GGGGAU, GGUGCC, GGCGGA, AGGCUC, ACAGAU, CCAUGG, AGUUGC, GGCUGC, ACUGGG, UGGCGG, GCGGUU, GGCGGC, GACAUC, GGGCUA, UGUAGU, GGAGCC, CCGACC, GGGCCA, GGGCUC, GGCGAU, AGGGGG, GGCCGG, AACAUC, GUCUGC, UGCCUG, GUCUCU, GUCCUC, CGUUCC, CUGGGA, GCGUGC, CGGGCU, GGCAGU, CGGGGU, GGUAGG, ACACCU, GUCAUC, GCCGGC, AGGGGC, GGCCUC, GGAGGG, GGUGUU, GGCAUG, UAUCCC, CGCCGC, AGGUGC, GACUGC, GCCUUC, AGGAGG, CGGAGG, GUCUGG, AGCUGC, GGCAUC, GCUGCU, CGGUGG, GUGUUC, GUCCAC, GGGCUU, GGCCGC, GGGUCU, GGCCGU, GGUAGU, ACAUCU, GCCGGU, AGCGGU, GGUUGG, AGGGUC, GGCUAG, AACCCC, GGUGAC, GUUGGG, GUAUCC, GGGGUU, GCUAUC, GGGGAG, CGGCGG, GAACUC, ACGGGC, GUAGGG, GGGUCC, CAGGCC, GGGAGG, GUUCAC, GGUGCG, ACAGGC, AGCGGG, ACAUGC, CAUGCU, CUUGGC, GUAGCU, CCGGGC, CGUAGC, GAAGCC, ACUUGG, GGCUCC, UGUAUC, GGCUUC, ACGACC, UCGGGC, GCCGAC, GGCUCA, GGCGAC, ACAGAC, CGGCUC, UCGUGC, GUUCCU, and GUCUGU.

The identified polynucleotides that exhibit toxicity to cancer cells may be formulated as a pharmaceutical compositions, for example, as pharmaceutical compositions for treating cell proliferative diseases and disorders such as cancer. The disclosed pharmaceutical compositions may be administered to a subject in need thereof, for example, a subject having a cell proliferative disease or disorder such as cancer.

ILLUSTRATIVE EMBODIMENTS

The following embodiments are illustrative should not be interpreted to limit the scope of the claimed subject matter.

Embodiment 1

A polynucleotide comprising a dsRNA sequence defined as follows:

```
5'-P01 P02 P03 P04 P05 P06 P07 P08 P09 P10 P11 P12 P13 P14 P15 P16 P17 P18 P19
    *   *   *   *   *   *   *   *   *   *   *   *   |   |   |   |   |   |   *
3'-G19 G18 G17 G16 G15 G14 G13 G12 G11 G10 G09 G08 G07 G06 G05 G04 G03 G02 G01
``` wherein:
G01 through G19 and P01 through P19 are any ribonucleotide selected from A, U/T, G, and C, provided that:
G01 is A or U/T;
G02, G03, G04, G05, G06, and G07 are complementary to P18, P17, P16, P15, P14, and P13, respectively;
the percentage GC content of the region from G02 to G07 is 50-100%, optionally or necessarily where G02 and G03 are G, optionally or necessarily where the GC content of G02 to G07 is ≥50%, ≥75%, ≥84%, or 100%, and optionally or necessarily where the G content of G02 to G07 is ≥50%, ≥75%, ≥84%, or 100%;
optionally, the percentage GC content of the region from G08 to G16 is 0-30%; optionally, the percentage GC content of the region from G17 to G19 is 31-100%.

Embodiment 2

The polynucleotide of claim 1, wherein the polynucleotide is an siRNA.

Embodiment 3

The polynucleotide of claim 1 or 2, wherein the polynucleotide is an siRNA defined as follows:

```
5'-        P01 P02 P03 P04 P05 P06 P07 P08 P09 P10 P11 P12 P13 P14 P15 P16 P17 P18 P19 P20 P21-3'
            *   *   *   *   *   *   *   *   *   *   *   *   |   |   |   |   |   |   *
3'-G21 G20 G19 G18 G17 G16 G15 G14 G13 G12 G11 G10 G09 G08 G07 G06 G05 G04 G03 G02 G01        -5'Phos
``` wherein:
G20, G21, P20 and P21 are any ribonucleotide.

Embodiment 4

The polynucleotide of claim 3, wherein G20, G21, P20, and P21 are deoxyribonucleotides.

Embodiment 5

The polynucleotide of any of the foregoing embodiments, wherein G02, G03, G04, G05, G06, and G07 comprise the sequence NNNNNN, which optionally is a polynucleotide sequence present in a tumor suppressor gene, optionally where NNNNNN has a sequence GGNNNN and optionally where NNNNNN has an overall GC content or G content of >80%.

Embodiment 6

The polynucleotide of any of the foregoing embodiments, wherein the polynucleotide downregulates expression of one or more survival genes when the polynucleotide is transfected or expressed in a cell.

Embodiment 7

The polynucleotide of embodiment 6, wherein the survival genes are selected from FUBP1, NAA50, SNRPE, CCT3, TFRC, PRELID3B and combinations thereof.

Embodiment 8

The polynucleotide of embodiment 6 or 7, wherein the cell is a cancer cell.

Embodiment 9

The polynucleotide of any of the foregoing embodiments, wherein the polynucleotide is an shRNA illustrated as follows:

```
5'-P01 P02 P03 P04 P05 P06 P07 P08 P09 P10 P11 P12 P13 P14 P15 P16 P17 P18 P19-Lo
    *   *   *   *   *   *   *   *   *   *   *   *   |   |   |   |   |   |   *   )
3'-G19 G18 G17 G16 G15 G14 G13 G12 G11 G10 G09 G08 G07 G06 G05 G04 G03 G02 G01-po
``` wherein:

$$L_0\brace P_0$$

comprises a polynucleotide loop sequence.

Embodiment 10

The polynucleotide of any of the foregoing embodiments, wherein the contiguous sequence of G02 through G07 is selected from the group consisting of GGGCAG, GGGGCU, GGGCUG, GGGCGA, GGGGGC, GGGGGU, GGGCGG, GGGUGG, GGUGGG, GGCUGG, GGGGCA, GGGGUC, GGCAGC, GAAGAU, GGUGGU, GGUGGA, GGGCAA, GGGCAU, GGAGGU, GGGGCC, GGGGCG, GUCUUC, GGAGCU, GGGAGA, GGGCGU, GGCGGU, GCAGGG, GGGAGU, CGGGGC, CUGGGC, GCAGGC, GGGCGC, GCUAAC, GGCGGG, GGGUGU, GGGUGC, GGGGGA, GAGGGU, GCGGGC, GUGGGC, GGGGUG, GGGAUC, GUAGUC, GACAGC, GCCUGU, GGUGCU, GGAGGA, GGGCCU, GCGGGG, GAGGGC, GGAUGC, GGGUGA, GCGGGU, UCUGGG, AGCUGG, GUGGGG, GGGCCG, GGAGGC, GGCUAU, CGUUGC, AGGGCC, GUUGCC, GAUGCU, GAGGGG, GUAGGC, GCUGGG, GUCUCC, AGUGGG, GGCUCU, GAAGUC, GUGGGU, GGCAGG, GGUGGC, GGCUAC, GCUAAU, GAUACC, GAUGCC, CCUGGG, GGGAGC, GAUGGC, CGGGUC, CGGGGG, UGGGGG, GUAGGU, GGGUAG, AGCGGC, GCGGCG, CGGGCC, CGCGGC, GUUUCC, GGCAUU, GGGGGG, GCUAGC, GCAGGU, GGGGAU, GGUGCC, GGCGGA, AGGCUC, ACAGAU, CCAUGG, AGUUGC, GGCUGC, ACUGGG, UGGCGG, GCGGUU, GGCGGC, GACAUC, GGGCUA, UGUAGU, GGAGCC, CCGACC, GGGCCA, GGGCUC, GGCGAU, AGGGGG, GGCCGG, AACAUC, GUCUGC, UGCCUG, GUCUCU, GUCCUC, CGUUCC, CUGGGA, GCGUGC, CGGGCU, GGCAGU, CGGGGU, GGUAGG, ACACCU, GUCAUC, GCCGGC, AGGGGC, GGCCUC, GGAGGG, GGUGUU, GGCAUG, UAUCCC, CGCCGC, AGGUGC, GACUGC, GCCUUC, AGGAGG, CGGAGG, GUCUGG, AGCUGG, GGCAUC, GCUGCU, CGGUGG, GUGUUC, GUCCAC, GGGCUU, GGCCGC, GGGUCU, GGCCGU, GGUAGU, ACAUCU, GCCGGU, AGCGGU, GGUUGG, AGGGUC, GGCUAG, AACCCC, GGUGAC, GUUGGG, GUAUCC, GGGGUU, GCUAUC, GGGGAG, CGGCGG, GAACUC, ACGGGC, GUAGGG, GGGUCC, CAGGCC, GGGAGG, GUUCAC, GGUGCG, ACAGGC, AGCGGG, ACAUGC, CAUGCU, CUUGGC, GUAGCU, CCGGGC, CGUAGC, GAAGCC, ACUUGG, GGCUCC, UGUAUC, GGCUUC, ACGACC, UCGGGC, GCCGAC, GGCUCA, GGCGAC, ACAGAC, CGGCUC, UCGUGC, GUUCCU, and GUCUGU.

Embodiment 11

An expression vector that expresses the polynucleotide of any of the foregoing embodiments or a single-stranded portion thereof.

Embodiment 12

The expression vector of embodiment 11 comprising a eukaryotic promoter operably linked to the polynucleotide or a DNA equivalent thereof.

Embodiment 13

The expression vector of embodiment 11 or 12, wherein the expression vector is a plasmid or a viral expression vector.

Embodiment 14

A pharmaceutical composition comprising the polynucleotide of any of embodiments 1-10 or a single-stranded portion thereof and a pharmaceutically acceptable excipient.

Embodiment 15

A pharmaceutical composition comprising the expression vector of any of embodiments 11-13 and a pharmaceutically acceptable excipient.

Embodiment 16

A nanoparticle comprising the polynucleotide of any of embodiments 1-10 or a single-stranded portion thereof.

Embodiment 17

The nanoparticle of embodiment 16, wherein the nanoparticle is a nanoparticle formed from lipoproteins and/or phospholipids (e.g., wherein the nanoparticle is a liposome or a micelle).

Embodiment 18

The nanoparticle of embodiment 16 or 17, wherein the polynucleotide is a siRNA and the siRNA is coupled to a lipoprotein of the nanoparticle.

Embodiment 19

A pharmaceutical composition comprising the nanoparticles of any of embodiments 16-18 and a pharmaceutically acceptable excipient.

Embodiment 20

A method for treating a disease or disorder in a subject in need thereof, the method comprising administering to the subject the pharmaceutical composition of embodiment 14, 15, or 19.

Embodiment 21

The method of embodiment 20, wherein the disease or disorder is a cell proliferative disease or disorder such as cancer.

Embodiment 22

A method of inhibiting the growth of a cancer cell or killing a cancer cell, the method comprising introducing or expressing the polynucleotide of any of embodiments 1-10 or a ssRNA portion thereof in the cancer cell.

Embodiment 23

A method of inhibiting the growth of a cancer cell or killing a cancer cell, the method comprising introducing the expression vector of any of embodiments 11-13 in the cancer cell.

Embodiment 24

A method of inhibiting the growth of a cancer cell or killing a cancer cell, the method comprising introducing the nanoparticles of any of embodiments 16-18 into the cancer cell.

EXAMPLES

The following Examples are illustrative and are not intended to limit the scope of the claimed subject matter.

Example 1—Many si/shRNAs can Kill Cancer Cells by Targeting Multiple Survival Genes Through an Off-Target Mechanism Reference is made to Putzback et al., Elife. 2017 Oct. 24; 6, 1-43, the content and supplemental content of which are incorporated herein by reference in their entireties Abstract Over 80% of multiple tested siRNAs and shRNAs targeting CD95 or CD95 ligand (CD95L) induce a form of cell death characterized by simultaneous activation of multiple cell death pathways preferentially killing transformed and cancer stem cells. We now show these si/shRNAs kill cancer cells through canonical RNAi by targeting the 3'UTR of critical survival genes in a unique form of off-target effect we call DISE (death induced by survival gene elimination). Drosha and Dicer deficient cells, devoid of most miRNAs, are hypersensitive to DISE, suggesting cellular miRNAs protect cells from this form of cell death. By testing 4666 shRNAs derived from the CD95 and CD95L mRNA sequences and an unrelated control gene, Venus, we have identified many toxic sequences—most of them located in the open reading frame of CD95L. We propose that using specific toxic RNAi-active seed sequences present in the genome can kill cancer cells.

Introduction

One of the most popular methods utilized to reduce gene expression in cells is RNA interference (RNAi). RNAi has been used in several studies to identify genes critical for the survival of human cancer cell lines (Cowley et al., 2014; Hadji et al., 2014; Hart, Brown, Sircoulomb, Rottapel, & Moffat, 2014; Morgens, Deans, Li, & Bassik, 2016; Wang et al., 2015). During RNAi, gene expression is inhibited by small interfering (si)RNAs, small hairpin (sh)RNAs or micro (mi)RNAs. miRNAs are generated as primary transcripts in the nucleus where they undergo processing to pre-miRNAs by the Drosha-DGCR8 complex before being exported to the cytosol by exportin 5 (Ha & Kim, 2014; Krol, Loedige, & Filipowicz, 2010). Once in the cytosol, pre-miRNAs and shRNAs are cleaved by Dicer, a type III RNase that functions in complex with the TAR RNA binding protein (TRBP), generating 21-23 nucleotide long fragments of double-stranded RNA (dsRNA) that have two nucleotide 3' overhangs (Zamore, Tuschl, Sharp, & Bartel, 2000). dsRNA fragments or chemically synthesized double stranded siRNAs are loaded into the RNA-induced silencing complex (RISC) as single stranded RNAs (the guide RNA) (Siomi & Siomi, 2009). A near-perfect complementarity between the guide strand of the si/miRNA and the target mRNA sequence results in cleavage of the mRNA (Pratt & MacRae, 2009). Incomplete complementarity results in inhibition of protein translation and contributes to mRNA degradation (Guo, Ingolia, Weissman, & Bartel, 2010). mRNA targeting is mostly determined by the seed sequence, positions 2-7/8 of the guide strand, which is fully complementary to the seed match in the 3'UTR of targeted mRNAs. Similar to miRNAs, although not fully explored, siRNAs and shRNAs also target multiple mRNAs besides the mRNAs they were designed to silence—a phenomenon commonly referred to as off-target effect (OTE)—that is generally sought to be avoided (Birmingham et al., 2006; Jackson et al., 2006; Lin et al., 2005).

The death receptor CD95 (Fas/APO-1) mediates induction of apoptosis when bound by its cognate CD95L, most prominently in the context of the immune system (Krammer, 2000). However, more recently, it has become apparent that the CD95/CD95L system has multiple tumor-promoting activities (Peter et al., 2007). CD95 signaling promotes cell growth (Chen et al., 2010), increases motility and invasiveness of cancer cells (Barnhart et al., 2004; Kleber et al., 2008), and promotes cancer stemness (Ceppi et al., 2014; Drachsler et al., 2016; Qadir et al., 2017). In fact, we reported tumors barely grew in vivo when the CD95 gene was deleted (Chen et al., 2010; Hadji et al., 2014). Therefore, it appeared consistent that multiple shRNAs and siRNAs targeting either CD95 or CD95L slowed down cancer cell growth (Chen et al., 2010) and engaged a distinct form of cell death characterized by the activation of multiple cell death pathways (Hadji et al., 2014). This unique form of cell death cannot be inhibited by conventional cell death or signaling pathway inhibitors or by knockdown of any single gene in the human genome (Hadji et al., 2014); it preferentially affects transformed cells (Hadji et al., 2014) including cancer stem cells (Ceppi et al., 2014). Here we report that loading of CD95 and CD95L derived sequences (si/shRNAs targeting CD95 or CD95L) into the RISC elicits a distinct form of cell death that results from the targeting of multiple survival genes in a unique form of OTE.

Results si/shRNAs Kill Cells in the Absence of the Targeted Site.

More than 80% of multiple tested shRNAs or siRNAs designed to target either CD95 or CD95L were toxic to multiple cancer cells (Hadji et al., 2014). We have now extended this analysis to Dicer substrate 27mer DsiRNAs designed to target CD95L. (D. H. Kim et al., 2005)). The tested DsiRNAs included Dsi13.x, DsiL3, Dsi-13.2, Dsi-13.3, Dsi-13.9, and a control non-targeting DsiRNA called Dsi-NC1. All five DsiRNAs displayed toxicity when introduced into HeyA8 cells at 5 nM reinforcing our previous observation that the majority of CD95 and CD95L targeting si/shRNAs are toxic to cancer cells (data not shown). We also analyzed a data set of a genome-wide analysis of 216 cells infected with a pooled library of the TRC shRNAs (Cowley et al., 2014). Most of the shRNAs we have tested were found to be depleted in the infected cell lines included in this study. The following shRNAs were found to be depleted in the listed percentage of the 216 cell lines tested: shL4 (99.5%), shL1 (96.8%), shR6 (88.9%), shR7 (75%), shL2 (67.1%), shR5 (38.4%, shL5 (26.4%), and shR8 (21.3%). Consistent with our data, shL1 and shR6 were found to be two of the most toxic shRNAs. Again in this independent analysis, the majority of tested shRNAs (67%) targeting either CD95 or CD95L killed more than half of all tested cancer cell lines.

Interestingly, a more recent RNAi screen did not report toxicity after expressing shRNAs against CD95 or CD95L (Morgens et al., 2016). The authors of this study used a second-generation shRNA platform based on a miR-30 backbone. To determine the source of the discrepancy in the data, we generated miR-30 based Tet-inducible versions of some of our most toxic shRNAs (shL1 (GCATCATCTTTG-GAGAAGCAA) (SEQ ID NO: 1), shL3

(ACTGGGCTGTACTTTGTATAT) (SEQ ID NO:2), shL4 (GCAGTGTTCAATCTTACCAGT) (SEQ ID NO:3), shR5 (GTTGCTAGATTATCGTCCAAA) (SEQ ID NO:4), shR6 (GTGCAGATGTAAACCAAACTT) (SEQ ID NO:5), and shR7 (CCTGAAACAGTGGCAATAAAT) (SEQ ID NO:6) and found none of them to be highly toxic to HeyA8 cells (data not shown). To determine their knockdown efficiency, we induced their expression in cells carrying sensor plasmids in which the fluorophore Venus was linked to either the CD95L or CD95 open reading frame (ORF). Expression of most of these miR-30-based shRNAs also did not efficiently silence Venus expression. In contrast, two of our most toxic shRNAs shL3 and shR6 when expressed in the Tet inducible pTIP vector not only killed HeyA8 cells, but also very efficiently suppressed Venus fluorescence in cells expressing the targeted Venus sensor. (FIG. 8). These data suggest that the levels of shRNAs produced from the miR-30 based vector may not be sufficient to be toxic to the cancer cells. Because expression levels of shRNAs are difficult to titer, we used siRNAs to determine the concentration of the toxic CD95L-derived siL3 required to kill HeyA8 cells (FIG. 9). Growth was effectively blocked (and cells died, data not shown) when siL3 was transfected at 1 nM—a concentration well below the commonly used and recommended siRNA concentration of 5-50 nM)—but not at 0.1 nM. These data suggest this form of toxicity does not require high amounts of si- or shRNAs; however, that the low expression we achieved from the miR-30 based shRNA vectors was not enough to effectively induce the toxicity. Because these miR-30 based shRNA vectors were developed to reduce off-target effects, the toxicity of CD95 and CD95L targeting si/shRNAs described by us and others could be due to an OTE. While this was a plausible explanation, the high percentage of toxic si/shRNAs derived from CD95 and CD95L seemed to exclude a standard OTE and pointed at a survival activity of CD95 and CD95L.

Figure 1:
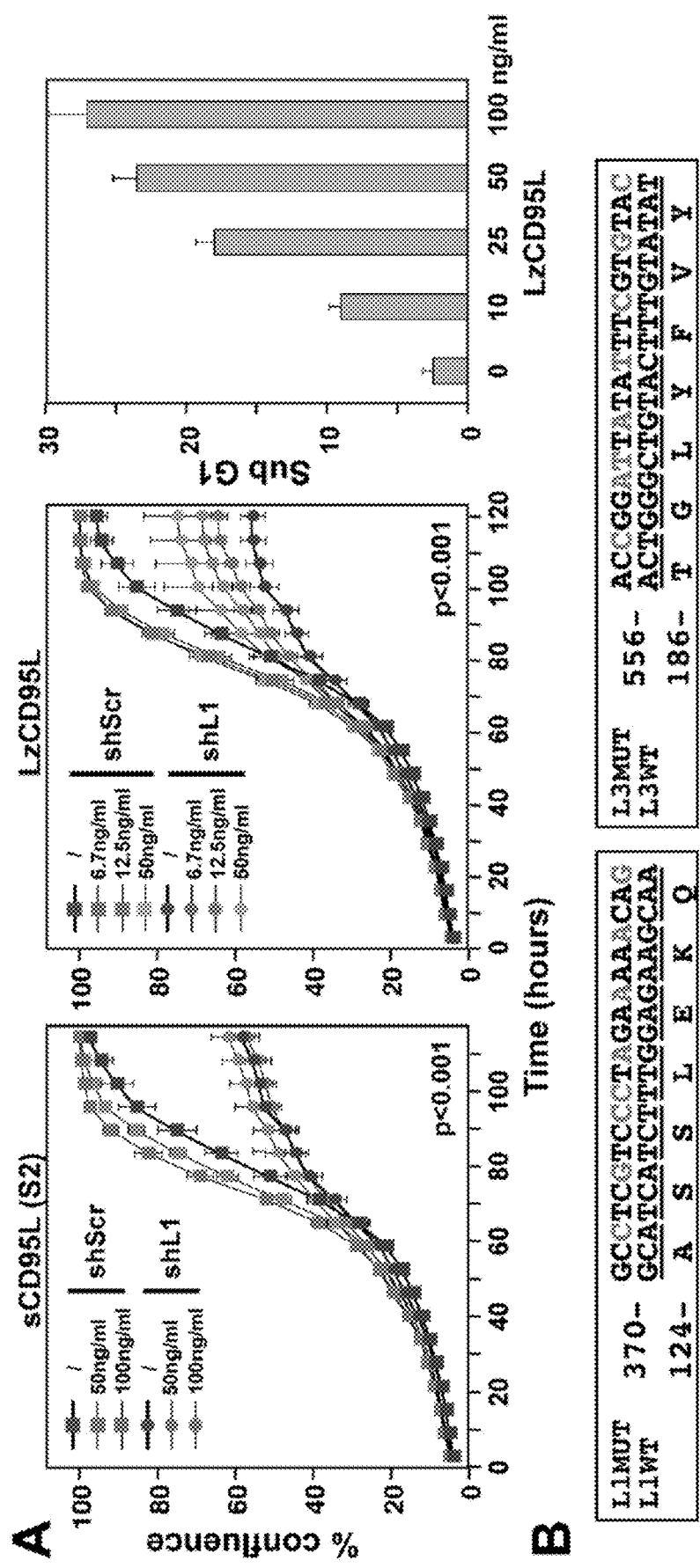
FIGS. 1. (A, B, C, D, E, F, and G). Exogenous CD95L or CD95 proteins do not protect cells from toxicity of CD95L/CD95 derived shRNAs. (A) Left: Percent cell confluence over time of NB7 cells after infection with either pLKO-shScr or pLKO-shL1 and concurrent treatment with different concentrations of soluble CD95L protein (S2). Two-way ANOVA was performed for pairwise comparisons of % confluence over time between shScr expressing cells untreated or treated with 100 ng/ml S2. Each data point represents mean±SE of three replicates. Center: Percent cell confluence over time of NB7 cells after infection with either pLKO-shScr or pLKO-shL1 and concurrent treatment with different concentrations of leucine zipper tagged (Lz) CD95L protein. Two-way ANOVA was performed for pairwise comparisons of % confluence over time between shScr expressing cells untreated or treated with 50 ng/ml LzCD95L. Each data point represents mean±SE of three replicates. Right: Percent nuclear PI staining of MCF-7 cells 24 hours after adding different amounts of LzCD95L. (B) Schematic of the eight silent mutations introduced to the shL1 and the shL3 target sites of CD95L. (Sequence Listing: GCATCATCTTTGGAGAAGCAA (SEQ ID NO:1); GCCTCGTCCCTAGAAAACAG (SEQ ID NO:47); ASSLEKQ (SEQ ID NO:145); ACTGGGCTGTAC-TTTGTATAT (SEQ ID NO:49); ACCGGATTATAT-TTCGTGTAC (SEQ ID NO:148); TGLYFVY (SEQ ID NO:146)). (C) Western blot analysis of CD95L and β-actin in NB7 cells over-expressing CD95L-WT, CD95L-L1MUT, or CD95L-L3MUT 3 days after infection with pLKO-shScr, pLKO-shL1, or pLKO-shL3. Shown is one of two repeats of this analysis. (D) Percent nuclear PI staining of NB7 cells expressing empty pLenti vector, CD95L-WT, CD95L-L1MUT, or CD95L-L3MUT 6 days after infection with either pLKO-shScr, pLKO-shL1, or pLKO-shL3. Each bar represents mean±SD of three replicates. (E) Schematic of the 8 silent mutations introduced at the shR6 site of CD95. (Sequence Listing: GTGCAGATGTAAACCAAACTT (SEQ ID NO: 149); ATGTCGCTGCAAGCCCAATTT (SEQ ID NO:8); CRCKPNF (SEQ ID NO:150)). (F) Western blot analysis of CD95 and β-actin in MCF-7 cells over-expressing CD95-WT or CD95-R6MUT. (G) Percent nuclear PI staining of MCF-7 cells expressing empty pLNCX2 vector, CD95-WT, or CD95-R6MUT 6 days after infection with pLKO-shScr, pLKO-shR6, or pLKO-shR7. Each bar represents mean±SD of three replicates.
Figure 1:
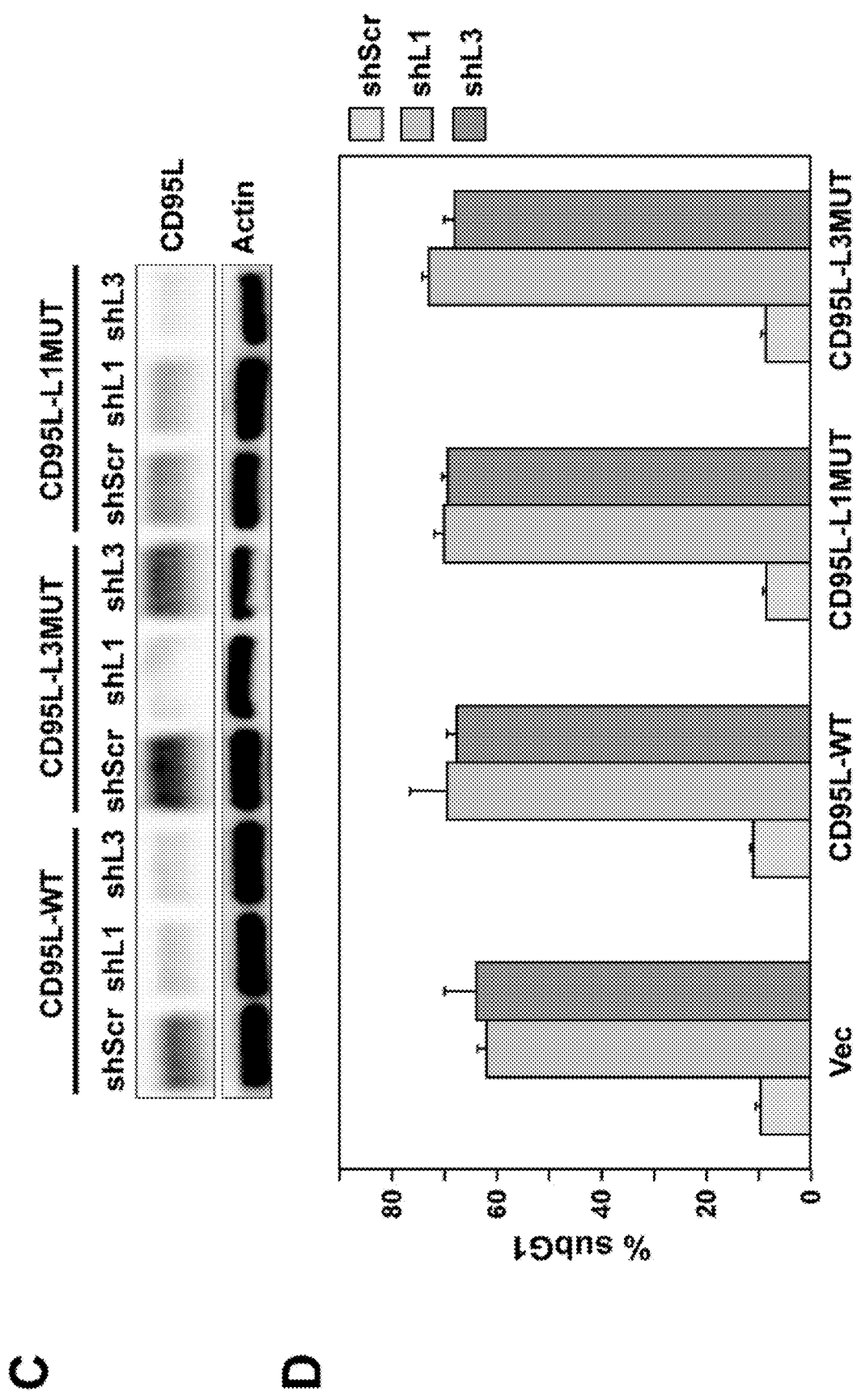
Figure 1:
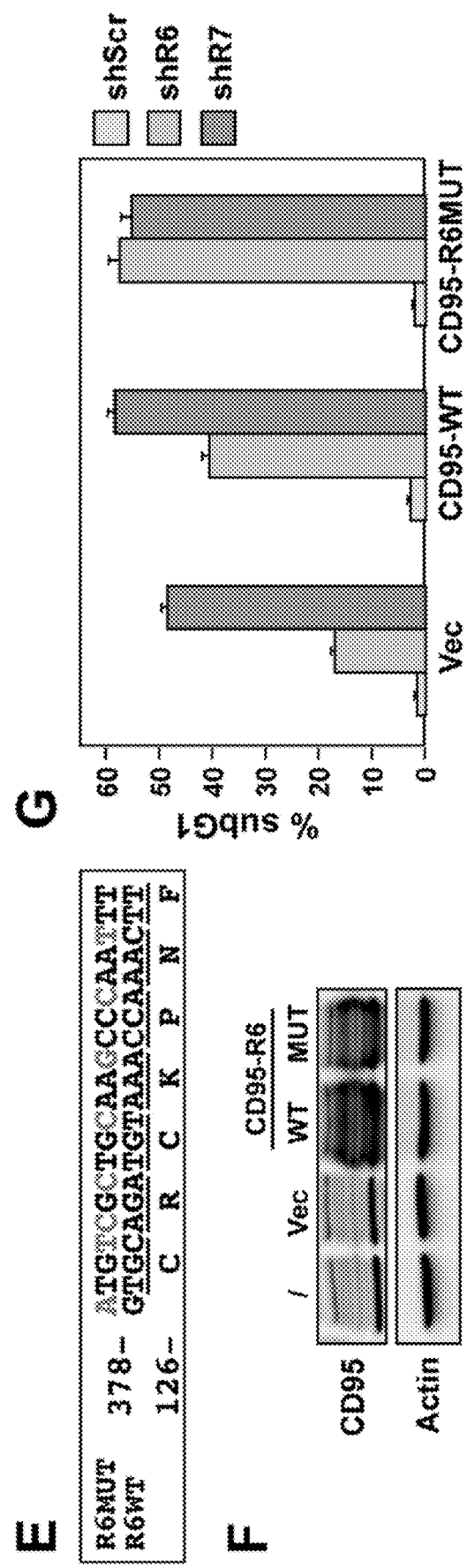

We therefore tested whether exogenously added recombinant CD95L protein could protect cells from the toxicity of CD95L-derived shRNAs. When NB7 cells were incubated with different concentrations of a soluble form of CD95L (S2), toxicity exerted by shL1 was not affected (FIG. 1A, left panel). NB7 neuroblastoma cells were chosen for these experiments because they lack expression of caspase-8 (Teitz et al., 2000) and hence are completely resistant to the apoptosis inducing effects of CD95L. An ostensible moderate and dose-dependent protection was detected when cells were treated with a highly active leucine-zipper tagged CD95L (LzCD95L) (FIG. 1A, center panel). However, this effect is likely due to the growth-promoting activities of soluble CD95L, which also significantly affected the growth of the cells expressing a scrambled control shRNA (seen for both S2 and LzCD95L). The recombinant LzCD95L protein was active, as demonstrated by its apoptosis-inducing capacity in CD95 apoptosis sensitive MCF-7 cells (FIG. 1A, right panel).

To test whether CD95L or CD95 proteins could protect cancer cells from death, we introduced silent mutations into the targeted sites of three very toxic shRNAs: shL1 and shL3 (both targeting CD95L) and shR6 (targeting CD95). We first introduced eight silent mutations into the sites targeted by either shL1 or shL3 (FIG. 1B) and expressed these proteins in NB7 cells (FIG. 1C). Both mutant constructs were highly resistant to knockdown by their cognate shRNA but still sensitive to knockdown by the other targeting shRNA (FIG. 1D). Overexpression of these shRNA-resistant versions of the CD95L ORF did not protect the cells from shL1 or shL3, respectively (FIG. 1D). Interestingly, expression of full length CD95L slowed down the growth of the NB7 cells right after infection with the lentivirus despite the absence of caspase-8 (data not shown). Infection with shRNAs was therefore performed 9 days after introducing CD95L when the cells had recovered and expressed significant CD95L protein levels (FIG. 1C). We then mutated the CD95 mRNA in the targeted site of shR6 (FIG. 1E). Neither expression of wild-type (wt) nor mutated (MUT) CD95 in MCF-7 cells (FIG. 1F) reduced the toxicity when cells were infected with the pLKO-shR6 or another toxic lentiviral shRNA, pLKO-shR7 (FIG. 1G). These data suggested that neither exogenously added recombinant CD95L or exogenously expressed CD95L or CD95 protein can protect cells from toxic shRNAs derived from these genes.

Figure 2:
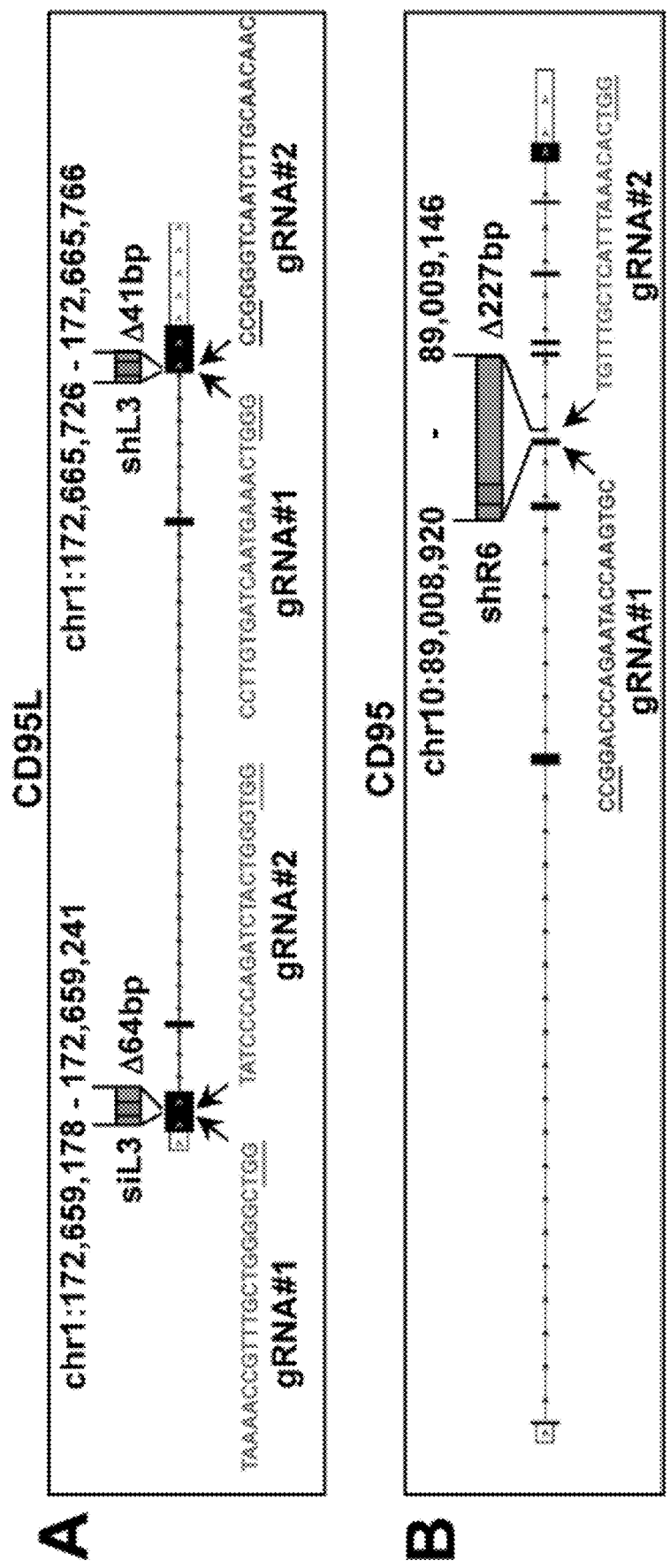
FIGS. 2. (A, B, C, D, E, F, G, H, and I) CD95 and CD95L derived si/shRNAs kill cells in the absence of the targeted sites in CD95 or CD95L. (A) Schematic of the genomic locations and sequences of the gRNAs used to excise the siL3 (Δ64 bp) and shL3 (Δ41 bp) target sites from CD95L. PAM site is underlined. (B) Schematic showing the genomic locations and sequences of the gRNAs used to excise the shR6 (Δ227 bp) target site. (C) PCR with flanking (top panels) and internal (bottom panels) primers used to confirm the Δ41 deletion in the shL3 site in one of the three homozygous deletion 293T clones generated. Cells transfected with Cas9 only (Cas9) are wild-type. (D) Quantitative PCR for endogenous CD95L with a primer downstream of the Δ41 shL3 deletion and another primer internal to the deleted region. nd, not detectable. Each bar represents mean±SD of three replicates. (E) PCR with flanking (top row) and internal (bottom row) primers used to confirm the presence of the shL3 Δ41 (top panel), siL3 Δ64 (middle panel), and shR6 Δ227 (bottom panel) deletions in HeyA8 clones. Mix, HeyA8 cells after transfection with Cas9 and gRNAs but before single cell cloning. (F) Quantitative PCR for CD95 in HeyA8 cells transfected with Cas9 plasmid (Cas9) alone, or the HeyA8 ΔshR6 clone #11. RNA was extracted 5 days after infection with pLKO-shScr, pLKO-shR6, pLKO-shR2, or pLKO-shR6' (targeting the 3'UTR). Each bar represents mean±SD of three replicates. (G) Percent cell confluence over time of 293T cells (left) and a pool of three 293T clones with a homozygous deletion of the shL3 target site (right) infected with pTIP-shScr or pTIP-shL3 and treatment with or without Dox. Data are representative of two independent experiments. Each data point represents mean±SE of six replicates. (H) Left: Percent confluence over time of HeyA8 cells infected with pLKO-shScr, pLKO-shR6, or pLKO-shL3. Center: Percent confluence over time of a HeyA8 clone with a homozygous deletion of the shR6 target site infected with either pLKO-shScr or pLKO-shR6. Right: Percent confluence over time of a pool of three HeyA8 clones with a homozygous deletion of the shL3 site infected with either pLKO-shScr or pLKO-shL3. Data are representative of two independent experiments. Each data point represents mean±SE of three replicates. (I) Percent confluence over time of a pool of three HeyA8 clones harboring a homozygous deletion of the siRNA siL3 target site after transfection with different concentrations of siScr or siL3. Data are representative of three independent experiments. Each data point represents mean±SE of three replicates. (Sequence Listing.
Figure 2:
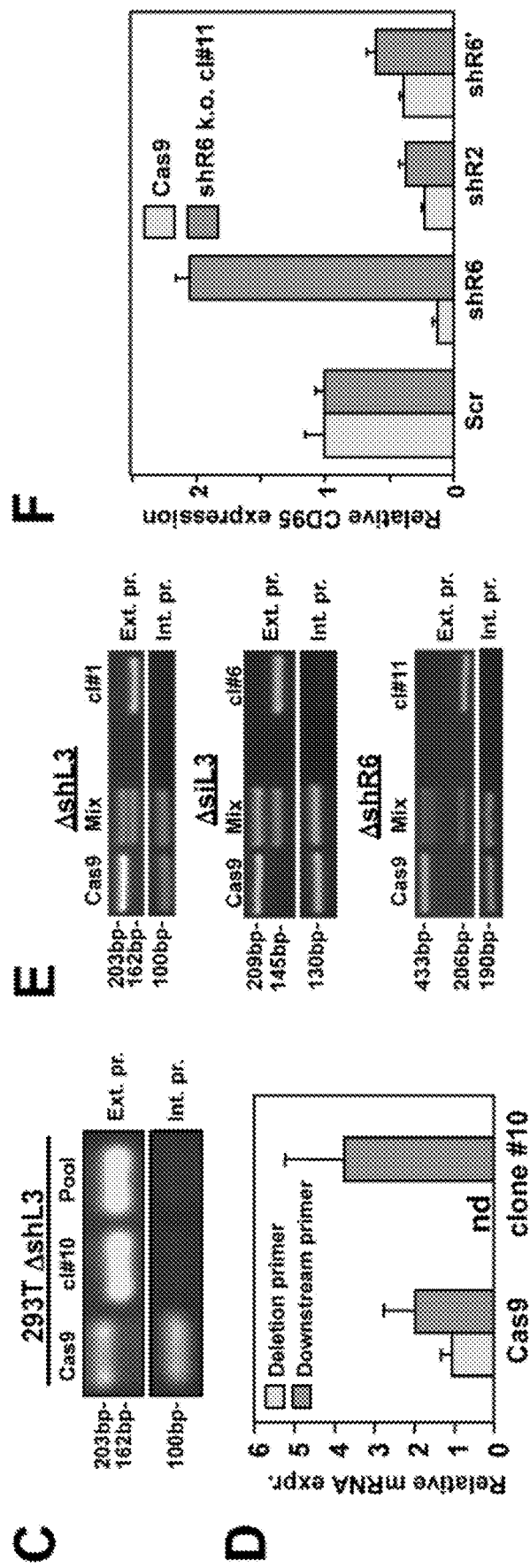
Figure 2:
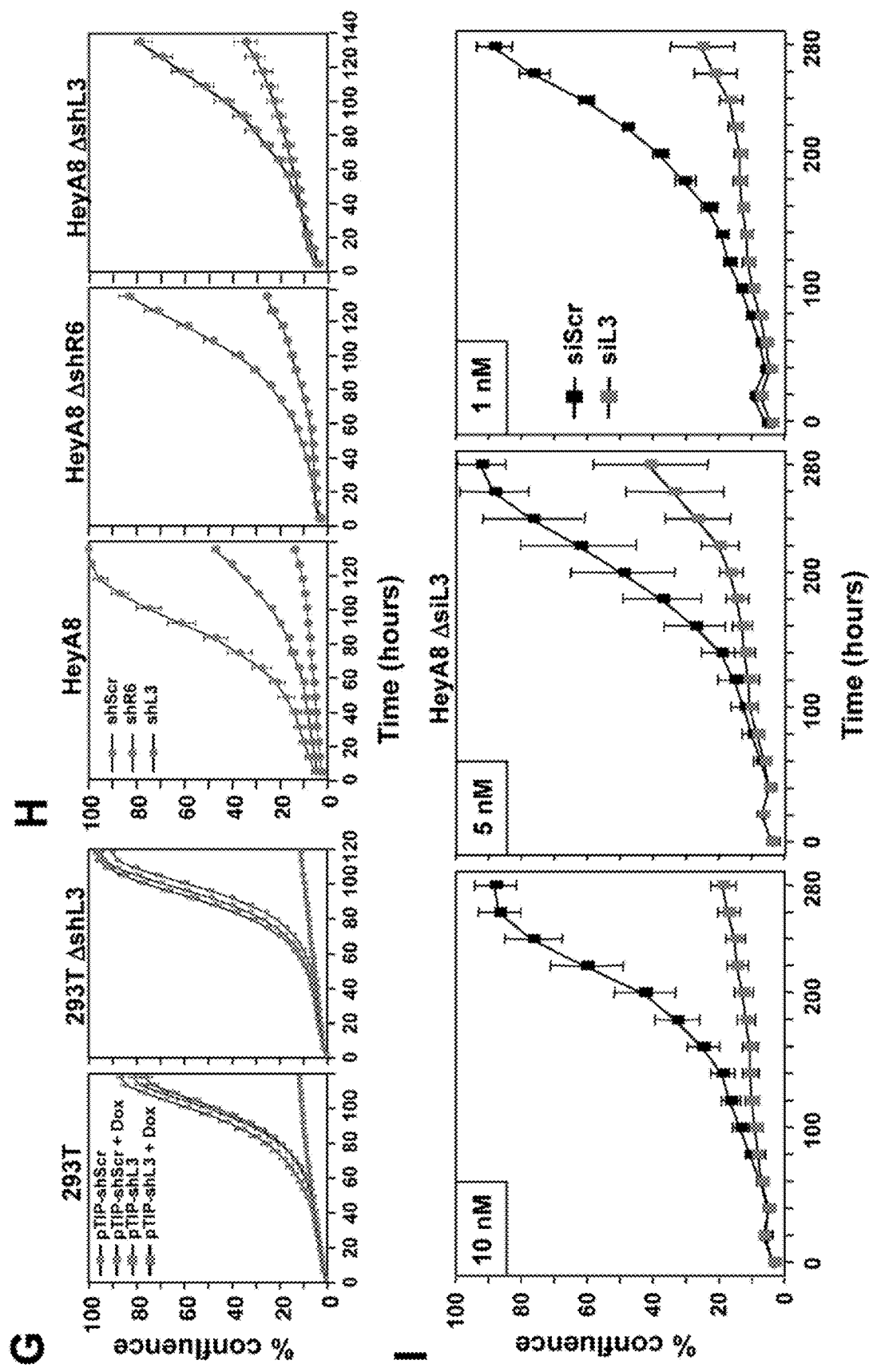

To determine whether we could prevent cancer cells from dying by this form of cell death by deleting the endogenous targeted sites, we used CRISPR/Cas9 gene-editing to excise sites targeted by different shRNAs and siRNAs in both alleles of the CD95 and CD95L genes. We first deleted a 41 nt piece of the CD95L gene in 293T cells, that contained the target site for shL3 (FIG. 2A, 2C). While internal primers could not detect CD95L mRNA in three tested clones, primers outside of the deleted area did detect CD95L mRNA (FIG. 2D, and data not shown). Three clones with this shL3 Δ41 deletion were pooled and tested for toxicity by shL3 expressed from a Tet-inducible plasmid (pTIP-shL3). Compared to a pool of control cells transfected only with the Cas9 plasmid, the 293T shL3 Δ41 cells were equally sensitive to the toxic shRNA (FIG. 2G). This was also observed when the clones were tested individually (data not shown).

To exclude the possibility that shL3 was inducing cell death due to a unique activity of shL3 and/or 293T cells, we deleted the same 41 nt in CD95L in the ovarian cancer cell line HeyA8; We also generated HeyA8 clones in which we either removed a 64 nt region containing the target site for the siRNA siL3 in the CD95L coding sequence or a 227 nt region containing the target site for shR6 in CD95 (FIG. 2A, 2B). In all cases, homozygous deletions were generated (FIG. 2E). To confirm the deletion of the shR6 target site, we infected HeyA8 cells treated with the Cas9 plasmid only and HeyA8 with a homozygous deletion of the shR6 site with shR6 and, as positive controls, with shR2 (targeting the CD95 ORF) and shR6' (targeting the CD95 3'UTR). Five days after infection, CD95 mRNA was quantified by real time PCR using a primer located outside the 227 bp deletion (FIG. 2F). The mutated CD95 mRNA was still detectable in the shR6 Δ227 cells. While shR2 and shR6' (both targeting outside the deleted region) caused knockdown of CD95 mRNA in both the Cas9 expressing control and the shR6 Δ227 cells, shR6 could only reduce mRNA expression in the Cas9 control cells. These data document that HeyA8 CD95 shR6 Δ227 cells no longer harbor the sequence targeted by shR6.

Now having HeyA8 cells lacking one of three RNAi-targeted sites in either CD95 or CD95L, we could test the role of the CD95 and CD95L gene products in protecting HeyA8 cells from the death induced by either shRNA (shL3 and shR6, two different vectors: pLKO or the Tet inducible pTIP) or the siRNA siL3. In all cases, the shRNA or siRNA that targeted the deleted region was still fully toxic to the target-site deleted cells (FIGS. 2H and 2I). We saw efficient growth reduction and cell death in siL3 site deleted cells transfected with as little as 1 nM siL3 (FIG. 2I, and data not shown). These data firmly establish that cells were not dying due to the knockdown of either CD95 or CD95L.

Involvement of Canonical RNAi.

shRNAs and early generation naked siRNAs showed general toxicity when introduced in large amounts, presumably by eliciting an interferon (IFN) response (Marques & Williams, 2005) or by saturating the RISC (Grimm et al., 2006). However, both chemically modified siRNAs at very low concentrations and lentiviral shRNAs at an MOI<1 were still toxic (data not shown). We therefore decided to test whether the observed toxicity involved canonical RNAi and activity of the RISC. To test shRNAs or siRNAs targeting CD95L, we introduced the Venus-CD95L sensor (inset in FIG. 3A, right panel) into HeyA8 CD95 protein k.o. cells we had generated in the process of deleting the shR6 site. Clone #2 was used for the following studies. While doublestranded (ds)-siL3 effectively silenced Venus expression and induced toxicity, neither the sense nor the antisense singlestranded (ss)RNAs significantly decreased Venus expression or induced toxicity (FIG. 3A). In addition, no activity was found when ds-siL3, synthesized as deoxyribo-oligonucleotides, was transfected into the cells (FIG. 3B). Using this type of analysis, we tested a number of modified siRNAs for RNAi activity and toxicity. For siRNAs to be fully active they require 3' overhangs on both strands (Bernstein, Caudy, Hammond, & Hannon, 2001). Converting siL3 to a bluntended duplex resulted in substantial loss of RNAi activity and toxicity (FIG. 3C). Due to the topology of the RISC, siRNA activity is decreased by modification of the 5' end of the antisense/guide strand (Chiu & Rana, 2003). To test whether cell death induced by siL3 would be affected by a bulky modification, we placed a Cy5 moiety at any of the four possible ends of the siL3 duplex. Only when the siL3 duplex carried a 5' modification in the guide strand did it prevent RNAi activity and toxicity; modifications in the three other positions had no effect (FIG. 3C). This was confirmed for another siRNA, siL2. To test whether the toxicity of siL3 required association with a macromolecular complex, which would be consistent with RISC involvement, we performed a competition experiment. HeyA8 cells were transfected with 10 nM of siL3, and a mutated nontoxic oligonucleotide, siL3MUT, was titered in (FIG. 3D). siL3MUT reduced the growth inhibitory activity of siL3 in a dose-dependent fashion suggesting that siL3 and siL3MUT compete for the same binding site in the cells, pointing at involvement of the RISC.

To determine involvement of RNAi pathway components in the toxicity of CD95 and CD95L-derived sequences, we tested HCT116 cells deficient for either Drosha or Dicer (Y. K. Kim, Kim, & Kim, 2016). Growth of parental HCT116 cells was impaired after infection with shL3 or shR6 viruses (FIG. 3E, left panel). Consistent with the requirement of Dicer to process shRNAs, Dicer$^{-/-}$ cells were completely resistant to the toxic shRNAs (FIG. 3E, center panel). This was also supported by the inability of shR6 to silence CD95 protein expression in these cells (FIG. 3F). Dicer$^{-/-}$ cells were not resistant to toxic siRNAs as these cells died when transfected with siL3, which is consistent with mature siRNAs not needing further processing by Dicer (FIG. 3G, center panel). Interestingly, Drosha$^{-/-}$ cells were hypersensitive to the two toxic shRNAs (FIG. 3E, right panel, p<0.0001, according to a polynomial fitting model), and shR6 efficiently knocked down CD95 expression in Drosha$^{-/-}$ cells (FIG. 3F). Both Drosha$^{-/-}$ and Dicer$^{-/-}$ cells were much more susceptible to the toxicity induced by siL3 than parental cells (FIG. 3G, center and right panel, p<0.0001, according to a polynomial fitting model). The hypersensitivity of the Drosha$^{-/-}$ cells to toxic si/shRNAs and of Dicer$^{-/-}$ cells to toxic siRNAs can be explained by Drosha$^{-/-}$ and Dicer$^{-/-}$ cells allowing much more efficient uptake of mature toxic RNAi-active species into the RISC because they are almost completely devoid of competing endogenous miRNAs (Y. K. Kim et al., 2016).

To determine the contribution of the siRNA seed sequence to their toxicity, we generated a set of chimeric siRNAs in which we systematically replaced nucleotides of the toxic siL3 siRNA with nucleotides of a nontoxic scrambled siRNA. We did this starting either from the seed end or from the opposite end (FIG. 3H). HeyA8 cells expressing both the Venus-CD95L sensor (to monitor level of knockdown) and a Nuc-Red plasmid to fluorescently label nuclei (to monitor the effects on cell growth) were transfected with 5 nM of the chimeric siRNAs; total green fluorescence and the number of red fluorescent nuclei were quantified over time. The siL3 control transfected cells showed an almost complete suppression of the green fluorescence and high toxicity. In the top panel of FIG. 3H, the data are summarized in which siL3 nucleotides were stepwise replaced with siScr nucleotides from the seed sequence end. Both RNAi and toxicity were profoundly reduced when three of the terminal siL3 nucleotides were replaced with the siScr nucleotides in those positions, suggesting the seed region (6mer highlighted) is critical for both activities. Consistently, as shown in the bottom panel of FIG. 3H, when siL3 nucleotides were replaced with siScr nucleotides from the non-seed end, neither RNAi nor the toxicity was diminished until replacements affected residues in the seed region. These data suggest the 6mer seed sequence of siL3 was critical for both RNAi activity and its toxicity.

Toxic si/shRNAs Cause Downregulation of Survival Genes.

A general OTE by RNAi has been reported (Birmingham et al., 2006; Jackson et al., 2006; Lin et al., 2005). However, this was been found to cause toxicity in most cases, and the targeted mRNAs were difficult to predict (Birmingham et al., 2006). The fact that 22 of the tested CD95 and CD95L-targeting sh- and si/DsiRNAs were toxic to many cancer cells evoking similar morphological and biological responses (Hadji et al., 2014) generated a conundrum: Could an OTE trigger a specific biology? To test this, we expressed two toxic shRNAs—one targeting CD95L (shL3) and one targeting CD95 (shR6)—in cells lacking their respective target sequences and subjected the RNA isolated from these cells to an RNA-Seq analysis. In order to detect effects that were independent of cell type, delivery method of the shRNA, or targeted gene, we expressed shL3 in 293T (ΔshL3) cells using the Tet-inducible vector pTIP and shR6 in HeyA8 (ΔshR6) cells using the pLKO vector. In each case, changes in RNA abundance were compared to cells in which expressing a non-targeting shRNA in matching vectors. Total RNA was harvested in all cases at either the 50-hour time point (before the onset of cell death) or at the 100-hour time point (during cell death) (FIG. 4A). To achieve high stringency, the data were then analyzed in two ways: first, using a conventional alignment-based analysis to identify genes for which the mRNA changed more than 1.5-fold (and an adjusted p-value of less than 0.05) and second, by a read-based method, in which we first identified all reads that changed >1.5-fold and then subjected each read to a BLAST search to identify the gene it was derived from. Only RNAs that were detected by both methods were considered. The combination of the analyses resulted in one mRNA that was upregulated (ATP13A3) and 11 mRNAs that were downregulated (GNB1, FUBP1, NAA50, SNRPE, CAPZA1, NUCKS1, CCT3, FSTL1, PRELID3B, and HIST1HIC) (FIG. 4B). Using an arrayed qPCR approach, most of these detected mRNA changes were validated for both cell lines (data not shown). Interestingly, for nine of the eleven genes, published data suggest they are either highly upregulated in cancer and/or critical for the survival of cancer cells, as their inhibition or knockdown resulted in either growth reduction or induction of various forms of cell death (Blomen et al., 2015; Wang et al., 2015)).

The following describes the 11 genes that were significantly downregulated after introducing the toxic shRNAs shL3 or shR6 into cancer cells and some of their cancer relevant activities:

1) CAPZA1 (capping actin protein of muscle Z-line alpha subunit 1) is an actin capping protein. CAPZA1 knockdown has been reported to cause disassembly of autophagosomes (Mi et al., 2015). It is overexpressed in malignant melanoma (Sun et al., 2011).

2) CCT3 (chaperonin containing TCP1 subunit 3) is part of a chaperone complex that folds various proteins including actin and tubulin. CCT3 is required for proper mitotic progression (Zhang et al., 2016).

3) FSTL1 (follistatin-like 1) is a putative activin-binding protein. Knockdown of FSTL1 in lung cancer cells resulted in mitotic arrest followed by apoptosis promoted by the activation of caspase-3 and -9 (Bae et al., 2016). FSTL1 is downregulated during cellular senescence of human mesenchymal stem cells (Yoo, Choi, & Kim, 2013).

4) FUBP1 (far upstream element binding protein 1). A lack of FUBP1 causes a cell-autonomous defect in the maintenance of fetal and adult hematopoietic stem cells (HSCs). FUBP1-deficient adult HSCs exhibit significant transcriptional changes, including upregulation of the cell-cycle inhibitor p21 and the pro-apoptotic Noxa molecule, suggesting they undergo apoptosis (Rabenhorst et al., 2015). In addition, FUBP1 binds to an upstream element of the c-myc promoter and regulates c-myc mRNA level, thus regulating proliferation (Jang et al., 2009). Finally, FUBP1 is upregulated in many tumors and acts as an oncoprotein by stimulating proliferation and inhibiting apoptosis (Baumgarten et al., 2014).

5) GNB 1 (G-protein beta submit 1) is tumor-promoting in breast cancer. Data suggest that GNB1 plays an important role in the mTOR-related anti-apoptosis pathway (Wazir, Jiang, Sharma, & Mokbel, 2013).

6) HIST1H1C. A specific role of this particular histone in cancer cell survival has not yet been described. (Knockdown causes cell cycle arrest in MCF-7 cells; (http://journals.plos.org/plosgenetics/article?id=10.1371%2Fjournal.pgen.1000227)).

7) NAA50 (N(alpha)-acetyltransferase 50, NatE catalytic subunit) is required for sister chromatid separation in vivo (Hou, Chu, Kong, Yokomori, & Zou, 2007).

8) NUCKS1 (nuclear casein kinase and cyclin dependent kinase substrate 1) is a chromatin-associated protein with a role in the DNA damage response. Knocking down NUCKS1 causes chromosomal breaks (Parplys et al., 2015).

9) PRELID3B (PRELI domain containing 3B) is an inner mitochondrial protein. Knocking down PRELID3B decreases cell viability (http://www.genecards.org/cgi-bin/carddisp.pl?gene=PRELID3B).

10) SNRPE (small nuclear ribonucleoprotein polypeptide E). siRNA-mediated depletion of SNRPE stimulated autophagy and led to a marked reduction of cell viability in breast, lung, and melanoma cancer cell lines, whereas it had little effect on the survival of the nonmalignant MCF-10A breast epithelial cells (Quidville et al., 2013).

11) TFRC (transferrin receptor). Blocking TFRC function with a neutralizing antibody inhibits cell proliferation and survival (Pham et al., 2014). Suppression of TFRC led to apoptosis of renal cells (Gui et al., 2013) and cell cycle arrest in esophageal squamous cell carcinoma cells (Chan et al., 2014).

Significantly, six of these eleven downregulated genes were recently identified in two independent genome-wide RNAi lethality screens to be critical for cancer cell survival (Blomen et al., 2015; Wang et al., 2015) (FIG. 4B). Considering these two screens only identified 6.6% of human genes to be critical for cell survival, we found a significant enrichment (54.5%, p-value=$3\times10^{-6}$ according to binomial distribution) of these survival genes among the genes downregulated during the cell death induced by either shL3 or shR6. All six survival genes are either highly amplified or mutated in human cancers. In addition to these six genes, GNB 1 and HIST1HIC were reported to be required fitness genes in a recent high-resolution CRISPR-based screen (Hart et al., 2015). A kinetic analysis showed most of the deregulated mRNAs were downregulated early with a significant effect already at 14 hours, more than two days before the onset of cell death (data not shown). This suggested the cells were dying because of the silencing of multiple critical survival genes, providing an explanation for why multiple cell death pathways were activated. We therefore call this type of cell death DISE (for Death Induced by Survival gene Elimination).

To confirm some of the downregulated genes were also critical survival genes for HeyA8 cells, we transfected HeyA8 cells with siRNA SmartPools targeting each of the eleven genes. Individual knockdown of seven of the targeted genes resulted in reduced cell growth when compared to cells transfected with a pool of scrambled siRNAs (data not shown). To mimic the effect of the CD95 and CD95L-derived shRNAs, we treated HeyA8 cells with a combination of siRNA pools targeting these seven genes. Remarkably, 1 nM of this siRNA mixture (35.7 pM of each individual siRNA) was sufficient to effectively reduce growth of the cells (FIG. 10) and also cause substantial cell death (FIG. 11), suggesting it is possible to kill cancer cells with very small amounts of siRNAs targeting a network of these survival genes.

To test the generality of this phenomenon, we inducibly expressed another CD95L derived shRNA, shL1, in 293T cells using the pTIP vector, and transfected HeyA8 cells with 25 nM siL3. We subjected the cells to RNA-Seq analysis 100 hours and 48 hours after addition of Dox or after transfection, respectively. To determine whether survival genes were downregulated in all cases of sh/siRNA induced cell death, we used a list of 1883 survival genes and 423 genes not required for survival (nonsurvival genes) recently identified in a CRISPR lethality screen. We subjected the four ranked RNA-Seq data sets to a gene set enrichment analysis using the two gene sets (data not shown). In all cases, survival genes were significantly enriched towards the top of the ranked lists (most downregulated). In contrast, nonsurvival genes were not enriched. One interesting feature of DISE that emerged was the substantial loss of histones. Of the 16 genes that were significantly downregulated in cells treated with any of the four sh/siRNAs, 12 were histones (FIG. 4C). While it might be expected that dying cells would downregulate highly expressed genes such as histones, we believe that losing histones is a specific aspect of DISE because a detailed analysis revealed the downregulated histones were not the most highly expressed genes in these cells (data not shown).

In addition, almost as many genes with similarly high expression were found to be upregulated in cells after DISE induction.

A Metascape analysis revealed genes involved in mitotic cell cycle, DNA conformation change, and macromolecular complex assembly were among the most significantly downregulated across all cells in which DISE was induced by any of the four sh/siRNAs (data not shown). These GO clusters are consistent with DISE being a form of mitotic catastrophe with cells unable to survive cell division (Hadji et al., 2014) and suggest a general degradation of macromolecular complexes.

Toxic si/shRNAs Target Survival Genes in their 3'UTR.

To test whether the toxic shRNAs directly targeted genes through canonical RNAi, we subjected the two gene lists obtained from the RNA-Seq analysis (the cell lines treated with either shL3 or shR6 at the 50 hour time point) to a Sylamer analysis (van Dongen, Abreu-Goodger, & Enright, 2008) designed to find an enrichment of miRNA/siRNA targeted sites in the 3'UTR of a list of genes ranked according to fold downregulation (data not shown). This analysis identified a strong enrichment of the cognate seed match for shL3 and shR6 in cells treated with either of these two shRNAs. The analyses with cells treated with shRNAs for 100 hours looked similar but less significant, suggesting early targeting by the shRNAs followed by secondary events (data not shown). Enrichment in 6mers and 8mers were both detected (only 8mers shown) in the 3'UTRs but not the ORF of the ranked genes (data not shown).

Interestingly, the seed matches detected by the Sylamer analysis were shifted by one nucleotide from the expected seed match based on the 21mer coded by the lentivirus. RNA-Seq analysis performed for the small RNA fraction confirmed in all cases (shScr and shL3 in pTIP, and shScr and shR6 in pLKO), the shRNAs in the cells were cleaved in a way resulting in the predominant formation of an siRNA shifted one nucleotide away from the shRNA loop region (black arrow heads in FIG. 12). This allowed us to design toxic mature siRNAs based on the sequences of shL3 and shR6. These shRNA-to-siRNA converts were toxic to HeyA8 cells (data not shown) confirming that the observed toxicity was not limited to the TRC shRNA platform, but based on a sequence-specific activity of the si/shRNAs.

The generalizability of the Sylamer results for shL3 and shR6 was tested with cells treated with either shL1 or siL3. In both cases, when the ranked RNA Seq data were subjected to a Sylamer analysis, the seed matches of the si/shRNA introduced were again significantly enriched in the 3'UTR of downregulated RNAs (data not shown). In none of the Sylamer analyses of the four data sets, did we see enrichment of seed matches in the 3'UTRs of downregulated RNAs that matched the passenger strand. In all cases, the only significantly enriched sequences matched the seed sequences in the guide strand of the si/shRNAs we introduced.

Our data suggested that DISE inducing si/shRNAs caused an early loss of survival genes, and at the same time downregulated RNAs through canonical RNAi targeting their 3'UTR. However, it was not clear whether the most highly downregulated survival genes were targeted in their 3'UTR by RNAi-active sequences. We determined as little as 6 nucleotides dictated whether an siRNA killed cancer cells (see FIG. 3H). 10 of the 11 targeted genes identified in the RNA-Seq analysis described in FIGS. 4A and 4B contained multiple 6mer seed matches for either shL3 and/or shR6 (FIG. 5, Top). It is therefore likely the two shRNAs, shL3 and shR6, killed cells by targeting a network of genes enriched in critical survival genes through RNAi. The only gene without an shL3 or shR6 seed match was HIST1H1C. Interestingly, only four of the histones downregulated in cells after treatment with any of the four tested sh/siRNAs had a 3'UTR (underlined in FIG. 4C) suggesting that most histones were not directly targeted by the sh/siRNAs.

Using multiplex qPCR, we tested whether other toxic shRNAs targeting either CD95 or CD95L also caused downregulation of some of the 11 genes silenced by shL3 and shR6. HeyA8 cells were transfected with the toxic siRNA siL3 (RNA harvested at 80 hours) or the toxic shRNAs shL1, shL3 or shR7 (RNA harvested at 100 hrs.). While shL1 did not have much of an effect on the expression of these genes, shR7 caused downregulation of 7 (CCT3, FUBP1, HIST1H1C, NAA50, NUCKS1, PRELID3B, SNRPE) of 11 of the same genes targeted by shL3 even though the 6mer seed matches of the two shRNAs are very different (CTTTGT for shL3 and GGAGGA for shR7).

To determine whether preferential targeting of survival genes was responsible for the death of the cells, we tested whether there was an association between the presence or absence of a predicted seed match in the 3'UTR for the si/shRNA introduced and whether a gene would be downregulated (>1.5 fold downregulated, p<0.05) among survival genes using the Fisher's Exact test (FIG. 5, Bottom). In almost all cases, this analysis revealed that survival genes containing a predicted seed match in their 3'UTR were statistically more likely to be downregulated than survival genes without such a motif. The analysis with shL1 treated cells did not reach statistical significance, likely due to the fact that this shRNA was found to be very toxic and the 100 hour time point may have been too late to observe evidence of significant targeting. This interpretation is supported by the observation that the significance for both shL3 and shR6 to target survival genes was higher at 50 hours when compared to the 100 hour time points (FIG. 5, Bottom) and that the Sylamer analysis of the shL1 treated cells was less significant after 100 hours of treatment than any of the other Sylamer analyses (data not shown).

Now that we had established that the toxicity of the studied shRNAs involved targeting of survival genes rather than CD95 or CD95L we had to assume that when studying a larger set of shRNAs that the level of knockdown of the targeted genes and the toxicity were not strictly correlated. This was confirmed for the TRC shRNAs targeting the ORF or 3'UTR of CD95 in CD95 high expressing HeyA8 cells (data not shown). While some of the toxic shRNAs efficiently silenced CD95 (i.e. shR6 and shR2) others did not (i.e. shR5). In summary, our analyses suggest that cells die by DISE due to an early and selective silencing of survival genes through targeting seed matches in their 3'UTR followed by the downregulation of histones.

Identification of Toxic shRNAs in the CD95L and CD95 mRNAs.

The majority of commercially available si- Dsi-, and shRNAs targeting either CD95 or CD95L were highly toxic to cancer cells. We therefore asked whether these two genes contained additional sequences with similar activity. To test all shRNAs derived from either CD95L or CD95, we synthesized all possible shRNAs, 21 nucleotides long, present in the ORF or the 3'UTR of either CD95L or CD95 starting with the first 21 nucleotides after the start codon, and then shifting the sequence by one nucleotide along the entire ORF and 3'UTR (FIG. 6A). We also included shRNAs from a gene not expressed in mammalian cells and not expected to contain toxic sequences, Venus. All 4666 oligonucleotides (700 Venus, 825 CD95L ORF, 837 CD95L 3'UTR, 987

CD95 ORF, and 1317 CD95 3'UTR shRNAs) were cloned into the Tet-inducible pTIP vector (FIG. 6B) as five individual pools. We first tested the activity of each individual pool to be toxic and to target the Venus sensor protein (fused to either the ORF of CD95 or CD95L). NB7 cells were again used because of their resistance to the Venus-CD95L sensor which was found to be slightly toxic to CD95 apoptosis competent cells. NB7-Venus-CD95L cells infected with the Venus-targeting shRNA pool showed some reduction in fluorescence when Dox was added, however, the shRNA pool derived from the CD95L ORF was much more active in knocking down Venus (FIG. 13A). No significant green fluorescence reduction was detected in cells after infection with the shRNA pool derived from the CD95L 3'UTR since the targeted sequences were not part of the sensor. Similar results were obtained when NB7-Venus-CD95 cells were infected with the Venus, CD95 ORF, and CD95 3'UTR targeting shRNA pools. To determine their ability to reduce cell growth (as a surrogate marker for toxicity), we infected NB7 parental cells with each of the five pools (parental cells were used for this experiment to avoid a possible sponge effect by expressing either CD95L or CD95 sequences that were part of the Venus sensors). Interestingly, the pool of 700 shRNAs derived from Venus did not cause any toxicity (FIG. 13B). In contrast, the pool of the shRNAs derived from CD95L significantly slowed down growth, while no toxicity was observed when cells were infected with the pool of shRNAs derived from the CD95L 3'UTR. In the case of CD95, both the shRNAs derived from the ORF and the 3'UTR showed some toxicity. However, the shRNAs derived from the 3'UTR caused greater toxicity compared to those derived from the ORF. The data suggests that overall the shRNAs derived from the CD95L ORF and the CD95 3'UTR contain the most toxic sequences.

To determine the toxicity of each of the shRNAs in the pools, NB7 cells were infected with the libraries of shRNA viruses (MOI<1), and after puromycin selection cells were pooled 1:1:1 (Venus ORF/CD95L ORF/CD95L 3'UTR pools or Venus ORF/CD95 ORF/CD95 3'UTR pools) to allow for competition between shRNAs when Dox was added (FIG. 6B). Cells were cultured for 9 days with and without Dox to allow for cell death to occur. To identify depleted shRNAs, shRNA barcodes were detected through next generation sequencing of PCR products to determine the relative abundance of each shRNA in three pools: 1) the cloned plasmid libraries, 2) cells after infection and culture for 9 days without Dox, and 3) cells infected and cultured with Dox for 9 days. A total of 71,168,032 reads were detected containing a complete sequence of one of the cloned shRNAs. Virtually all shRNAs were substantially represented in the cloned plasmids (data not shown). The shRNAs in the CD95L pool (comprised of the Venus, CD95L ORF, and CD95L 3'UTR subpools) and the CD95 pool (comprised of the Venus, CD95 ORF, and CD95 3'UTR subpools) were ranked from highest (most toxic) to lowest underrepresentation. During this and subsequent analyses, we noticed in many cases, Dox addition did cause a reduction of shRNAs, indicating an increase in toxicity; however, in other instances, infection alone and without the addition of Dox was toxic. This effect was likely due to the well-described leakiness of the Tet-on system (Pham, Moretti, Goodall, & Pitson, 2008), which we confirmed for shR6 in NB7 cells (data not shown). To capture all toxic shRNAs, we therefore decided to split the analysis into two halves: 1) the changes in abundance after infection compared to the composition in the plasmid pool (infection −Dox) and 2) the changes in abundance after Dox addition compared to the infected −Dox cells (infection+ Dox). In subsequent analyses shRNAs underrepresented after infection are boxed (FIG. 6C) or otherwise shown (FIG. 6D, 7B, and data not shown) and the ones underrepresented after Dox addition are either boxed or otherwise shown. Grey dots represent all shRNAs and other illustrated dots represent only the ones that were significantly underrepresented at least 5-fold. Interestingly, the highest abundance of downregulated shRNAs was found in the CD95L ORF and the CD95 3'UTR pools of shRNAs, which is consistent with the increased toxicity observed when NB7 cells were infected with either of these two pools individually (see FIG. 13B). The shRNAs of these two toxic pools were highly enriched in the underrepresented shRNAs in the two pooled experiments (CD95L and CD95). Their toxicity was also evident when all shRNAs in each pool (2362 shRNAs in the CD95L and 3004 shRNAs in the CD95 pool) were ranked according to the highest fold downregulation (FIG. 6C). The three subpools in each experiment are shown separately. Thus, again this analysis identified the ORF of CD95L and the 3'UTR of CD95 as the subpool in each analysis with the highest enrichment of underrepresented shRNAs (FIG. 6C).

This analysis allowed us to describe the toxicity landscape of CD95L and CD95 ORFs and their 3'UTRs (FIG. 6D). All shRNAs significantly underrepresented at least five-fold are shown along the CD95L pool (FIG. 6D, left) and the CD95 pool (FIG. 6D, right) sequences. For both CD95L and CD95, toxic shRNAs localized into distinct clusters. The highest density of toxic sequences was found in the stretch of RNA that codes for the intracellular domain of CD95L (underlined in FIG. 6D).

Predicting shRNA Toxicity—the Toxicity Index (TI) and GC Content.

Our data suggest toxic shRNAs derived from either CD95L or CD95 kill cancer cells by targeting a network of genes critical for survival through canonical RNAi. Therefore, we wondered how many 8mer seed sequences derived from these toxic shRNAs would have corresponding seed matches in the 3'UTR of critical survival genes in the human genome. Would it be possible to predict with some certainty in an in silico analysis what shRNAs would be toxic to cells? To calculate such a hypothetical toxicity index, we used the ranked CRISPR data set (Wang et al., 2015) with 1883 survival genes (SGs) and 423 nonSGs. Based on our RNA-Seq analyses, we hypothesized the survival genes contained more putative seed matches for toxic shRNAs in their 3'UTRs than the nonsurvival genes (FIG. 7A, Top) and that the number of seed matches in the 3'UTRs of survival genes divided by the number of seed matches in the 3'UTR of nonsurvival genes would, to some extent, predict toxicity of an si/shRNA (FIG. 7A, Bottom).

To establish a Toxicity Index (TI) for each shRNA, we first gathered 3'UTR sequences for 1846 of the survival genes and 416 of the nonsurvival genes. We then generated a list containing a normalized ratio of occurrences of every possible 8mer seed match in the 3'UTRs of the survival and non-survival gene groups. This resulted in a ratio for each of the 65,536 possible 8mer combinations (data not shown), the TI. We then assigned to each of the 4666 shRNAs in our screen its TI, and ranked each pool within the two experiments of our screen according to the highest TI (stippled lines in FIG. 7B). We then further separated the shRNAs into two groups: those that were toxic just after infection and those toxic after addition of Dox (FIG. 7B, and data not shown). In each ranked list, we could now assess whether the experimentally determined toxicity of shRNAs correlated with the in silico predicted TI. Remarkably, the highest enrichment of toxic shRNAs was found amongst those with higher TI for the subpool of shRNAs targeting the CD95L ORF followed by shRNAs in the subpool targeting the CD95 3'UTR. To confirm the significance of this finding, we repeated the analysis 10,000 times by randomly assigning 8mers and their associated TIs to the two shRNA pools and again sorted the data from highest to lowest TI. The reported p-values were calculated based on these permutated datasets using Mann-Whitney U tests.

We noticed that survival genes tend to be more highly expressed than nonsurvival genes (data not shown). To address the question whether toxic si/shRNAs only target survival genes or all genes that are highly expressed, we recalculated the TI based on a set of 850 highly expressed and expression matched survival and nonsurvival genes (FIG. 14A). This alternative TI tracked slightly less well with the toxic shRNAs we identified, but the enrichment of toxic shRNAs towards the top of the list ranked according to the new TI was still statistically significant (FIG. 14B). This analysis demonstrates survival genes contain more seed matches for toxic shRNAs in their 3'UTR than nonsurvival genes regardless of the expression level. This suggests, to a certain extent, it is possible to predict the experimental toxicity of shRNAs based on the in silico calculated TI.

Our data suggest DISE results from a sequence-specific off-target activity that depends on the presence of certain seed matches in the 3'UTR of survival genes. Thus, DISE inducing RISC associated small RNAs behave in manner similar to miRNAs. This raised the question whether these seed matches have special properties. While we did not find a sequence motif that was present in all toxic si/shRNAs, we did find that sequence composition, specifically GC content, which has been reported to affect the specificity of shRNAs (Gu et al., 2014; Ui-Tei et al., 2004), correlated with the toxicity of shRNAs. When the GC content of the 6mer seed sequences of all underrepresented shRNAs detected in the shRNA screen across the CD95L ORF was plotted we found a significant correlation between the GC content and higher toxicity (indicated by underrepresentation) (FIGS. 7C and 7D). This correlation was even more pronounced when plotting GC content versus the 6mer toxicity index (FIG. 7E, and data not shown). While not an absolute requirement, higher GC content made shRNAs more toxic, consistent with reports demonstrating that shRNAs with high GC content in the seed region showed decreased on-target and increased off-target activity (Gu et al., 2014; Ui-Tei et al., 2004). In summary, our data suggest that si- and/or shRNAs with certain seed sequences are toxic to cancer cells by targeting critical survival genes through an RNAi mechanism independent of both Drosha and Dicer. Furthermore, the data suggest high miRNA content, presumably through competing for occupancy in the RISC, might render cells less sensitive to DISE.

Discussion

Most current uses of RNAi are aimed toward highly specific silencing with little OTE. In fact, OTEs represent one of the largest impediments to the use of RNAi in phenotypic screening applications. We now demonstrate DISE is a unique form of OTE that results in the simultaneous activation of multiple cell death pathways in cancer cells. The discovery that DISE involves loss of multiple survival genes now provides an explanation for the unique properties we described for this form of cell death, especially the observation that cancer cells have a hard time developing resistance to this cell death mechanism (Hadji et al., 2014; Murmann et al., 2017).

DISE Represents a Specific Form of RNAi OTE.

There are a number of rules that have been elucidated for designing si/shRNAs (Bramsen et al., 2009) to avoid undesired effects such as OTE (Petri & Meister, 2013), general toxicity due to the presence of toxic sequence motifs (Fedorov et al., 2006; Petri & Meister, 2013), poisoning/saturating of the RISC (Grimm et al., 2006), or evocation of an IFN response (Marques & Williams, 2005). The following arguments and evidence support our prediction that DISE is a manifestation of a novel, functionally important, conserved mechanism of genome regulation, and not the result of one of the above-mentioned effects:

1) The Sheer Number of Toxic shRNAs Embedded in CD95L or CD95.

A number of genome-wide shRNA and siRNA lethality screens have revealed that 2-5% of shRNAs targeting human genes are toxic to cells. We recently reported in 12 independent arrayed shRNA lethality screens the identification of 651 genes out of about 18,000 targeted genes that are critical for the survival of 8 different cancer cell lines (Hadji et al., 2014). Many of the genes targeted by these shRNAs were actually established survival genes (as discussed in (Hadji et al., 2014)). That means that the number of shRNAs that are toxic due to a possible OTE or general toxicity would be expected to be very small. In contrast, we found that >80% of the shRNAs and siRNAs that were designed to target either CD95 or CD95L exhibited toxicity in multiple cell lines. Consistent with our data analysis a parallel genome-scale loss of function screen confirmed that the majority of the tested shRNAs derived from either CD95L and CD95 were toxic to a majority of the tested 216 cell lines when used as a pooled library (Cowley et al., 2014). These also included a number of hematopoietic cell lines suggesting that the DISE effect is not limited to solid cancers. Interestingly, in this study the authors did not consider the data on most of the CD95L and CD95 targeting shRNAs to be significant as they received a low consistency score. A high consistency score predicts the observed phenotype (cell death or growth reduction in this case) is caused by knocking down the targeted gene (Shao et al., 2013). However, we have demonstrated here that the toxicity of an shRNA is solely dependent on its seed and the transcriptome of the treated cells. Therefore, the results of every shRNA should be considered individually as far as the DISE inducing effect is concerned.

2) High Concentrations of siRNAs can Saturate the RISC, Preventing the Access of Crucial Endogenous miRNAs (Khan et al., 2009).

We have demonstrated that, in general, 5 nM of CD95L-derived siRNAs are sufficient to kill cancer cells. We have even seen very efficient cell death with as little as 1 nM of siRNA (see FIG. 21 and FIG. 9). It is therefore unlikely we are poisoning the RISC. It has been reported that in siRNA overexpression experiments, changes in mRNA expression can be caused by blocked access of endogenous miRNAs to the RISC, such as the highly expressed miRNA family, let-7 (Khan et al., 2009). However, we can exclude such an effect in our analysis, as there was no significant enrichment (or depletion) of the let-7 seed match motif (or that of any other miRNA) in our analyses (data not shown).

3) No IFN Response was Observed.

We have performed multiple RNA-Seq and gene array analyses of cells in which DISE was induced by multiple si/shRNAs targeting CD95 or CD95L. In none of these analyses did we detect an increase in any of the known IFN response genes (Schoggins et al., 2011) (data not shown). In addition, we demonstrated the latest generation of Dicer optimized 27mer DsiRNAs that do not elicit an IFN response (D. H. Kim et al., 2005) and the shRNAs expressed from within the cells shown to have low IFN triggering activity (Robbins et al., 2006) have the same toxic activities as the standard 21mer siRNAs (data not shown).

4) Mutation of Just One Position Destroys Activity.

A major argument against DISE toxicity being caused by overloading the RISC, an IFN response or the presence of known toxic sequences, lies in the analysis of the chimeras we generated between siL3 and a non-toxic scrambled oligonucleotide (see FIG. 3H). This analysis demonstrated that the seed match positions of siL3 are critical for its toxicity. In fact, just replacing one nucleotide in a critical position in the center of the seed match almost completely abolished toxicity of the siRNA.

What are the Requirements for an si/shRNA to Induce DISE?

Our data provide strong evidence that the toxicity observed is a sequence-specific event caused by seed matches present in the targets of the toxic si/shRNAs rather than by a toxic motif enriched in all toxic si/shRNAs (i.e. the UGGC motif described before (Fedorov et al., 2006)). We did find a correlation between the toxicity of shRNAs (both predicted by the TI and experimentally determined in the shRNA screen) and the GC content in their seed region. While this correlation was significant, it was not a requirement as some of the most toxic si- and shRNAs had a low 8mer seed GC content (shL3, 25%; shR6, 25%; siL3, 37.5%). Our data suggests that survival genes may contain different types of seed matches (based on base composition or sequence) when compared to nonsurvival genes. Such a distinction has indeed been described before (Stark, Brennecke, Bushati, Russell, & Cohen, 2005). In a study in *Drosophila*, it was determined that survival genes are depleted of seed matches targeted by highly expressed miRNAs. These authors concluded that evolution must have selected against the presence of seed matches for highly expressed miRNAs in the 3'UTR of survival genes. It is therefore not surprising that a gene ontology (GO) analysis of all miRNA targets (the "targets") in this study described these genes as being involved in development and differentiation (Stark et al., 2005). In contrast, genes not targeted by miRNAs (the "antitargets") grouped in GO clusters that were consistent with cell survival (Stark et al., 2005). A similar phenomenon was also shown in mammalian cells; genes with fewer miRNA target sites, as predicted by Targetscan, contained distinct enriched GO terms from those enriched in genes with many predicted target sites. The genes with fewer sites were enriched in GO terms like ribosomal subunits and respiratory chain, whereas target-heavy genes were more enriched in regulatory-related GO terms (Zare, Khodursky, & Sartorelli, 2014). It is possible the DISE inducing si/shRNAs carry seed sequences that preferentially target seed matches present in the 3'UTRs of the "anti-targets". However, as our data on the miR-30 based shRNAs suggest, DISE-inducing shRNAs must be expressed at a certain level to be toxic.

DISE is Caused by Loading of the Guide Strand of Toxic si/shRNAs into the RISC.

Part of our data was generated using a widely used first generation stem loop shRNA platform, the TRC library. The TRC shRNAs have recently been found to be prone to cause OTE. Gu et al. showed that the loop design of this system results in imprecise Dicer cleavage and, consequently, the production of different mature small-RNA species that increase passenger loading, one major source of OTE (Gu et al., 2012). More recently it was reported that most guide RNAs derived from the TRC hairpin were shifted by 4 nt 3' of the expected 5' start site (Watanabe, Cuellar, & Haley, 2016). While we did see a shift in processing of these stem loop shRNAs, we did not see such a high level of imprecision in the cleavage of our toxic shRNAs. In fact, 99.4% of the shR6 guide RNAs started at the same nucleotide position (FIG. 12). The majority of the processing of both our pTIP and pLKO-based shRNAs was shifted by one nucleotide (FIG. 12). This shift was consistent with the defined seed matches that were detected in the Sylamer analyses. In general, one major seed match was detected with one other minor species (this was less obvious for shL1, data not shown). Furthermore, all four Sylamer analyses only detected enrichments in the 3'UTR of downregulated mRNAs that were consistent with only the guide strand targeting the mRNA and not the passenger strand. In all cases, including in cells transfected with the siRNA siL3, the primary enriched sequence motifs were either 7, or 8mers present in the 3'UTR of the targeted mRNAs.

DISE has Features of the RNAi OTE Previously Reported.

Our data on DISE are consistent with a number of properties of RNAi OTE that have previously been reported. Similar to DISE, OTE mediated silencing requires a 6/7nt seed sequence of complementarity (Birmingham et al., 2006; Jackson et al., 2006; Lin et al., 2005) and it targets mRNAs in the 3'UTR (Birmingham et al., 2006). Our data on shRNAs, siRNAs, and DsiRNAs suggest that DISE is not limited to one platform and requires sequence specific targeting. This conclusion is also consistent with a previous report that suggested that sequence-dependent off-target transcript regulation is independent of the delivery method (Jackson et al., 2006). The authors found the same enrichment of 6mers and 7mers in 3'UTRs of targeted mRNAs for siRNAs and shRNAs (Jackson et al., 2006).

The Role of Dicer in DISE.

We previously reported that Dicer$^{Exo5-/-}$ HCT116 cells (with deleted Exon 5) were at least as sensitive to induction of DISE (by either shL3 or shR6) than wt cells suggesting that Dicer deficient cells could be killed by DISE (Hadji et al., 2014). It is has been reported that these Dicer deficient cells are hypomorphs (Ting et al., 2008) and indeed, we detected low residual Dicer expression by Western blotting (Hadji et al., 2014). We have now revisited this issue with HCT116 cells rendered completely deficient for Dicer using CRISPR/Cas9 gene editing (Y. K. Kim et al., 2016). The fact that these Dicer$^{-/-}$ cells were now completely resistant to the toxic effects of shL3 or shR6 demonstrates the complete absence of Dicer protein and activity. Similar to the Drosha$^{-/-}$ cells, in the absence of mature miRNAs, which seem to attenuate DISE, Dicer$^{-/-}$ cells are hypersensitive to DISE induced by siRNAs.

Open Questions Regarding the Relevance of DISE.

We are proposing an entirely new concept of killing cancer cells that is based on the toxicity of CD95 and CD95L derived small RNAs. Naturally, there are many open questions:

1) Is DISE Part of an Anti-Cancer Mechanism?

We are proposing that DISE kills cancer cells in a way that they usually cannot escape from. We have not found a way to block cancer cells from dying by DISE. We provide strong evidence to suggest this is due to the simultaneous targeting of multiple survival genes that result in the activation of multiple cell death pathways. It will be difficult to prove cells are dying due to the preferential targeting of survival genes. It may never be possible to express multiple siRNA resistant survival genes at the same time at physiological levels to render cancer cells resistant to the action of countless small RNAs. This prediction alone makes DISE a promising new strategy to kill cancer cells.

2) Does CD95L Induce DISE In Vivo?

We recently found that overexpression of the CD95L ORF is toxic to cancer cells and that this kills cancer cells in a manner very similar to DISE induction (unpublished data). We and others have noticed upregulation of CD95L in multiple stress related conditions such as treatment with chemotherapy ((Friesen, Fulda, & Debatin, 1999) and data not shown). While the amount of CD95L RNA and the level of upregulation alone may not be enough to induce DISE, it could result from the combined expression of multiple RNAs that when generated kill cells by DISE. We view CD95L as just one of many RNAs that have this activity.

3) Are there Other Genes in the Human Genome Containing Toxic Seed Sequences?

We recently identified other genes in the genome that contain DISE inducing shRNAs (Patel & Peter, 2017). It is therefore possible that when cells are subjected to genotoxic or oncogenic stress that they generate numerous small RNAs that can be taken up by the RISC and in combination execute DISE. Hence, our analysis of CD95/CD95L will likely be applicable to other genes.

A Model for why DISE Preferentially Kills Cancer Cells.

We interpret the hypersensitivity of both Drosha$^{-/-}$ and Dicer$^{-/-}$ cells to DISE in the following way: Most of the small RNAs in the cells that are loaded into the RISC are miRNAs. Using AGO pull-down experiments we determined 98.4% of AGO associated RNAs in HCT116 cells to be miRNAs (99.3% in HeyA8 cells, data not shown). It was recently reported that Drosha$^{-/-}$ cells showed a reduction of miRNA content from roughly 70-80% to 5-6%, and Dicer$^{-/-}$ cells showed a reduction down to 14-21% (Y. K. Kim et al., 2016). Since neither Drosha$^{-/-}$ nor Dicer$^{-/-}$ cells express reduced AGO2 protein levels (see subset FIG. 3E), it is reasonable to assume that their RISC can take up many more of the toxic DISE inducing RNAs than the RISC in wt cells explaining the super toxicity of both DISE inducing si/shRNAs and CD95L mRNAs in these cells.

We previously showed expression of either shL3 and shR6 induced DISE in immortalized normal ovarian fibroblasts much more efficiently than in matching nonimmortalized cells (Hadji et al., 2014), suggesting that this form of cell death preferentially affects transformed cells. Our data now provide an interesting model to explain the higher sensitivity of cancer cells to DISE when compared to normal cells. It is well documented that cancer cells in general have global downregulation of miRNAs when compared to normal tissues (Lu et al., 2005). This might free up the RISC for DISE inducing RNAs and would imply that miRNAs may protect normal cells from DISE.

Overall our data allow us to predict that any small RNA with DISE inducing RNAi activity that does not require Dicer processing can kill cancer cells regardless of Dicer or Drosha status. In fact, in an accompanying manuscript we demonstrate that DISE can be triggered in vivo to treat ovarian cancer in mouse xenografts by delivering CD95L-derived siRNAs using nanoparticles (Murmann et al., 2017). No toxicity was observed in the treated mice. These data suggest that it might be possible to develop a novel form of cancer therapy based on the DISE OTE mechanism Materials and Methods Reagents and Antibodies.

Primary antibodies for Western blot: anti-β-actin antibody (Santa Cruz #sc-47778, RRID:AB_626632), anti-human CD95L (BD Biosciences #556387, RRID:AB_396402), and anti-human CD95 (Santa Cruz #sc-715, RRID: AB_2100386), anti-human AGO2 (Abcam #AB186733, RRID:AB_2713978), anti-human Drosha (Cell Signaling #3364, RRID:AB_10828827), and anti-Dicer (Cell Signaling #3363, RRID:AB_2093073). Secondary antibodies for Western blot: Goat anti-rabbit; IgG-HRP (Southern Biotech #SB-4030-05, RRID:AB_2687483 and Cell Signaling #7074, RRID:AB_2099233) and Goat anti-mouse; IgG1-HRP; (Southern BioTech #1070-05, RRID:AB_2650509). Conjugated antibody isotype control for CD95 surface staining were FITC-mouse anti-human CD95 (BD Biosciences #556640, RRID:AB_396506) and FITC-mouse IgG1, K isotype control (BD Biosciences #551954, RRID: AB_394297). Recombinant soluble S2 CD95L and leucine-zipper tagged (Lz)CD95L were described before (Algeciras-Schimnich et al., 2003). Reagents used: propidium iodide (Sigma-Aldrich #P4864), puromycin (Sigma-Aldrich #P9620), G418 (Affymetrix #11379), zVAD-fmk (Sigma-Aldrich #V116, used at 20 μM), doxycycline (Dox) (Sigma-Aldrich #9891), Lipofectamine 2000 (ThermoFisher Scientific #11668027), and Lipofectamine RNAiMAX (ThermoFisher Scientific #13778150).

Cell lines. The ovarian cancer cell line HeyA8 (RRID: CVCL_8878), the neuroblastoma cell line NB7 (RRID: CVCL_8824), and the breast cancer cell line MCF-7 (RRID: CVCL_0031) were grown in RPMI 1640 medium (Cellgro #10-040-CM), 10% heat-inactivated FBS (Sigma-Aldrich), 1% L-glutamine (Mediatech Inc), and 1% penicillin/streptomycin (Mediatech Inc). The human embryonic kidney cell line 293T (RRID:CVCL_0063) and Phoenix AMPHO (RRID:CVCL_H716) cells were cultured in DMEM (Cellgro #10-013-CM), 10% heat-inactivated FBS, 1% L-Glutamine, and 1% penicillin/streptomycin.

HCT116 Drosha$^{-/-}$ and Dicer$^{-/-}$ cells were generated by Narry Kim (Y. K. Kim et al., 2016). HCT116 parental (cat #HC19023, RRID:CVCL_0291), a Drosha$^{-/-}$ clone (clone #40, cat #HC19020) and two Dicer clones (clone #43, cat #HC19023 and clone #45, cat #HC19024) were purchased from Korean Collection for Type Cultures (KCTC). All HCT116 cells were cultured in McCoy's medium (ATCC, cat #30-2007), 10% heat-inactivated FBS, 1% L-Glutamine, and 1% penicillin/streptomycin. All cell lines were authenticated using STR profiling and tested monthly for mycoplasm using PlasmoTest (Invitrogen).

All lentiviruses were generated in 293T cells using pCMV-dR8.9 and pMD.G packaging plasmids. Retroviruses were generated in Phoenix AMPHO cells using the VSVg packaging plasmid.

NB7 cells overexpressing wild type and mutant CD95L cDNAs used in FIGS. 1C and D were generated by infecting cells seeded at 50,000 to 100,000 cells per well on a 6-well plate with empty pLenti, pLenti-CD95L-WT, pLenti-CD95L-L1MUT, and pLenti-CD95L-L3MUT (described below) with 8 μg/ml polybrene. Selection was done with 3 μg/ml puromycin for at least 48 hours.

MCF-7 cells overexpressing CD95 cDNAs used in FIG. 1F were generated by seeding cells at 50,000 per well in a 6-well plate followed by infection with pLNCX2-CD95 or pLNCX2-CD95R6MUT (described below) in the presence of 8 μg/ml polybrene. Selection was done with 200 μg/ml G418 48 hours after infection for 2 weeks.

The HeyA8 cells used in FIG. 3D carried a lentiviral Venus-siL3 sensor vector (Murmann et al., 2017) and were infected with NucLight Red lentivirus (Essen Bioscience #4476) with 8 μg/ml polybrene and selected with 3 μg/ml puromycin and sorted for high Venus expression 48 hours later. HeyA8 ΔshR6 clone #2 sensor cells used in FIG. 3A to 3C were infected with lentiviruses generated from the Venus-CD95L sensor vector (described below) to overexpress the Venus-CD95L chimeric transcript. Cells were sorted for high Venus expression 48 hours later. NB7 cells over-expressing either the Venus-CD95L sensor or the Venus-CD95 sensor (described below) used in FIG. 13A were similarly generated.

Plasmids and Constructs.

The Venus-CD95L ORF and Venus-CD95 ORF (full length) sensor vectors were created by sub-cloning the Venus-CD95L or the Venus-CD95 inserts (synthesized as a minigene by IDT with flanking XbaI RE site on the 5' end and EcoRI RE site at the 3' end in the pIDTblue vector), which are composed of the Venus ORF followed by either the CD95L ORF (accession number NM_000639.2) or the CD95 ORF (accession number BC012479.1) as an artificial 3'UTR (both lacking the A in the start codon), respectively, into the modified CD510B vector (Ceppi et al., 2014) using XbaI and EcoRI. Ligation was done with T4 DNA ligase.

The pLNCX2-CD95R6MUT vector was synthesized by replacing a 403 bp fragment of the CD95 ORF insert from the pLNCX2-CD95-WT vector (Hadji et al., 2014) with a corresponding 403 bp fragment that had 8 silent mutation substitutions at the shR6 site (5'-GTGTCGCTGTAAAC-CAAACTT (SEQ ID NO:7)→5'-ATGTCGCTGCAAGCC-CAATTT-3' (SEQ ID NO:8)) using BstXI (NEB #R0113) and BamHI (NEB #R3136) restriction enzymes (mutant insert was synthesized in a pIDTblue vector with 5' end BstXI site and 3' end BamHI RE site).

Dox-inducible vectors expressing shRNAs were constructed by subcloning an annealed double-stranded DNA insert containing the sequence encoding the shRNA hairpin (sense strand: 5'-TGGCTTTATATATCTCCCTATCAGT-GATAGAGATCGNNNNNNNNNNNNNNNNN NNNC-TCGAGnnnnnnnnnnnnnnnnnnnnnTTTTTGTACCGAG-CTCGGATCCACTAGTCCA GTGTGGGCATGCTG-CGTTGACATTGATT-3' (SEQ ID NO:9)) into the pTIP-shR6 vector (Hadji et al., 2014). BsaBI (NEB #R0537) and SphI-HF (NEB #R3182) were used to digest both the pTIP-shR6 vector (to excise the shR6 insert) and the double-stranded shRNA DNA cassette insert followed by ligation with T4 DNA ligase. The template oligos were purchased from IDT. The poly-N represents the two 21 bp sequences that transcribe for the sense (N) and antisense (n) shRNA.

miR-30 based shRNAs were generated by The Gene Editing & Screening Core, at Memorial Sloan Kettering, N.Y., by converting the 21mers expressed in the pLKO and pTIP vectors into 22mers followed by cloning into the Dox-inducible LT3REPIR vector as described (Dow et al., 2012). A vector expressing an shRNA against *Renilla* luciferase was used as control (Dow et al., 2012).

Crispr Deletions.

We identified two gRNAs that target upstream and downstream of the site to be deleted. These gRNAs were expected to result in the deletion of a DNA piece just large enough to remove the target site. The CRISPR gRNA scaffold gene blocks were from IDT and consisted of the DNA sequence 5'-TGTACAAAAAAGCAGGCTTTAAAGGAACCAAT-TCAGTCGACTGGATCCGGTA CCAAGGTCGGGCAG-GAAGAGGGCCTATTTCCCATGATTCCTTCATATTTG-CATAT ACGATACAAGGCTGTTAGAGAGATAATTA-GAATTAATTTGACTGTAAACACAAA GATATTAGTA-CAAAATACGTGACGTAGAAAGTAATAATTTCTTGG-GTAGTTTGCA GTTTTAAAATTATGTTTTAAAATGGA-CTATCATATGCTTACCGTAACTTGAAAGTA TTTC-GATTTCTTGGCTTTATATATCTTGTGGAAAGGACG-AAACACCGNNNNNNNN NNNNNNNNNNNNGTTT-TAGAGCTAGAAATAGCAAGTTAAAATAAGGCTAG-TCCGT TATCAACTTGAAAAAGTGGCACCGAG-TCGGTGCTTTTTTTCTAGACCCAGCTTTCT TGTA-CAAAGTTGGCATTA-3' (SEQ ID NO:10) (Mali et al., 2013); The poly-NNNNNNNNNNNNNNNNNNN represents the 19nt target sequence. The two 19nt target sequences for excision of the shL3 site (Δ41 deletion) were 5'-CCTTGTGATCAATGAAACT-3' (SEQ NO: 11) (gRNA #1) and 5'-GTTGTTGCAAGATTGACCC-3' (SEQ ID NO:12) (gRNA #2). The two target sequences for the Δ227 deletion of the shR6 site were 5'-GCACTTGGTAT-TCTGGGTC-3' (SEQ ID NO:13) and 5'-TGTTTGCTCAT-TTAAACAC-3' (SEQ ID NO:14). The two target sequences for Δ64 deletion of the siL3 site were 5'-TAAAACCGTTTGCTGGGGC-3' (SEQ ID NO:15) and 5'-TATCCCCAGATCTACTGGG-3' (SEQ ID NO: 16). Target sequences were identified using the CRISPR gRNA algorithm found at http://crispr.mit.edu/; only gRNAs with scores over 50 were used. These 6 gene blocks were subcloned into the pSC-B-amp/kan plasmid using the Strata-Clone Blunt PCR Cloning kit (Agilent Technologies #240207).

The target sites of siL3, shL3, and shR6 were homozygously deleted from target cells by co-transfecting Cas9 plasmid with each corresponding pair of pSC-B-gRNA plasmids. Briefly, 400,000 cells were seeded per well on a 6-well plate the day prior to transfection. Each well was transfected with 940 ng of Cas9-GFP plasmid (pMJ920) (Jinek et al., 2013) and 450 ng of each pSC-B-gRNA plasmid using Lipofectamine 2000. Media was replaced next day. One to two days later, cells were sorted for the top 50% population with the highest green fluorescence. Those cells were cultured for an additional week to let them recover. The cells were then sorted by FACS (BD FACSAria SORP system) directly into 96-well plates containing a 1:1 ratio of fresh media:conditioned media for single cell cloning. Approximately two to three weeks later, single cell clones were expanded and subjected to genotyping. PCR using both a primer pair that flanked the region to be deleted and another pair containing one flanking primer and one internal primer was used to screen clones for homozygous deletion. For detection of the Δ41 deletion of the shL3 site, the flanking external primers were 5'-TCTGGAATGGGAA-GACACCT-3' (SEQ ID NO:17) (Fr primer) and 5'-CCTC-CATCATCACCAGATCC-3' (SEQ ID NO:18) (Rev primer), and the internal Rev primer was 5'-ATATA-CAAAGTACAGCCCAGT-3' (SEQ ID NO:19). For detection of the Δ227 deletion of the shR6 site, the flanking external primers were 5'-GGTGTCATGCTGTGAC-TGTTG-3' (SEQ ID NO:20) (Fr primer) and 5'-TTTAGCT-TAAGTGGCCAGCAA-3' (SEQ ID NO:21) (Rev primer), and the internal Rev primer was 5'-AAGTTGGTTTA-CATCTGCAC-3' (SEQ ID NO:22). For detection of the Δ64 deletion of the siL3 site, the flanking external primers were 5'-CTTGAGCAGTCAGCAACAGG-3' (SEQ ID NO:23) (Fr primer) and 5'-CAGAGGTTGGACAGGGAAGA-3' (SEQ ID NO:24) (Rev primer), and the internal Rev primer was 5'-ATATGGGTAATTGAAGGGCTG-3' (SEQ ID NO:25). After screening the clones, Sanger sequencing was performed to confirm that the proper deletion had occurred. Three clones were pooled for each si/shRNA target site deletion except for HeyA8 ΔshR6 for which only clone #11 showed homozygous deletion of the shR6 site; clones #1 and 2 were not complete shR6 deletion mutants, but frame-shift mutations did occur in each allele (as in clone #11) making them CD95 knockout clones.

Knockdown with pLKO Lentiviruses.

Cells were infected with the following pLKO.2 MISSION Lentiviral Transduction Particles (Sigma): pLKO.2-puro non-targeting (scramble) shRNA particles (#SHC002V), 8 non-overlapping shRNAs against human CD95L mRNA (accession number #NM_000639), TRCN0000058998 (shL1: GCATCATCTTTGGAGAAGCAA) (SEQ ID NO:1), TRCN0000058999 (shL2: CCCATTTAACAGGCAAGTCCA) (SEQ ID NO:26), TRCN0000059000 (shL3: ACTGGGCTGTACTTTGTATAT) (SEQ ID NO:2), TRCN0000059001 (shL4: GCAGTGTTCAATCTTACCAGT) (SEQ ID NO:3), TRCN0000059002 (shL5: CTGTGTCTCCTTGTGATGTTT) (SEQ ID NO:27), TRCN0000372231 (shL6: TGAGCTCTCTCTGGTCAATTT) (SEQ ID NO:28), TRCN0000372232 (shL2': TAGCTCCTCAACTCACCTAAT) (SEQ ID NO:29), and TRCN0000372175 (shL5': GACTAGAGGCTTGCATAATAA) (SEQ ID NO:30), and 9 non-overlapping shRNAs against human CD95 mRNA (accession number NM_000043), TRCN0000218492 (shR2: CTATCATCCTCAAGGACATTA) (SEQ ID NO:31), TRCN00000 38695 (shR5: GTTGCTAGATTATCGTCCAAA) (SEQ ID NO:4), TRCN0000038696 (shR6: GTGCAGATGTAAACCAAACTT) (SEQ ID NO:5), TRCN0000038697 (shR7: CCTGAAACAGTGGCAATAAAT) (SEQ ID NO:6), TRCN0000038698 (shR8: GCAAAGAGGAAGGATCCAGAT) (SEQ ID NO:32), TRCN0000265627 (shR27': TTTTACTGGGTACATTTTATC) (SEQ ID NO:33), TRCN0000255406 (shR6': CCCTTGTGTTTGGAATTATAA) (SEQ ID NO:34), TRCN0000255407 (shR7': TTAAATTATAATGTTTGACTA) (SEQ ID NO:35), and TRCN0000255408 (shR8': ATATCTTTGAAAGTTTGTATT) (SEQ ID NO:36). Infection was carried out according to the manufacturer's protocol. In brief, 50,000 to 100,000 cells seeded the day before in a 6-well plate were infected with each lentivirus at an M.O.I of 3 in the presence of 8 µg/ml polybrene overnight. Media change was done the next day, followed by selection with 3 µg/ml puromycin 24 hours later. Selection was done for at least 48 hours until puromycin killed the non-infected control cells. For infection of NB7 cells over-expressing pLenti-CD95L cDNAs with pLKO lentiviral particles as in FIGS. 1C and D, cells were seeded at 5,000 per well on a 24-well plate and infected with an M.O.I. of 20 to ensure complete infection. For infection of MCF-7 cells over-expressing pLNCX2-CD95 cDNAs with pLKO lentiviruses as in FIG. 1G, cells were seeded at 7,000 per well on a 24-well plate and infected at an M.O.I. of three. 3 µg/ml puromycin was added 48 hours after infection. For infection of HCT116, Drosha$^{-/-}$, and Dicer$^{-/-}$ cells in FIG. 3E, cells were seeded at 100,000 per well in a 24-well plate and infected at an M.O.I of three. 3 µg/ml puromycin was added 48 hours after infection.

Knockdown with pTIP-shRNA Viruses.

Cells were plated at 50,000 to 100,000 cells per well in a 6-well plate. Cells were infected with lentivirus generated in 293T cells from the desired pTIP-shRNA vector in the presence of 8 µg/ml Polybrene. Media was replaced 24 hours later. Selection was done 48 hours after infection with 3 µg/ml puromycin. Induction of shRNA expression was achieved by adding 100 ng/ml Dox to the media. For infection with the LT3REPIR-shRNA viruses cells were plated and infected as described above for pTIP-shRNA viruses. After selection with 3 µg/ml puromycin was complete, they were plated in 96-well plates and the shRNA expression was induced by adding Dox (100 ng/ml) to the media. The cell confluency over time was measured using Incucyte.

Transfection with Short Oligonucleotides.

siRNAs were either purchased from Dharmacon (FIG. 2I and data not shown) or synthesized by IDT (FIG. 3A) as sense and antisense RNA (or DNA for FIG. 3B, and data not shown) oligos and annealed. The sense RNA oligonucleotides had 3' 2 deoxy-T overhangs. The antisense RNA oligos were phosphorylated at the 5' end and had 3' 2 deoxy-A overhangs. siRNAs targeting CD95L (and controls) were as follows: siRNA (Scr, sense: UGGUUUACAUGUUGUGUGA) (SEQ ID NO:37), siL1 (sense: UACCAGUGCUGAUCAUUUA) (SEQ ID NO:38), siL2 (sense: CAACGUAUCUGAGCUCUCU) (SEQ ID NO:39), siL3 (sense: GCCCUUCAAUUACCCAUAU) (SEQ ID NO:40), siL4 (sense: GGAAAGUGGCCCAUUUAAC) (SEQ ID NO:41), and siL3MUT (sense: GGACUUCAACUAGACAUCU) (SEQ ID NO:42). The siL3 DNA oligos (sense: GCCCTTCAATTACCCATAT) (SEQ ID NO:43) and Scr DNA oligos (sense: TGGTTTACATGTTGTGTGA) (SEQ ID NO:44) were used in FIG. 3B. Blunt siL3 and siScr RNA oligos without the deoxynucleotide overhangs as well as siL2 and siL3 RNA oligos with Cy5-labelled 5' or 3' ends (IDT) were used in FIG. 3C. DsiRNA used were as follows: Dsi13.X (sense RNA oligo: CAGGACUGAGAAGAAGUAAAACCdGdT (SEQ ID NO:45), antisense RNA oligo: ACGGUUUUACUUCUUCUCAGUCCUGUA (SEQ ID NO:46)), DsiL3 (sense RNA oligo: CAGCCCUUCAAUUACCCAUAUCCdCdC (SEQ ID NO:47), antisense RNA oligo: GGGGAUAUGGGUAAUUGAAGGGCUGCU (SEQ ID NO:48)), Dsi-13.2 (sense RNA oligo: AUCUUACCAGUGCUGAUCAUUUAdTdA (SEQ ID NO:49), antisense RNA oligo: UAUAAAUGAUCAGCACUGGUAAGAUUG (SEQ ID NO:50)), Dsi-13.3 (sense RNA oligo: AAAGUAUACUUCCGGGGUCAAUCdTdT (SEQ ID NO:51), antisense RNA oligo: AAGAUUGACCCCGGAAGUAUACUUUGG (SEQ ID NO:52)), Dsi-13.9 (sense RNA oligo: CUUCCGGGGUCAAUCUUGCAACAdAdC (SEQ ID NO:53), antisense RNA oligo: GUUGUUGC AAGAUUGACCCCGGAAGUA (SEQ ID NO:54)), and a non-targeting DsiRNA control Dsi-NC1 (Sense:5'-CGUUAAUCGCGUAUAAUACGCGUdAdT (SEQ ID NO:55), antisense:5'-AUACGCGUAUUAUACGCGAUUAACGAC (SEQ ID NO:56), IDT #51-01-14-03). Predesigned siRNA SmartPools targeting the 11 downregulated genes were obtained from Dharmacon and used in FIG. 11 and FIG. 12. Each siRNA SmartPool consisted of 4 siRNAs with On-Targetplus modification. The following SmartPools were used: L-014208-02 (NUCKS1); L-012212-00 (CAPZA1); L-018339-00 (CCT3); L-013615-00 (FSTL1); L-011548-00 (FUBP1); L-017242-00 (GNB1); L-014597-01 (NAA50); L-020893-01 (PRELID3B); L-019719-02 (SNRPE); L-003941-00 (TFRC); L-006630-00 (HIST1H1C). On-Targetplus non-targeting control pool (D-001810-10) was used as negative control. Transfection efficiency was assessed by transfecting cells with siGLO Red (Dharmacon) followed by FACS analysis.

HeyA8 cells (and modified cells derived from parental HeyA8 cells) were seeded at 750 cells per well on a 96-well plate one day before transfection. Cells were transfected using 0.1 µl of Lipofectamine RNAiMAX reagent per well. HCT116 cells (and modified cells derived from parental HCT116 cells) were seeded at 4000 cells per well on a 96-well plate one day before transfection. 0.2 µl of Lipofectamine RNAiMAX was used for transfection. Media was changed the day after transfection.

Soluble CD95L Protein Rescue Experiments.

NB7 cells were seeded at 500 cells per well in a 96-well plate. Next day, cells were infected with the scrambled pLKO lentiviruses or pLKO-shL1 lentiviruses at an M.O.I. of 20 (to achieve 100% transduction efficiency under conditions omitting the puromycin selection step) in the presence of 8 µg/ml polybrene and 100 ng/ml of S2 CD95L or LzCD95L for 16 hrs. Media was replaced the next day with media containing varying concentrations of recombinant CD95L.

Real-Time PCR.

Total RNA was extracted and purified using QIAZOL Lysis reagent (QIAGEN) and the miRNeasy kit (QIAGEN). 200 ng of total RNA was used to generate cDNA using the High-Capacity cDNA reverse Transcription kit (Applied Biosystems #4368814). cDNA was quantified using Taqman Gene expression master mix (ThermoFisher Scientific #4369016) with specific primers from ThermoFisher Scientific for GAPDH (Hs00266705_g1), human CD95 (Hs00163653_m1), human CD95 3'UTR in FIG. 2F (custom probe, Fr primer: GGCTAACCCCACTCTATGAATCAAT (SEQ ID NO:57), Rev primer: GGCCTGCCTGTTCAGTAACT (SEQ ID NO:58), Probe: CCTTTTGCTGAAATATC (SEQ ID NO:59)), human CD95L (Hs00181226_g1 and Hs00181225_m1), the shL3 target site in CD95L in FIG. 2D (custom probe, Fr primer: GGTGGCCTTGTGATCAATGAAA (SEQ ID NO:60), Rev primer: GCAAGATTGACCCCGGAAGTATA (SEQ ID NO:61), Probe: CTGGGCTGTACTTTGTATATT (SEQ ID NO:62)), and downstream of the shL3 site in FIG. 2D (custom probe, Fr primer: CCCCAGGATCTGGTGAT-GATG (SEQ ID NO:63), Rev primer: ACTGCCCCCAGGTAGCT (SEQ ID NO:64), Probe: CCCACATCTGCCCAGTAGT (SEQ ID NO:65)).

To perform arrayed real-time PCR, total RNA was extracted and used to make cDNA as described for standard real-time PCR. For Taqman Low Density Array (TLDA) profiling, custom-designed 384-well TLDA cards (Applied Biosystems #43422489) were used and processed according to the manufacturer's instructions. Briefly, 50 al cDNA from each sample (200 ng total input RNA) was combined with 50 al TaqMan Universal PCR Master Mix (Applied Biosystems) and hence a total volume of 100 al of each sample was loaded into each of the 8 sample loading ports on the TLDA cards that were preloaded with assays from Thermofisher Scientific for human GAPDH control (Hs99999905_m1) and for detection of ATP13A3 (Hs00225950_m1), CAPZA1 (Hs00855355_g1), CCT3 (Hs00195623_m1), FSTL1 (Hs00907496_m1), FUBP1 (Hs00900762_m1), GNB 1 (Hs00929799_m1), HISTH1C (Hs00271185_s1), NAA50 (Hs00363889_m1), NUCKS1 (Hs01068059_g1), PRELID3B (Hs00429845_m1), SNRPE (Hs01635040_s1), and TFRC (Hs00951083_m1) after the cards reached room temperature. The PCR reactions were performed using Quantstudio 7 (ThermoFisher Scientific). Since each of the port loads each sample in duplicates on the TLDA card and because two biological replicates of each sample were loaded onto two separate ports, quadruplicate Ct values were obtained for each sample. Statistical analysis was performed using Student's t test. Cells were plated at 600,000 per 15 mm dish (Greiner CELLSTAR, cat #P7237, Sigma) after one day of puromycin selection. Total RNA was harvested at 50 hours after plating for RNAseq analysis.

Western Blot Analysis.

Protein extracts were collected by lysing cells with RIPA lysis buffer (1% SDS, 1% Triton X-100, 1% deoxycholic acid). Protein concentration was quantified using the DC Protein Assay kit (Bio-Rad). 30 µg of protein were resolved on 8-12% SDS-PAGE gels and transferred to nitrocellulose membranes (Protran, Whatman) overnight at 25 mA. Membranes were incubated with blocking buffer (5% non-fat milk in 0.1% TBS/Tween-20) for 1 hour at room temperature. Membranes were then incubated with the primary antibody diluted in blocking buffer over night at 4° C. Membranes were washed 3 times with 0.1% TBS/Tween-20. Secondary antibodies were diluted in blocking buffer and applied to membranes for 1 hour at room temperature. After 3 more additional washes, detection was performed using the ECL reagent (Amersham Pharmacia Biotech) and visualized with the chemiluminescence imager G:BOX Chemi XT4 (Synoptics).

CD95 Surface Staining.

Cell pellets of about 300,00 cells were resuspended in about 100 µl of PBS on ice. After resuspension, 5 µl of either anti-CD95 primary antibody (BD #556640) conjugated with fluorescein isothiocyanate (FitC), or the matching Isotype control (BD #551954), Mouse IgG1 κ conjugated with FitC, were added. Cells were incubated on ice at 4° C., in the dark, for 25 minutes, washed twice with PBS, and percent green cells were determined by flow cytometry (Becton, Dickinson).

Cell Death Quantification (DNA Fragmentation).

A cell pellet (500,000 cells) was resuspended in 0.1% sodium citrate, pH 7.4, 0.05% Triton X-100, and 50 µg/ml propidium iodide. After resuspension, cells were incubated 2 to 4 hours in the dark at 4° C. The percent of subG1 nuclei (fragmented DNA) was determined by flow cytometry.

Cell Growth and Fluorescence Over Time.

After treatment/infection, cells were seeded at 500 to 4,000 per well in a 96-well plate at least in triplicate. Images were captured at indicated time points using the IncuCyte ZOOM live cell imaging system (Essen BioScience) with a 10× objective lens. Percent confluence, red object count, and the green object integrated intensity were calculated using the IncuCyte ZOOM software (version 2015A).

RNA-Seq Analysis.

The following describes the culture conditions used to produce samples for RNA-Seq in FIG. 4. HeyA8 ΔshR6 clone #11 cells were infected with pLKO-shScr or pLKO-shR6. A pool of three 293T ΔshL3 clones was infected with either pTIP-shScr or pTIP-shL3. After selection with puromycin for 2 days, the pTIP-infected 293T cells were plated with Dox in duplicate at 500,000 cells per T175 flask. The pLKO-infected HeyA8 cells were plated at 500,000 cells per flask. Total RNA was harvested 50 hours and 100 hours after plating. In addition, 293T cells were infected with either pLKO-shScr or pLKO-shL1 and RNA was isolated (100 hrs after plating) as described above for the infection with shR6. Finally, HeyA8 cells were transfected with RNAiMAX in 6-wells with siScr (NT2) or siL3 oligonucleotides (Dharmacon) at 25 nM. The transfection mix was removed after 9 hours.

Total RNA was isolated 48 hours after initial transfection using the miRNeasy Mini Kit (Qiagen, Cat. No. 74004)) following the manufacturer's instructions. An on-column digestion step using the RNAse-free DNAse Set (Qiagen, Cat. No.: 79254) was included for all RNA-Seq samples.

RNA libraries were generated and sequenced (Genomics Core facility at the University of Chicago). The quality and quantity of the RNA samples were checked using an Agilent bio-analyzer. Paired end RNA-SEQ libraries were generated using Illumina TruSEQ TotalRNA kits using the Illumina provided protocol (including a RiboZero rRNA removal step). Small RNA-SEQ libraries were generated using Illumina small RNA SEQ kits using the Illumina provided protocol. Two types of small RNA-SEQ sub-libraries were generated: one containing library fragments 140-150 bp in size and one containing library fragments 150-200 bp in size (both including the sequencing adaptor of about 130 bp). All three types of libraries (one RNA-SEQ and two small RNA-SEQ) were sequenced on an Illumina HiSEQ4000 using Illumina provided reagents and protocols. Adaptor sequences were removed from sequenced reads using TrimGalore (https://www.bioinformatics.babraham.ac.uk/projects/trim_galore), and the trimmed reads were mapped to the hg38 assembly of the human genome with Tophat and bowtie2. Raw read counts were then assigned to genes using HTSeq. Differential gene expression was analyzed with the R Bioconductor DESeq2 package (Love, Huber, & Anders, 2014) using shrinkage estimation for dispersions and fold changes to improve stability and interpretability of estimates. P values and adjusted P values were calculated using the DESeq2 package.

To identify differentially abundant RNAs in cells expressing either shL3 or shR6, using a method unbiased by genome annotation, we also analyzed the raw 100 bp reads for differential abundance. First, the second end in each paired end read was reverse complemented, so that both reads were on the same strand. Reads were then sorted and counted using the core UNIX utilities sort and uniq. Reads with fewer than 128 counts across all 16 samples were discarded. A table with all of the remaining reads was then compiled, summing counts from each sequence file corresponding to the same sample. This table contained a little over 100,000 reads. The R package edgeR (http://bioinformatics.oxfordjournals.org/content/26/1/139) was used to identify differentially abundant reads, and then these reads were mapped to the human genome using blat (http://genome.cshlp.org/content/12/4/656.abstract) to determine chromosomal location whenever possible. Homer (http://homer.salk.edu/homer/) was used to annotate chromosomal locations with overlapping genomic elements (such as genes). Raw read counts in each sequence file were normalized by the total number of unique reads in the file.

To identify the most significant changes in expression of RNAs both methods of RNAs-Seq analyses (alignment and read based) were used to reach high stringency. All samples were prepared in duplicate and for each RNA the average of the two duplicates was used for further analysis. In the alignment-based analysis, only RNAs that had a base mean of >2000 reads and were significantly deregulated between the groups (adjusted p-value <0.05) were considered for further analysis. RNAs were scored as deregulated when they were more than 1.5 fold changed in the shL3 expressing cells at both time points and in the shR6 expressing cells at either time points (each compared to shScr expressing cells) (data not shown). This was done because we found that the pLKO driven expression of shR6 was a lot lower than the pTIP driven expression of shL3. This likely was a result of the reduced cellular responses in the shR6 expressing cells. In the read based analysis, reads were only considered if they had both normalized read numbers of >10 across the samples in each treatment, as well as less than 2 fold variation between duplicates and >1.5 fold change between treatment groups at both time points and both cell lines (data not shown). After filtering, reads were mapped to the genome and associated with genes based on chromosomal localization. Finally, All RNAs were counted that showed deregulation in the same direction with both methods. This resulted in the identification of 11 RNAs that were down and 1 that was upregulated in cells exposed to the shRNAs shL3 and shR6. To determine the number of seed matches in the 3'UTR of downregulated genes, the 3'UTRs of the 11 mRNAs were extracted from the *Homo sapiens* gene (GRCh38.p7) dataset of the Ensembl 86 database using the Ensembl Biomart data mining tool. For each gene, only the longest deposited 3'UTR was considered. Seed matches were counted in all 3'UTRs using in-house Perl scripts.

GSEA was performed using the GSEA v2.2.4 software from the Broad Institute (www.http://software.broadinstitute.org/gsea); 1000 permutations were used. The Sabatini gene lists (Wang, 2015) were set as custom gene sets to determine enrichment of survival genes versus the nonsurvival control genes in downregulated genes from the RNA seq data; Adjusted p-values below 0.05 were considered significantly enriched. The GO enrichment analysis was performed using all genes that after alignment and normalization were found to be at least 1.5 fold downregulated with an adjusted p values of <0.05, using the software available on www.Metascape.org and default running parameters.

Conversion of shL3 and shR6 to siRNAs.

From the RNA-Seq analysis with HeyA8 ΔshR6 infected with pLKO-shR6 and 293T ΔshL3 clones infected pTIP-shL3, we analyzed the mature double-stranded RNAs derived from pLKO-shR6 and pTIP-shL3 and found that the most abundant RNA forms were both shifted by one nucleotide. Based on these most abundant species observed after cellular processing, we converted shL3 and shR6 sequences to siRNAs. The genomic target sequence in shL3 (21nt) is 5'-ACUGGGCUGUACUUUGUAUAU-3' (SEQ ID NO:66). For the shL3=>siL3 sense strand, one G was added before the A on the 5' end while the last U on the 3' end was deleted, and second and third to the last ribonucleotides on the 3' end (UA) were replaced with deoxyribonucleotides for stabilization. For shL3=>siL3 antisense strand, the last three nucleotides on the 5' end (AUA) were deleted and one U and two dTs (UdTdT) were added after the last U on the 3'end. The shL3=>siL3 sense strand is 5'-GACUGGGCUGUAC-UUUGUAdTdA-3' (SEQ ID NO:67) and antisense strand is 5'-/5Phos/UACAAAGUACAGCCCAGUUdTdT-3' (SEQ ID NO:68). The shR6=>siRNA was designed in a similar fashion except that two Gs instead of one G were added to the 5' end of the sense strand while UUdTdT instead of UdTdT was added to the 3' end of the antisense strand. The genomic target sequence in shR6 (21nt) is 5'-GUGCAGAU-GUAAACCAAACUU-3' (SEQ ID NO:69). The shR6=>siR6 sense strand is 5'-GGGUGCAGAUGUAAAC-CAAAdCdT-3' (SEQ ID NO:70) and antisense strand is 5'-/5Phos/UUUGGUUUACAUCUGCACUUdTdT-3' (SEQ ID NO:71). Both shL3=>siL3 and ShR6=>siR6 siRNA duplexes were purchased from Dharmacon.

Construction of pTIP-shRNA Libraries.

The pTIP-shRNA libraries were constructed by subcloning libraries of 143nt PCR inserts of the form 5'-XXXXXXXXXXXXXXXXXXXXXXXXXATAGA-GATCGNNNNNNNNNNNNNNNN NNNNNCTCGAG-NNNNNNNNNNNNNNNNNNNNNTTTTTGTACCGA-GCTCGGATCC ACTAGTCCAGTGTGGGCATGCTGC-GTTGACATTGATT-3' (SEQ ID NO:72) into the pTIP-shR6 vector after excising the shR6 insert. The poly-N region represents the 21-mer sense and antisense shRNA hairpin. The intervening CTCGAG is the loop region of the shRNA. The 5 libraries targeting Venus, CD95L ORF, CD95L 3'UTR, CD95 ORF, or CD95 3'UTR were composed of every possible 21-mer shRNA (i.e. each nearest neighbor shRNA was shifted by 1 nucleotide). These libraries were synthesized together on a chip as 143 bp single-stranded DNA oligos (CustomArray Inc, Custom 12K oligo pool). Each shRNA pool had its own unique 5' end represented by the poly-X region. This allowed selective amplification of a particular pool using 1 of 5 unique Fr primers (CD95L ORF:

5'-TGGCTTTATATATCTCCCTATCAGTG-3' (SEQ ID NO:73), CD95L 3' UTR: 5'-GGTCGTCCTATCTATTATT-ATTCACG-3' (SEQ ID NO:74), CD95 ORF: 5'-TCTTGTGTCCAGACCAATTTATTTCG-3' (SEQ ID NO:75), CD95 3'UTR: 5'-CTCATTGACTATCGTTT-TAGCTACTG-3' (SEQ ID NO:76), Venus: 5'-TAT-CATCTTTCATGATGACTTTCCGG-3') (SEQ ID NO:77) and the common reverse primer 5'-AATCAATGT-CAACGCAGCAT-3' (SEQ ID NO:78). Phusion High Fidelity Polymerase (NEB #M0530) was used to amplify each library pool; standard PCR conditions were used with an annealing temperature of 61° C. and 15 cycles. PCR reactions were purified using PCR Cleanup kit (QIAGEN). The pTIP-shR6 vector and each of the amplified libraries were digested with SphI-HF and BsaBI. Digested PCR products were run on either a 2% Agarose gel or a 20% polyacrylamide (29:1) gel made with 0.5×TBE buffer. PCR products were extracted using either Gel Extraction kit (QIAGEN) for extraction from Agarose gels or via electro-elution using D-Tube Dialyzer Mini columns (Novagen #71504). Purified PCR inserts were then ligated to the linearized pTIP vector with T4 DNA ligase for 24 hours at 16° C. The ligation mixtures were transformed via electroporation in MegaX DH10B T1 cells (Invitrogen #C6400) and plated on 24 cm ampicillin dishes. At least 10 colonies per pool were picked and sequenced to verify successful library construction. After verification, all colonies per library were pooled together and plasmid DNA extracted using the MaxiPrep kit (QIAGEN). The 5 pTIP-shRNA library DNA preps were used to produce virus in 293T cells.

Lethality Screen with pTIP-shRNA Libraries.

NB7 cells were seeded at $1.5 \times 10^6$ per 145 cm$^2$ dish. Two dishes were infected with each of the 5 libraries with a transduction efficiency of about 10 to 20%. Media was replaced next day. Infected cells were selected with 1.5 μg/ml puromycin. Cells infected with the Venus, CD95L ORF, and CD95L 3'UTR-targeting libraries were pooled in a 1:1:1 ratio to make the CD95L cell pool. Likewise, cells infected with the Venus, CD95 ORF, and CD95 3'UTR-targeting libraries were pooled to make the CD95 receptor cell pool. The CD95 and the CD95L cell pools were plated separately each in 2 sets of duplicates seeded at 600,000 cells per 145 cm$^2$ dish. One set received 100 ng/ml Dox, and the other one was left untreated (total of 4 dishes per combined pool; 2 received no treatment and 2 received Dox). Cells infected with the different libraries were also plated individually in triplicate with or without Dox on a 96-well plate to assess the overall toxicity of each pool. DNA was collected from each 145 cm$^2$ dish 9 days after Dox addition.

The shRNA barcodes were amplified from the harvested DNA template using NEB Phusion Polymerase with 4 different pairs of primers (referred to as N, N+1, N+2, and N+3) in separate reactions per DNA sample. The N pair consisted of the primers originally used to amplify the CD95L ORF library (Fr: 5'-TGGCTTTATATATCTCCC-TATCAGTG-3' (SEQ ID NO:73) and Rev: 5'-AAT-CAATGTCAACGCAGCAT-3' (SEQ ID NO:78)). The N+1 primers had a single nucleotide extension at each 5' end of the N primers corresponding to the pTIP vector sequence (Fr: 5'-TTGGCTTTATATATCTCCCTATCAGTG-3' (SEQ ID NO:79) and Rev: 5'-TAATCAATGTCAACGCAGCAT-3' (SEQ ID NO:80)). The N+2 primers had 2 nucleotide extensions (Fr: 5'-CTTGGCTTTATATATCTCCC-TATCAGTG-3' (SEQ ID NO:81) and Rev: 5'-ATAAT-CAATGTCAACGCAGCAT-3' (SEQ ID NO:82)), and the N+3 primers had 3 nucleotide extensions (Fr: 5'-TCTTGGCTTTATATATCTCCCTATCAGTG-3' (SEQ ID NO:83) and Rev: 5'-AATAATCAATGTCAACGCAG-CAT-3' (SEQ ID NO:84)). The barcodes from the pTIP-shRNA library plasmid preparations were also amplified using Phusion Polymerase with the N, N+1, N+2, and N+3 primer pairs. The shRNA barcode PCR products were purified from a 2% Agarose gel and submitted for 100 bp paired-end deep sequencing (Genomics Core facility at the University of Chicago). DNA was quantitated using the Qubit. The 4 separate PCR products amplified using N, N+1, N+2, and N+3 were combined in equimolar amounts for each sample. Libraries were generated using the Illumina TruSeq PCR-free kit using the Illumina provided protocol. The libraries were sequenced using the HiSEQ4000 with Illumina provided reagents and protocols. Raw sequence counts for DNAs were calculated by HTSeq. shRNA sequences in the PCR pieces of genomic DNA were identified by searching all reads for the sense sequence of the mature shRNA plus the loop sequence CTCGAG. To avoid a division by zero problem during the subsequent analyses all counts of zero in the raw data were replaced with 1. A few sequences with a total read number <10 across all plasmids reads were not further considered. In the CD95L pool this was only one shRNA (out of 2362 shRNAs) (L792') and in the CD95 20 shRNAs (out of 3004 shRNAs) were not represented (R88, R295, R493, R494, R496, R497, R498, R499, R213', R215', R216', R217', R220', R221', R222', R223', R225', R226', R258', R946', R1197', R423'). While most shRNAs in both pools had a unique sequence two sequences occurred 6 times (L605', L607', L609', L611', L613', L615', and L604', L606', L608', L610', L612', L614'). In these cases, read counts were divided by 6. Two shRNAs could not be evaluated: 1) shR6 in the CD95 pool. It had a significant background due to the fact that pTIP-shR6 was used as a starting point to clone all other shRNAs. 2) shL3 was found to be a minor but significant contaminant during the infection of some of the samples. For each condition, two technical duplicates and two biological duplicates were available. To normalize reads to determine the change in relative representation of shRNAs between conditions, the counts of each shRNA in a subpool (all replicates and all conditions) was divided by the total number of shRNAs in each subpool (%). First, the mean of the technical replicates (R1 and R2) was taken. To analyze the biological replicates and to determine the changes between conditions, two analyses were performed: 1) The change in shRNA representation between the cloned plasmid library and cells infected with the library and then cultured for 9 days without Dox (infection –Dox). Fold downregulation was calculated for each subpool as [(plasmid %/–Dox1%+plasmid %/–Dox2%)/2]. 2) The difference in shRNA composition between the infected cells cultured with (infection+Dox) and without Dox. Fold downregulation was calculated for each subpool as [(–Dox1%/+Dox1%)+(–Dox1%/+Dox2%)+(–Dox2%/+Dox1%)+(–Dox2%/+Dox2%)/4]. Only shRNAs were considered that were at least 5-fold underrepresented in either of the two analyses (data not shown).

The Toxicity Index (TI) and GC Content Analysis.

The TI in FIG. 7A is defined by the sum of the counts of a 6mer or 8mer seed match in the 3'UTRs of critical survival genes divided by the seed match counts in the 3'UTRs of nonsurvival genes. We used the 1882 survival genes recently described in a CRISPR/Cas9 lethality screen by Wang et al. (Wang et al., 2015). The survival genes were defined by having a CRISPR score of <–0.1 and an adjusted p-value of <0.05. We chose as a control group to these top essential genes the bottom essential genes using inverse criteria (CRISPR score of >0.1 and adjusted p-value of <0.05) and are referring to them as the "nonsurvival genes". Both counts were normalized for the numbers of genes in each gene set. 3'UTRs were retrieved as described above. For the survival genes 1846 and for the nonsurvival genes 416 3'UTRs were found. For each gene, only seed matches in the longest 3'UTR were counted. The TI was calculated for each of the 4096 possible 6mer combinations and each of the 65536 possible 8mer combinations (data not shown). These numbers were then assigned to the results of the shRNA screen (data not shown). An alternative TI was calculated in FIG. 14B and is based on the top 850 most highly expressed survival genes (all expressed >1000 average reads) and 850 expression matched genes not described to be critical for cancer cell survival were selected as controls.

For the analyses in FIGS. 7C and D, the GC content % was calculated for every 6mer in the CD95L ORF shRNA pool. The GC content % was then plotted against the log(Fold down) for each shRNA in the CD95L ORF shRNA after infection (compared to the plasmid composition) in FIG. 7C and after addition of Dox (compared to cells infected but not treated with Dox) in FIG. 7D. In FIG. 7E, the log(TI) and GC content % was extracted for every possible 6mer and plotted. Pearson correlation coefficient and associated p-value were calculated in R3.3.1.

Sylamer Analysis.

Sylamer is a tool to test for the presence of RNAi-type regulation effects from a list of differentially expressed genes, independently from small RNA measurements (van Dongen et al., 2008) (http://www.ebi.ac.uk/research/enright/software/sylamer). For short stretches of RNA (in this case length 6, 7, and 8 in length corresponding to the lengths of the determinants of seed region binding in RNAi-type binding events), Sylamer tests for all possible motifs of this length whether the motif occurrences are shifted in sequences associated with the list under consideration, typically 3'UTRs when analyzing RNAi-type binding events. A shift or enrichment of such a motif towards the downregulated end of the gene list is consistent with upregulation of a small RNA that has the motif as the seed region. Sylamer tests in small increments along the list of genes, using a hypergeometric test on the counts of a given word, comparing the leading part of the gene list to the universe of all genes in the list. For full details refer to (van Dongen et al., 2008). Enriched motifs stand out from the back-ground of all motifs tested, as visible in the Sylamer plot. The plot consist of many different lines, each line representing the outcomes of a series of tests for a single word, performed along regularly spaced intervals (increments of 200 genes) of the gene list. Each test yields the log-transformed P-value arising from a hypergeometric test as indicated above. If the word is enriched in the leading interval the log-transformed value has its value plotted on the positive y-axis (sign changed), if the word is depleted the log-transformed value is plotted on the negative y-axis. 3' UTRs were used from Ensembl, version 76. As required by Sylamer, they were cleaned of low-complexity sequences and repetitive fragments using respectively Dust (Morgulis, Gertz, Schaffer, & Agarwala, 2006) with default parameters and the RSAT interface (Medina-Rivera et al., 2015) to the Vmatch program, also run with default parameters. Sylamer (version 12-342) was run with the Markov correction parameter set to 4.

Statistical Analyses.

Continuous data were summarized as means and standard deviations (except for all IncuCyte experiments where standard errors are shown) and dichotomous data as proportions. Continuous data were compared using t-tests for two independent groups and one-way ANOVA for 3 or more groups. For evaluation of continuous outcomes over time, two-way ANOVA was used with one factor for the treatment conditions of primary interest and a second factor for time treated as a categorical variable to allow for non-linearity. Comparisons of single proportions to hypothesized null values were evaluated using binomial tests. Statistical tests of two independent proportions were used to compare dichotomous observations across groups.

The effects of treatment on wild-type versus either $Dicer^{-/-}$ or $Drosha^{-/-}$ cells were statistically assessed by fitting regression models that included linear and quadratic terms for value over time, main effects for treatment and cell type, and two- and three-way interactions for treatment, cell-type and time. The three-way interaction on the polynomial terms with treatment and cell type was evaluated for statistical significance since this represents the difference in treatment effects over the course of the experiment for the varying cell types.

To test if higher TI is enriched in shRNAs that were highly downregulated, p-values were calculated based on permutated datasets using Mann-Whitney U tests. The ranking of TI was randomly shuffled 10,000 times and the W statistic from our dataset was compared to the distribution of the W statistic of the permuted datasets. Test of enrichment was based on the filtered data of at least 5-fold difference, which we define as a biologically meaningful. Fisher Exact Tests were performed to assess enrichment of downregulated genes (i.e. >1.5 downregulated with adjusted p-value <0.05) amongst genes with at least one si/shRNA seed match. All statistical analyses were conducted in Stata 14 (RRID: SCR_012763) or R 3.3.1 in Rstudio (RRID:SCR_000432).

Data Availability

The accession number for the RNA-Seq and expression data reported in this manuscript are GSE87817.

REFERENCES

Algeciras-Schimnich, A., Pietras, E. M., Barnhart, B. C., Legembre, P., Vijayan, S., Holbeck, S. L., & Peter, M. E. (2003). Two CD95 tumor classes with different sensitivities to antitumor drugs. Proc Natl Acad Sci USA, 100(20), 11445-11450.

Bae, K., Park, K. E., Han, J., Kim, J., Kim, K., & Yoon, K. A. (2016). Mitotic cell death caused by follistatin-like 1 inhibition is associated with up-regulated Bim by inactivated Erk1/2 in human lung cancer cells. Oncotarget, 7(14), 18076-18084. doi: 10.18632/oncotarget.6729

Barnhart, B. C., Legembre, P., Pietras, E., Bubici, C., Franzoso, G., & Peter, M. E. (2004). CD95 ligand induces motility and invasiveness of apoptosis-resistant tumor cells. EMBO J, 23(15), 3175-3185.

Baumgarten, P., Harter, P. N., Tonjes, M., Capper, D., Blank, A. E., Sahm, F., . . . Mittelbronn, M. (2014). Loss of FUBP1 expression in gliomas predicts FUBP1 mutation and is associated with oligodendroglial differentiation, IDH1 mutation and 1p/19q loss of heterozygosity. Neuropathol Appl Neurobiol, 40(2), 205-216. doi: 10.1111/nan.12088

Bernstein, E., Caudy, A. A., Hammond, S. M., & Hannon, G. J. (2001). Role for a bidentate ribonuclease in the initiation step of RNA interference. Nature, 409(6818), 363-366. doi:10.1038/35053110

Birmingham, A., Anderson, E. M., Reynolds, A., Ilsley-Tyree, D., Leake, D., Fedorov, Y., . . . Khvorova, A. (2006). 3' UTR seed matches, but not overall identity, are associated with RNAi off-targets. Nat Methods, 3(3), 199-204. doi:10.1038/nmeth854

Blomen, V. A., Majek, P., Jae, L. T., Bigenzahn, J. W., Nieuwenhuis, J., Staring, J., . . . Brummelkamp, T. R. (2015). Gene essentiality and synthetic lethality in haploid human cells. Science, 350(6264), 1092-1096. doi: 10.1126/science.aac7557

Bramsen, J. B., Laursen, M. B., Nielsen, A. F., Hansen, T. B., Bus, C., Langkjaer, N., . . . Kjems, J. (2009). A large-scale chemical modification screen identifies design rules to generate siRNAs with high activity, high stability and low toxicity. Nucleic Acids Res, 37(9), 2867-2881. doi: 10.1093/nar/gkp 106

Ceppi, P., Hadji, A., Kohlhapp, F., Pattanayak, A., Hau, A., Xia, L., . . . Peter, M. E. (2014). CD95 and CD95L promote and protect cancer stem cells. Nature Commun, 5, 5238.

Cerami, E., Gao, J., Dogrusoz, U., Gross, B. E., Sumer, S. O., Aksoy, B. A., . . . Schultz, N. (2012). The cBio cancer genomics portal: an open platform for exploring multidimensional cancer genomics data. Cancer Discov, 2(5), 401-404. doi:10.1158/2159-8290.CD-12-0095

Chan, K. T., Choi, M. Y., Lai, K. K., Tan, W., Tung, L. N., Lam, H. Y., . . . Law, S. (2014). Overexpression of transferrin receptor CD71 and its tumorigenic properties in esophageal squamous cell carcinoma. Oncol Rep, 31(3), 1296-1304. doi: 10.3892/or.2014.2981

Chen, L., Park, S. M., Tumanov, A. V., Hau, A., Sawada, K., Feig, C., . . . Peter, M. E. (2010). CD95 promotes tumour growth. Nature, 465(7297), 492-496.

Chiu, Y. L., & Rana, T. M. (2003). siRNA function in RNAi: a chemical modification analysis. RNA, 9(9), 1034-1048.

Cowley, G. S., Weir, B. A., Vazquez, F., Tamayo, P., Scott, J. A., Rusin, S., . . . Hahn, W. C. (2014). Parallel genome-scale loss of function screens in 216 cancer cell lines for the identification of context-specific genetic dependencies. Sci Data, 1, 140035. doi: 10.1038/sdata.2014.35

Dow, L. E., Premsrirut, P. K., Zuber, J., Fellmann, C., McJunkin, K., Miething, C., . . . Lowe, S. W. (2012). A pipeline for the generation of shRNA transgenic mice. Nat Protoc, 7(2), 374-393. doi: 10.1038/nprot.2011.446

Drachsler, M., Kleber, S., Mateos, A., Volk, K., Mohr, N., Chen, S., . . . Martin-Villalba, A. (2016). CD95 maintains stem cell-like and non-classical EMT programs in primary human glioblastoma cells. Cell death & disease, 7, e2209. doi: 10.1038/cddis.2016.102

Fedorov, Y., Anderson, E. M., Birmingham, A., Reynolds, A., Karpilow, J., Robinson, K., . . . Khvorova, A. (2006). Off-target effects by siRNA can induce toxic phenotype. RNA, 12(7), 1188-1196. doi: 10.1261/rna.28106

Friesen, C., Fulda, S., & Debatin, K. M. (1999). Cytotoxic drugs and the CD95 pathway. Leukemia, 13(11), 1854-1858.

Gao, J., Aksoy, B. A., Dogrusoz, U., Dresdner, G., Gross, B., Sumer, S. O., . . . Schultz, N. (2013). Integrative analysis of complex cancer genomics and clinical profiles using the cBioPortal. Science signaling, 6(269), pl1. doi: 10.1126/scisignal.2004088

Grimm, D., Streetz, K. L., Jopling, C. L., Storm, T. A., Pandey, K., Davis, C. R., . . . Kay, M. A. (2006). Fatality in mice due to oversaturation of cellular microRNA/short hairpin RNA pathways. Nature, 441(7092), 537-541. doi: 10.1038/nature04791

Gu, S., Jin, L., Zhang, Y., Huang, Y., Zhang, F., Valdmanis, P. N., & Kay, M. A. (2012). The loop position of shRNAs and pre-miRNAs is critical for the accuracy of dicer processing in vivo. Cell, 151(4), 900-911. doi: 10.1016/j.cell.2012.09.042

Gu, S., Zhang, Y., Jin, L., Huang, Y., Zhang, F., Bassik, M. C., . . . Kay, M. A. (2014). Weak base pairing in both seed and 3' regions reduces RNAi off-targets and enhances si/shRNA designs. Nucleic Acids Res, 42(19), 12169-12176. doi: 10.1093/nar/gku854

Gui, S., Sang, X., Zheng, L., Ze, Y., Zhao, X., Sheng, L., . . . Tang, M. (2013). Intragastric exposure to titanium dioxide nanoparticles induced nephrotoxicity in mice, assessed by physiological and gene expression modifications. Part Fibre Toxicol, 10, 4. doi: 10.1186/1743-8977-10-4

Guo, H., Ingolia, N. T., Weissman, J. S., & Bartel, D. P. (2010). Mammalian microRNAs predominantly act to decrease target mRNA levels. Nature, 466(7308), 835-840.

Ha, M., & Kim, V. N. (2014). Regulation of microRNA biogenesis. Nat Rev Mol Cell Biol, 15(8), 509-524. doi: 10.1038/nrm3838

Hadji, A., Ceppi, P., Murmann, A. E., Brockway, S., Pattanayak, A., Bhinder, B., . . . Peter, M. E. (2014). Death induced by CD95 or CD95 ligand elimination. Cell Reports, 10, 208-222.\

Hart, T., Brown, K. R., Sircoulomb, F., Rottapel, R., & Moffat, J. (2014). Measuring error rates in genomic perturbation screens: gold standards for human functional genomics. Mol Syst Biol, 10, 733. doi:10.15252/msb.20145216

Hart, T., Chandrashekhar, M., Aregger, M., Steinhart, Z., Brown, K. R., MacLeod, G., . . . Moffat, J. (2015). High-Resolution CRISPR Screens Reveal Fitness Genes and Genotype-Specific Cancer Liabilities. Cell, 163(6), 1515-1526. doi:10.1016/j.cell.2015.11.015

Hou, F., Chu, C. W., Kong, X., Yokomori, K., & Zou, H. (2007). The acetyltransferase activity of San stabilizes the mitotic cohesin at the centromeres in a shugoshin-independent manner. J Cell Biol, 177(4), 587-597. doi: 10.1083/jcb.200701043

Jackson, A. L., Burchard, J., Schelter, J., Chau, B. N., Cleary, M., Lim, L., & Linsley, P. S. (2006). Widespread siRNA "off-target" transcript silencing mediated by seed region sequence complementarity. RNA, 12(7), 1179-1187. doi: 10.1261/rna.25706

Jang, M., Park, B. C., Kang, S., Chi, S. W., Cho, S., Chung, S. J., . . . Park, S. G. (2009). Far upstream element-binding protein-1, a novel caspase substrate, acts as a cross-talker between apoptosis and the c-myc oncogene. Oncogene, 28(12), 1529-1536. doi: 10. 1038/onc.2009. 11

Jinek, M., East, A., Cheng, A., Lin, S., Ma, E., & Doudna, J. (2013). RNA-programmed genome editing in human cells. Elife, 2, e00471. doi: 10.7554/eLife.00471

Khan, A. A., Betel, D., Miller, M. L., Sander, C., Leslie, C. S., & Marks, D. S. (2009). Transfection of small RNAs globally perturbs gene regulation by endogenous microRNAs. Nat Biotechnol, 27(6), 549-555.

Kim, D. H., Behlke, M. A., Rose, S. D., Chang, M. S., Choi, S., & Rossi, J. J. (2005). Synthetic dsRNA Dicer substrates enhance RNAi potency and efficacy. Nat Biotechnol, 23(2), 222-226. doi: 10.1038/nbt1051

Kim, Y. K., Kim, B., & Kim, V. N. (2016). Re-evaluation of the roles of DROSHA, Export in 5, and DICER in microRNA biogenesis. Proc Natl Acad Sci USA, 113(13), E1881-1889. doi:10.1073/pnas.1602552113

Kleber, S., Sancho-Martinez, I., Wiestler, B., Beisel, A., Gieffers, C., Hill, O., . . . Martin-Villalba, A. (2008). Yes and PI3K Bind CD95 to Signal Invasion of Glioblastoma. Cancer Cell, 13(3), 235-248.

Krammer, P. H. (2000). CD95's deadly mission in the immune system. Nature, 407(6805), 789-795.

Krol, J., Loedige, I., & Filipowicz, W. (2010). The widespread regulation of microRNA biogenesis, function and decay. Nat Rev Genet, 11(9), 597-610.

Lin, X., Ruan, X., Anderson, M. G., McDowell, J. A., Kroeger, P. E., Fesik, S. W., & Shen, Y. (2005). siRNA-mediated off-target gene silencing triggered by a 7 nt complementation. Nucleic Acids Res, 33(14), 4527-4535. doi: 10. 1093/nar/gki762

Love, M. I., Huber, W., & Anders, S. (2014). Moderated estimation of fold change and dispersion for RNA-seq data with DESeq2. Genome Biol, 15(12), 550. doi: 10.1186/s13059-014-0550-8

Lu, J., Getz, G., Miska, E. A., varez-Saavedra, E., Lamb, J., Peck, D., . . . Golub, T. R. (2005). MicroRNA expression profiles classify human cancers. Nature, 435(7043), 834-838.

*Mali*, P., Yang, L., Esvelt, K. M., Aach, J., Guell, M., DiCarlo, J. E., . . . Church, G. M. (2013). RNA-guided human genome engineering via Cas9. Science, 339 (6121), 823-826. doi:10.1126/science.1232033 Marques, J. T., & Williams, B. R. (2005). Activation of the mammalian immune system by siRNAs. Nat Biotechnol, 23(11), 1399-1405. doi: 10. 1038/nbt1 161

Medina-Rivera, A., Defrance, M., Sand, O., Herrmann, C., Castro-Mondragon, J. A., Delerce, J., . . . van Helden, J. (2015). RSAT 2015: Regulatory Sequence Analysis Tools. Nucleic Acids Res, 43(W1), W50-56. doi:10.1093/nar/gkv362

Mi, N., Chen, Y., Wang, S., Chen, M., Zhao, M., Yang, G., . . . Yu, L. (2015). CapZ regulates autophagosomal membrane shaping by promoting actin assembly inside the isolation membrane. Nat Cell Biol, 17(9), 1112-1123. doi: 10.1038/ncb3215

Morgens, D. W., Deans, R. M., Li, A., & Bassik, M. C. (2016). Systematic comparison of CRISPR/Cas9 and RNAi screens for essential genes. Nat Biotechnol, 34(6), 634-636. doi: 10.1038/nbt.3567

Morgulis, A., Gertz, E. M., Schaffer, A. A., & Agarwala, R. (2006). A fast and symmetric DUST implementation to mask low-complexity DNA sequences. J Comput Biol, 13(5), 1028-1040. doi:10.1089/cmb.2006.13.1028

Murmann, A. E., McMahon, K. M., Halluck-Kangas, A., Ravindran, N., Patel, M., Law, C., . . . Peter, M. E. (2017). Induction of DISE in ovarian cancer cells in vivo. BioRxive, https://doi.org/10.1101/141945.

Parplys, A. C., Zhao, W., Sharma, N., Groesser, T., Liang, F., Maranon, D. G., . . . Wiese, C. (2015). NUCKS1 is a novel RAD51AP1 paralog important for homologous recombination and genome stability. Nucleic Acids Res, 43(20), 9817-9834. doi: 10.1093/nar/gkv859

Patel, M., & Peter, M. E. (2017). Identification of DISE-inducing shRNAs by monitoring cellular responses. BioRxive, https://doi.org/10.1101/186890.

Peter, M. E., Budd, R. C., Desbarats, J., Hedrick, S. M., Hueber, A. O., Newell, M. K., . . . Lynch, D. H. (2007). The CD95 receptor: apoptosis revisited. Cell, 129(3), 447-450.

Petri, S., & Meister, G. (2013). siRNA design principles and off-target effects. Methods Mol Biol, 986, 59-71. doi: 10.1007/978-1-62703-311-4_4

Pham, D. H., Moretti, P. A., Goodall, G. J., & Pitson, S. M. (2008). Attenuation of leakiness in doxycycline-inducible expression via incorporation of 3' AU-rich mRNA destabilizing elements. Biotechniques, 45(2), 155-156. doi: 10.2144/000112896

Pham, D. H., Powell, J. A., Gliddon, B. L., Moretti, P. A., Tsykin, A., Van der Hoek, M., . . . Pitson, S. M. (2014). Enhanced expression of transferrin receptor 1 contributes to oncogenic signalling by sphingosine kinase 1. Oncogene, 33(48), 5559-5568. doi: 10.1038/onc.2013.502

Pratt, A. J., & MacRae, I. J. (2009). The RNA-induced silencing complex: a versatile gene-silencing machine. J Biol Chem, 284(27), 17897-17901. doi: 10. 1074/jbc.R900012200

Qadir, A. S., Ceppi, P., Brockway, S., Law, C., Mu, L., Khodarev, N. N., . . . Peter, M. E. (2017). CD95/Fas Increases Stemness in Cancer Cells by Inducing a STAT1-Dependent Type I Interferon Response. Cell Rep, 18(10), 2373-2386. doi: 10.1016/j.celrep.2017.02.037

Quidville, V., Alsafadi, S., Goubar, A., Commo, F., Scott, V., Pioche-Durieu, C., . . . Andre, F. (2013). Targeting the deregulated spliceosome core machinery in cancer cells triggers mTOR blockade and autophagy. Cancer Res, 73(7), 2247-2258. doi: 10.1158/0008-5472.CAN-12-2501

Rabenhorst, U., Thalheimer, F. B., Gerlach, K., Kijonka, M., Bohm, S., Krause, D. S., . . . Zornig, M. (2015). Single-Stranded DNA-Binding Transcriptional Regulator FUBP1 Is Essential for Fetal and Adult Hematopoietic Stem Cell Self-Renewal. Cell Rep, 11(12), 1847-1855. doi: 10.1016/j.celrep.2015.05.038

Robbins, M. A., Li, M., Leung, I., Li, H., Boyer, D. V., Song, Y., . . . Rossi, J. J. (2006). Stable expression of shRNAs in human CD34+ progenitor cells can avoid induction of interferon responses to siRNAs in vitro. Nat Biotechnol, 24(5), 566-571. doi: 10.1038/nbt1206

Schoggins, J. W., Wilson, S. J., Panis, M., Murphy, M. Y., Jones, C. T., Bieniasz, P., & Rice, C. M. (2011). A diverse range of gene products are effectors of the type I interferon antiviral response. Nature, 472(7344), 481-485. doi: 10.1038/nature09907

Shao, D. D., Tsherniak, A., Gopal, S., Weir, B. A., Tamayo, P., Stransky, N., . . . Mesirov, J. P. (2013). ATARiS: computational quantification of gene suppression phenotypes from multisample RNAi screens. Genome Res, 23(4), 665-678. doi: 10.1101/gr. 143586.112

Siomi, H., & Siomi, M. C. (2009). On the road to reading the RNA-interference code. Nature, 457(7228), 396-404. doi: 10.1038/nature07754

Stark, A., Brennecke, J., Bushati, N., Russell, R. B., & Cohen, S. M. (2005). Animal MicroRNAs confer robustness to gene expression and have a significant impact on 3'UTR evolution. Cell, 123(6), 1133-1146. doi: 10.1016/j.cell.2005.11.023

Sun, D., Zhou, M., Kowolik, C. M., Trisal, V., Huang, Q., Kernstine, K. H., . . . Shen, B. (2011). Differential expression patterns of capping protein, protein phosphatase 1, and casein kinase 1 may serve as diagnostic markers for malignant melanoma. Melanoma Res, 21(4), 335-343. doi:10.1097/CMR.0b013e328346b715

Teitz, T., Wei, T., Valentine, M. B., Vanin, E. F., Grenet, J., Valentine, V. A., . . . Kidd, V. J. (2000). Caspase 8 is deleted or silenced preferentially in childhood neuroblastomas with amplification of MYCN. Nat Med, 6(5), 529-535.

Ting, A. H., Suzuki, H., Cope, L., Schuebel, K. E., Lee, B. H., Toyota, M., . . . Baylin, S. B. (2008). A requirement for DICER to maintain full promoter CpG island hypermethylation in human cancer cells. Cancer Res, 68(8), 2570-2575. doi:10.1158/0008-5472.CAN-07-6405
Ui-Tei, K., Naito, Y., Takahashi, F., Haraguchi, T., Ohki-Hamazaki, H., Juni, A., . . . Saigo, K. (2004). Guidelines for the selection of highly effective siRNA sequences for mammalian and chick RNA interference. Nucleic Acids Res, 32(3), 936-948. doi: 10.1093/nar/gkh247
van Dongen, S., Abreu-Goodger, C., & Enright, A. J. (2008). Detecting microRNA binding and siRNA off-target effects from expression data. Nat Methods, 5(12), 1023-1025. doi: 10.1038/nmeth. 1267
Wang, T., Birsoy, K., Hughes, N. W., Krupczak, K. M., Post, Y., Wei, J. J., . . . Sabatini, D. M. (2015). Identification and characterization of essential genes in the human genome. Science, 350(6264), 1096-1101. doi: 10.1126/science.aac7041
Watanabe, C., Cuellar, T. L., & Haley, B. (2016). Quantitative evaluation of first, second, and third generation hairpin systems reveals the limit of mammalian vector-based RNAi. RNA Biol, 13(1), 25-33. doi: 10. 1080/ 15476286.2015.1128062
Wazir, U., Jiang, W. G., Sharma, A. K., & Mokbel, K. (2013). Guanine nucleotide binding protein beta 1: a novel transduction protein with a possible role in human breast cancer. Cancer Genomics Proteomics, 10(2), 69-73.
Yoo, J. K., Choi, S. J., & Kim, J. K. (2013). Expression profiles of subtracted mRNAs during cellular senescence in human mesenchymal stem cells derived from bone marrow. Exp Gerontol, 48(5), 464-471. doi:10.1016/ j.exger.2013.02.022
Zamore, P. D., Tuschl, T., Sharp, P. A., & Bartel, D. P. (2000). RNAi: double-stranded RNA directs the ATP-dependent cleavage of mRNA at 21 to 23 nucleotide intervals. Cell, 101(1), 25-33. doi: 10.1016/S0092-8674 (00)80620-0
Zare, H., Khodursky, A., & Sartorelli, V. (2014). An evolutionarily biased distribution of miRNA sites toward regulatory genes with high promoter-driven intrinsic transcriptional noise. BMC Evol Biol, 14, 74. doi:10.1186/1471-2148-14-74
Zhang, Y., Wang, Y., Wei, Y., Wu, J., Zhang, P., Shen, S., . . . Yu, L. (2016). Molecular chaperone CCT3 supports proper mitotic progression and cell proliferation in hepatocellular carcinoma cells. Cancer Lett, 372(1), 101-109. doi: 10.1016/j.canlet.2015.12.029

Example 2—Identification of DISE-Inducing shRNAs by Monitoring Cellular Responses Reference is made to Patel et al., "Identification of DISE-inducing shRNAs by monitoring cellular responses," Cell Cycle 2017 Nov. 1, 2017, the content and supplemental content of which are incorporated herein by reference in their entireties.

Abstract

Off-target effects (OTE) are an undesired side effect of RNA interference (RNAi) caused by partial complementarity between the targeting siRNA and mRNAs other than the gene to be silenced. The death receptor CD95 and its ligand CD95L contain multiple sequences that when expressed as either si- or shRNAs kill cancer cells through a defined OTE that targets critical survival genes. Death induced by survival gene elimination (DISE) is characterized by specific morphological changes such as elongated cell shapes, senescence-like enlarged cells, appearance of large intracellular vesicles, release of mitochondrial ROS followed by activation of caspase-2, and induction of a necrotic form of mitotic catastrophe. Using genome-wide shRNA lethality screens with eight different cancer cell lines, we recently identified 651 genes as critical for the survival of cancer cells. To determine whether the toxic shRNAs targeting these 651 genes contained shRNAs that kill cancer cell through DISE rather than by silencing their respective target genes, we tested all shRNAs in the TRC library derived from a subset of these genes targeting tumor suppressors (TS). We now report that only by monitoring the responses of cancer cells following expression of shRNAs derived from these putative TS it was possible to identify DISE-inducing shRNAs in five of the genes. These data indicate that DISE in general is not an undefined toxic response of cells caused by a random OTE but rather a specific cellular response with shared features that point at a specific biological function involving multiple genes in the genome.

Introduction

RNA interference is a widely used tool to reduce the expression of mRNAs. RNAi is initiated by double-stranded (ds)RNAs or pre-microRNAs, which are cleaved by Dicer, an RNase III enzyme, producing 21-23 nucleotide short interfering (si)RNAs or micro (mi)RNAs respectively, containing 2nt 3' overhangs[1,2]. The antisense (guide) strand is then loaded onto the endonuclease argonaute 2 (Ago2) in the RNA-induced silencing complex (RISC) and directs the downstream targeting events mostly through complete complementarity between positions 2-8 (the seed region) at the 5' end of the guide strand and a matching sequence (seed match) in the 3'UTR of targeted mRNAs[3-6]. While in case of miRNAs, the guide strand recruits the RISC to the 3' untranslated regions (UTRs) of partially complementary mRNAs to promote translation repression or mRNA cleavage[7,8], the guide strand of an siRNA is designed to be fully complementary to the target mRNA and directs the enzymatic cleavage of the mRNA by the Ago2 protein[9-11]. RNAi can be induced by either transfecting cells with siRNAs, or by introducing short hairpin (sh)RNAs in the form of expression vectors or viruses. Apart from the intended target, the guide strands of siRNAs also recognize many mRNAs with partial complementarity in a manner similar to miRNAs, mostly involving the guide RNA seed, and studies have suggested that 3'UTR complementarity to si/shRNA seed sequences can mediate gene silencing based on an off-target effect (OTE) both through translational repression and mRNA degradation[12-15]. In addition, improper loading of the sense/passenger strand can also lead to OTEs[16]. This can be caused by imprecise cleavage of shRNAs by Dicer prior to RISC loading[16]. The main causes of OTE are therefore cross-reactivities of either the guide RNA or the passenger strand loaded into the RISC[17,18] with transcripts of undesired genes in the genome. The goal for virtually all RNAi projects is to selectively silence targeted genes with little or no OTE. In fact, most of the latest generation siRNAs are chemically modified to increase their stability, specificity, and to reduce OTE[19], and shRNAs are expressed using optimized vector systems that allow preferential loading of guide strand into the RISC[18,20].

We recently reported that >80% of 22 different nonoverlapping si-, Dsi- or shRNAs derived from either CD95L or CD95 killed cancer cells by activating multiple cell death pathways[21,22]. Activation of the CD95/Fas surface receptor upon binding to its cognate ligand (CD95L) induces apoptosis. The CD95/CD95L system is used by immune cells to eliminate virus-infected and cancer cells through the secretion of CD95 ligand (CD95L)[23]. Hence, the CD95/CD95L system has a tumor suppressive function. Interestingly, what at first appeared to be cancer cell death caused by silencing the expression of these two genes, actually turned out to be initiated by a mechanism completely independent of the presence of CD95 or CD95L gene products[22]. We demonstrated that the toxic si- or shRNAs derived from either CD95 or CD95L killed cells in what appeared to be a combination of apoptosis, necrosis and mitotic catastrophe, mediated by the release of mitochondrial ROS, activation of caspase-2, and DNA damage. Morphologically, most cells responded by forming oddly shaped elongated cell structures, with likely stress induced large vesicles, and anaphase bridges[21]. While some cells died as early as one day after introducing the toxic shRNAs, most cells died when attempting to divide[21]. This form of cell death could not be inhibited and cancer cells had a hard time developing resistance both in vitro and in vivo[21, 24]. We recently presented data to suggest that cells actually die through an OTE that results in the preferential targeting of the 3'UTRs of a set of critical survival genes[22]. We have therefore named this form of cell death DISE (for death induced by survival gene elimination).

The discovery of DISE raised a number of puzzling questions: Why did the cancer cells appear to respond to the toxic shRNAs in a highly similar way? Why would an OTE not result in a variety of unintended cellular responses, depending on what gene or sets of genes are affected? In this study we set out to identify novel toxic shRNAs derived from a small subset of putative tumor suppressor genes other than CD95 and CD95L. Solely by monitoring cellular responses (morphology, biochemical changes, and ability to divide) by the cancer cells we have identified shRNAs derived from 5 putative tumor suppressive genes that can kill multiple cancer cells by an OTE in the absence of the coded protein that resembles DISE. We propose that these RNAi active sequences can be used to kill cancer cells.

Results

A Subset of Genes Recently Found to be Critical for the Survival of Cancer Cells are Tumor Suppressors.

Previously, based on 12 shRNA-based lethality screens of 8 human cancer cell lines/cell line variants (HeLa, S3, HeLa N10, CHP-100, FU-UR-1, HEK293, A549 EGFRB, A549, H2030), we nominated 651 out of ~18,0000 genes targeted (by ~78,000 shRNAs, individually tested) as critical survival factors for cancer cells[21]. Included were all genes for which at least 3 out of 5 shRNAs (H factor=60) reduced cell viability more than 95% in at least 9 out of 12 independent screens[21]. Most of the 651 genes had genuine survival functions and included genes coding for ribosomal proteins, cell cycle regulators or all three RAS genes (see Table S2 in Hadji et al. 2014). However, a survival function was not immediately obvious for a number of these genes and therefore they could be sources of DISE-inducing shRNAs. To increase the chance of finding such toxic shRNAs, we decided to focus on a subset of genes most unlikely to be required for cancer cell survival: tumor suppressors (TS). To identify potential TS among the 651 genes identified as survival genes, we compared the 651 genes with a curated list of 637 putative TS genes[25]. This analysis resulted in 17 putative TS genes (ARMC10, BECLIN1, CHEK1, DDX3X, DPP4, EFNA5, ITGAV, MAPKAPK5, NGFR, PAFAH1B1, PHB, PTCH2, SOCS3, THY1, TMEFF1, TGFBR2, ZNF366, plus CD95L (i.e., "FASLG")) for which up to 94% of the targeting shRNAs killed a number of cancer cell lines in the shRNA lethality screen. For each of the 17 genes, tumor suppressive activities have been described for various cancers (see legend of FIG. 19).

Identification of RNAi Active Toxic Sequences Derived from Certain Tumor suppressors.

The finding that shRNAs derived from TS can kill cancer cells suggested that they may not act by reducing protein levels of their targeted genes, but by another mechanism, possibly DISE. We therefore decided to first validate the toxicity by testing five shRNAs per gene, a total of 85 shRNAs. Because we were only interested in shRNAs that killed all cancer cells, we chose three additional cell lines for this test, which were not part of the original shRNA lethality screen: HeyA8 (ovarian cancer), T89G (glioblastoma), and HCT116 (colon cancer). The latter two cell lines were chosen because we used them before to study and biochemically characterize DISE[21]. We decided on a sequential strategy: test the shRNAs on HeyA8 cells, then test the toxic ones on T98G cells and test all shRNAs that killed these two cell lines on HCT116 cells. To identify two shRNAs per gene that killed HeyA8 cells, the 85 shRNAs (in the pLKO backbone) were screened in 96 well plates targeting the 17 TSs using a Thermo Multidrop Combi and a Tecan Freedom EVO200 for infecting cells at an MOI of five. After puromycin selection the effect on growth was monitored in the IncuCyte Zoom. For each gene, the two shRNAs that caused the strongest growth reduction were identified and used for further analysis (data not shown). This resulted in the identification of 34 toxic shRNAs targeting the 17 TS.

Because we were interested in determining if these shRNAs had similar activities and elicited cellular responses similar to the DISE-inducing shRNAs derived from CD95 or CD95L, we retested these 34 toxic shRNAs at an MOI of three on HeyA8, T98G and HCT116 cells. This was done again in the IncuCyte Zoom and growth reduction (50% reduction compared to cells infected with a nontargeting shRNA at half maximal confluency) was used as an initial surrogate marker for cell death. All 34 shRNAs targeting the 17 TS were identified as toxic to HeyA8 cells, validating the original screen. (FIG. 15). Not surprisingly, while shRNAs against the tested TS were toxic, when we tested 4-5 shRNAs targeting two of the most widely studied and most highly mutated TS in human cancers, p53 and PTEN, none of them qualified as toxic shRNAs using the threshold we had defined (data not shown). This suggested that only certain TS contain RNAi active sequences that can kill cancer cells. Of the 34 shRNAs targeting the 17 TS genes, 30 shRNAs were also toxic to T98G cells targeting 15 of the TSs (ARMC10, CHEK1, DDX3X, DPP4, ITGAV, MAPKAPK5, NGFR, PAFAH1B1, PHB, PTCH2, SOCS3, THY1, TMEFF1, TGFBR2, ZNF366) (data not shown). Because we were only interested in shRNAs that kill all three cancer cells, we only tested these 30 shRNAs on HCT116 cells. This reduced the number of shRNAs that killed all three cell lines to 26 shRNAs (targeting 13 TS: ARMC10, CHEK1, DDX3X, DPP4, ITGAV, MAPKAPK5, PAFAH1B1, PHB, PTCH2, SOCS3, THY1, TMEFF1, TGFBR2).

Toxic TS Derived shRNAs Trigger DISE-Like Cell Death.

To determine which of the shRNAs killed the three cell lines in a fashion similar to DISE induction observed with CD95L derived shRNAs, we compared the morphological changes seen in HeyA8 and T98G cells after infection with a lentiviral shRNA with that seen in cells infected with the CD95L derived shL3. We were unable to perform a morphological analysis in HCT116 cells since the cells were too small and without clear morphological features to distinguish. In HeyA8 cells, 3-7 days after infection, we detected the typical stress-induced elongated cell shapes (FIG. 16A), appearance of large intracellular vesicles, and enlargement and senescence-like cell flattening (FIG. 16B). 8 of the 13 remaining TS genes had shRNAs that both elicited these changes (ARMC10, DPP4, MAPKAPK5, PAFAH1B1, PTCH2, SOCS3, TGFBR2, and TMEFF1) (FIG. 16). In T98G cells, for the same 8 genes (all of the 16 shRNAs), we observed that the cells attempted to divide and immediately after that they rounded up and died (data not shown).

In order to determine whether the remaining 16 shRNAs induced cell death biochemically similar to DISE, we tested whether these shRNAs caused ROS production and caspase-2 activation in HeyA8 cells—two characteristic features of DISE seen in HeyA8 cells after infection with shL3 and also observed in multiple other cell lines after introducing multiple CD95L or CD95 targeting shRNAs[21]. For 7 of the remaining TS, both shRNAs caused significant induction of ROS and caspase-2 activation (ARMC10, MAPKAPK5, PAFAH1B1, PTCH2, SOCS3, TGFBR2, and TMEFF1) (FIGS. 17A and 17B). Our sequential analysis in three cancer cell lines also allowed us to narrow down the list of potential shRNAs that killed cancer cells by DISE to seven (ARMC10, MAPKAPK5, PAFAH1B1, PTCH2, SOCS3, TGFBR2, and TMEFF1). To confirm that all shRNAs derived from these seven genes did not just result in growth reduction but actually killed cancer cells, we quantified DNA fragmentation in HeyA8 cells 8 days after lentiviral infection (FIG. 17C). Indeed, all 14 shRNAs caused a significant increase in subG1 DNA, suggesting that they all at various levels killed cancer cells.

Toxic shRNAs Derived from Five TS Genes Kill Cancer Cells Through DISE.

One of the most surprising properties of DISE-inducing shRNAs is that they kill cancer cells independent of targeting the mRNA they were designed to silence; instead we reported that these sequences are toxic to cells through a unique form of OTE that targets a network of critical survival genes[22]. We narrowed down our list of toxic shRNAs to only include shRNAs that killed cancer cells in a way that was similar to DISE in morphology and biochemistry; we now considered whether these TS genes were enriched in shRNAs that kill cancer cells in a way independent of the expression of the coding protein, which would be indicative of the toxic OTE that is DISE. We chose to study this using HAP1 cells for two reasons: 1) They are available as knock-out cells (generated by using CRISPR/Cas9 gene editing) for most human genes (that are not essential for cell survival) and 2) We recently demonstrated that DISE-inducing shRNAs derived from either CD95 or CD95L could still kill CD95 or CD95L deficient HAP1 cells (data not shown). For five of the seven genes, both shRNAs reduced growth of unmodified HAP1 cells >50% (FIG. 20); hence these five genes could be tested in HAP1 CRISPR/Cas9 modified cells. In all HAP1 cells using CRISPR/Cas9 gene editing a frame shift mutation was introduced downstream of the translational start codon. Two of the mutant clones, ARMC10 and MAPKAPK5, were validated by Western blotting to be protein knock outs (data not shown). Two of the genes, SOCS3 and TMEFF1, are not expressed in HAP1 cells (Transcripts Per Kilobase Million (TPM) of less than 3 in RNA Seq analysis are considered undetectable[26]). All of the 5 CRISPR/Cas9 modified cell lines still died after the introduction of shRNAs derived from these genes (FIG. 18). Indeed, all shRNAs derived from these 5 genes caused a significant increase in subG1 DNA (data not shown) suggesting that they all at various levels killed cancer cells.

Because for two of the genes the Western blot confirmation of a complete knockout was inconclusive (MAPKAPK5—multiple bands; and TGFBR2—no band), an additional k.o clone was generated and tested. For MAPKAPK5 an out-of-frame deletion was introduced into exon 8 and for TGFBR2 in exon 4 (data not shown). Both clones were as sensitive to the two toxic shRNAs derived from these genes as wt cells (data not shown). The data indicate that all of the toxic shRNAs we identified derived from the five TS killed the cells through an OTE. Because the result of this OTE is cell death and because this cell death in all tested cell lines resembled DISE we conclude that these genes contain toxic sequences that can kill cancer cells by DISE. These data suggest that CD95 and CD95L are not unique and that the human genome likely contains multiple genes that contain sequences that have DISE inducing activities when expressed as small double stranded RNAs.

Discussion

RNAi has become one of the most utilized methods to study the function of genes. Countless reports of gene-specific silencing and genome-wide screens document the power of RNAi[21, 27-30]. However, one caveat of RNAi screens is the OTE. This can be caused by cross-reactivities between the guide strand of the siRNA and the target mRNAs due to partial complementarity. In addition, OTE can be caused by unintended loading of the passenger strand into the RISC. OTE has been described to occur[16] and was found to affect many genes and to only require a complementarity of 6-7 nucleotides between the targeting si/shRNA and the affected mRNAs[12-14]. However, studies were unable to predict which genes would be and which genes would not be affected by OTE[13]. This finding is consistent with the assumption that OTEs are truly random. When all OTEs are truly random, one would expect cells to respond in various ways depending on the mRNAs affected by the OTE. Similarly, when OTEs lead to cell death, one would assume that different forms of cell death with different morphologies and different signaling pathways would be activated.

We recently identified a general OTE that results in the death of most tested cancer cells. It was found to preferentially affect transformed cells[21], and among them cancer stem cells[31]. Interestingly, this OTE preferentially affected genes that are critical for cancer cell survival. We named this from of cell death DISE (death induced by survival gene elimination). Cells dying by DISE, in most cases, display similar morphologies and share a number of biochemical responses suggesting that DISE is not a random occurrence but has an underlying specific biological purpose which we are currently studying.

DISE was discovered by testing a large number of si- and shRNAs derived from either CD95 or CD95L. Since it was a sequence-specific OTE, it was likely that other genes also contained sequences that when expressed as shRNAs would induce DISE. We have now confirmed that shRNAs derived from a number of TS can induce a form of cell death that resembles DISE, with the same morphology, elongated cell shapes, ROS production, activation of caspase-2, inability to properly divide followed by DNA degradation and cell death. Solely by scoring similarities between the responses of cells to different toxic shRNAs did we identify 10 shRNAs (targeting 5 TS) that all killed cancer cells in which the gene was either disabled by CRISPR/Cas9 gene editing (protein knockout confirmed for two of them) or not expressed. In contrast, none of the shRNAs designed to silence the two most highly studied TS, p53 and PTEN caused significant cell death, suggesting that it is a selective group of genes that contain toxic RNAi active sequences.

Our data do not allow us to conclude that shRNAs derived from TS are particularly prone to inducing DISE. TS were merely chosen as a group of genes that were most unlikely to be critical for the survival of cancer cells. Hence, the shRNAs derived from our lethality screens designed to target TS were expected to be enriched in shRNAs that induce cell death by an OTE. Our data now suggest that certain TS-derived shRNAs can kill cancer cells through DISE and in five cases, we provide evidence to suggest that these shRNAs killed the cells in the absence of functional protein consistent with the action of the DISE mechanism. Based on these data, we propose that DISE is a general mechanism through which toxic shRNAs derived from multiple genes kill cancer cells.

Materials and Methods

Reagents.

Propidium iodide (#P4864) and puromycin (#P9620) were purchased from Sigma-Aldrich. Antibodies used for western blot were: anti-MAPKAPK5 (D70A10) rabbit mAb from Cell Signaling (#7419); anti-ARMC10 (#NBP1-81127) rabbit pAb from Novus Biologicals; and goat anti-rabbit IgG human adsorbed-HRP #4010-05) was from Southern Biotech.

Cell Lines.

The ovarian cancer cell line HeyA8, and the colon cancer cell line HCT116 were grown in RPMI 1640 medium (Mediatech Inc), supplemented with 10% heat-inactivated FBS (Sigma-Aldrich), 1% L-glutamine (Mediatech Inc), and 1% penicillin/streptomycin (Mediatech Inc). The glioblastoma cell line T98G was grown in EMEM (ATCC #30-2003), containing 10% heat-inactivated FBS, 1% L-Glutamine, and 1% penicillin/streptomycin. The chronic myelogenous leukemia cell line HAP1 (Horizon Discovery #C631), HAP1 ARMC10 k.o. (Horizon Discovery #HZGH005198c009, 2 bp deletion in exon 2, k.o. validated by Western blotting), HAP1 TGFBR2 k.o. (Horizon Discovery #HZGHC000035c015, 13 bp deletion in exon 1, and cat #HZGHC006289c002-7 bp deletion in exon 4, protein not detectable by Western blotting), HAP1 TMEFF1 k.o. (Horizon Discovery #HZGHC005199c011, 2 bp deletion in exon 2, k.o. not validated by Western blotting), HAP1 SOCS3 k.o. (Horizon Discovery #HZGHC005447c010, 25 bp deletion in exon 2, protein not detectable by Western blotting), and HAP1 MAPKAPK5 k.o. (Horizon Discovery #HZGHC000217c004, 4 bp deletion in exon 2, and cat #HZGHC006287c012-4 bp deletion in exon 8, k.o. validated by Western blotting) cell lines, were cultured in Gibco IMDM (Life Technologies #12440053), supplemented with 10% heat-inactivated FBS, 1% L-Glutamine, and 1% penicillin/streptomycin.

Knockdown Via Lentiviral shRNAs.

Cells were infected with the following MISSION® Lentiviral Transduction Particles (Sigma): pLKO.1-puro Control Transduction Particle coding for a nontargeting (scrambled) shRNA (#SHC002V), shRNAs against mRNA NM_000430 (*Homo sapiens* PAFAH1B1) TRCN0000050966 (#1: TGACCATTAAACTATGGGATT (SEQ ID NO:85)) and TRCN0000050964 (#7: CGTATGGGATTACAAGAACAA (SEQ ID NO:86)), shRNAs against mRNA NM_002507 (*Homo sapiens* NGFR) TRCN00000058155 (#3: CCTCCAGAACAAGACCTCATA (SEQ ID NO:87)) and TRCN00000058157 (#5: GCCTACGGCTACTACCAGGAT (SEQ ID NO:88)), shRNAs against mRNA NM_002210 (*Homo sapiens* ITGAV) TRCN0000010768 (#4: GTGAGGTCGAAACAGGATAAA (SEQ ID NO:89)) and TRCN0000010769 (#5: CGACAGGCTCACATTCTACTT (SEQ ID NO:90)), shRNAs against mRNA NM_001935 (*Homo sapiens* DPP4) TRCN0000050773 (#1: GCCCAATTTAACGACACAGAA (SEQ ID NO:91)) and TRCN0000050776 (#7: GACTGAAGTTATACTCCTTAA (SEQ ID NO:92)), shRNAs against mRNA NM_010109 (*Homo sapiens* EFNA5) TRCN0000058218 (#1: GAGACCAACAAATAGCTGTAT (SEQ ID NO:93)) and TRCN0000058220 (#3: CGCGGCACAAACACCAAGGAT (SEQ ID NO:94)), shRNAs against mRNA NM_003692 (*Homo sapiens* TMEFF1) TRCN0000073510 (#3: CATGCCAATTTCAGTGCCATA (SEQ ID NO:95)) and TRCN0000073511 (#4: GCCAATTTCAGTGCCATACAA (SEQ ID NO:96)), shRNAs against mRNA NM_001274 (*Homo sapiens* CHEK1) TRCN0000009947 (#2: GACAGAATAGAGCCAGACATA (SEQ ID NO:97)) and TRCN0000039856 (#3: GCCCACATGTCCTGATCATAT (SEQ ID NO:98)), shRNAs against mRNA NM_003738 (*Homo sapiens* PTCH2) TRCN0000033327 (#9: GCTGCATTACACCAAGGAGAA (SEQ ID NO:99)) and TRCN0000033328 (#10: CGTACTCACATCCATCAACAA (SEQ ID NO:100)), shRNAs against mRNA NM_031905 (*Homo sapiens* ARMC10) TRCN0000130777 (#3: GCACATGCTTCACAGTTACAT (SEQ ID NO:101)) and TRCN0000128466 (#5: GCTTTAGTTGATCACCATGAT (SEQ ID NO:102)), shRNAs against mRNA NM_003766 (*Homo sapiens* BECN1) TRCN0000033552 (#2: CTCAAGTTCATGCTGACGAAT (SEQ ID NO:103)) and TRCN0000033553 (#8: GCTTGGGTGTCCTCACAATTT (SEQ ID NO:104)), shRNAs against mRNA NM_001356 (*Homo sapiens* DDX3X) TRCN0000000002 (#2: CGGAGTGATTACGATGGCATT (SEQ ID NO:105)) and TRCN0000000003 (#3: CGTAGAATAGTCGAACAAGAT (SEQ ID NO:106)), shRNAs against mRNA NM_006288 (*Homo sapiens* THY1) TRCN0000057023 (#1: GCCATGAGAATACCAGCAGTT (SEQ ID NO:107)) and TRCN0000057024 (#2: CGAACCAACTTCACCAGCAAA (SEQ ID NO:108)), shRNAs against mRNA NM_002634 (*Homo sapiens* PHB) TRCN0000029204 (#1: CCCAGAAATCACTGTGAAATT (SEQ ID NO:109)) and TRCN0000029208 (#5: GAGTTCACAGAAGCGGTGGAA (SEQ ID NO:110)), shRNAs against mRNA NM_003955 (*Homo sapiens* SOCS3) TRCN0000057073 (#1: CCACCTGGACTCCTATGAGAA (SEQ ID NO:111)) and TRCN0000057076 (#4: CGGCTTCTACTGGAGCGCAGT (SEQ ID NO:112)), shRNAs against mRNA NM_152625 (*Homo sapiens* ZNF366) TRCN0000020134 (#1: AGGCAGTTCAAATATAGCTTT (SEQ ID NO:113)) and TRCN0000020135 (#2: GCCCACAAAGATGCCCTATAA (SEQ ID NO:114)), shRNAs against mRNA NM_003668 (Home *sapiens* MAPKAPK5) TRCN0000000681 (#1: GCGGCACTGTCACTTGTTAAA (SEQ ID NO:115)) and TRCN0000195129 (#4: CAGTATCAATTGGACTCAGAA (SEQ ID NO:116)), shRNAs against mRNA NM_003242 (*Homo sapiens* TGFBR2) TRCN0000195606 (#4: CGACATGATAGTCACTGACAA (SEQ ID NO:117)) and TRCN0000197056 (#5: GACCTCAAGAGCTCCAATATC (SEQ ID NO:118)), shRNA targeting mRNA NM_000639 (*Homo sapiens* FasLG) TRCN0000059000 (shL3: ACTGGGCTGTACTTTGTATAT (SEQ ID NO:119)), 5 shRNAs targeting mRNA NM_000314 (*Homo sapiens* PTEN) TRCN0000355840 (#1: GGCACAAGAGGCCCTAGATTT (SEQ ID NO:120)), TRCN0000355841 (#2: ACAGTAGAGGAGCCGTCAAAT (SEQ ID NO:121)), TRCN0000355842 (#3: GACTTAGACTTGACCTATATT (SEQ ID NO:122)), TRCN0000355843 (#4: GACGAACTGGTGTAATGATAT (SEQ ID NO:123)), TRCN0000355946 (#5: ACATTATGACACCGCCAAATT (SEQ ID NO:124)), 4 shRNAs targeting mRNA NM_000546 (*Homo sapiens* TP53) TRCN0000342334 (#1: CACCATCCACTACAACTACAT (SEQ ID NO:125)), TRCN0000342335 (#2: CGGCGCACAGAGGAAGAGAAT (SEQ ID NO:126)), TRCN0000003754 (#3: TCAGACCTATGGAAACTACTT (SEQ ID NO:127)), TRCN0000342259 (#4: GTCCAGAT-GAAGCTCCCAGAA (SEQ ID NO: 128)).

Infection was performed according to the manufacturer's protocol. Briefly, 50,000 cells seeded the day before on a 6-well plate were infected with each lentivirus at an MOI of 3 in presence of 8 µg/mL polybrene overnight. Media was changed the next day, followed by selection with 3 µg/mL puromycin 24 hours later. Cells were selected for at least 48 hours, then seeded on a 96-well plate and placed in the IncuCyte (Essen Bioscience) to measure confluence or expanded for 4 days to assess cell viability with propidium iodide staining.

ROS Measurement.

Intracellular ROS production was measured after 8 days of infection with lentiviral shRNAs by incubating cells with 10 µM CM-H2DCFDA (C6827; Invitrogen Molecular Probes) in media at 37° C. for 30 min. CM-H2DCFDA, a cell-permeable fluorogenic probe, is cleaved by intracellular esterases forming DCFH, which in presence of ROS, gets oxidized to the fluorescent compound DCF. Following incubation, cells were washed three times with PBS, and ROS was quantified by flow cytometry.

Caspase-2 Activity Measurement.

Intracellular caspase-2 activity was detected in situ using FAM-VDVAD-FMK (ImmunoChemistry Technologies, LLC) according to the manufacturer's instructions. Briefly, cells were harvested 8 days after infection with lentiviral shRNAs. The pellet was resuspended in 290 µl of medium, to which 10 µl of 30×FAM-VDVAD-FMK was added. Cells were incubated at 37° C. for 1 hour, washed with PBS, and resuspended in 300 µl of medium. Cells were kept on ice protected from light and immediately analyzed by flow cytometry.

Cell Death Assay (Propidium Iodide Staining).

Cells infected with lentiviral shRNAs were plated in triplicates on 12 well plates after 2 days of puromycin selection, and plates were incubated at 37° C. for 4 days. The total cell pellet consisting of live and dead cells was resuspended in Nicoletti buffer (0.1% sodium citrate, pH 7.4, 0.05% Triton X-100, 50 µg/ml propidium iodide). After incubating for 2-4 hours in the dark at 4° C., percent cell death was quantified by flow cytometry.

Western Blot Analysis.

Cells were lysed using RIPA lysis buffer (1% SDS, 1% Triton X-100, 1% deoxycholic acid) and protein concentration was determined using the DC Protein Assay kit (Bio-Rad). Equal amounts of protein (30 µg) were resolved on 10% SDS-PAGE gels and transferred to nitrocellulose membrane (Amersham Protran 0.45 am, GE Healthcare Life Science). The membranes were blocked with 5% non-fat dry milk in 0.1% Tween-20/TBS and then incubated in primary antibodies at 4° C. overnight. After washing 3 times with TBST, membranes were incubated with secondary antibodies followed by washing again. Detection was performed using the ECL™ Western Blotting Detection Reagents reagent (GE Healthcare) and developed using a chemiluminescence imager, G:BOX Chemi XT4 (Syngene). Both primary and secondary antibodies were diluted in the blocking buffer (5% milk in 0.1% Tween-20/TBS) as follows: anti-ARMC10 (1:250), anti-MAPKAPK5 (1:1000) and goat anti-rabbit IgG human adsorbed-HRP (1:5000).

Statistical Analyses.

Growth reduction was scored as significant when cell growth was inhibited at least 50% at the half maximal growth of shScr infected cells. Percent growth reduction values were calculated using the formula: $[(y_1-c_1)-(y_2-c_2)]/[(y_1-c_1)]*100$ where $y_1$ is the half maximal confluency for cells infected with shScr (i.e. if the cells grew from 5% to 100% then $y_1=[(100+5)/2]$); $c_1$ is the starting confluency for cells infected with shScr. STATA1C software was then used to obtain the time ($t_1$) for $y_1$ and also to obtain the value of $y_2$, which is the confluency of cells infected with TS shRNAs at $t_1$, and $c_2$ is their starting confluency. Experiments were performed in triplicates and the data were expressed as mean±SD. Statistical analysis was performed using Student's two-tailed t-test. A value of $p<0.05$ was considered to be significant.

REFERENCES

1. Zamore P D, Tuschl T, Sharp P A, Bartel D P. RNAi: double-stranded RNA directs the ATP-dependent cleavage of mRNA at 21 to 23 nucleotide intervals. Cell 2000; 101:25-33.
2. Bernstein P L, Herrick D J, Prokipcak R D, Ross J. Control of c-myc mRNA half-life in vitro by a protein capable of binding to a coding region stability determinant. Genes Dev 1992; 6:642-54.
3. Kawamata T, Seitz H, Tomari Y. Structural determinants of miRNAs for RISC loading and slicer-independent unwinding. Nat Struct Mol Biol 2009; 16:953-60.
4. Matranga C, Tomari Y, Shin C, Bartel D P, Zamore P D. Passenger-strand cleavage facilitates assembly of siRNA into Ago2-containing RNAi enzyme complexes. Cell 2005; 123:607-20.
5. Rivas F V, Tolia N H, Song J J, Aragon J P, Liu J, Hannon G J, et al. Purified Argonaute2 and an siRNA form recombinant human RISC. Nat Struct Mol Biol 2005; 12:340-9.
6. Yoda M, Kawamata T, Paroo Z, Ye X, Iwasaki S, Liu Q, et al. ATP-dependent human RISC assembly pathways. Nat Struct Mol Biol 2010; 17:17-23.
7. Bartel D P. MicroRNAs: genomics, biogenesis, mechanism, and function. Cell 2004; 116:281-97.
8. Carthew R W, Sontheimer E J. Origins and Mechanisms of miRNAs and siRNAs. Cell 2009; 136:642-55.
9. Hammond S M, Bernstein E, Beach D, Hannon G J. An RNA-directed nuclease mediates post-transcriptional gene silencing in *Drosophila* cells. Nature 2000; 404:293-6.
10. Elbashir S M, Lendeckel W, Tuschl T. RNA interference is mediated by 21- and 22-nucleotide RNAs. Genes Dev 2001; 15:188-200.
11. Nykanen A, Haley B, Zamore P D. ATP requirements and small interfering RNA structure in the RNA interference pathway. Cell 2001; 107:309-21.
12. Jackson A L, Burchard J, Schelter J, Chau B N, Cleary M, Lim L, et al. Widespread siRNA "off-target" transcript silencing mediated by seed region sequence complementarity. RNA 2006; 12:1179-87.
13. Birmingham A, Anderson E M, Reynolds A, Ilsley-Tyree D, Leake D, Fedorov Y, et al. 3' UTR seed matches, but not overall identity, are associated with RNAi off-targets. Nat Methods 2006; 3:199-204.
14. Lin X, Ruan X, Anderson M G, McDowell J A, Kroeger P E, Fesik S W, et al. siRNA-mediated off-target gene silencing triggered by a 7 nt complementation. Nucleic Acids Res 2005; 33:4527-35.

15. Lim L P, Lau N C, Garrett-Engele P, Grimson A, Schelter J M, Castle J, et al. Microarray analysis shows that some microRNAs downregulate large numbers of target mRNAs. Nature 2005; 433:769-73.
16. Gu S, Jin L, Zhang Y, Huang Y, Zhang F, Valdmanis P N, et al. The loop position of shRNAs and pre-miRNAs is critical for the accuracy of dicer processing in vivo. Cell 2012; 151:900-11.
17. Petri S, Meister G. siRNA design principles and off-target effects. Methods Mol Biol 2013; 986:59-71.
18. Fellmann C, Hoffmann T, Sridhar V, Hopfgartner B, Muhar M, Roth M, et al. An optimized microRNA backbone for effective single-copy RNAi. Cell Rep 2013; 5:1704-13.
19. Deleavey G F, Damha M J. Designing chemically modified oligonucleotides for targeted gene silencing. Chem Biol 2012; 19:937-54.
20. Chang K, Marran K, Valentine A, Hannon G J. Creating an miR30-based shRNA vector. Cold Spring Harbor protocols 2013; 2013:631-5.
21. Hadji A, Ceppi P, Murmann A E, Brockway S, Pattanayak A, Bhinder B, et al. Death induced by CD95 or CD95 ligand elimination. Cell Reports 2014; 10:208-22.
22. Putzbach W, Gao Q Q, Patel M, van Dongen S, Haluck-Kangas A, Sarshad A A, et al. Toxic si/shRNAs that kill cancer cells by targeting survival genes BioRxive 2017: BIORXIV/2017/141952.
23. Krammer P H. CD95's deadly mission in the immune system. Nature 2000; 407:789-95.
24. Murmann A E, McMahon K M, Halluck-Kangas A, Ravindran N, Patel M, Law C, et al. Induction of DISE in ovarian cancer cells in vivo. BioRxive 2017:BIORXIV/2017/141945.
25. Zhao M, Sun J, Zhao Z. TSGene: a web resource for tumor suppressor genes. Nucleic Acids Res 2013; 41:D970-6.
26. Essletzbichler P, Konopka T, Santoro F, Chen D, Gapp B V, Kralovics R, et al. Megabase-scale deletion using CRISPR/Cas9 to generate a fully haploid human cell line. Genome Res 2014; 24:2059-65.
27. Wang T, Birsoy K, Hughes N W, Krupczak K M, Post Y, Wei J J, et al. Identification and characterization of essential genes in the human genome. Science 2015; 350:1096-101.
28. Hart T, Brown K R, Sircoulomb F, Rottapel R, Moffat J. Measuring error rates in genomic perturbation screens: gold standards for human functional genomics. Mol Syst Biol 2014; 10:733.
29. Morgens D W, Deans R M, Li A, Bassik M C. Systematic comparison of CRISPR/Cas9 and RNAi screens for essential genes. Nat Biotechnol 2016; 34:634-6.
30. Cowley G S, Weir B A, Vazquez F, Tamayo P, Scott J A, Rusin S, et al. Parallel genome-scale loss of function screens in 216 cancer cell lines for the identification of context-specific genetic dependencies. Scientific data 2014; 1:140035.
31. Ceppi P, Hadji A, Kohlhapp F, Pattanayak A, Hau A, Xia L, et al. CD95 and CD95L promote and protect cancer stem cells. Nature Commun 2014; 5:5238.
32. Xing Z, Tang X, Gao Y, Da L, Song H, Wang S, et al. The human LIS1 is downregulated in hepatocellular carcinoma and plays a tumor suppressor function. Biochem Biophys Res Commun 2011; 409:193-9.
33. Yuanlong H, Haifeng J, Xiaoyin Z, Jialin S, Jie L, Li Y, et al. The inhibitory effect of p75 neurotrophin receptor on growth of human hepatocellular carcinoma cells. Cancer Lett 2008; 268:110-9.
34. Dimaras H, Gallie B L. The p75 NTR neurotrophin receptor is a tumor suppressor in human and murine retinoblastoma development. Int J Cancer 2008; 122:2023-9.
35. Khwaja F, Tabassum A, Allen J, Djakiew D. The p75(NTR) tumor suppressor induces cell cycle arrest facilitating caspase mediated apoptosis in prostate tumor cells. Biochem Biophys Res Commun 2006; 341:1184-92.
36. Tabassum A, Khwaja F, Djakiew D. The p75(NTR) tumor suppressor induces caspase-mediated apoptosis in bladder tumor cells. Int J Cancer 2003; 105:47-52.
37. Kaur S, Kenny H A, Jagadeeswaran S, Zillhardt M R, Montag A G, Kistner E, et al. {beta}3-integrin expression on tumor cells inhibits tumor progression, reduces metastasis, and is associated with a favorable prognosis in patients with ovarian cancer. Am J Pathol 2009; 175:2184-96.
38. McCarty J H, Barry M, Crowley D, Bronson R T, Lacy-Hulbert A, Hynes R O. Genetic ablation of alphav integrins in epithelial cells of the eyelid skin and conjunctiva leads to squamous cell carcinoma. Am J Pathol 2008; 172:1740-7.
39. Wesley U V, Tiwari S, Houghton A N. Role for dipeptidyl peptidase IV in tumor suppression of human non small cell lung carcinoma cells. Int J Cancer 2004; 109:855-66.
40. Li J J, Liu D P, Liu G T, Xie D. EphrinA5 acts as a tumor suppressor in glioma by negative regulation of epidermal growth factor receptor. Oncogene 2009; 28:1759-68.
41. Gery S, Yin D, Xie D, Black K L, Koeffler H P. TMEFF1 and brain tumors. Oncogene 2003; 22:2723-7.
42. Sinha S, Singh R K, Bhattacharya N, Mukherjee N, Ghosh S, Alam N, et al. Frequent alterations of LOH11CR2A, PIG8 and CHEK1 genes at chromosomal 11q24.1-24.2 region in breast carcinoma: clinical and prognostic implications. Mol Oncol 2011; 5:454-64.
43. Lam M H, Liu Q, Elledge S J, Rosen J M. Chk1 is haploinsufficient for multiple functions critical to tumor suppression. Cancer Cell 2004; 6:45-59.
44. Smyth I, Narang M A, Evans T, Heimann C, Nakamura Y, Chenevix-Trench G, et al. Isolation and characterization of human patched 2 (PTCH2), a putative tumour suppressor gene inbasal cell carcinoma and medulloblastoma on chromosome 1p32. Human Mol Gen 1999; 8:291-7.
45. Zhou X, Yang G, Huang R, Chen X, Hu G. SVH-B interacts directly with p53 and suppresses the transcriptional activity of p53. FEBS Lett 2007; 581:4943-8.
46. Curtiss N P, Bonifas J M, Lauchle J O, Balkman J D, Kratz C P, Emerling B M, et al. Isolation and analysis of candidate myeloid tumor suppressor genes from a commonly deleted segment of 7q22. Genomics 2005; 85:600-7.
47. Furuya N, Yu J, Byfield M, Pattingre S, Levine B. The evolutionarily conserved domain of Beclin 1 is required for Vps34 binding, autophagy and tumor suppressor function. Autophagy 2005; 1:46-52.
48. Liang X H, Yu J, Brown K, Levine B. Beclin 1 contains a leucine-rich nuclear export signal that is required for its autophagy and tumor suppressor function. Cancer Res 2001; 61:3443-9.
49. Aita V M, Liang X H, Murty V V, Pincus D L, Yu W, Cayanis E, et al. Cloning and genomic organization of beclin 1, a candidate tumor suppressor gene on chromosome 17q21. Genomics 1999; 59:59-65.

50. Muschen M, Warskulat U, Beckmann M W. Defining CD95 as a tumor suppressor gene. J Mol Med (Berl) 2000; 78:312-25.
51. Shih J W, Tsai T Y, Chao C H, Wu Lee Y H. Candidate tumor suppressor DDX3 RNA helicase specifically represses cap-dependent translation by acting as an eIF4E inhibitory protein. Oncogene 2008; 27:700-14.
52. Chao C H, Chen C M, Cheng P L, Shih J W, Tsou A P, Lee Y H. DDX3, a DEAD box RNA helicase with tumor growth-suppressive property and transcriptional regulation activity of the p21waf1/cip1 promoter, is a candidate tumor suppressor. Cancer Res 2006; 66:6579-88.
53. Lung H L, Cheung A K, Cheng Y, Kwong F M, Lo P H, Law E W, et al. Functional characterization of THY1 as a tumor suppressor gene with antiinvasive activity in nasopharyngeal carcinoma. Int J Cancer 2010; 127:304-12.
54. Abeysinghe H R, Pollock S J, Guckert N L, Veyberman Y, Keng P, Halterman M, et al. The role of the THY1 gene in human ovarian cancer suppression based on transfection studies. Cancer Genet Cytogenet 2004; 149:1-10.
55. Abeysinghe H R, Cao Q, Xu J, Pollock S, Veyberman Y, Guckert N L, et al. THY1 expression is associated with tumor suppression of human ovarian cancer. Cancer Genet Cytogenet 2003; 143:125-32.
56. Dart D A, Spencer-Dene B, Gamble S C, Waxman J, Bevan C L. Manipulating prohibitin levels provides evidence for an in vivo role in androgen regulation of prostate tumours. Endocr Relat Cancer 2009; 16:1157-69.
57. Ko K S, Tomasi M L, Iglesias-Ara A, French B A, French S W, Ramani K, et al. Liver-specific deletion of prohibitin 1 results in spontaneous liver injury, fibrosis, and hepatocellular carcinoma in mice. Hepatology 2010; 52:2096-108.
58. Barclay J L, Anderson S T, Waters M J, Curlewis J D. SOCS3 as a tumor suppressor in breast cancer cells, and its regulation by PRL. Int J Cancer 2009; 124:1756-66.
59. Ansems M, Hontelez S, Karthaus N, Span P N, Adema G J. Crosstalk and DC-SCRIPT: expanding nuclear receptor modulation. Biochim Biophys Acta 2010; 1806:193-9.
60. Kress T R, Cannell I G, Brenkman A B, Samans B, Gaestel M, Roepman P, et al. The MK5/PRAK kinase and Myc form a negative feedback loop that is disrupted during colorectal tumorigenesis. Mol Cell 2011; 41:445-57.
61. Sun P, Yoshizuka N, New L, Moser B A, Li Y, Liao R, et al. PRAK is essential for ras-induced senescence and tumor suppression. Cell 2007; 128:295-308.
62. Riehle K J, Campbell J S, McMahan R S, Johnson M M, Beyer R P, Bammler T K, et al. Regulation of liver regeneration and hepatocarcinogenesis by suppressor of cytokine signaling 3. J Exp Med 2008; 205:91-103.
63. Forrester E, Chytil A, Bierie B, Aakre M, Gorska A E, Sharif-Afshar A R, et al. Effect of conditional knockout of the type II TGF-beta receptor gene in mammary epithelia on mammary gland development and polyomavirus middle T antigen induced tumor formation and metastasis. Cancer Res 2005; 65:2296-302.
64. Shida N, Ikeda H, Yoshimoto T, Oshima M, Taketo M M, Miyoshi I. Estrogen-induced tumorigenesis in the pituitary gland of TGF-beta(+/−) knockout mice. Biochim Biophys Acta 1998; 1407:79-83.
65. Zhao M, Sun J, Zhao Z. TSGene: a web resource for tumor suppressor genes. Nucleic Acids Res 2013; 41:D970-6.

Example 3—Induction of DISE in Ovarian Cancer Cell In Vivo

Reference is made to Murmann et al., "Induction of DISE in ovarian cancer cells in vivo," Oncotarget 2017 Oct. 4; 8(49):84643-84658, the content and supplemental content of which are incorporated herein by reference in their entireties.

Abstract

The death receptor CD95/Fas can be activated by immune cells to kill cancer cells. shRNAs and siRNAs derived from CD95 or CD95 ligand (CD95L) are highly toxic to most cancer cells. We recently found that these sh/siRNAs kill cancer cells in the absence of the target by targeting the 3'UTRs of critical survival genes through canonical RNAi. We have named this unique form of off-target effect DISE (for death induced by survival gene elimination). DISE preferentially kills transformed cells and cancer stem cells. We demonstrate that DISE induction occurs in cancer cells in vivo after introducing a lentiviral CD95L derived shRNA (shL3) into HeyA8 ovarian cancer cells grown as i.p. xenografts in mice, when compared to a scrambled shRNA. To demonstrate the possibility of therapeutically inducing DISE, we coupled siRNAs to templated lipoprotein nano particles (TLP). In vitro, TLPs loaded with a CD95L derived siRNA (siL3) selectively silenced a biosensor comprised of Venus and CD95L ORF and killed ovarian cancer cells. In vivo, two siRNA-TLPs (siL2-TLP and siL3-TLP) reduced tumor growth similarly as observed for cells expressing the shL3 vector. These data suggest that it is possible to kill ovarian cancer cells in vivo via DISE induction using siRNA-TLPs.

Introduction

CD95/Fas is a death receptor that, together with its ligand CD95L, regulates immune homeostasis [1, 2]. Immune cells such as cytotoxic killer and natural killer (NK) cells use CD95L to kill virus infected and cancer cells [3]. However, we, and others, reported that CD95 and CD95L have multiple tumor promoting activities [4-6] and tissue specific deletion of CD95 in the liver or the ovaries of mice strongly reduced or prevented tumor formation in these tissues [7, 8]. We found that >80% of 22 different siRNAs, DsiRNAs or shRNAs targeting either CD95 or CD95L killed cancer cells [8, 9] through a process we had coined DICE (for death induced by CD95/CD95L elimination). DICE is independent of caspase-8, RIPK1, MLKL, and p53, is not inhibited by Bcl-$x_L$ expression, and it preferentially affects cancer cells [8]. It is characterized by an increase in cell size and production of mitochondrial ROS, which is followed by DNA damage. It resembles a necrotic form of mitotic catastrophe. No single drug was found to completely block this form of cell death, and DICE could also not be blocked by the knockdown of any single gene, making it a promising new way to kill cancer cells [8]. More recently, we reported that DICE preferentially affects cancer stem cells [10] suggesting a physiological role of DICE in targeting neoplastically transformed cells.

Surprisingly, we recently discovered that DICE occurs even in the complete absence of CD95 and CD95L [9]. DICE is, therefore, a highly selective form of an RNAi off target effect (OTE). We found that CD95 and CD95L mRNAs contain dozens of sequences that target a network of genes found to be critical for the survival of cancer cells and that are often upregulated in cancer [9]. These sequences, when introduced into cancer cells in the form of transfected siRNAs or lentiviral shRNAs, act through canonical RNAi, targeting the survival genes through short seed matches in their 3'UTRs. The cancer cells likely die due to the loss of multiple survival genes. We have therefore called this form of cell death DISE (for death induced by survival gene elimination) [9]. The complex nature of this toxicity may explain why cancer cells have difficulties developing resistance to DISE.

We have now explored how inducing DISE may be a novel form of cancer therapy. We first demonstrated that DISE induction works in an in vivo model whereby mice harbor xenografted ovarian cancer cells expressing a CD95L derived shRNA (shL3). We then delivered two siRNAs derived from CD95L (siL2 and siL3) to mice with ovarian cancer xenografts using a nanoparticle platform demonstrated previously to deliver siRNA in vivo [11, 12]. Templated lipoprotein particles (TLP) stabilize siRNA and are dependent upon SR-B1 expression for efficient siRNA delivery. The TLPs were delivered i.p., taken up by the tumor cells, and acted through canonical RNAi, substantially reducing tumor growth.

The in vivo study was terminated once the control treated mice showed signs of discomfort due to large tumors and/or ascites formation. The remaining tumor cells from the nanoparticle delivered siL3 group were resected, cultured, and transfected with siL3 in culture using a commercially available cationic lipid-based transfection reagent in order to determine if the cells became insensitive to DISE. In this context, the tumor cells were still fully susceptible to DISE, suggesting that treatment optimization (i.e. dose and time) may allow for full eradication of tumor growth. Collectively, these data demonstrate that DISE induction is a promising new approach for treating cancer.

Results

Induction of DISE Using shRNAs In Vivo.

In multiple cancer cells tested in vitro, including ovarian cancer cell lines (FIG. 27A), DISE induction is a potent mechanism for cancer cell treatment [8]. To test whether DISE is a viable mechanism for in vivo treatment, we chose an orthotopic mouse model of ovarian cancer. We selected the highly active shRNA shL3, which we have previously demonstrated kills cancer cells by targeting survival genes [9]. In vitro, cells were selected with puromycin after lentiviral infection. However, because puromycin selection could not be used in vivo, prior to in vivo experiments we tested the efficiency of shRNA virus infection and DISE induction in HeyA8 Venus-siL3-pfuL2T cells with and without puromycin selection (FIG. 21A). Cell growth was reduced in cells treated using a MOI of 5 (without puromycin treatment) and was comparable to cells selected by treatment with puromycin (after infection with a MOI of 3). The in vitro data demonstrate that DISE induction occurs roughly 2-3 days after introducing the shRNA [8]. To determine the effects of DISE in vivo, we injected NSG mice i.p. with cells infected with either pLKO-shScr or pLKO-shL3 virus without puromycin treatment (FIG. 21B, left panel) or treated for one day with puromycin before injection (FIG. 21B, right panel). Tumor growth was monitored over two weeks and tumor cells expressing shL3 grew slower when compared to tumors expressing shScr. Upon histological inspection of the tumors by a pathologist, 13 days after cancer cell injection, shScr control treated tumors showed large areas of central necrosis in larger tumors, presumably caused by hypoxia (FIG. 21C-a, b, top panel), and demonstrated signs of tumor cells invading the omentum with no signs of necrosis (FIG. 21C-c, top panel). The shL3 expressing tumors showed signs of necrosis in smaller tumors than seen in the shScr expressing tumor cells (FIG. 21C-d). Clear signs of tumor regression were seen with small areas of residual tumors. Our data demonstrate that cancer cells, when grown in vivo, are susceptible to DISE, confirming that DISE induction may be a potent therapy for cancer.

To induce shRNA expression after injection of tumor cells, we used the Tet inducible pTIP vector [8]. HeyA8-pFuL2G cells were stably infected with either pTIP-shScr or pTIP-shL3 in the presence and absence of puromycin selection and then treated with Doxycycline (Dox) to induce shRNA expression. shL3 expression significantly slowed down growth of cells compared to shScr (FIG. 22A). Puromycin treatment did not have an effect on cell growth in the absence of Dox. HeyA8 cells treated with Dox to induce shL3 showed little to no growth and most cells demonstrated cell death when compared to shScr cells (data now shown). The pTIP-shScr and pTIP-shL3 cells were injected i.p. into NSG mice and one day after tumor injection half the mice were given Dox in their drinking water. Small animal imaging showed that tumor growth was significantly reduced in mice injected with cells expressing pTIP-shL3 that received Dox (FIG. 22B, left panel). The level of growth reduction was more pronounced when the tumors were excised and weighed (FIG. 22B, right panel).

Because there was remaining pTIP-shL3 tumor at the end of the study, we wanted to determine if the cells were no longer responsive to shL3 due to a mutation, had become resistant to DISE, had reduced function of the RNAi machinery, or no longer responded to Dox. Therefore, we isolated cells from tumors of four mice and cultured them in puromycin for 2 days to eliminate any host cells. Three resected tumors were from pTIP-shL3 mice that had received Dox, and the fourth tumor was from a mouse carrying a pTIP-shScr expressing tumor. All four cultured tumors expressed roughly the same amount of GFP documenting that a substantial number of cells in each culture were HeyA8 cells with the pTIP vector (data not shown). When these cells were plated in the presence of Dox all four of them grew in vitro (FIG. 22C). To determine if mutations present in the cell culture were responsible for the apparent resistance to toxic activity of shL3, we cultured HeyA8-pTIP-shScr and HeyA8-pTIP-shL3 cells in vitro in the presence of Dox for an extended period of time. Interestingly, every clone plated grew out (FIG. 22D and data not shown). However, it was unlikely that rare mutations occurred in every well that contributed to the clone growth, because only 250 cells were plated per well. To determine if cells had become resistant to the DISE inducing activity of shL3 we introduced the shL3 shRNA in a different form into one of the resistant clones (H5) using the pLKO vector in the presence of Dox and puromycin (FIG. 22E). While the H5 cells were impaired in their growth compared to cells isolated from a well with cells expressing shScr, they were not resistant to DISE induced by either shR6 (a shRNA targeting CD95) or shL3 shRNA (FIG. 22E, right panel). These data suggest that RNAi was still fully active in the resistant clone. This was also confirmed by the demonstration that shR6 knocked down CD95 as efficiently in the H5 clone as in the control cells (FIG. 22F). Most important however, was the observation that the H5 clone which was resistant to Dox induction of shL3 driven from the pTIP vector was still fully susceptible to the very same shRNA when induced using a different vector. The in vitro data suggest that tumor cells did not develop resistance to DISE but rather to the vector or to Dox used to induce the shRNA. Similar data were also obtained in vitro and in vivo when the pTIP-shL3 vector was used in a breast cancer mouse model in which we injected MB-MDA-231 cells expressing pTIPshScr or pTIP-shL3 into the fat pad and cultured the cells ex vivo (data not shown). This suggests that the resistance that developed is not specific to HeyA8 cells but could be a more fundamental effect seen with the pTIP vector.

siL3 Kills Ovarian Cancer Cells by Targeting a Network of Survival Genes.

These data suggested that it might be possible to induce DISE in vivo by delivering siRNAs to tumor cells. We recently showed that the majority of the tested shRNAs, siRNAs and DsiRNAs that are derived from CD95L induced DISE [9]. We selected two toxic siRNAs, siL2 and siL3, derived from CD95L. Both were active in silencing their cognate target [8] and in reducing growth of HeyA8 cells (FIG. 23A). To monitor delivery and RNAi activity of siL3 in vivo we developed a biosensor plasmid that carried a CD95L mini gene of 50 nt with the center comprised of the 20 nt sequence that is targeted by siL3. This minigene was linked to a Venus fluorophore (FIG. 23B). We generated a mutant form of the sensor whereby the siL3 target site was mutated in 6 positions. HeyA8 cells were generated either expressing the siL3WT or the siL3MUT sensor. These cells were transfected with a nontargeting siRNA (siScr), siL3 or siL3MUT and, after 2 days, cells were analyzed by flow cytometry (FIG. 23C). The green fluorescence in the cells carrying the two sensor constructs was only reduced upon transfection with the siRNA that was completely complementary to the sequence in the sensor. This established the sensor system as a sensitive tool to detect the activity of the CD95L targeting siL3. Finally, we monitored the change in fluorescence, cell morphology and confluency (as a surrogate marker of cell viability) over time upon transfection with the different siRNAs (data not shown). When HeyA8 cells expressing the siL3WT Venus sensor were transfected with siL3MUT they remained green and became confluent after 6 days (data not shown). The same cells transfected with siL3 lost green fluorescence after about 2 days and never reached confluency due to DISE induction (data not shown). In contrast, when HeyA8 cells expressing the siL3MUT sensor were transfected with the complementary siL3MUT siRNA they lost green fluorescence after 2 days but became confluent (data not shown), when transfected with siL3 they remained green but did not reach confluency due to DISE induction (data not shown). These experiments confirmed that siL3 induces DISE in a sequence specific manner.

We recently showed that a number of siRNAs and shRNAs derived from either CD95 or CD95L are toxic to cancer cells because they target a network of genes that are critical for the survival of the cells. We demonstrated that siL3 can kill HeyA8 cells even after homozygously deleting the siL3 targeted site in HeyA8 cells [9]. To test whether the naked siL3 oligonucleotides we planned to couple to nanoparticles killed cancer cells by targeting survival genes we subjected HeyA8 cells with no detectable expression of CD95L (data not shown) and transfected with unmodified siScr or siL3 and then performed RNA Seq analysis. The most downregulated genes in the siL3 treated cells when compared to the cells treated with control siScr were enriched in genes recently described in a genome wide CRISPR based lethality screen [13] as survival genes (data not shown) but not enriched in nonsurvival genes. In fact, survival genes were about two times more likely targeted than nonsurvival genes (data not shown). Performing a Sylamer analysis which identifies seed matches of si- and miRNAs that are enriched in the 3'UTRs of a ranked list of genes, confirmed an enrichment of the siL3 seed match in the 3'UTRs of the downregulated genes (data not shown). The data were very similar to the ones obtained for cells treated with chemically modified siL3 suggesting that the naked siRNA had comparable activities [9]. To test whether an independent toxic siRNA, siL2, derived from CD95L also induced DISE we generated 293T cells lacking the entire CD95L locus using CRISPR/Cas9 gene editing (data not shown). Transfection of these 293T CD95L k.o. cells with either siL3 and siL2 resulted in substantial cell growth inhibition (a surrogate marker of cell death) (FIG. 23D) suggesting that siL2, just like siL3, is a toxic siRNA derived from the CD95L gene that kills cancer cells by DISE.

Induction of DISE in Cancer Cells Using TLP Nanoparticles In Vitro and In Vivo.

We have recently developed a new form of siRNA delivery using TLP nanoparticles [11]. We described that uptake of the TLPs was dependent on expression of the scavenger receptor SR-B1 [11]. To test which of the cancer cell lines expressed SR-B1, we subjected a number of solid and blood cancer cell lines to Western blot analysis (FIG. 24A). SR-B1 was expressed in all tested cancer cell lines at varying levels, except for Jurkat cells. We then tested uptake of TLPs coupled with a Cy5 labeled siL3 oligonucleotide (data now shown). Both fluorescence microscopy and FACS analysis demonstrated efficient uptake of the labeled particles in 17 different cancer cell lines. Particles were taken up within 1 hour and when excess particles were washed away detection of labeled siL3 slowly dissipated (FIG. 24B). We next tested whether uptake of siL3 loaded TLPs resulted in reduction of green fluorescence and induction of DISE in HeyA8-Venus-siL3 cells (FIG. 24C). The siL3-TLP, but not the siL3MUT-TLP or empty TLPs, had a strong effect on green fluorescence (FIG. 24C and data not shown). Incubation of these cells with the siL3-TLP also induced DISE (FIG. 24C and data now shown). This was found for the p53 mutant ovarian cancer cell line OVCAR3 and for another epithelial ovarian cancer cell line OVCAR4 (FIG. 27B).

To test whether siRNA-TLPs could be used to induce DISE in vivo, HeyA8-Venus-siL3 cells also expressing a Tomato red luciferase construct were injected i.p. into NSG mice and a day after injection mice were subjected to IVIS analysis. Based on the bioluminescence signal they were sorted into three groups (10 mice per group) so that each group had a similar signal distribution. Mice were injected 5 times over 9 days with water, siScr-TLP or siL3-TLP (FIG. 25A). Tumors of a small group of additional mice were analyzed by flow cytometry 10 days after tumor injection (after 4 injections with TLCs). The red/green ratio as a measure of targeting the Venus siL3 sensor was determined (FIG. 25B). Together with a reduction in green fluorescence in the tumors treated with siL3-TLP when compared to tumors treated with siScr-TLP (data not shown) provided evidence that the TLPs had entered the tumor tissue and were actively inducing RNAi in the case of siL3-TLP. We also noticed an increase in the side scatter of red tumor cells taken from three tumors from a mouse treated with siL3-TLP when compared to cells of three tumors from a mouse treated with siScr-TLP (FIG. 25C, left panel), a phenomenon also observed in vitro in HeyA8 cells after transfection with siL3 (FIG. 25C, right panel, and data not shown). The most likely reason for this observation is an increase in granularity of the cells caused by the appearance of massive stress granules caused by DISE induction in these cells [8]. Finally, data show a significant reduction in IVIS signal from the tumor cells at both the second and third measurement (FIG. 25D) when treated with the siL3-TLP, but not when treated with water or siScr-TLP. The data suggest that it is possible to deliver a DISE inducing siRNA to tumor cells in vivo.

To test whether a longer treatment and another DISE inducing siRNA would promote a more pronounced tumor growth reduction, we treated mice (n=10/group) with siScr-TLP, siL3-TLP and siL2-TLP for three weeks (FIG. 26A). To be able to detect CD95L specific RNAi by the two siRNAs we used HeyA8 cells expressing a Venus sensor that contained the entire CD95L open reading frame [9]. In addition, to be able to distinguish tumor from host tissues in the mice we also stably expressed a red fluorophore localized to the nucleus in the tumor cells. Mice were i.p. injected with $5 \times 10^5$ cells and treated with TLP nanoparticles as indicated (FIG. 26A). Both siL2-TLP and siL3-TLP substantially reduced tumor growth (FIG. 26B). Mice had to be sacrificed at 23 days due to the aggressive growth of HeyA8 cells in siScr-TLP treated mice. To determine whether particles were taken up by the tumor cells and whether the siRNAs acted through RNAi we isolated and froze tumor tissue from three mice in each treatment group and determined by immunofluorescence microscopy the level of reduction in green fluorescence. Overall, reduction in green fluorescence was detectable throughout the tumors of mice treated with the siL2-TLP or siL3-TLP (data not shown). While the nanoparticles accumulated on the tumors (data not shown) no particles were obvious on the livers or the kidneys of the treated mice and no signs of toxicity were detected (data not shown). This was corroborated by the analysis of the serum of treated mice. No elevation in liver enzymes was measured (FIG. 28A). Due to the mechanism of DISE induction we found cross-reactivity of human derived sh- and siRNAs to targeted survival genes in mouse cells (data not shown) and transfection of siL3 into mouse ovarian cancer cell line ID8 slowed down their growth (FIG. 28B). These data suggest that siL3-TLP was not toxic to the mice but reduced tumor growth by inducing DISE in the tumor cells.

Similar to the experiments in which we expressed shRNAs in cancer cells in vivo to reduce tumor growth, treatment of the HeyA8 tumors with TLP nanoparticles also did not completely eliminate the cancer cells. To determine the mechanism of treatment resistance we isolated tumor cells from mice that had been treated with either siScr-TLP or siL3-TLP particles (three mice each) and after establishing tissue culture in vitro we introduced the siL3 siRNA into the cells by transfection (FIGS. 26C and 26D). In all cases, regardless of whether cells were derived from siScr-TLP or siL3-TLP treated mice, when siL3 was introduced it efficiently reduced the Venus fluorescence to zero (FIG. 26C) and effectively killed the cells (FIG. 26D). These data demonstrated that similar to the Dox treated HeyA8-pTIP-siL3 cells, the cells did not become resistant to the induction of DISE when they were isolated ex vivo and cultured under standard laboratory conditions. In summary, our data suggest that it is possible to induce DISE in vivo. Further work is needed to understand the mechanism of DISE induction, and to optimize strategies aimed at inducing DISE in vivo.

Discussion

Most targeted cancer therapy is based on small molecule inhibitors or biological reagents that target an oncogene often overexpressed in cancer cells. However, such targeted therapy has not resulted in a cure for the majority of cancer patients with advanced cancer. Most often patients develop resistance to the treatment, either because tumors in relapsing patients carry mutations in the targeted gene or the tumors upregulate factors that render them resistant to the therapy [14, 15]. Using more of the same therapy is futile and thus attempts are being made to find alternative targets for therapy or to re-sensitize cancer cells to the targeted therapy. In fact, it has been suggested that we will need to find "a radically different therapeutic modality" [16]. It has also been argued that rather than targeting individual genes, one needs to identify and disrupt networks of genes [17]. We are now providing such an approach, a radically different way of attacking cancer, that affects networks of survival genes.

We recently identified toxic RNAi active sequences in the genes of CD95 and CD95L [9]. We had reported earlier that introducing such sequences in the form of siRNAs or shRNAs induces a combination of multiple cell death pathways (we now call DISE) that cancer cells have a hard time developing resistance to [8]. Our new data on treating mice with nanoparticles by delivering two of these siRNAs in vivo now suggest that, in theory, it should be possible to induce this mechanism selectively in tumor cells in vivo. While we did detect resistance to treatment both when DISE was initiated in mice by expressing an inducible CD95L derived shRNA and when delivering CD95L derived siRNAs using nanoparticles, in both cases cells retained their intrinsic sensitivity to DISE. Tumor cell sensitivity was confirmed ex vivo as seemly resistant tumor cells treated both with lentiviral shRNAs or with commercially available siRNAs under standard culture conditions, both exhibited growth reduction upon reintroduction of treatment. Ultimately, further study is required to maximize the therapeutic efficacy of DISE. We chose ovarian cancer in an attempt to somewhat localize the nanoparticles to one tissue site in the animals. Indeed, when injected i.p., few nanoparticles could be detected on the liver of the animals but most of them were found to decorate or localize within the tumors (data not shown).

A key question remaining to be addressed is the issue of general toxicity, whether normal cells will die by DISE. While our siRNAs were derived from human CD95L, due to the mechanism through which DISE works it is very likely (and we now demonstrate for siL3) that the siRNAs will also kill mouse cells. In fact DISE was first seen in the mouse cell line CT26 stably expressing human CD95L when we overexpressed human CD95L derived shL3 [8]. Only later we discovered that shL3 very efficiently killed these mouse cells by targeting a network of critical survival genes in the mouse cells (data not shown). Recently, we reported data to suggest that normal cells are protected from DISE by the cellular miRNAs [9] which are known to be globally downregulated in human cancers when compared to their normal tissues [18]. However, the question whether DISE affects normal cells requires further research.

We showed that DISE preferentially affects cancer stem cells (CSCs) [10]. This selective sensitivity suggested that the DISE mechanism may have a physiological role in protecting stem cells from neoplastic transformation and that it can be used to target CSCs. The question arising as with every therapy directed at CSCs is whether it will affect somatic stem cells. This will have to be tested.

We propose that DISE will predominantly affect cancer cells making it unnecessary to specifically deliver the drugs to the cancer cells. In this case, the TLP nanoparticles used in our study are dependent on the expression of the SR-B1 scavenger receptor, a receptor expressed by numerous cancer types. Our data support that siRNA-TLP may be used to induce DISE in different types of cancer via local or systemic administration. Further, other targeted vesicles, such as exosomes, may be loaded with DISE-inducing siRNAs whereby systemic delivery may be accomplished. Finally, generating exosomes or nanoparticles with mixtures of toxic siRNAs derived from CD95/CD95L [9], or other genes that contain such sequences, may allow more potent targeting of cancer cells. While the siRNAs used in our study are toxic to cancer cells, recent work from our group suggests that the human genome is filled with genes that contain such toxic sequences allowing screening for the ones that are most toxic to cancer cells and least toxic to normal cells and then using aforementioned delivery strategies for in vivo therapy.

Materials and Methods

Cell Lines and Tissue Culture.

Base media were supplemented with 10% heat-inactivated fetal bovine serum (FBS; Sigma-Aldrich) and 1% 100× penicillin/streptomycin and L-Glutamine (Mediatech Inc.). Adherent cells were dissociated with 0.25% (w/v) Trypsin-0.53 mM EDTA solution (Mediatech Inc.). Cells were cultured in an atmosphere of air, 95% and 5% carbon dioxide ($CO_2$) at 37° C. For lentivirus production 293T cells were used. 293T cells were cultured in Dulbecco's Modified Eagle's Medium (DMEM). The following cell lines were used: breast cancer: MCF-7 (NCI60 cell panel), MDA-MB-231 (ATCC HTB-26), and HCC-70 (ATCC CRL-2315) were cultured in supplemented RPMI1640 Medium (Mediatech Inc.), SKBR-3 (ATCC HTB-30), in McCoy's 5a Medium Modified (ATCC); Ovarian cancer: OVCAR-3, OVCAR-4, OVCAR-5, and OVCAR-8 (all Tumor Biology Core, Northwestern University) were cultured in RPMI1640; Caov-3 (ATCC HTB-75) in DMEM. HeyA8, Monty-1, and SKOV3IP1 were obtained from Dr. E. Lengyel, University of Chicago. HeyA8 was cultured in RPMI1640, Monty-1 and SKOV3IP1 in DMEM that was further supplemented with 1% non-essential amino Acids 100× (BioWhittaker), 1% Sodium Pyruvate 100 mM (BioWhittaker), and 1% MEM Vitamins 100× solution (Mediatech Inc.). Glioblastoma cell lines T98G (ATCC CRL1690) and U-87 MG (ATCC HTB-14) were cultured in Eagle's Minimum Essential Medium (EMEM) (ATCC). The neuroblastoma cell line NB-7, the colorectal cancer cell line HCT116 (ATCC CCL-247), and JA3 (a subclone of Jurkat, an acute T-cell leukemia cell line, University of Heidelberg, Germany) were cultured in RPMI1640. The hepatocellular carcinoma cell line HepG2 (ATCC HB-80645) was cultured in EMEM (ATCC). ID8, a mouse ovarian cancer cell line, was cultured in DMEM supplemented with 4% FBS, and 10 mg/l Insulin, 5.5 mg/l Transferrin, 6.7 µg/ml Selenium (ITS, Mediatech, Inc., 1:10 diluted).

Lentiviral Infection.

50,000 to 100,000 cells per 6-well were plated and infected the following day. When the lentivirus titer was known, the cells were infected at a multiplicity of infection (MOI) of 3 or 5 in the presence of 8 µg/ml polybrene, for 24 hours. Otherwise virus mix was produced by transfecting 293T cells. 3-4 million 293T cells were plated in a 10 cm dish in antibiotics free medium. Next day, in one tube 60 µl of Lipofectamine® 2000 Transfection Reagent was mixed with 1 ml Opti-MEM medium (Gibco), and this tube was incubated for 5 min at RT. In a second tube, a lentiviral vector, a packaging plasmid pCMVDR8.9, and an envelope plasmid pMD.G (VSV.G-envelope protein encoding plasmid) were mixed at a ratio of 12 µg:6 µg:6 µg in 1 ml Opti-MEM I. The two tubes were then mixed and incubated for 20 mins after which the transfection mix was added drop wise to the 10 cm dish of 293T cells. After 9 hours, the transfection mix was removed, and replaced with fresh full medium. The virus mix was collected 48 hours after transfection, sterile filtered, and aliquots were stored at −80° C. until use. Cells were infected using a volume of 0.5 to 2 ml of this virus mix per 6-well. Where applicable, infected cells were selected with 3 µg/ml puromycin. To induce the expression of shRNAs from pTIP vectors the tetracycline analogue Doxycycline (Dox) was added to the culture at a final concentration of 0.1 µg/ml. To label nuclei red cells were infected with a puromycine selectible NucLight Red lentivirus (Essen Bioscience).

Lentiviral Vectors.

To determine whether RNAi active sequences are taken up by the cells and active, cells were infected with lentivirus Venus sensors. They contain either a minisensor comprised of the 50 nucleotides surrounding the siL3 target site in CD95L (Venus-siL3WT), the mutated siL3 target site (Venus-siL3MUT) (described below), or the entire open reading frame of the CD95L-gene (NCBI accession number NM_000639.1) as recently described [9].

The Venus-siL3 sensor vector was created by subcloning an insert containing the Venus ORF followed by an artificial 3'UTR composed of a 62 bp portion of the CD95L cDNA containing the siL3 target site (5'-GCCCTTCAATTACC-CATAT-3') (SEQ ID NO:43) into a modified pCD510B vector (System Bioscience) as the backbone. IDT synthesized the insert as both a sense and antisense DNA strand containing an XbaI restriction enzyme (RE) site at the 5' end and an EcoRI RE site at the 3' end. The annealed insert and the modified pCD510B vector were digested with XbaI (NEB #R0145) and EcoRI (NEB #R0101). Subsequent ligation with T4 DNA ligase (NEB #M0202) created the pCD510B Venus-siL3 sensor vector. The Venus-siL3MUT sensor was generated by subcloning the Venus-siL3MUT insert into a modified CD510B-1 backbone [10] using XbaI and EcoRI. The insert was ordered as a synthetic gene from IDT containing an XbaI site and EcoRI site at the 5' and 3' ends, respectively and was composed of the Venus open reading frame followed by the sequence 5'-CTCGAGAGCTGCCGTGCAGCAGGACTTCAACTA-GACATCTCCCCAGATCTACTGG G-3' (SEQ ID NO: 129), which contains the mutant siL3 sense sequence.

To monitor the growth of tumor cells in NSG mice by quantifying bioluminescence, the cells were infected with lentivirus pFU-Luc2-eGFP (pFUL2G), pFU-Luc2-tdTomato (pFUL2T) (a kind gift of Dr. Sanjiv Sam Gambhir at Stanford University, Stanford Calif.), or FUW-LucNeo (LucNeo) (G418 selectable) (Received from Dr. Jian-Jun Wei, Northwestern University). To express shRNAs derived from the CD95 or CD95L gene, cells were infected with the following MISSION Lentiviral Transduction Particles (the active sequence is underlined in each sh-RNA loop sequence): plko-shSCR=MISSION® pLKO.1-puro Control Non-Mammalian shRNA control Transduction articles (Sigma, SHC002V) as non targeting control (CCGG CAACAAGATGAAGAGCACCAACTCGAGTTGGTG-CTCTTCATCTTGTTGTTT TT (SEQ ID NO:130)). Plko-shL3: MISSION® shRNA Lentiviral Transduction Particle for human CD95L (Sigma, Cat. No. SHCLNV-NM_000639 on exon 4, RCN0000059000) (CCGG ACTGGGCTGTACTTTGTATATCTCGAGATATACAA-AGTACAGCCCAGTTTT TTG (SEQ ID NO:131)). Plko-shR6: MISSION® shRNA Lentiviral Transduction Particle for human CD95 (Sigma, Cat. No. SHCLNV-NM_000043 on exon 4, TRCN0000038696) (CCGG GTGCAGATGTAAACCAAACTTCTCGAGAAGTTTG-GTTTACATCTGCACTTT TTG (SEQ ID NO:132)). These same shRNA sequences were cloned into the tetracycline inducible expression vector pTIP as previously described [8]. Cancer cells were infected with lentivirus for pTIP-shScr, or pTIP-shL3.

Western Blot Analysis.

Protein extracts were collected by lysing cells with RIPA lysis buffer [150 mM NaCl, 10 mM Tris HCl ph7.2, 1%

SDS, 1% Triton X-100, 1% deoxycholic acid, 5 mM EDTA, Protein inhibitor cocktail tablet (1 tablet per 10 ml lysis buffer)]. 200 µM PMSF was added to the lysis buffer prior to use. Protein concentration was quantified using the DC™ Protein Assay (Bio-Rad). 30 µg of protein were resolved on 10% SDS-PAGE gels and transferred to nitrocellulose membranes (Amersham™ Protran™, pre size 0.45 m GE Healthcare Life Science) overnight at 25 mA. To verify the protein bands, a protein size marker was included on the gel, Amersham ECL Rainbow Molecular Weight Marker (GE Healthcare Life Science, Cat. No.: RPN800E). Membranes were incubated with blocking buffer (5% non-fat milk in PBST (PBS+0.1% Tween-20) for 1 hour at room temperature. Membranes were then incubated with the primary antibody diluted in blocking buffer over night at 4° C. Membranes were washed 3 times with PBST. Secondary antibodies were diluted in blocking buffer and applied to membranes for 1 hour at room temperature. After 3 more additional washes, detection was performed using the ECL™ Western Blotting Detection Reagents reagent (GE Healthcare) or SuperSignal™ West Dura Extended Duration Substrate (ThermoFisher Sci.) and visualized with the chemiluminescence imager G:BOX Chemi XT4 (Syngene). All primary and secondary antibodies were diluted in a blocking buffer (5% non-fat milk in PBST) at different dilutions. The following primary antibodies were used: anti-human Fas antibody (C-20) Polyclonal rabbit IgG (Santa Cruz Biotechnology Inc., Cat. No.: sc-715, 1:500), anti-Scavenger receptor type B-1 rabbit IgG monoclonal [EP1556Y] (Abcam, Cat. No.: ab52629, 1:2000), and anti-Actin (1-19) goat polyclonal IgG (Santa Cruz Biotechnology Inc., Cat. No.: sc-1616, 1:2000). All secondary antibodies labeled with horse radish peroxidase: goat anti-rabbit IgG-HRP (Santa Cruz Biotechnology, Inc.; Cat. No.: sc-2004; 1:8000), rabbit anti goat IgG (Human adsorbed)-HRP (Santa Cruz Biotechnology Inc. sc-2768; 1:8000), goat-anti-rabbit-Ig human adsorbed-HRP (Southern Biotech; Cat. No.: 4010-05, 1:10000), or rabbit-anti-goat IgG(H+L) human adsorbed-HRP (Southern Biotech; Cat. No.: 6164-05, 1:10000).

CRISPR/CAS9 Genome Editing to Delete the Entire CD95L Gene in 293T Cells.

The procedure to generate specific mutant cells using two guide RNAs was recently described [9]. In short, the pMJ920 Cas9 vector (expressing a Cas9-GFP conjugate) was transfected using Lipofectamine™ 2000 (Invitrogen, Cat #11668-019) with two guide RNA scaffolds containing guide RNA sequences targeting both 5' and 3' of the FASLG mRNA sequence to generate genomic human CD95L knock out cells. The following guide RNA were designed using the online CRISPR design tool (crispr.mit.edu described in [19]. Guide sequences with a quality score >70 were tested. The final guides used to generate FASLG knockouts are as follows (PAM sequence is underlined): 5' guide sequence (TTGTGGGCGGAAACTTCCAGGG (SEQ ID NO:133)), 3' guide sequence (GTACTGCCTATGTAAGCACTGG (SEQ ID NO:134)), were transfected as G-blocks (IDT) into 293T cells. As a control, the Cas9 vector was transfected alone, without the addition of G-blocks encoding guide RNAs. The G block sequences were adopted from [20] and are as follows:

5' Guide-
(SEQ ID NO: 135)
TGTACAAAAAAGCAGGCTTTAAAGGAACCAATTCAGTCGACTGGAT

CCGGTACCAAGGTCGGGCAGGAAGAGGGCCTATTTCCCATGATTCCTTCA

TATTTGCATATACGATACAAGGCTGTTAGAGAGATAATTAGAATTAATTT

GACTGTAAACACAAAGATATTAGTACAAAATACGTGACGTAGAAAGTAAT

AATTTCTTGGGTAGTTTGCAGTTTTAAAATTATGTTTTAAAATGGACTAT

CATATGCTTACCGTAACTTGAAAGTATTTCGATTTCTTGGCTTTATATAT

CTTGTGGAAAGGACGAAACACCGTTGTGGGCGGAAACTTCCAGTTTTAGA

GCTAGAAATAGCAAGTTAAAATAAGGCTAGTCCGTTATCAACTTGAAAAA

GTGGCACCGAGTCGGTGCTTTTTTTCTAGACCCAGCTTTCTTGTACAAAG

TTGGCATTA.

3' Guide-
(SEQ ID NO: 136)
TGTACAAAAAAGCAGGCTTTAAAGGAACCAATTCAGTCGACTGGAT

CCGGTACCAAGGTCGGGCAGGAAGAGGGCCTATTTCCCATGATTCCTTCA

TATTTGCATATACGATACAAGGCTGTTAGAGAGATAATTAGAATTAATTT

GACTGTAAACACAAAGATATTAGTACAAAATACGTGACGTAGAAAGTAAT

AATTTCTTGGGTAGTTTGCAGTTTTAAAATTATGTTTTAAAATGGACTAT

CATATGCTTACCGTAACTTGAAAGTATTTCGATTTCTTGGCTTTATATAT

CTTGTGGAAAGGACGAAACACCGTAATAGAGTGGCTTAGTAGGTTTTAGA

GCTAGAAATAGCAAGTTAAAATAAGGCTAGTCCGTTATCAACTTGAAAAA

GTGGCACCGAGTCGGTGCTTTTTTTCTAGACCCAGCTTTCTTGTACAAAG

TTGGCATTA.

Cells successfully transfected were enriched by FACS sorting the top 20% GFP fluorescing cells three days after transfection (Day 1 transfection, Day 2 change media, Day 4 enrichment). The BD FACSAria SORP system was used. The cells were replated to recover. After 13 days in culture, single cells were sorted into 96 well plates containing conditioned media. Homozygous knockout clones were identified 3-4 weeks later by genomic PCR. The genotype of the 293T clones was determined by genomic PCR with external primers designed using Primer3: Lg5P_del_F (CATAAAATTATAGCCCCACTGACC (SEQ ID NO:137)) and Lg5P_del_R (CTGGGATGACAGCTTAAAGAAAAT (SEQ ID NO:138)), and internal primers FasLg_(int)_F (GTGGTAGGCTATTGTCCCTGGAAT (SEQ ID NO:139)) and FasLg_(int)_R (TGCAAGATTGACCCCG-AAGTATA (SEQ ID NO:140)) (IDT).

Transfection with Short Oligonucleotides.

For transfection of cancer cells with siRNAs Lipofectamine® RNAiMAX or 2000 transfection reagent was used at a concentration that was optimized for each cell line, following the instructions of the vendor. The same sequences were ordered from two different vendors, Dharmacon and Integrated DNA Technologies (IDT): Dharmacon: Lyophilized ON-Target plus siRNA were resuspended in 1×siRNA buffer (using 5× buffer from Dharmacon, through Thermo Fisher Scientific Biosciences, Cat. No.: B-002000-UB, diluted with RNAse/DNAse free water, to 60 mM KCl, 6 mM HEPES-pH 7.5, 0.2 mM $MgCl_2$) to a concentration of 20 µM. IDT: Individual RNA oligos were ordered for the sense and antisense oligo; the sense strand had Ts added to the 3' end; antisense strand had 2 deoxy As at the 3' end, and phosphate residue on the 5' end. For the visualization of siRNA-uptake a Cy5 label was attached to the 5' end of the sense strand. Sense and antisense oligos were first resuspended in water at 500 µM (stock), then sense and antisense oligos were mixed with nuclease free Duplex buffer (IDT, Cat. No #11-01-03-01; 100 mM Potassium Acetate, 30 mM HEPES, pH 7.5) to 20 µM (working solution), heated up for 2 minutes at 94° C., then the oligos were allowed to cool down to room temperature for 30 minutes. All siRNA solutions were aliquoted and stored at −80° C. The cells were transfected with siRNAs at a final concentration of 5 nM-25 nM. The following siRNA sequences were used: siNT #2: UGGUUUACAUGU-CGACUAA (SEQ ID NO:141) (Dharmacon D-001810-02, non targeting in mammalian cells), siL2: CAACGUAUCUGAGCUCUCU (SEQ ID NO:142) (Dharmacon J-011130-06, human CD95L exon 4), siL3: GCCC-UUCAAUUACCCAUAU (SEQ ID NO:143) (Dharmacon J-011130-07, human CD95L exon 1.), siL3MUT: G<u>GA</u>CUUCAACUAGACAUCU (SEQ ID NO:144) (siL3 sequence with 6 changes), siL3-Cy5: GCCCUU-CAAUUACCCAUAU-Cy5 (SEQ ID NO: 143) (siL3 sequence with Cy5 fluorophore).

Total RNA Isolation and RNA-Seq Analysis.

HeyA8 cells were transfected in 6-wells with IDT siNT2 or siL3 oligonucleotides at 25 nM. The transfection mix was removed after 9 hours. Total RNA was isolated 48 hours after initial transfection using the miRNeasy Mini Kit (Qiagen, Cat. No. 74004)) following the manufacturers instructions. An on column digestion step using the RNAse-free DNAse Set (Qiagen, Cat. No.: 79254) was included. NGS RNA-SEQ library making and sequencing was performed by the University of Chicago Genomics Facility. The quality and quantity of RNA samples was assessed using an Agilent bio-analyzer. RNA-SEQ libraries were generated using Illumina Stranded TotalRNA TruSeq kits using the Illumina provided protocol and sequencing was performed using the Illumina HiSEQ4000 using Illumina provided protocols and reagents. Sequences were aligned to the human genome and analyzed as recently described [9]. The accession number for the RNA-Seq and expression data reported in this paper is GSE101167.

Monitoring Growth and Fluorescence Expression Over Time.

To monitor cell growth over time, cells were seeded between 125 or 10,000 per well in a 96-well plate in triplicates. The plate was then scanned using the IncuCyte ZOOM live cell imaging system (Essen BioScience). Images were captured at regular intervals, at the indicated time points, using an 10× objective. Cell confluence, red object count, and the green object integrated intensity were calculated using the IncuCyte ZOOM software (version 2015A).

Synthesis of Templated Lipoprotein Particles (TLP) and siRNA-TLPs.

For TLP synthesis, an aqueous solution of citrate stabilized gold nanoparticles (Au NP) (80 nM, 5±0.75 nm, Ted Pella, Inc.) was mixed with a 5-fold molar excess of purified human apolipoprotein A-I (apoA-I) (400 nM, Meridian Life Sciences, >95% pure by SDS PAGE) in a glass vial. The AuNP/apo A-I mixture was incubated overnight at room temperature (RT) in a flat bottom shaker at low speed. Next, a 1:1 ratio of two phospholipids: 1,2-dipalmitoyl-sn-glycero-3-phosphoethanolamine-N-[3-(2-pyridyldithio) propionate] (PDP-PE) and 1,2-dioleoyl-sn-glycero-3-phosphocholine (DOPC) (Avanti Polar Lipids), each dissolved in chloroform ($CHCl_3$, 1 mM), were added to the AuNP/apo A-I solution in 250-fold molar excess to the AuNP. PDP-PE was added first and the solution was vortexed prior to adding DOPC. Next, cholesterol dissolved in $CHCl_3$ (1 mM, Sigma Aldrich) was added in 25-fold molar excess to the AuNP. The mixture was vortexed and briefly sonicated (~2 min) causing the solution to become opaque and pink in color. The resulting mixture was gradually heated to ~65° C. with constant stirring to evaporate $CHCl_3$ and to transfer the phospholipids onto the particle surface and into the aqueous phase (~20 minutes). The reaction was complete when the solution returned to a transparent red color. The resultant TLPs were incubated overnight at RT and then purified via centrifugation (15,870×g, 50 min) or tangential flow filtration (TFF). The supernatant was removed in the case of centrifugation and the resulting purified and concentrated TLPs were combined into a single vial. TLPs were stored at 4° C. until use. The concentration of the TLPs was measured using UV-Vis spectroscopy (Agilent 8453) where AuNPs have a characteristic absorption at $\lambda_{max}$=520 nm, and the extinction coefficient for 5 nm AuNPs is $9.696 \times 10^6$ $M^{-1}$ $cm^{-1}$.

To synthesize siRNA-TLP, RNA and 1,2-dioleoyl-3-trimethylammonium-propane (DOTAP) were first mixed. Individual sense and antisense RNA sequences of the siL2, siL3, or scrambled (siScr) (IDT) were re-suspended in nuclease free water (500 µM, final). Complement pairs were then mixed in nuclease free water at a concentration enabling direct addition to TLPs (100 nM) at 25-fold molar excess of each RNA sequence (2.5 µM, final per RNA sequence). An ethanolic (EtOH) solution of DOTAP was then added to the RNA mixture to desired DOTAP:RNA molar ratios. In each case the resulting solvent ratio was 9:1, EtOH:water (v/v). The mixture of DOTAP and RNA was briefly sonicated and vortexed (×3) and then incubated at RT for 15 minutes prior to addition to a solution of TLPs in water. After the DOTAP-RNA mixture was added to the TLPs, the solvent mixture was 9:1, water:EtOH (v/v). The solution was incubated overnight at RT with gentle shaking on a flat bottom shaker at low speed. Resulting siRNA-TLPs were purified via centrifugation (15,870×g, 50 min), the supernatant with unbound starting materials was removed, the pellets were briefly sonicated and then combined in a single tube to concentrate the siRNA-TLPs. The concentration of the siRNA-TLPs was calculated as described for TLP. For siRNA-TLPs, a strong absorption at $\lambda_{max}$=260 nm confirmed the presence of RNA.

Monitoring of Cy5-Labeled Particle Uptake.

For FACS analysis, cells were plated at 50,000 cells per 12-well plate in 1 ml medium. After about 16 hours the entire medium was replaced with medium containing 10 nM TLP. After 24 hours incubation with the particles, the cells were harvested, trypsinized when necessary, and analyzed with FACS. For IncuCyte monitoring, cells were plated at 10000, 5000, 2500, and 1250 cells per 96-well. Images for phase, and the red channel were taken every 2.5 hours.

Intra Peritoneal (i.p.) Injection of Ovarian Cancer Cells into NSG Mice and in Vivo Imaging.

$10^5$-$10^6$ modified HeyA8 (always infected with a luciferase lentivirus) were injected i.p. into 6-week-old female NSG mice (NOD scid gamma, NOD-scid $IL2Rg^{null}$, NOD-scid $IL2Rgamma^{null}$) (Jackson Laboratory, Cat. No.: 005557) following the Northwestern University Institutional Animal Care and Use Committee (IACUC)-approved protocol. The growth of tumor cells in the mice over time was monitored non-invasively using the IVIS® Spectrum in vivo imaging system (Perkin Elmer). The tumor load was quantified by the luminescence of the regions of interest (the same area for each mouse encompassing the entire abdomen) using the Living Image software. To visualize the tumor load in the mice, 200 µl of the sterile Luciferin stock solution (15 mg/ml in Dulbeccos's phosphate buffered Saline without $Mg^{2+}$ and $Ca^{2+}$) was i.p. injected per mouse (which equals approximately 10 µl of luciferin stock per g of body weight). The mice were imaged 15 minutes after injection. Total Flux values of the different treatment groups were compared.

H&E Staining.

Tissue samples or tumors were fixed in 10% Normal Buffered Formalin (VWR, Cat. No.: 16004-128) for 16 hrs, and further processed by the Northwestern University Mouse Histology & Phenotyping Laboratory (MHPL) (paraffin embedding, sectioning at 4 µM, slide preparation, and staining). Histology services were provided by the Northwestern University Research Histology and Phenotyping Laboratory at the Robert H Lurie Comprehensive Cancer Center.

Microscopy and Imaging.

The following microscopes were used for imaging: Zeiss Axioscope with Nuance camera (Nuance multispectral imaging system) with the software called Nuance 3.0.0. to image Venus green and tdTomato Red. Imaging work on this microscope was performed at the Northwestern University Center for Advanced Microscopy. A Zeiss Axiovert S100 fluorescence microscope equipped with an Axiocam digital camera, and the software AxioVision Rel 4.8. was used to image samples with Venus green and Red Fluorescent protein. Images of histological slides, H&E images were taken on a Leica DM 4000B Light microscope D (Leica Microsystems) equipped with a Leica DFC320 color digital camera (Leica Microsystems). The Software program used to capture the images was called Leica Application Suite version 44.0 (Build: 454).

RNAi Targeting of Venus-Sensor—Analysis by FACS.

To analyze tumors by FACS, tumors were isolated from the peritoneal cavity of a mouse, washed in PBS, and dissociated with Trypsin. After the cell suspension was strained over a 70 m Fisherbrand® nylon mesh (Fisher Scientific, Cat. No.: 22363548), the suspension over the cells were analyzed by FACS. BD LSRFortessa Analyser at the Flow Cytometry Core, Northwestern University, was used for flow analyses. The data was analyzed using the program FlowJo 8.8.6. To ensure that only tumor cells were analyzed, only the red events (NucRed or pFUL2T infected cancer cells) were considered. The percentage of high green and low green expressing cells were quantified. For assessing the granularity of the tumors cells, the values of the side scatter area were compared between treatments.

RNAi Targeting of Venus-Sensor—Analysis by Fluorescent Microscopy.

Tumors were fixed in 4% Paraformaldehyde (A 32% Paraformaldehyde stock solution, EM grade (Electron Microcopy Sciences, Cat. No.: 15714-S) was diluted with deionized water) over night, followed by a sucrose gradient (10% sucrose for 2 hours, 20% sucrose for 2 hours, 30% sucrose overnight), before they were shock frozen in TissuePlus® O.C.T. Compound Embedding medium (Scigen Scientific Gardena, Calif., Cat. No.: 4583) following standard tissue freezing procedures. The frozen O.C.T blocks were sectioned at 6 um, mounted on slides by the MHPL (Northwestern University), and stored at −80° C. until use. To assess the effect of the treatment on the Venus-fluorescence, slides with the section was thawed at room temperature, washed gently three times with PBS buffer, and mounted with a coverslip using Antifade VectaShield+DAPI (Vector Laboratories Inc., CA, Cat. No.: H-1200). Images of tumors with different treatments were taken on the Zeiss Axiovert S100 fluorescence microscope with the identical settings. Tumor cells only expressed a red fluorophore, which allowed to compare tumor areas with high as well as low green fluorescent Venus-sensor expression.

Serum Collection and Toxicity Test.

Two mice from each TLP treatment group were selected as representatives to assess TLP toxicity. Whole blood was collected from each mouse via retro-orbital bleeding using disposable glass Pasteur pipettes when mice were sedated. Blood was then allowed to gravity drip into Greiner BioOne™ MiniCollect™ Capillary Blood Collection System Tubes (Fisher Scientific, Cat. No.: 22-030-400) that were kept on ice. The collection tubes containing the serum were spun at 3000 g for 10 minutes at 15° C. After completion of the spin, two layers formed in the tube. The top layer containing the whole serum was collected, volume measured, transferred to new sterile Eppendorf™ Snap-Cap Microcentrifuge Safe-Lock™ Tubes (Fisher Scientific, Cat. No.: 05-402-25), frozen, and stored at −20° C. The serum samples were analyzed using a Complete Chemistry Profile Test performed by the Charles River Research Animal Diagnostic Services (Wilmington, Mass.).

Statistical Methods.

Two-way analysis of variances (ANOVA) were performed using the STATA14 software to compare growth curves. One-tail student t-test was performed in the software package R to compare tumor load between treatment groups. Wilcoxon Rank Sum test was performed in R to compare IVIS signal between treatment groups.

Example 4—Induction of DISE by Tumor Suppressive microRNAs

Reference is made to Quan Q. Gao, William E. Putzbach, Andrea E. Murmann, Siquan Chen, Aishe A. Sarshad, Ambrosini, G, Elizabeth T. Bartom, Markus Hafner, and Marcus E. Peter, "Induction of DISE by tumor suppressive microRNAs," in preparation.

Abstract

Many siRNAs and shRNAs induce a form of cell death in all cancer cells by silencing a set of critical survival genes in a process called death induced by survival gene elimination (DISE). Mechanistically, a 6mer seed sequence (position 2-7 of the guide strand) is sufficient to confer DISE-inducing activity. We have now performed a strand-specific screen testing the toxicity of all 4096 possible 6mer seed sequences in a neutral double-stranded siRNA backbone. We found an asymmetric preference for guanine in positions 1-3 of the 6mer seed in the most toxic siRNAs, which target survival genes that are GC rich in their 3'UTR. During over 800 millions years of evolution, miRNAs have evolved to avoid guanine in their seed sequences. However, two tumor suppressive miRNAs were found to be killing cancer cells through DISE using G rich toxic seeds in cells exposed to genotoxic stress: 1) the p53 inducible miR-34 family and most of its cell death inducing activity comes form its 6mer seed; and 2) miR-320a, a noncanonical miRNA that is still expressed in cancer cells when miRNA processing genes are mutated. Ago-bound miR-320a is converted from a poorly to a highly toxic miRNA by removal of two adenine nucleotides from its 5' end. Our data suggest that most miRNAs have evolved to avoid induction of DISE but certain tumor suppressive miRNAs utilize this mechanism to kill cancer cells.

Introduction

RNAi is a form of post-transcriptional regulation exerted by 19-21nt long double stranded RNAs that represses expression of target mRNAs that harbor reverse complementary to the antisense/guide strand of the small RNA. Hybridization between the guide RNA strand and the target recruits the RNA-induced silencing complex (RISC), which directly cleaves the target RNA. RNAi active RNAs can be endogenous siRNAs and micro(mi)RNAs. Today, nearly 1,900 miRNAs in humans are catalogued in the public database miRbase (see miRBase organization website) (1). miRNAs control everything from proliferation (2) and apoptosis (3) to differentiation and development (4). It is estimated over 60% of all human genes are conserved targets of at least one miRNA (5).

For a miRNA, the RNAi pathway begins in the nucleus with transcription of a miRNA precursor (pri-miRNA) (6). Pri-miRNAs are first processed by the Drosha/DGCR8 Microprocessor complex (7). Both newly-transcribed short hairpin(sh)RNAs and processed pre-microRNAs are exported from the nucleus to the cytoplasm by Exportin 5 (8). Once in the cytoplasm, Dicer processes them further, along with other dsRNA duplex structures (9, 10). Mature dsRNA duplexes are then loaded into Argonaute proteins to form the RISC (11). Once loaded, the sense/passenger strand is ejected/degraded, while the guide strand remains associated with the RISC (12). In humans, AGO2 degrades targeted mRNAs through its slicer activity (13). However, Argonaute protein can also execute RNAi through deadenylation/degradation or translational repression via interaction with Glycine-Tryptophan Protein Of 182 KDa (GW182) (14).

Although artificial si/shRNAs are usually designed with 100% reverse complementarity to their intended targets, cleavage-independent RNAi can be initiated with as little as six nucleotide base-pairing between a guide RNA's so-called seed sequence (positions 2 to 7/8) and the target RNA (15). This seed-based targeting is restricted to binding sites located in the 3' UTR, whereas full-complementary binding sites can initiate RNAi whether located in the ORF or UTR regions of an mRNA (16, 17).

miRNAs play important roles in cancer. Such-called "oncomiRs" can act as either tumor suppressors or oncogenes (18, 19). While the function of a miRNA depends on the nature of its targets, some miRNA families have predominantly tumor suppressive or oncogenic activities. Some of the most oncogenic miRNAs include the miR-17-93 family, miR-21, miR-155 and miR-221/222 (19). Almost always tumor suppressive are the miR-34 family (three members), the let-7 family (13 members) and the miR-15/16 family (3 members) (18, 19). The miR-34 family is a p53 induced miRNA exerting its activity upon genotoxic stress by targeting a large number of targets that are involved in cell survival and cell proliferation (20). Hundreds of cell- and animal-based studies support the function of miR-34a as a master regulator of tumor suppression and provided the rationale for miR-34a as a potential therapeutic strategy (21).

We recently discovered that many si- and shRNAs can kill all cancer cells through RNAi by targeting the 3'UTR of critical survival genes (22). We termed this form of cell death DISE (for death induced by survival, gene elimination). DISE induction involves activation of multiple cell death pathways in parallel, with a ROS mediated necrotic form of mitotic catastrophe at its core (23). In addition, cells suffer from extreme stress followed by signs of genomic instability and aneuploidy. Finally, cancer cells have a hard time developing resistance to this treatment both in vitro and when treated in vivo using DISE-inducing siRNAs coupled to nanoparticles (24). We reported that a seed sequence in the toxic siRNAs of as little as 6 nucleotides is sufficient for effective killing (22).

We have now performed a strand specific siRNA screen with a library of siRNAs representing all 4096 possible 6mer seed sequences. We report that the most toxic DISE-inducing seeds are G rich with the highest G concentration towards the 5' end of the seed. We demonstrate that their toxicity can be explained by targeting survival genes with high GC content in their 3'UTR. We also report that tumor suppressing miRNAs (miR-15/16 or miR-34a) contain G rich 6mers seeds and which are more toxic in our screen than the seeds of oncogenic miRNAs (i.e. miR-17-93). miR-34a was found to be one of the most toxic miRNAs and we show that most of its toxicity comes from its 6mer seed sequence. Upon genotoxic stress this p53 regulated miRNA is upregulated in the RISC of HCT116 cells. Drosha$^{-/-}$ cells which lack most canonical miRNAs, including miR-34a, are hypersensitive to genotoxic drugs suggesting an RNAi component in the toxicity of this form of cell death. Under these conditions the only inducible miRNA found in the RISC was the tumor suppressive miRNA miR-320a which does not require Drosha for its biogenesis. Genotoxic stress caused 5' trimming of mature miR-320a converting it from low to a highly toxic miRNA. In general, older more conserved miRNAs contain less toxic seeds. Our data also allow to explain why certain miRNAs predominantly express the 5p arm whereas others express mostly the 3p arm. We demonstrate that for most miRNAs including the oncogenic miRNAs the mature form expressed corresponds to the arm that contains the less toxic seed. In contrast, for major tumor suppressive miRNAs the mature miRNA is derived from the arm that contains the more toxic seed. Our data allow us to conclude that while most miRNAs have evolved to avoid targeting survival and house keeping genes, certain tumor suppressive miRNAs kill cancer cells through induction of DISE especially after genotoxic stress.

Results

Identifying the Most Toxic DISE-Inducing 6Mer Seeds.

Our previous work demonstrated that a short seed sequence of 6 nucleotides in si- and shRNAs is sufficient to mediate a toxicity of siRNAs that kill all cancer cells through targeting the 3'UTRs of multiple survival genes resulting in the simultaneous activation of multiple cell death pathways. We called this form of cell death DISE, for death induced by survival gene elimination (22, 25). We recently designed a 19mer oligonucleotide scaffold with two nucleotide 3' overhangs to test the activity of any 6mer seed sequence in the guide strand of an siRNA (26). The 6mer was added at positions 2-7 of the guide strand and the passenger strand was modified in positions 1 and 2 by 2'-O-methylation, which blocked its loading into the RISC (FIG. 29A). By using this scaffold, we found that virtually all of the activity of the most toxic siRNA derived from CD95L, siL3, stemmed from its 6mer seed sequence as the 6mer seed construct (siL3$^{seed}$) was as toxic as the entire siRNA derived from the sequence of CD95L (26). To determine the general rules of targeting that underlie DISE, we tested the toxicity of all possible 4096 6mer seed sequences in this 19mer scaffold with blocked passenger stand loading (FIG. 29B). The tested siRNAs showed varying levels of toxicity when transfected into the ovarian cancer cell line HeyA8 at 10 nM (FIG. 29B). This toxicity was due to RNAi as knockdown of AGO2 prevented the two most toxic siRNA duplexes from being toxic (FIG. 29C). Consistent with the role of the 6mer in the toxicity of the siRNAs the seeds of the 4 previously tested siRNAs derived from CD95L (23) were about as toxic as the full length siRNAs with siL3$^{seed}$ being most toxic followed by siL2$^{seed}$ and less or no toxicity associated with siL4$^{seed}$ and siL1$^{seed}$ (FIG. 29B). We also saw a significant correlation between the predicted DISE toxicity of siRNAs, the 6mer toxicity index (TI) (22) and the observed toxicity of the 6mer seed siRNAs (data not shown). The TI for each siRNA is calculated as the number of seed matches present in the 3'UTR of a set of ~1800 survival genes when compared to the number of seed matches found in a set of ~400 nonsurvival genes. A similar correlation was also found between the toxicity of the most toxic CD95L derived shRNAs, determined in a screen of all possible CD95L derived shRNAs (22) and the matching 6mer seed siRNAs (FIG. 29D, left). 139 of the tested 825 shRNAs derived from CD95L were found to be downregulated at least 5 fold (=toxic) in this screen and a substantially higher number of the seeds in these shRNAs were super toxic (>90% loss in viability, red dots in FIG. 29D, right) when compared to a control set of 139 shRNA that were not downregulated. These data establish that the 6mer seed alone determine toxicity to cancer cells and the observed toxicity significantly tracks with the in silico predicted toxicity (TI) and an experimentally determined toxicity using a set of shRNAs. This suggests that many of the 6mer seeds are toxic due to DISE induction.

There was substantial agreement in the toxicity of the 4096 seeds duplexes when the mouse liver cancer cell line M565 was tested with all 4096 duplexes (FIG. 29E) suggesting that some of the rules governing DISE were conserved between mouse and human. This was also supported with the comparison of the results with the TI based on mouse survival genes (data not shown). We noticed that the nucleotide composition of the two seeds of the toxic CD95L derived siRNAs (siL3 and siL2) had a higher G content than that the seeds of the two non toxic siRNAs (siL4 and siL1 (FIG. 29B). We previously found a significant correlation between the GC content of the seed and the toxicity of the screened shRNAs (22). This was now confirmed by analyzing the screen result of the 4096 seeds in both the human and the mouse cell line (FIG. 29F). However, upon closer inspection we found a substantial difference in toxicity between seeds with high G and seeds with high C content. G containing seeds appeared to be more toxic than C containing seeds. The least toxicity was found with seeds with a high A content. These data suggested that the DISE inducing toxicity relied on a specific nucleotide composition.

DISE-Inducing Seeds have a G Rich Nucleotide Composition.

The screen of the 4096 seed duplexes suggested that seeds with a high G content would be most toxic to a human and a mouse cancer cell line. In order to test this directly for each of the four nucleotides we selected the 19 seed duplexes with the highest G content (83.3-100%) and tested these 76 duplexes on four cell lines, two human (HeyA8 and H460, lung cancer) and two mouse (M565 and 3LL, lung cancer) (FIG. 30A). The reanalysis of these cherry picked seeds also allowed us to determine the reproducibility of the results obtained in the large screen (which for technical reasons had to be performed in three sets). Both the data on the HeyA8 and the M565 cells were highly reproducible especially in the most toxic seeds (data not shown). When the data on the four cell lines were compared it became apparent that in all cell lines the G-rich seeds were by far the most toxic followed by the C rich, U rich and A-rich seeds (FIG. 30A). This indicates that it is not so much the GC content of the seed but the G content that determines DISE toxicity. Most analyses to determine toxicity of certain siRNA duplexes were performed using existing sets of si- and shRNAs that cover all genes in the genome (27-29). In all cases these si/shRNA sets were designed following certain rules to reduce off target effects (30). This resulted in large siRNA and shRNAs sets lacking certain seeds. An example of the nucleotide representation in each of the 6 seed positions in one of the commercial siRNA libraries is shown in FIG. 30B (left panel). Such libraries designed to study functions of individual genes are highly underrepresented in Gs and Cs. In contrast our complete set of 6mer seed duplexes allowed to test the contributions of all four nucleotides in each of the 6 seed positions (FIG. 30B, right panel). That the nucleotide composition in different seed positions could matter became clear when we analyzed the results of the screen of the most C-rich seeds (purple box in FIG. 30A). Their toxicity decreased in all four cells lines with C to A replacement moved from the 5' to the 3' end of the seed (stippled grey lines in FIG. 30A). To determine the nucleotide content of the most toxic seed we averaged the nucleotide content at each of the 6 positions of either the 200 most or 200 least toxic seed duplexes for HeyA8 cells (highlighted in FIG. 29B) or for M565 cells (data not shown). In both cell lines we noticed that a high G content towards the 5' end of the seed was most toxic while in position 6 C predominated (FIG. 30C). In contrast, nontoxic seeds were much more A and U rich again with an asymmetry with U predominating toward the 5' end and A more frequent at the 3' end of the seed.

siRNAs with toxic seeds target house keeping genes enriched in C-rich Sequences.

Seeds Sequences Rich in Gs Towards their 5' End were Most Toxic Suggesting that they targeted genes important for cell survival carrying seed matches rich in Cs at their 3' end. To determine whether such genes existed we performed a Matrix Motif search using the PMWScore tool (PMW-Tools, http://vital-it.ch/pwmtools). To be most stringent the nucleotide composition of the 20 most toxic seeds (FIG. 31A) was used to generate a matrix and all human 3'UTRs were screened for the best single hits (results not shown). When this list ranked according to the highest score was subjected to a gene ontology analysis using GOrilla the GO terms with the lowest p-values ($<10^{-11}$) were consistent with the affected genes being important for cell survival (FIG. 31B, top). They included a number of biosynthetic and metabolic processes. This was not found when the list was reversed ranked according to the lowest PMW score (FIG. 31B, bottom). To determine whether survival genes carried specific seed matches or be targeted by G rich seeds or were overall GC rich, we determined the nucleotide content of the genes with the highest score (>400, 4287 genes) with a group of the lowest scoring genes of a similar size (<90, 4835 genes) (results not shown). Compared to the average nucleotide content of all 3'UTRs which are known to be rich in A and U (31), the genes with a score >400 had a much higher G and C content (with a subtle but significant overrepresentation of C) when compared to the genes with a score <90. This suggested that the genes targeted by G rich seed-containing siRNAs did contain genes with a higher C content but they were also overall rich in G and C. This also suggested that survival/housekeeping genes would have a higher GC content than nonsurvival genes. An analysis of a group of ~1800 survival genes and ~400 nonsurvival genes confirmed this prediction (results not shown). To determine whether GC rich sites occurred at a special location within 3'UTRs in otherwise AU rich 3'UTRs, we plotted the best first position of the sequences identified with either the toxic or the nontoxic matrix (results not shown). Consistent with an analysis of single nucleotide distribution in all human coding genes (32) we found the first best matches of GC rich targets complementary to the toxic matrix to be within 100 nts of the stop codon whereas sequence motifs complementary to the nontoxic matrix were further away (>200 nts). When testing the subset of survival and non survival genes, even as it did not reach statistical significance it appears that best first seed matches with the toxic matrix in the 3'UTRs of survival genes were closer to the 3'UTR start then in non survival genes. This difference was not seen when the analysis was repeated with the nontoxic matrix (results not shown).

We had previously postulated that DISE was an anticancer mechanism and predicted that small siRNA active sRNAs would be involved in killing cancer cells (25). Consistent with this hypothesis an analysis published data on point mutations in the exomes of 27 different human cancer showed that losing a C is the predominant point mutation across all cancers (33). Frequencies of such point mutations ranged from >60% (in acute myeloid leukemia) to >90% (in cervical cancer) (FIG. 31C). Remarkably, the frequency of the loss of Cs was independent of the mutational load of cancers.

Interestingly, two of the five significantly enriched Top Regulator Effect Networks of genes that were identified in the PWM analysis when analyzed with an Ingenuity Pathway Analysis (IPA) were regulated by two miRNAs with a G-rich seed sequence (FIG. 35). They are predicted to repress expression of genes that are required for cell proliferation of tumor cells, DNA and RNA transcription and cellular homeostasis. The two 6mer seeds of the miRNAs were highly toxic in our screen (FIG. 35). This result raised the question of whether miRNAs could be utilizing the seed toxicity we have now defined to kill cancer cells through induction of DISE by targeting survival and house keeping genes.

Tumor Suppressive miRNAs with Toxic DISE-Inducing 6Mer Seeds.

To test whether certain miRNAs could kill cancer ells through toxic 6mers we identified, we compared the seed toxicity determined in our screen for the most highly expressed arm (3p or 5p) of the 500 main miRNAs (FIG. 32A and results not shown). While none of the 6mer seeds present in the most oncogenic miRNAs (miR-221/222, miR-21, miR-155, the miR-17-92 cluster (miR-17, miR-18a, miR-19a, miR-20a, miR-19b-1, and miR-92a) and its paralogues the miR-106b-25 cluster (miR-106b, miR-93 and miR-25) and the miR-106a~363 cluster (miR-106a, mR-18b, miR-20b, miR-19b-2, miR-92-2 and miR-363) (34)) were toxic (reduced viability >50%, stippled line in FIG. 32A), two of the major tumor suppressive miRNA families, miR-15/16 and miR-34a/c and miR-34b contained highly toxic seeds (labeled in red). This suggests that these two families were killing cancer cells through induction of DISE. Interestingly, two major tumor suppressive families, let-7 and miR-200 (35), were not found to contain toxic G rich seeds suggesting that they may be tumor suppressive through other mechanisms. The most toxic seed in a major tumor suppressive miRNA was found in miR-34a. Interestingly, the three miR-34 family members are p53 induced genes and are considered master regulators of tumor suppression (21). Similar to DISE-inducing siRNAs (24) they have been shown to have no toxicity to normal cells (36). When transfecting the pre-miRs of miR-34a, miR-15a and let-7a into HeyA8 cells potency of these three miRNAs to reduce cell growth mimicked the toxicity of their 6mer seeds (FIG. 32B). This suggested that a large part of their toxicity may come from the composition of positions 2-7. To test this directly for the most toxic miRNA, we compared the activity of pre-miR-34a and miR-34a$^{seed}$ (FIG. 32C). Strikingly the effect on cells were virtually identical. Cells showed the typical morphology we found in other cells undergoing DISE (FIG. 32D) (22, 23, 37). While optimal miRNA targeting requires at least a 7mer seed interaction and also involves nucleotides at positions 13-16 of the miRNA (38), DISE induction only requires a 6mer seed. This suggests that miR-34a may have targets that are not involved in keeping cells alive. A recent phase I clinical trial was stopped when five of patients developed side effects in form of a severe cytokine release syndrome. Could these adverse effects be due to miR-34a inducing DISE or to its activity to silence other targets that require more than a 6mer seed to be targeted? To test this, we will perform an RNA-Seq analysis on HeyA8 cells transfected with either pre-miR-34a of just its toxic seed (miR-34a$^{seed}$). We expect to find that there will be a substantial overlap in downregulated genes between pre-miR-34a and the miR-34a$^{seed}$ transfected cells and that a number of genes will be downregulated only in the pre-miR-34a treated cells. While miR-34a may have additional activities, its DISE inducing activity may only require the 6mer seed.

Genotoxic Stress Upregulates Toxic miRNAs.

Our data on miR-34a containing a DISE inducing seed and the fact that miR-34a is being upregulated after genotoxic stress (20), we were wondering whether miR-34a would contribute to cell death induced by genotoxic drugs (such as doxorubicin (Doxo), carboplatin (Carbo), or etoposide (Eto)) and whether this type of cell death has similarities to DISE. This would be consistent with the observation that many genotoxic drugs induce multiple cell death pathways (39-43), and treated cells display morphologies similar to cells undergoing DISE (44, 45) (FIG. 36). To compare cell death induced by different chemotherapeutic agents with that of toxic si/shRNAs we treated the ovarian cancer cell line HeyA8 with Doxo, Carbo or Eto to perform an RNA-Seq analysis. Drug concentrations were chosen so that 80 hrs of treatment caused a slow down in cell growth and signs of stress without major cell death occurring (data not shown). The goal was to identify RNA changes that could potentially be causative and not the result of ongoing cell death. Interestingly, the morphological changes in the cells treated with the drugs were very similar to the ones seen in cells treated with si/shRNAs (FIG. 36).

The ranked lists of downregulated RNAs isolated from HeyA8 cells treated with the three drugs were subjected to a gene set enrichment analysis (GSEA) to determine whether the set of ~1800 survival genes was enriched in the downregulated genes (results not shown), an effect we described in cells in which we induced DISE using CD95/CD95L derived siRNAs (22). There was strong enrichment of downregulated survival genes towards the top of the ranked list with no enrichment in the control set of ~400 nonsurvival genes. 102 of the survival genes were downregulated in cells treated with either of the three drugs (results not shown). In a DAVID gene ontology analysis they strongly enriched in a few clusters all consistent with their involvement in chromosome segregation, DNA replication, cell cycle regulation, and mitosis (data not shown). To determine whether downregulation of these survival genes was the likely cause of cells dying during the drug treatment, we quantified 30 of the 102 survival genes in HeyA8 cells treated with Doxo for different times using an arrayed PCR (results not shown). 25 of the 30 genes mRNAs were significantly downregulated as early as 7 hours after treatment with no further reduction beyond 15 hrs after treatment suggesting that their loss was the cause of cell dying rather than a consequence.

Supporting the similarity between genotoxic drug induced cell death and DISE, we found that 11 out of 12 genes significantly downregulated (>2 fold, adjusted p-value <0.05) in cells after treatment with the three drugs or any of four DISE-inducing si/shRNAs (22) to be histones (FIG. 37). The high similarity of the response of cancer cells to the sh/siRNAs and the three genotoxic drugs suggested similarities in the mechanism of cell death. A Metascape analysis of all 7 RNA Seq data pairs confirmed this similarity (data not shown). The GO clusters that were most significantly downregulated in cells treated with either of the three genotoxic drugs or the four DISE inducing si/shRNAs derived from CD95/CD95L were again related to DNA repair, cell cycle, and mitosis, consistent with DISE being a necrotic form of mitotic catastrophe (23).

To test whether treatment of cells with genotoxic drugs causes the production of small RNAs, in particular miRNAs that can be found in the RISC, HeyA8 cells were treated with Doxo for 80 hrs or cultured without drug. RNA was extracted and subjected to RNA Seq analysis of small RNAs (results not shown). The composition of the total miRNA content in the cells was not affected in a major way by the Doxo treatment. Four miRNAs (miR-21, miR-10a, miR-30a and miR-10b) represented more than 50% of all miRNAs in these cells and virtually the same 20 miRNAs represented more than 90% of all miRNAs in the untreated and Doxo treated cells (results not shown). To determine what small RNAs were loaded onto the RISC we precipitated all 4 Ago proteins using a GW182 peptide as described (73). HeyA8 were treated with Doxo for 0, 20, 40 and 80 hrs. Interestingly, while the amount of AGO2 pulled down was the same at all time points the amount of bound miRNA-sized RNAs increased with longer treatment times (FIGS. 33A and 33B). This was not only due to a more efficient binding of AGO proteins loaded with guide RNAs to the GW182 protein as reported (46) but most likely the result of an overall increase in total small RNAs in the treated cells (FIG. 33B). After Doxo treatment most of the Ago bound small RNAs were again miRNAs (results not shown). Interestingly, miR-34a which was a minor miRNA in the total small RNA pool now contributed a much more substantial fraction of the Ago bound miRNAs (results not shown). miR-34a, b and c bound to Ago proteins were upregulated at all time points (FIG. 33C). While some reports demonstrated that inhibiting miR-34a rendered cancer cells more resistant to cell death induced by genotoxic stress ((47) and refs), one report found no effect of knocking out miR-34a on the sensitivity of HCT116 or MCF-7 cells to Doxo (48). To determine the contribution of miR-34a and other miRNAs to the toxicity seen in cells exposed to the genotoxic drugs, we treated Drosha$^{-/-}$ cells which are devoid of most canonical miRNAs (Kim et al) with the three genotoxic drugs (FIG. 33D). Interestingly, these cells were hypersensitive to the toxicity induced by any of the three drugs. We recently reported that Drosha$^{-/-}$ cells were hypersensitive to toxic siRNAs (22, 26). We had interpreted this result with the RISC complex in these cells being more available to the uptake of small toxic RNAs. Our data suggested that not only is miR-34a not essential for the cell death induced by genotoxic drugs in HCT116 cells but also none of the other canonical miRNAs.

The hypersensitivity of the Drosha$^{-/-}$ cells suggested an involvement of the RISC in the toxicity of the drugs. We therefore wondered whether in the absence of most canonical miRNAs other miRNAs with toxic seeds could be loaded into the RISC ensuring the death of the cells. Indeed the composition of small RNAs found bound to Ago proteins dramatically varied between wild-type and Drosha$^{-/-}$ cells (FIG. 33E). In the absence of most canonical miRNAs miR-320a which was previously shown to not require either Drosha or Dicer for its biogenesis (49) represented more than 86% of all miRNAs). We compared the levels of RISC bound miR-34a and miR-320a in either HCT116 wild-type or Drosha$^{-/-}$ cells after treatment with Doxo (FIG. 33F). Similar to HeyA8 cells miR-34a bound to Ago proteins was upregulated in the wild-type but not in the knock-out cells. In contrast, miR-320a which in the absence of most other miRNAs represented a substantially higher percentage of RISC bound small RNAs in the knock-out cells was slightly upregulated.

Processing of miR-320a Converts it into a Highly Toxic miRNA.

We noticed that the main form of RISC bound miR-320a upregulated in HCT116 cells after Doxo treatment was shorted by two nucleotides at its 5' end when compared to the predicted, and most abundant, sequence of mature miR-320a (FIG. 34A). This effect was not observed for the three most highly upregulated miRNAs where the most highly upregulated and the most abundant species overall had the same 5' end and hence the same seed. The trimming of miR-320a at the 5' end was even more pronounced in HCT116 Drosha$^{-/-}$ cells where miR-320a represented almost all RISC bound miRNAs. Interestingly, the removal of two As at the 5' end of miR-320a-3p according to our seed screen predicted a conversion of miR-320a from a slightly toxic into a hyper toxic miRNA, more toxic than even miR-34a (see FIG. 32A). To test this we transfected HeyA8 cells with either the authentic pre-miR-320a or an miR-320a$^{seed}$ duplex that corresponded to the shortened miR-320a sequence (miR-320a$^{Ago}$) (FIG. 34B). While pre-miR-320a was not toxic, miR-320a$^{Ago}$ was highly toxic to the cells. These data suggested that in the absence of other small RNAs that could kill cells through DISE miR-320a (and possibly other small RNAs) may act as back up to ensure that genotoxic stressors can kill cells with defective miRNA processing often observed in cancer (50, 51) through DISE. By analyzing the potential seed sequences (2-7) in all small Ago-bound RNAs in HCT116 wt and Drosha$^{-/-}$ cells we noticed that the G content in the 6mer seed was significantly higher in the upregulated sequences than in the downregulated ones (data not shown) suggesting that cell under genotoxic stress produce small RNAi active RNAs that could contribute to the cell death through DISE induction. To test whether in cells treated with these drugs there was evidence of downregulated genes carrying C rich 6mers that could be targeted by small G rich RNAs we analyzed the ranked list of deregulated RNAs from the HeyA8 cells treated with the three drugs from highest downregulation to highest upregulation using the Sylamer analysis. We consider all sequence motifs that were either significantly enriched or depleted in the most downregulated mRNAs (data not shown). This analysis revealed that the downregulated RNAs contained enriched 6mer seed matches for predicted 6mer seeds that were significantly more toxic than the seeds that target the motifs depleted in the downregulated mRNAs (FIG. 34C). These data are consistent with G rich sequences being released in the treated cells. By analysis of the 6 positions in the 6mer seed matches of the down-regulated mRNAs, we found that in positions 1/2 and 5/6 C and G predominated (results not shown). In contrast the 6mer motif underrepresented in the most downregulated mRNAs was almost devoid of Gs and Cs in these four positions (results not shown). This analysis provide indirect evidence that genotoxic drugs cause an upregulation of toxic RNAi active RNAs that target mRNAs with C and G rich 6mers and that DISE induction contributes to the cell death seen in treated cells. These RNAs may not all be miRNAs.

When analyzing small Ago bound HeyA8, HCT116 and HCT116 Drosha$^{-/-}$ cells treated with Doxo we identified only 7 small RNAs that were upregulated more than 1.5 fold in all three cells when treated with Doxo (data not shown). They corresponded to 5 unique 5' ends. Two of them (#1 and 2) were derived from 45S rRNA, two came from unknown regions on the human genome (#3 and 4) and the fifth was miR-320a$^{Ago}$. We now tested all 5 sequences as siRNA duplexes after transfection into the four cancer cell lines used before (HeyA8, H460, 3LL and M565). All 5 duplexes showed significant toxicity in all four cell lines when compared to the established toxicity of siL3 with miR-320a$^{Ago}$ being the most toxic sequence (FIG. 34D). Our data suggest that certain tumor suppressive miRNAs, such as miR-34 and miR-320a exert their tumor suppressive activities by carrying toxic 6mer seeds sequences that can kill cancer cells through DISE. This activity may contribute to the cell death induced by genotoxic drugs used to treat various cancers.

DISE and the Evolution of miRNAs.

Our strand specific seed screen now allows to not only to predict what si/miRNAs are toxic to cells but if endogenous small RNAs such as miRNAs use this mechanism to be toxic to cancer cells. Similar to miRNAs the DISE mechanism may therefore be highly conserved during evolution. It was previously determined that miRNAs have evolved to target genes required for various cell functions, however that the 3'UTRs of house keeping genes are depleted of most miRNA targets (52). Based on the composition of DISE-inducing seeds we determined and the enrichment of GC rich sequence motifs in survival genes, we can now ask if and when miRNAs evolved that contain toxic G rich sequences in positions 2-7 of their seeds. Such miRNAs could be tumor suppressive by inducing DISE. When comparing all miRNAs that are analyzed in TargetScan we noticed that miRNAs in highly conserved miRNA families contain seed sequences that were much less toxic in our screen than seeds in poorly conserved miRNAs (data not shown). Consistent with our analysis on the effect of nucleotide content on seed toxicity, the 6mer seed of poorly conserved miRNAs had a balanced nucleotide composition in all 6 seed positions with a slight excess of Gs (FIG. 38, far left). In contrast miRNAs that were highly conserved from humans to zebrafish had replaced Gs in the first three seed positions with the nontoxic A (FIG. 38, far right). Interestingly, the loss of G in these positions is consistent with the asymmetry we found in the seed with respect to Gs being more toxic when positioned towards the 5' end of the seed (see FIG. 31A). In addition, highly conserved miRNAs somewhat avoid either G or C in position number 6. Weakly conserved miRNAs would be expected to be younger in evolutionary age than highly conserved ones. Consistent with this assumption we found that the 6mer seeds of younger miRNAs (<10 million years old) were more likely to be toxic to cells than the ones of older miRNAs (>800 million years old) (53) (data not shown). Most importantly, when comparing miRNAs of different ages it became apparent that seeds of miRNAs over the last 800 million years were gradually depleted of Gs beginning at the 5' end and eventually also affecting positions 3-5 until in the oldest ones G was no longer the most abundant nucleotide in any of the 6 positions (data not shown). It became replaced by A and Us. These analyses indicated that miRNAs that are highly conserved and highly expressed in cells avoid Gs in potentially toxic seed positions.

miRNAs are expressed as pre-miRs and usually only one major species of mature miRNA (either the 5p or the 3p arm) is found in cells produced from one of the two strands of the premiR stem (54). Consistent with the assumption that cells cannot tolerated toxic DISE-inducing seeds we now found that for the major miRNAs the lesser expressed arm is predicted to be more toxic than the highly expressed one (data not shown). This not only confirmed that miRNAs with toxic seeds exist and are not readily expressed but it also allowed us to provide and explanation for why certain miRNAs are detected only as 3p or 5p forms. However, our analysis did not consider the possibility that certain miRNAs such as miR-34a or miR-320a may have evolved to kill cancer cells using a toxic seed. In these cases one would actually expect the more abundant arm to carry the toxic seed. To test this assumption we ranked all major miRNAs known to give rise to both 3p and 5p versions according their to the ratio of toxicity (loss of viability) of the predominant to toxicity of the lesser arm (data not shown). When we labeled the major tumor suppressive and oncogenic miRNAs we noticed that for most of the oncogenic miRNAs the highly expressed arm contains a 6mer seed that was not toxic in our screen (data not shown). In contrast, for almost all tumor suppressive miRNAs the highly expressed arm contained a seed much more toxic than the lesser arm (data not shown). The overall difference in ratio between the two groups of miRNAs was highly significant. A more detailed analysis of these data revealed that the three oncogenic miRNAs with the highest relative expression, miR-363, miR-92-2, and miR-25 were almost exclusively expressed as the nontoxic 3p form (data not shown). In contrast, the three miRNAs with the highest use of the arm with the toxic seed were miR-34a. miR-34c, and miR-449b (data not shown). Interestingly, miR-449b has the same seed sequence as miR-34a and has been suggested to act as a back up miRNA for miR-34a. This could be seen in miR-34a knock out mice (55). These data lend support to the hypothesis that the most tumor suppressive miRNAs us the DISE mechanism to kill cancer cells and suggest that the DISE mechanism developed hundreds of millions years ago.

Discussion

The Toxic Seed Screen.

We recently postulated the existence of small RNAi active sequences that are toxic to cancer cells but not normal cells (25). However, testing all possible siRNA sequences for toxicity is not possible as a 19mer duplex siRNA would have 270 billion different sequence combinations. While miRNAs effectively target through stable 7mer seed pairing (16,348 combinations), effective targeting also involves 3' sequences in the guide strand (38) again precluding a systematic screen for toxic sequence elements. We recently discovered that a fundamental cell type and species-independent form of seed sequence specific toxicity, we called DISE, is determined by a 6mer seed sequence in si-/shRNAs (22, 25). To test the activity of seeds, we recently modified a neutral nontoxic 19mer siRNA backbone in a way that allows testing of only the guide strand by adding two 2'-O-methylation groups to positions 1 and 2 of the passenger strand (26). This blocked loading of the passenger strand into the RISC. This has now allowed us to test all 4096 possible 6mer sequences in a neutral siRNA duplex scaffold to determine the rules that govern DISE induction. By ranking the 4096 6mer seeds from most toxic to least toxic we could determine the most toxic seed composition for human and mouse cells.

Sequence specific RNAi toxicity has been reported before (56, 57). However, most of these studies involved either testing all possible si/shRNAs targeting one specific gene (58, 59) or using genome-wide siRNA libraries (27-29). These studies were limited by the nucleotide sequences of the targeted genes or the composition of the siRNA libraries. Almost all commercial siRNA libraries are designed using specific rules that ensure efficient and target specific knockdown (30). They lack GC-rich sequences in their seeds as these were found to be ineffective in mediating RNAi (60, 61). Our comprehensive screen now allows us to assign to all si- and shRNA a toxicity score and we provide evidence that this score can also be applied to miRNAs.

The Rules of Targeting.

Based on a limited set of shRNAs present in the genes CD95 and CD95L we had reported previously that the toxicity tracked with the GC content of the seed (22). Our comprehensive and strand specific analysis now confirmed this, however it also revealed that G rich seeds are much more toxic than C rich seeds, followed by U rich seeds and no detected toxicity in highly A rich seeds. The preference for G richness in highly toxic seeds was confirmed with four different cell lines representing different species, cancer and tissue of origin. Interestingly, the toxicity of miRNAs could also be predicted solely on the basis of their 6mer seed sequences, suggesting the rules of DISE induction are not limited to artificial si/shRNAs. When analyzing the most toxic seeds we found an asymmetry of high G content towards the 5' end of the seed and higher C content in position 6 of the seed. The enrichment of Gs in the first 2-3 positions of the seed is consistent with the way Ago proteins scan mRNAs as targets. This involves mainly the first few nucleotides (positions 1-3) of the seed (62). Using a matrix based on the most and least toxic 6mer seeds we scanned 3'UTRs of survival and non survival genes. We found that survival are enriched in CG rich regions with are close to the 3'UTR start when compared to nonsurvival genes or when using the nontoxic AU rich matrix.

Tumor Suppressive miRNAs as DISE Inducers.

When miRNA were discovered to play a role in cancer they were categorized into tumor promoting and tumor suppressing miRNAs (18). While many miRNAs were found to have multiple sometimes contradictory activities, depending on the nature of their targets in a given cell, a number of miRNAs were found to be predominantly oncogenic or tumor suppressive in most cancers. miR-34a is arguably the most tumor suppressive miRNA as it has been shown to be toxic to most cancer cells (63). Our strand specific 6mer seed screen revealed that the seed of miR-34a accounts for most of its toxicity to cancer cells.

Traditionally, scientists have attempted to explain tumor promoting or tumor suppressive activities of miRNAs by identifying targets that either oncogenic or tumor suppressive (18). Examples of targets of tumor suppressive miRNAs are the oncogenes Bcl-2 for miR-15/16 (64) or miR-34a or c-Myc for miR-34a (65). However, particularly for miR-34a, the major oncogenic targets has never been identified. Intense studies have resulted in a bewildering list of potential targets (summarized in (65)). Over 700 targets implicated in cancer cell proliferation, survival and resistance to therapy have been described (65). Our data now suggest that tumor suppressive miRNAs such as miR-34a engage the DISE mechanism to target hundreds of house keeping genes. While miRNAs have always been viewed as targeting entire networks of genes in most cases they are still being studied by identifying single important targets. Our data now provide the means to rationally design new miRNA based anti-cancer reagents that attack networks of survival genes.

Different Ways miRNAs are Tumor Suppressive.

Interestingly, our data also point at miRNAs exerting tumor suppressive activities in different ways. Let-7 is one of the most abundant miRNAs in most normal tissues (35) and can therefore not be coexpressed with critical survival genes that harbor its seed match in the 3'UTR. We interpret the results of low toxicity of let-7 as let-7 exerting its tumor suppression predominantly not through induction of DISE but through its activities in inducing redifferentiation of cancer cells (35, 66). Another family of miRNAs that has tumor suppressive activities are the 5 members of the miR-200 family (miR-200a, b, c, 141 and 429) (67). The fact that they contain 6mers seeds that were not toxic in our screen is consistent with them being very highly expressed in epithelial and fully differentiated tissues (67). Similar to let-7, miR-200 causes redifferentiation of cancer stem cells and renders cells more sensitive to treatment (35). These two major miRNA families seem to be tumor suppressive not through induction of cell death but by maintaining cells in highly differentiated states (35).

miR-34a and its Clinical Utility.

Two important properties of miR-34a are consistent with it exerting its tumor suppressive activity through its toxic 6mer seed and induction of DISE:

1) miR-34a is highly conserved miRNA first discovered in *C. elegans* (68). In man miR-34a is highly expressed in many tissues (http://mirnamap.mbc.nctu.edu.tw). Consistently, miR-34a exhibits low toxicity to normal cells in vitro and in vivo (36). If one assumes that most of its toxicity comes from its DISE inducing seed sequence these reports are consistent with our observation that mice treated with DISE inducing siRNAs while slowing down tumor growth showed no signs of toxicity to normal tissues (24).

2) miR-34a was reported to be especially active in killing cancer stem cells (summarized in (21)). This activity is consistent with our data that demonstrated that DISE preferentially affects CSCs (69).

In 2013 miR34a (MRX34) became the first miRNA to be tested in a phase I clinical trial of unresectable primary liver cancer (70). The study was recently terminated and reported immune-related adverse effects in several individuals. It was suggested that these adverse effects may have been caused by either a reaction to the liposome-based carrier or the use of double-stranded RNA (65). In addition, they may be due to an undesired gene modulation by miR-34a itself. Different forms of delivery were suggested to possibly improve this negative outcome (65).

Our data now suggest that miR-34a is a DISE-inducing miRNA and its 700 known targets may be part of the network of survival genes that are targeted during DISE. We demonstrated that most of the toxic activity of miR-34a is due to its toxic 6mer seed. Our RNA-Seq analysis of mRNAs downregulated in cells treated with either pre-miR-34a or miR-34$^{seed}$ allowed us to separate the mRNAs that might be involved in DISE induction (targeted by both pre-miR-34a or miR-34$^{seed}$) from the ones that require additional sequences in miR-34a to be efficiently targeted. Our data would suggest to analyze the treated patients to determine whether the toxicity seen in the patients treated with the miR-34a mimetic was due to targets specific to pre-miR-34a or caused by the DISE inducing miR-34a seed. The comparison of the RNA Seq data of cells treated with either the premiR or the seed now allows to determine whether these two activities can be separated.

DISE May Contribute to the Cell Death Induced by Genotoxic Drugs.

Our data provide evidence that genotoxic drugs kill cancer cells at least in part by triggering the DISE mechanism. Exposure of cancer cells to such drugs resulted in upregulation of tumor suppressing miRNAs, most prominently of the miR-34 family of miRNAs. This mechanism may be highly redundant and may involve many miRNAs and other small RNAs that can be taken up by the RISC. We realized it would not be possible to delete all miRNAs in a cells that can kill cells through DISE to determine their contribution. However, in Drosha$^{-/-}$ cells which lack most canonical mature miRNAs we found the atypical tumor suppressive miR-320a to be highly abundant. miR-320a is generated independent of both Drosha or Dicer (49). It was not only upregulated in response to genotoxic stress but when analyzing AGO bound miR-320a it was found to be shorted at the 5' end by up to two nucleotides. This processing step resulted in the loss of two As at the 5' end converting miR-320a into a miRNA more toxic than even the toxic miR-34a. miR-320a may therefore act as a back up miRNA that can still respond in case other miRNAs are absent, for instance in cases of mutations in miRNA biogenesis associated genes (50). miRNAs may not be the only mediators of DISE in cells after genotoxic stress. Treatment with a number of genotoxic drugs were reported to result in degradation of rRNAs possibly resulting in formation of RNAi active small RNAs (71). Our data on two rRNA derived small RNAs upregulated in all cells treated with Doxo being toxic to cells when provided in a form that are loaded into the RISC would be consistent with that assumption.

The Evolution of miRNAs.

It was shown before that miRNAs overall avoid seed sequences that target the 3'UTR of survival/house keeping genes (52, 72). Survival genes therefore are depleted in seed matched for the most abundant miRNAs in a cell. That also means that 3'UTRs of survival genes must be enriched in sequences not targeted by the seeds in most miRNAs. Our combined data now suggest that it is these sequences that toxic siRNAs and tumor suppressive miRNAs with DISE-inducing seeds are targeting. Our analysis also suggest that most miRNAs have evolved over the last 800 millions year by gradually avoiding Gs in their seeds beginning with the 5' end (data not shown). While evolution has selected to reduce the number of seed matches in the 3'UTR of survival genes for abundant miRNAs, we realized that every cell has a powerful suicide mechanism built in: the production of small RNAi active sequences that target the sites that are avoided by most miRNAs. Expressing miRNAs with such toxic seeds could be an effective way to eliminate unwanted cells. After characterizing the most potent DISE-inducing seeds we identified miRNAs that mediate toxicity through inducing this death mechanism. In addition, we discovered the reason for the strand selectivity of many miRNAs. All miRNAs are processed from the premiR stem loop structure and the mature miRNA that acts as guide strand once loaded into the RISC can be derived from either the 5' (5p) and in the 3' arm (3p) while the other arm is degraded. Our data now suggest that during evolution most abundant miRNAs have evolved to use the arm with the lower DISE-inducing seed toxicity as the active guide strand, presumably to avoid being toxic. Only in a number of tumor suppressive miRNAs the strand that contains the toxic seed is used as the predominant strand. In fact just by ranking major miRNAs according to whether they express the arm with the seed of higher toxicity we could separate established oncogenic from tumor suppressive miRNAs. Using this method it should now be possible to identify novel tumor suppressive miRNAs.

In summary, we have determined the rules of RNAi targeting that results in DISE induction. These rules allow to predict with some certainty which si/shRNA sequence and which miRNA has the potential to kill cells through DISE. Interestingly, toxic seeds are present in a number of tumor suppressive miRNAs that can kill cancer cells. Our data also provide new insights into the evolution of miRNAs and provide a new rationale to explain miRNA strand selection.

REFERENCES

1. Kozomara A, Griffiths-Jones S. (2014). miRBase: annotating high confidence microRNAs using deep sequencing data. Nucleic acids research. 42:D68-73
2. Lenkala D, LaCroix B, Gamazon E R, Geeleher P, Im H K, Huang R S. (2014). The impact of microRNA expression on cellular proliferation. Human genetics. 133:931-8
3. Hau A, Ceppi P, Peter M E. (2012). CD95 is part of a let-7/p53/miR-34 regulatory network. PloS one. 7:e49636.
4. Schickel R, Boyerinas B, Park S M, Peter M E. (2008). MicroRNAs: key players in the immune system, differentiation, tumorigenesis and cell death. Oncogene. 27:5959-74.
5. Friedman R C, Farh K K, Burge C B, Bartel D P. (2009). Most mammalian mRNAs are conserved targets of microRNAs. Genome Res. 19:92-105.
6. Lee Y, Kim M, Han J, Yeom K H, Lee S, Baek S H, Kim V N. (2004).
MicroRNA genes are transcribed by RNA polymerase I I. EMBO J. 23:4051-60.
7. Han J, Lee Y, Yeom K H, Kim Y K, Jin H, Kim V N. (2004). The Drosha-DGCR8 complex in primary microRNA processing. Genes Dev. 18:3016-27.
8. Yi R, Qin Y, Macara I G, Cullen B R. (2003). Exportin-5 mediates the nuclear export of pre-microRNAs and short hairpin RNAs. Genes Dev. 17:3011-6.
9. Bernstein E, Caudy A A, Hammond S M, Hannon G J. (2001). Role for a bidentate ribonuclease in the initiation step of RNA interference. Nature. 409:363-6.
10. Hutvagner G, McLachlan J, Pasquinelli A E, Balint E, Tuschl T, Zamore P D. (2001). A cellular function for the RNA-interference enzyme Dicer in the maturation of the let-7 small temporal RNA. Science (New York, N.Y.). 293:834-8.
11. Wang Y, Sheng G, Juranek S, Tuschl T, Patel D J. (2008). Structure of the guide-strand-containing argonaute silencing complex. Nature. 456:209-13.
12. Leuschner P J, Ameres S L, Kueng S, Martinez J. (2006). Cleavage of the siRNA passenger strand during RISC assembly in human cells. EMBO reports. 7:314-20.
13. Schirle N T, MacRae I J. (2012). The crystal structure of human Argonaute2. Science (New York, N.Y.). 336:1037-40.
14. Eulalio A, Huntzinger E, Izaurralde E. (2008). GW182 interaction with Argonaute is essential for miRNA-mediated translational repression and mRNA decay. Nature structural & molecular biology. 15:346-53.
15. Lewis B P, Burge C B, Bartel D P. (2005). Conserved seed pairing, often flanked by adenosines, indicates that thousands of human genes are microRNA targets. Cell. 120:15-20.

16. Selbach M, Schwanhausser B, Thierfelder N, Fang Z, Khanin R, Rajewsky N. (2008). Widespread changes in protein synthesis induced by microRNAs. Nature. 455:58-63.
17. Baek D, Villen J, Shin C, Camargo F D, Gygi S P, Bartel D P. (2008). The impact of microRNAs on protein output. Nature. 455:64-71.
18. Esquela-Kerscher A, Slack F J. (2006). Oncomirs—microRNAs with a role in cancer. Nat Rev Cancer. 6:259-69.
19. Hua Y J, Larsen N, Kalyana-Sundaram S, Kjems J, Chinnaiyan A M, Peter M E. (2013). miRConnect 2.0: Identification of antagonistic, oncogenic miRNA families in three human cancers. BMC Genomics. 14:179.
20. He X, He L, Hannon G J. (2007). The guardian's little helper: microRNAs in the p53 tumor suppressor network. Cancer Res. 67:11099-101.
21. Agostini M, Knight R A. (2014). miR-34: from bench to bedside. Oncotarget. 5:872-81.
22. Putzbach W, Gao Q Q, Patel M, van Dongen S, Haluck-Kangas A, Sarshad A A, Bartom E, Kim K Y, Scholtens D M, Hafner M, Zhao J C, Murmann A E, Peter M E. (2017). Many si/shRNAs can kill cancer cells by targeting multiple survival genes through an off-target mechanism. eLife. 6: e29702.
23. Hadji A, Ceppi P, Murmann A E, Brockway S, Pattanayak A, Bhinder B, Hau A, De Chant S, Parimi V, Kolesza P, Richards J S, Chandel N, Djaballah H, Peter M E. (2014). Death induced by CD95 or CD95 ligand elimination. Cell Reports. 10:208-22.
24. Murmann A E, McMahon K M, Halluck-Kangas A, Ravindran N, Patel M, Law C, Brockway S, Wei J J, Thaxton C S, Peter M E. (2017). Induction of DISE in ovarian cancer cells in vivo. Oncotarget. 8:84643-58.
25. Putzbach W, Gao Q Q, Patel M, Haluck-Kangas A, Murmann A E, Peter M E. (2017). DISE—A Seed Dependent RNAi Off-Target Effect that Kills Cancer Cells. Trends in Cancer. In press.
26. Murmann A E, Gao Q Q, Putzbach W T, Patel M, Bartom E T, Law C Y, Bridgeman B, Chen S, McMahon K M, Thaxton C S, Peter M E. (2018). Small interfering RNAs based on huntingtin trinucleotide repeats are highly toxic to cancer cells. In revision.
27. Karlas A, Berre S, Couderc T, Varjak M, Braun P, Meyer M, Gangneux N, Karo-Astover L, Weege F, Raftery M, Schonrich G, Klemm U, Wurzlbauer A, Bracher F, Merits A, Meyer T F, Lecuit M. (2016). A human genome-wide loss-of-function screen identifies effective chikungunya antiviral drugs. Nat Commun. 7:11320.
28. Whitehurst A W, Bodemann B O, Cardenas J, Ferguson D, Girard L, Peyton M, Minna J D, Michnoff C, Hao W, Roth M G, Xie X J, White M A. (2007). Synthetic lethal screen identification of chemosensitizer loci in cancer cells. Nature. 446:815-9.
29. Mohr S E, Smith J A, Shamu C E, Neumuller R A, Perrimon N. (2014). RNAi screening comes of age: improved techniques and complementary approaches. Nat Rev Mol Cell Biol. 15:591-600.
30. Bramsen J B, Laursen M B, Nielsen A F, Hansen T B, Bus C, Langkjaer N, Babu B R, Hojland T, Abramov M, Van Aerschot A, Odadzic D, Smicius R, Haas J, Andree C, Barman J, Wenska M, Srivastava P, Zhou C, Honcharenko D, Hess S, Muller E, Bobkov G V, Mikhailov S N, Fava E, Meyer T F, Chattopadhyaya J, Zerial M, Engels J W, Herdewijn P, Wengel J, Kjems J. (2009). A large-scale chemical modification screen identifies design rules to generate siRNAs with high activity, high stability and low toxicity. Nucleic Acids Res. 37:2867-81.
31. Mignone F, Gissi C, Liuni S, Pesole G. (2002). Untranslated regions of mRNAs. Genome Biol. 3:REVIEWS0004.
32. Louie E, Ott J, Majewski J. (2003). Nucleotide frequency variation across human genes. Genome Res. 13:2594-601.
33. Lawrence M S, Stojanov P, Polak P, Kryukov G V, Cibulskis K, Sivachenko A, Carter S L, Stewart C, Mermel C H, Roberts S A, Kiezun A, Hammerman P S, McKenna A, Drier Y, Zou L, Ramos A H, Pugh T J, Stransky N, Helman E, Kim J, Sougnez C, Ambrogio L, Nickerson E, Shefler E, Cortes M L, Auclair D, Saksena G, Voet D, Noble M, DiCara D, Lin P, Lichtenstein L, Heiman D I, Fennell T, Imielinski M, Hernandez B, Hodis E, Baca S, Dulak A M, Lohr J, Landau D A, Wu C J, Melendez-Zajgla J, Hidalgo-Miranda A, Koren A, McCarroll S A, Mora J, Crompton B, Onofrio R, Parkin M, Winckler W, Ardlie K, Gabriel S B, Roberts C W M, Biegel J A, Stegmaier K, Bass A J, Garraway L A, Meyerson M, Golub T R, Gordenin D A, Sunyaev S, Lander E S, Getz G. (2013). Mutational heterogeneity in cancer and the search for new cancer-associated genes. Nature. 499:214-8.
34. Concepcion C P, Bonetti C, Ventura A. (2012). The microRNA-17-92 family of microRNA clusters in development and disease. Cancer journal. 18:262-7.
35. Peter M E. (2009). Let-7 and miR-200 microRNAs: guardians against pluripotency and cancer progression. Cell Cycle. 8:843-52.
36. Di Martino M T, Leone E, Amodio N, Foresta U, Lionetti M, Pitari M R, Cantafio M E, Gulla A, Conforti F, Morelli E, Tomaino V, Rossi M, Negrini M, Ferrarini M, Caraglia M, Shammas M A, Munshi N C, Anderson K C, Neri A, Tagliaferri P, Tassone P. (2012). Synthetic miR-34a mimics as a novel therapeutic agent for multiple myeloma: in vitro and in vivo evidence. Clin Cancer Res. 18:6260-70.
37. Patel M, Peter M E. (2017). Identification of DISE-inducing shRNAs by monitoring cellular responses. Cell Cycle. doi: 10.1080/15384101.2017.1383576.
38. Grimson A, Farh K K, Johnston W K, Garrett-Engele P, Lim L P, Bartel D P. (2007). MicroRNA targeting specificity in mammals: determinants beyond seed pairing. Mol Cell. 27:91-105.
39. Meredith A M, Dass C R. (2016). Increasing role of the cancer chemotherapeutic doxorubicin in cellular metabolism. J Pharm Pharmacol. 68:729-41.
40. Yeung T K, Germond C, Chen X, Wang Z. (1999). The mode of action of taxol: apoptosis at low concentration and necrosis at high concentration. Biochem Biophys Res Commun. 263:398-404.
41. Yoo S H, Yoon Y G, Lee J S, Song Y S, Oh J S, Park B S, Kwon T K, Park C, Choi Y H, Yoo Y H. (2012). Etoposide induces a mixed type of programmed cell death and overcomes the resistance conferred by Bcl-2 in Hep3B hepatoma cells. Int J Oncol. 41:1443-54.
42. Kwon H K, Shin H J, Lee J H, Park S H, Kwon M C, Panneerselvam S, Lee C G, Kim S G, Kim J H, Choi S. (2015). Etoposide Induces Necrosis Through p53-Mediated Antiapoptosis in Human Kidney Proximal Tubule Cells. Toxicol Sci. 148:204-19.
43. Wang D, Lippard S J. (2005). Cellular processing of platinum anticancer drugs. Nat Rev Drug Discov. 4:307-20.
44. Chang B D, Broude E V, Dokmanovic M, Zhu H, Ruth A, Xuan Y, Kandel E S, Lausch E, Christov K, Roninson I B. (1999). A senescence-like phenotype distinguishes tumor cells that undergo terminal proliferation arrest after exposure to anticancer agents. Cancer Res. 59:3761-7.
45. Eom Y W, Kim M A, Park S S, Goo M J, Kwon H J, Sohn S, Kim W H, Yoon G, Choi K S. (2005). Two distinct modes of cell death induced by doxorubicin: apoptosis and cell death through mitotic catastrophe accompanied by senescence-like phenotype. Oncogene. 24:4765-77.
46. Elkayam E, Faehnle C R, Morales M, Sun J, Li H, Joshua-Tor L. (2017). Multivalent Recruitment of Human Argonaute by GW182. Mol Cell. 67:646-58 e3.
47. Cao W, Yang W, Fan R, Li H, Jiang J, Geng M, Jin Y, Wu Y. (2014). miR-34a regulates cisplatin-induce gastric cancer cell death by modulating PI3K/AKT/survivin pathway. Tumour Biol. 35:1287-95.
48. Navarro F, Lieberman J. (2015). miR-34 and p53: New Insights into a Complex Functional Relationship. PLoS One. 10:e0132767.
49. Kim Y K, Kim B, Kim V N. (2016). Re-evaluation of the roles of DROSHA, Export in 5, and DICER in microRNA biogenesis. Proc Natl Acad Sci USA. 113:E1881-9.
50. Walz A L, Ooms A, Gadd S, Gerhard D S, Smith M A, Guidry Auvil J M, Meerzaman D, Chen Q R, Hsu C H, Yan C, Nguyen C, Hu Y, Bowlby R, Brooks D, Ma Y, Mungall A J, Moore R A, Schein J, Marra M A, Huff V, Dome J S, Chi Y Y, Mullighan C G, Ma J, Wheeler D A, Hampton O A, Jafari N, Ross N, Gastier-Foster J M, Perlman E J. (2015). Recurrent DGCR8, DROSHA, and SIX homeodomain mutations in favorable histology Wilms tumors. Cancer Cell. 27:286-97.
51. Kumar M S, Lu J, Mercer K L, Golub T R, Jacks T. (2007). Impaired microRNA processing enhances cellular transformation and tumorigenesis. Nat Genet. 39:673-7.
52. Stark A, Brennecke J, Bushati N, Russell R B, Cohen S M. (2005). Animal MicroRNAs confer robustness to gene expression and have a significant impact on 3'UTR evolution. Cell. 123:1133-46.
53. Patel V D, Capra J A. (2017). Ancient human miRNAs are more likely to have broad functions and disease associations than young miRNAs. BMC Genomics. 18:672.
54. Meijer H A, Smith E M, Bushell M. (2014). Regulation of miRNA strand selection: follow the leader? Biochem Soc Trans. 42:1135-40.
55. Concepcion C P, Han Y C, Mu P, Bonetti C, Yao E, D'Andrea A, Vidigal J A, Maughan W P, Ogrodowski P, Ventura A. (2012). Intact p53-dependent responses in miR-34-deficient mice. PLoS Genet. 8:e1002797.
56. Fedorov Y, Anderson E M, Birmingham A, Reynolds A, Karpilow J, Robinson K, Leake D, Marshall W S, Khvorova A. (2006). Off-target effects by siRNA can induce toxic phenotype. RNA. 12:1188-96.
57. Petri S, Meister G. (2013). siRNA design principles and off-target effects. Methods Mol Biol. 986:59-71.
58. Jackson A L, Bartz S R, Schelter J, Kobayashi S V, Burchard J, Mao M, Li B, Cavet G, Linsley P S. (2003). Expression profiling reveals off-target gene regulation by RNAi. Nat Biotechnol. 21:635-7.
59. Birmingham A, Anderson E M, Reynolds A, Ilsley-Tyree D, Leake D, Fedorov Y, Baskerville S, Maksimova E, Robinson K, Karpilow J, Marshall W S, Khvorova A. (2006). 3' UTR seed matches, but not overall identity, are associated with RNAi off-targets. Nat Methods. 3:199-204.
60. Gu S, Zhang Y, Jin L, Huang Y, Zhang F, Bassik M C, Kampmann M, Kay M A. (2014). Weak base pairing in both seed and 3' regions reduces RNAi off-targets and enhances si/shRNA designs. Nucleic Acids Res. 42:12169-76.
61. Ui-Tei K, Naito Y, Takahashi F, Haraguchi T, Ohki-Hamazaki H, Juni A, Ueda R, Saigo K. (2004). Guidelines for the selection of highly effective siRNA sequences for mammalian and chick RNA interference. Nucleic Acids Res. 32:936-48.
62. Chandradoss S D, Schirle N T, Szczepaniak M, MacRae I J, Joo C. (2015). A Dynamic Search Process Underlies MicroRNA Targeting. Cell. 162:96-107.
63. Hermeking H. (2010). The miR-34 family in cancer and apoptosis. Cell Death Differ. 17:193-9.
64. Balatti V, Pekarky Y, Rizzotto L, Croce C M. (2013). miR deregulation in CLL. Adv Exp Med Biol. 792:309-25.
65. Slabakova E, Culig Z, Remsik J, Soucek K. (2017). Alternative mechanisms of miR-34a regulation in cancer. Cell Death Dis. 8:e3100.
66. Park S M, Shell S, Radjabi A R, Schickel R, Feig C, Boyerinas B, Dinulescu D M, Lengyel E, Peter M E. (2007). Let-7 Prevents Early Cancer Progression by Suppressing Expression of the Embryonic Gene HMGA2. Cell Cycle. 6:2585-90.
67. Park S M, Gaur A B, Lengyel E, Peter M E. (2008). The miR-200 family determines the epithelial phenotype of cancer cells by targeting the E-cadherin repressors, ZEB1 and ZEB2. Genes Dev. 22:894-907.
68. Yang J, Chen D, He Y, Melendez A, Feng Z, Hong Q, Bai X, Li Q, Cai G, Wang J, Chen X. (2013). MiR-34 modulates *Caenorhabditis elegans* lifespan via repressing the autophagy gene atg9. Age. 35:11-22.
69. Ceppi P, Hadji A, Kohlhapp F, Pattanayak A, Hau A, Xia L, Liu H, Murmann A E, Peter M E. (2014). CD95 and CD95L promote and protect cancer stem cells. Nature Commun. 5:5238.
70. Beg M S, Brenner A J, Sachdev J, Borad M, Kang Y K, Stoudemire J, Smith S, Bader A G, Kim S, Hong D S. (2017). Phase I study of MRX34, a liposomal miR-34a mimic, administered twice weekly in patients with advanced solid tumors. Invest New Drugs. 35:180-8.
71. Narendrula R, Mispel-Beyer K, Guo B, Parissenti A M, Pritzker L B, Pritzker K, Masilamani T, Wang X, Lanner C. (2016). RNA disruption is associated with response to multiple classes of chemotherapy drugs in tumor cell lines. BMC Cancer. 16:146.
72. Zare H, Khodursky A, Sartorelli V. (2014). An evolutionarily biased distribution of miRNA sites toward regulatory genes with high promoter-driven intrinsic transcriptional noise. BMC Evol Biol. 14:74.
73. Hauptmann J, Schraivogel D, Bruckmann A, Manickavel S, Jakob L, Eichner N, Pfaff J, Urban M, Sprunck S, Hafner M, Tuschl T, Deutzmann R, Meister G. (2015). Biochemical isolation of Argonaute protein complexes by Ago-APP. Proc Natl Acad Sci USA. 112:11841-5.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:

1. A polynucleotide comprising a dsRNA sequence defined as follows:

```
5'- P01 P02 P03 P04 P05 P06 P07 P08 P09
    |   |   |   |   |   |   |   |   |
3'- G19 G18 G17 G16 G15 G14 G13 G12 G11

P10 P11 P12 P13 P14 P15 P16 P17 P18 P19
    |   |   |   |   |   |   |   |   |   |
    G10 G09 G08 G07 G06 G05 G04 G03 G02 G01
``` wherein:
- (a) G01 through G19 and P01 through P19 are any ribonucleotide selected from A, U, G, and C provided that P01 through P19 are complementary to G19 through G01, respectively;
- (b) P19 is selected from A and U and G01 is selected from U and A, respectively; and (c) the sequence of

```
P13  P14  P15  P16  P17  P18
 |    |    |    |    |    |
G07  G06  G05  G04  G03  G02
``` is

```
(i) G C C C C C
    | | | | | |
    C G G G G G.
```

2. The polynucleotide of claim 1, wherein the polynucleotide is an siRNA.

3. A polynucleotide comprising a dsRNA sequence defined as follows:

```
5'- P01 P02 P03 P04 P05 P06 P07 P08 P09 P10 P11 P12 P13 P14 P15 P16 P17 P18 P19
    |   |   |   |   |   |   |   |   |   |   |   |   |   |   |   |   |   |   |
3'- G19 G18 G17 G16 G15 G14 G13 G12 G11 G10 G09 G08 G07 G06 G05 G04 G03 G02 G01
``` wherein:
- (a) G01 through G19 and P01 through P19 are any ribonucleotide selected from A, U, G, and C provided that P01 through P19 are complementary to G19 through G01, respectively;
- (b) P19 is selected from A and U and G01 is selected from U and A, respectively; and (c) the sequence of

```
P13  P14  P15  P16  P17  P18
 |    |    |    |    |    |
G07  G06  G05  G04  G03  G02
``` is selected from

```
(i) G C C C C C
    | | | | | |
    C G G G G G, and (ii) C C A C C C
     | | | | | |
     G G U G G G,
``` wherein the polynucleotide is an siRNA, and
wherein P01 is an O-methylated cytosine.

4. The polynucleotide of claim 2, wherein the siRNA has 2-nucleotide 3' overhangs and a sequence defined as follows:

```
5'-     P01 P02 P03 P04 P05 P06 P07 P08 P09 P10 P11 P12 P13 P14 P15 P16 P17 P18 P19 P20 P21
        |   |   |   |   |   |   |   |   |   |   |   |   |   |   |   |   |   |   |   |   |
3'- G21 G20 G19 G18 G17 G16 G15 G14 G13 G12 G11 G10 G09 G08 G07 G06 G05 G04 G03 G02 G01
``` wherein:
G20, and G21 are deoxyribonucleotides.

5. The polynucleotide of claim 4, wherein G20 and G21 are dA, and P20 and P21 are T.

6. A polynucleotide comprising a dsRNA sequence defined as follows:

```
5'- P01 P02 P03 P04 P05 P06 P07 P08 P09 P10 P11 P12 P13 P14 P15 P16 P17 P18 P19
    |   |   |   |   |   |   |   |   |   |   |   |   |   |   |   |   |   |   |
3'- G19 G18 G17 G16 G15 G14 G13 G12 G11 G10 G09 G08 G07 G06 G05 G04 G03 G02 G01
``` wherein:
- (a) G01 through G19 and P01 through P19 are any ribonucleotide selected from A, U, G, and C provided that P01 through P19 are complementary to G19 through G01, respectively;
- (b) P19 is selected from A and U and G01 is selected from U and A, respectively; and
- (c) the sequence of

```
P13  P14  P15  P16  P17  P18
 |    |    |    |    |    |
G07  G06  G05  G04  G03  G02
``` is selected from

```
(i) G C C C C C
    | | | | | |
    C G G G G G, and
```

```
(ii) C C A C C C
     | | | | |
     G G U G G,
``` wherein the polynucleotide is an siRNA comprising a 5' O-methylated cytosine and 2-nucleotide 3' overhangs.

7. The polynucleotide of claim 1, wherein the polynucleotide is an shRNA illustrated as follows:

```
5'- P01 P02 P03 P04 P05 P06 P07 P08 P09 P10 P11 P12 P13 P14 P15 P16 P17 P18 P19 - Lo
    |   |   |   |   |   |   |   |   |   |   |   |   |   |   |   |   |   |   |      )
3'- G19 G18 G17 G16 G15 G14 G13 G12 G11 G10 G09 G08 G07 G06 G05 G04 G03 G02 G01 - po
``` wherein:

```
                Lo
                 )
                po
``` comprises a polynucleotide loop sequence.

8. The polynucleotide of claim 7, wherein the loop sequences is 5'-CUCGAG-3'.

9. An expression vector that expresses the polynucleotide of claim 7.

10. The polynucleotide of claim 1, wherein the polynucleotide downregulates expression of one or more survival genes when the polynucleotide is transfected or expressed in a cell.

11. A pharmaceutical composition comprising the polynucleotide of claim 1 and a pharmaceutically acceptable excipient.

12. A pharmaceutical composition comprising the expression vector of claim 9 and a pharmaceutically acceptable excipient.

13. A nanoparticle comprising the polynucleotide of claim 1.

14. The nanoparticle of claim 13, wherein the nanoparticle is a nanoparticle formed from lipoproteins.

15. The nanoparticle of claim 13, wherein the polynucleotide is a siRNA and the siRNA is coupled to a lipoprotein of the nanoparticle.

16. A method of inhibiting the growth of a cancer cell or killing a cancer cell, the method comprising introducing or expressing the polynucleotide of claim 1 in the cancer cell.

17. A method of inhibiting the growth of a cancer cell or killing a cancer cell, the method comprising introducing or expressing the polynucleotide of claim 7 in the cancer cell.

18. A method of inhibiting the growth of a cancer cell or killing a cancer cell, the method comprising introducing the expression vector of claim 9 into the cancer cell.

19. A nanoparticle comprising the polynucleotide of claim 3.

20. A nanoparticle comprising the polynucleotide of claim 6.

* * * * *

SEQUENCE LISTING

```
<160> NUMBER OF SEQ ID NOS: 172

<210> SEQ ID NO 1
<211> LENGTH: 21
<212> TYPE: DNA
<213> ORGANISM: Homo sapiens

<400> SEQUENCE: 1
gcatcatctt tggagaagca a                                               21

<210> SEQ ID NO 2
<211> LENGTH: 21
<212> TYPE: DNA
<213> ORGANISM: Homo sapiens

<400> SEQUENCE: 2
actgggctgt actttgtata t                                               21

<210> SEQ ID NO 3
<211> LENGTH: 21
<212> TYPE: DNA
<213> ORGANISM: Homo sapiens

<400> SEQUENCE: 3
gcagtgttca atcttaccag t                                               21

<210> SEQ ID NO 4
<211> LENGTH: 21
<212> TYPE: DNA
<213> ORGANISM: Homo sapiens

<400> SEQUENCE: 4
gttgctagat tatcgtccaa a                                               21

<210> SEQ ID NO 5
<211> LENGTH: 21
<212> TYPE: DNA
<213> ORGANISM: Homo sapiens

<400> SEQUENCE: 5
gtgcagatgt aaaccaaact t                                               21

<210> SEQ ID NO 6
<211> LENGTH: 21
<212> TYPE: DNA
<213> ORGANISM: Homo sapiens

<400> SEQUENCE: 6
cctgaaacag tggcaataaa t                                               21

<210> SEQ ID NO 7
<211> LENGTH: 21
<212> TYPE: DNA
<213> ORGANISM: Homo sapiens
```

<400> SEQUENCE: 7
gtgtcgctgt aaaccaaact t                                        21

<210> SEQ ID NO 8
<211> LENGTH: 21
<212> TYPE: DNA
<213> ORGANISM: Artificial
<220> FEATURE:
<223> OTHER INFORMATION: Sequence targeting human CD95 ORF mutated to
      include 8 silent mutations

<400> SEQUENCE: 8
atgtcgctgc aagcccaatt t                                        21

<210> SEQ ID NO 9
<211> LENGTH: 143
<212> TYPE: DNA
<213> ORGANISM: Artificial
<220> FEATURE:
<223> OTHER INFORMATION: Sequence encoding the shRNA hairpin for
      expressing shRNAs
<220> FEATURE:
<221> NAME/KEY: misc_feature
<222> LOCATION: (37)..(57)
<223> OTHER INFORMATION: n is a, c, g, or t
<220> FEATURE:
<221> NAME/KEY: misc_feature
<222> LOCATION: (64)..(84)
<223> OTHER INFORMATION: n is a, c, g, or t

<400> SEQUENCE: 9
tggctttata tatctcccta tcagtgatag agatcgnnnn nnnnnnnnnn nnnnnnnctc    60
gagnnnnnnn nnnnnnnnnn nnnnttttg taccgagctc ggatccacta gtccagtgtg   120
ggcatgctgc gttgacattg att                                          143

<210> SEQ ID NO 10
<211> LENGTH: 455
<212> TYPE: DNA
<213> ORGANISM: Artificial
<220> FEATURE:
<223> OTHER INFORMATION: gRNA scaffold gene block for generating gRNA
      for CRISPR of human CD95L
<220> FEATURE:
<221> NAME/KEY: misc_feature
<222> LOCATION: (320)..(338)
<223> OTHER INFORMATION: n is a, c, g, or t

<400> SEQUENCE: 10
tgtacaaaaa agcaggcttt aaaggaacca attcagtcga ctggatccgg taccaaggtc    60
gggcaggaag agggcctatt tcccatgatt ccttcatatt tgcatatacg atacaaggct   120
gttagagaga taattagaat taatttgact gtaaacacaa agatattagt acaaaatacg   180
tgacgtagaa agtaataatt tcttgggtag tttgcagttt taaaattatg ttttaaaatg   240
gactatcata tgcttaccgt aacttgaaag tatttcgatt tcttggcttt atatatcttg   300
tggaaaggac gaaacaccgn nnnnnnnnn nnnnnnnngt tttagagcta gaaatagcaa   360
gttaaaataa ggctagtccg ttatcaactt gaaaaagtgg caccgagtcg gtgcttttttt   420 tctagaccca gctttcttgt acaaagttgg catta                               455

<210> SEQ ID NO 11
<211> LENGTH: 19
<212> TYPE: DNA
<213> ORGANISM: Artificial
<220> FEATURE:

```
<223> OTHER INFORMATION: Target sequence for excision of of the shL3
      site of human CD95L

<400> SEQUENCE: 11
ccttgtgatc aatgaaact                                              19

<210> SEQ ID NO 12
<211> LENGTH: 19
<212> TYPE: DNA
<213> ORGANISM: Artificial
<220> FEATURE:
<223> OTHER INFORMATION: Target sequence for excision of shL3 site of
      human CD95L

<400> SEQUENCE: 12
gttgttgcaa gattgaccc                                              19

<210> SEQ ID NO 13
<211> LENGTH: 19
<212> TYPE: DNA
<213> ORGANISM: Artificial
<220> FEATURE:
<223> OTHER INFORMATION: Target sequence for excision of the shR6 site
      of human CD95

<400> SEQUENCE: 13
gcacttggta ttctgggtc                                              19

<210> SEQ ID NO 14
<211> LENGTH: 19
<212> TYPE: DNA
<213> ORGANISM: Artificial
<220> FEATURE:
<223> OTHER INFORMATION: Target sequence for excision of shR6 site of
      human CD95

<400> SEQUENCE: 14
tgtttgctca tttaaacac                                              19

<210> SEQ ID NO 15
<211> LENGTH: 19
<212> TYPE: DNA
<213> ORGANISM: Artificial
<220> FEATURE:
<223> OTHER INFORMATION: Target sequence for excision of siL3 site of
      human CD95L

<400> SEQUENCE: 15
taaaaccgtt tgctggggc                                              19

<210> SEQ ID NO 16
<211> LENGTH: 19
<212> TYPE: DNA
<213> ORGANISM: Artificial
<220> FEATURE:
<223> OTHER INFORMATION: Target sequence for excision of siL3 site of
      human CD95L

<400> SEQUENCE: 16
tatccccaga tctactggg                                              19

<210> SEQ ID NO 17
<211> LENGTH: 20
<212> TYPE: DNA
<213> ORGANISM: Artificial
<220> FEATURE:
<223> OTHER INFORMATION: Forward primer for detection of deletion of
``` shL3 site in human CD95L

<400> SEQUENCE: 17
tctggaatgg gaagacacct                                               20

<210> SEQ ID NO 18
<211> LENGTH: 20
<212> TYPE: DNA
<213> ORGANISM: Artificial
<220> FEATURE:
<223> OTHER INFORMATION: Reverse primer for detection of deletion of the
      shL3 site in human CD95L

<400> SEQUENCE: 18
cctccatcat caccagatcc                                               20

<210> SEQ ID NO 19
<211> LENGTH: 21
<212> TYPE: DNA
<213> ORGANISM: Artificial
<220> FEATURE:
<223> OTHER INFORMATION: Reverse primer for detection of deletion of
      shL3 site of human CD95L

<400> SEQUENCE: 19
atatacaaag tacagcccag t                                             21

<210> SEQ ID NO 20
<211> LENGTH: 21
<212> TYPE: DNA
<213> ORGANISM: Artificial
<220> FEATURE:
<223> OTHER INFORMATION: Forward primer for detection of deletion of the
      shR6 site of human CD95

<400> SEQUENCE: 20
ggtgtcatgc tgtgactgtt g                                             21

<210> SEQ ID NO 21
<211> LENGTH: 20
<212> TYPE: DNA
<213> ORGANISM: Artificial
<220> FEATURE:
<223> OTHER INFORMATION: Reverse primer for detection of deletion of
      shR6 site of human CD95

<400> SEQUENCE: 21
tttagcttaa gtggccagca                                               20

<210> SEQ ID NO 22
<211> LENGTH: 20
<212> TYPE: DNA
<213> ORGANISM: Artificial
<220> FEATURE:
<223> OTHER INFORMATION: Reverse primer for detection of deletion of
      shR6 site of human CD95

<400> SEQUENCE: 22
aagttggttt acatctgcac                                               20

<210> SEQ ID NO 23
<211> LENGTH: 20
<212> TYPE: DNA
<213> ORGANISM: Artificial
<220> FEATURE:
<223> OTHER INFORMATION: Forward primer for detection of deletion of
      siL3 site of human CD95L

```
<400> SEQUENCE: 23
cttgagcagt cagcaacagg                                           20

<210> SEQ ID NO 24
<211> LENGTH: 20
<212> TYPE: DNA
<213> ORGANISM: Artificial
<220> FEATURE:
<223> OTHER INFORMATION: Reverse primer for detection of deletion of
      siL3 site of human CD95L

<400> SEQUENCE: 24
cagaggttgg acagggaaga                                           20

<210> SEQ ID NO 25
<211> LENGTH: 21
<212> TYPE: DNA
<213> ORGANISM: Artificial
<220> FEATURE:
<223> OTHER INFORMATION: Reverse primer for detection of deletion of
      siL3 site of human CD95L

<400> SEQUENCE: 25
atatgggtaa ttgaagggct g                                         21

<210> SEQ ID NO 26
<211> LENGTH: 21
<212> TYPE: DNA
<213> ORGANISM: Homo sapiens

<400> SEQUENCE: 26
cccatttaac aggcaagtcc a                                         21

<210> SEQ ID NO 27
<211> LENGTH: 21
<212> TYPE: DNA
<213> ORGANISM: Homo sapiens

<400> SEQUENCE: 27
ctgtgtctcc ttgtgatgtt t                                         21

<210> SEQ ID NO 28
<211> LENGTH: 21
<212> TYPE: DNA
<213> ORGANISM: Homo sapiens

<400> SEQUENCE: 28
tgagctctct ctggtcaatt t                                         21

<210> SEQ ID NO 29
<211> LENGTH: 21
<212> TYPE: DNA
<213> ORGANISM: Homo sapiens

<400> SEQUENCE: 29
tagctcctca actcacctaa t                                         21

<210> SEQ ID NO 30
<211> LENGTH: 21
<212> TYPE: DNA
<213> ORGANISM: Homo sapiens

<400> SEQUENCE: 30
```

-continued gactagaggc ttgcataata a                                              21

<210> SEQ ID NO 31
<211> LENGTH: 21
<212> TYPE: DNA
<213> ORGANISM: Homo sapiens

<400> SEQUENCE: 31
ctatcatcct caaggacatt a                                              21

<210> SEQ ID NO 32
<211> LENGTH: 21
<212> TYPE: DNA
<213> ORGANISM: Homo sapiens

<400> SEQUENCE: 32
gcaaagagga aggatccaga t                                              21

<210> SEQ ID NO 33
<211> LENGTH: 21
<212> TYPE: DNA
<213> ORGANISM: Homo sapiens

<400> SEQUENCE: 33
ttttactggg tacattttat c                                              21

<210> SEQ ID NO 34
<211> LENGTH: 21
<212> TYPE: DNA
<213> ORGANISM: Homo sapiens

<400> SEQUENCE: 34
cccttgtgtt tggaattata a                                              21

<210> SEQ ID NO 35
<211> LENGTH: 21
<212> TYPE: DNA
<213> ORGANISM: Homo sapiens

<400> SEQUENCE: 35
ttaaattata atgtttgact a                                              21

<210> SEQ ID NO 36
<211> LENGTH: 21
<212> TYPE: DNA
<213> ORGANISM: Homo sapiens

<400> SEQUENCE: 36
atatctttga aagtttgtat t                                              21

<210> SEQ ID NO 37
<211> LENGTH: 19
<212> TYPE: RNA
<213> ORGANISM: Artificial
<220> FEATURE:
<223> OTHER INFORMATION: Scrambled siRNA sequence

<400> SEQUENCE: 37
ugguuuacau guuguguga                                                 19

<210> SEQ ID NO 38
<211> LENGTH: 19
<212> TYPE: RNA
<213> ORGANISM: Homo sapiens

```
<400> SEQUENCE: 38
uaccagugcu gaucauuua                                                  19

<210> SEQ ID NO 39
<211> LENGTH: 19
<212> TYPE: RNA
<213> ORGANISM: Homo sapiens

<400> SEQUENCE: 39
caacguaucu gagcucucu                                                  19

<210> SEQ ID NO 40
<211> LENGTH: 19
<212> TYPE: RNA
<213> ORGANISM: Homo sapiens

<400> SEQUENCE: 40
gcccuucaau uacccauau                                                  19

<210> SEQ ID NO 41
<211> LENGTH: 19
<212> TYPE: RNA
<213> ORGANISM: Homo sapiens

<400> SEQUENCE: 41
ggaaaguggc ccauuuaac                                                  19

<210> SEQ ID NO 42
<211> LENGTH: 19
<212> TYPE: RNA
<213> ORGANISM: Artificial
<220> FEATURE:
<223> OTHER INFORMATION: Sequence targeted to siL3 of human CD95L
      mutated to disrupt targeting sequence

<400> SEQUENCE: 42
ggacuucaac uagacaucu                                                  19

<210> SEQ ID NO 43
<211> LENGTH: 19
<212> TYPE: DNA
<213> ORGANISM: Homo sapiens

<400> SEQUENCE: 43
gcccttcaat tacccatat                                                  19

<210> SEQ ID NO 44
<211> LENGTH: 19
<212> TYPE: DNA
<213> ORGANISM: Artificial
<220> FEATURE:
<223> OTHER INFORMATION: Scrambled DNA sequence corresponding to siRNA
      of SEQ ID NO:37

<400> SEQUENCE: 44
tggtttacat gttgtgtga                                                  19

<210> SEQ ID NO 45
<211> LENGTH: 25
<212> TYPE: DNA
<213> ORGANISM: Artificial
<220> FEATURE:
<223> OTHER INFORMATION: Sense RNA oligo for dsiRNA targeting human
      CD95L including terminal deoxyguanine and deoxythymidine
```

```
<400> SEQUENCE: 45
caggacugag aagaaguaaa accgt                                            25

<210> SEQ ID NO 46
<211> LENGTH: 27
<212> TYPE: RNA
<213> ORGANISM: Artificial
<220> FEATURE:
<223> OTHER INFORMATION: Antisense RNA oligo for dsiRNA targeting human
      CD95L

<400> SEQUENCE: 46
acgguuuuac uucuucucag uccugua                                          27

<210> SEQ ID NO 47
<211> LENGTH: 25
<212> TYPE: DNA
<213> ORGANISM: Artificial
<220> FEATURE:
<223> OTHER INFORMATION: Sense RNA oligo for siRNA targeting human CD95L
      including terminal dideoxycytidines

<400> SEQUENCE: 47
cagcccuuca auuacccaua ucccc                                            25

<210> SEQ ID NO 48
<211> LENGTH: 27
<212> TYPE: RNA
<213> ORGANISM: Artificial
<220> FEATURE:
<223> OTHER INFORMATION: Antisense RNA oligo for dsiRNA targeting human
      CD95L

<400> SEQUENCE: 48
ggggauaugg guaauugaag ggcugcu                                          27

<210> SEQ ID NO 49
<211> LENGTH: 25
<212> TYPE: DNA
<213> ORGANISM: Artificial
<220> FEATURE:
<223> OTHER INFORMATION: Sense RNA oligo for dsiRNA targeting human
      CD95L including terminal deoxythymidine and deoxyadenine

<400> SEQUENCE: 49
aucuuaccag ugcugaucau uuata                                            25

<210> SEQ ID NO 50
<211> LENGTH: 27
<212> TYPE: RNA
<213> ORGANISM: Artificial
<220> FEATURE:
<223> OTHER INFORMATION: Antisense RNA oligo for dsiRNA targeting human
      CD95L

<400> SEQUENCE: 50
uauaaaugau cagcacuggu aagauug                                          27

<210> SEQ ID NO 51
<211> LENGTH: 25
<212> TYPE: DNA
<213> ORGANISM: Artificial
<220> FEATURE:
<223> OTHER INFORMATION: Sense RNA oligo for dsiRNA targeting human
      CD95L including terminal dideoxythymidines
```

```
<400> SEQUENCE: 51
aaaguauacu uccggggguca aucuu                                              25

<210> SEQ ID NO 52
<211> LENGTH: 27
<212> TYPE: RNA
<213> ORGANISM: Artificial
<220> FEATURE:
<223> OTHER INFORMATION: Antisense RNA oligos for dsiRNA targeting human
      CD95L

<400> SEQUENCE: 52
aagauugacc ccggaaguau acuuugg                                             27

<210> SEQ ID NO 53
<211> LENGTH: 25
<212> TYPE: DNA
<213> ORGANISM: Artificial
<220> FEATURE:
<223> OTHER INFORMATION: Sense RNA oligo for dsiRNA targeting human
      CD95L including terminal deoxyadenine and deoxycytidine

<400> SEQUENCE: 53
cuuccggggu caaucuugca acaac                                               25

<210> SEQ ID NO 54
<211> LENGTH: 27
<212> TYPE: RNA
<213> ORGANISM: Artificial
<220> FEATURE:
<223> OTHER INFORMATION: Antisense RNA oligo for dsiRNA targeting human
      CD95L

<400> SEQUENCE: 54
guuguugcaa gauugacccc ggaagua                                             27

<210> SEQ ID NO 55
<211> LENGTH: 25
<212> TYPE: DNA
<213> ORGANISM: Artificial
<220> FEATURE:
<223> OTHER INFORMATION: Sense RNA oligos for dsiRNA non-targeting
      control for human CD95L including terminal deoxyadenine and
      deoxythymidine

<400> SEQUENCE: 55
cguuaaucgc guauaauacg cguat                                               25

<210> SEQ ID NO 56
<211> LENGTH: 27
<212> TYPE: RNA
<213> ORGANISM: Artificial
<220> FEATURE:
<223> OTHER INFORMATION: Antisense RNA oligo for dsiRNA non-targeting
      control for human CD95L

<400> SEQUENCE: 56
auacgcguau uauacgcgau uaacgac                                             27

<210> SEQ ID NO 57
<211> LENGTH: 25
<212> TYPE: DNA
<213> ORGANISM: Artificial
<220> FEATURE:
<223> OTHER INFORMATION: Forward primer for 3'UTR of human CD95

<400> SEQUENCE: 57
```

```
ggctaacccc actctatgaa tcaat                                        25
```

<210> SEQ ID NO 58
<211> LENGTH: 20
<212> TYPE: DNA
<213> ORGANISM: Artificial
<220> FEATURE:
<223> OTHER INFORMATION: Reverse primer for 3'UTR of human CD95

<400> SEQUENCE: 58

```
ggcctgcctg ttcagtaact                                              20
```

<210> SEQ ID NO 59
<211> LENGTH: 17
<212> TYPE: DNA
<213> ORGANISM: Homo sapiens

<400> SEQUENCE: 59

```
cctttttgctg aaatatc                                                17
```

<210> SEQ ID NO 60
<211> LENGTH: 22
<212> TYPE: DNA
<213> ORGANISM: Artificial
<220> FEATURE:
<223> OTHER INFORMATION: Forward primer for human CD95L

<400> SEQUENCE: 60

```
ggtggccttg tgatcaatga aa                                           22
```

<210> SEQ ID NO 61
<211> LENGTH: 23
<212> TYPE: DNA
<213> ORGANISM: Artificial
<220> FEATURE:
<223> OTHER INFORMATION: Reverse primer for human CD95L

<400> SEQUENCE: 61

```
gcaagattga ccccggaagt ata                                          23
```

<210> SEQ ID NO 62
<211> LENGTH: 21
<212> TYPE: DNA
<213> ORGANISM: Homo sapiens

<400> SEQUENCE: 62

```
ctgggctgta ctttgtatat t                                            21
```

<210> SEQ ID NO 63
<211> LENGTH: 21
<212> TYPE: DNA
<213> ORGANISM: Artificial
<220> FEATURE:
<223> OTHER INFORMATION: Forward primer for human CD95L

<400> SEQUENCE: 63

```
ccccaggatc tggtgatgat g                                            21
```

<210> SEQ ID NO 64
<211> LENGTH: 17
<212> TYPE: DNA
<213> ORGANISM: Artificial
<220> FEATURE:
<223> OTHER INFORMATION: Reverse primer for human CD95L

```
<400> SEQUENCE: 64
actgccccca ggtagct                                                      17

<210> SEQ ID NO 65
<211> LENGTH: 19
<212> TYPE: DNA
<213> ORGANISM: Homo sapiens

<400> SEQUENCE: 65
cccacatctg cccagtagt                                                    19

<210> SEQ ID NO 66
<211> LENGTH: 21
<212> TYPE: RNA
<213> ORGANISM: Homo sapiens

<400> SEQUENCE: 66
acugggcugu acuuuguaua u                                                 21

<210> SEQ ID NO 67
<211> LENGTH: 21
<212> TYPE: DNA
<213> ORGANISM: Artificial
<220> FEATURE:
<223> OTHER INFORMATION: Sense RNA oligo for dsiRNA targeting human
      CD95L including terminal deoxythymidine and deoxyadenine

<400> SEQUENCE: 67
gacugggcug uacuuuguat a                                                 21

<210> SEQ ID NO 68
<211> LENGTH: 21
<212> TYPE: DNA
<213> ORGANISM: Artificial
<220> FEATURE:
<223> OTHER INFORMATION: Antisense RNA oligo for dsiRNA targeting human
      CD95L including terminal dideoxythymidines

<400> SEQUENCE: 68
uacaaaguac agcccaguut t                                                 21

<210> SEQ ID NO 69
<211> LENGTH: 21
<212> TYPE: RNA
<213> ORGANISM: Homo sapiens

<400> SEQUENCE: 69
gugcagaugu aaaccaaacu u                                                 21

<210> SEQ ID NO 70
<211> LENGTH: 22
<212> TYPE: DNA
<213> ORGANISM: Artificial
<220> FEATURE:
<223> OTHER INFORMATION: Sense RNA oligo for dsiRNA targeting human CD95
      including terminal deoxycytidine and deoxythymidine

<400> SEQUENCE: 70
gggugcagau guaaaccaaa ct                                                22

<210> SEQ ID NO 71
<211> LENGTH: 22
<212> TYPE: DNA
<213> ORGANISM: Artificial
<220> FEATURE:
```

```
<223> OTHER INFORMATION: Antisense RNA oligo for dsiRNA targeting human
      CD95 including terminal dideoxythymidines

<400> SEQUENCE: 71
uuugguuuac aucugcacuu tt                                             22

<210> SEQ ID NO 72
<211> LENGTH: 143
<212> TYPE: DNA
<213> ORGANISM: Artificial
<220> FEATURE:
<223> OTHER INFORMATION: PCR inserts for generating shRNA libraries
      against human CD95 or CD95L
<220> FEATURE:
<221> NAME/KEY: misc_feature
<222> LOCATION: (1)..(26)
<223> OTHER INFORMATION: n is a, c, g, or t
<220> FEATURE:
<221> NAME/KEY: misc_feature
<222> LOCATION: (37)..(57)
<223> OTHER INFORMATION: n is a, c, g, or t
<220> FEATURE:
<221> NAME/KEY: misc_feature
<222> LOCATION: (64)..(84)
<223> OTHER INFORMATION: n is a, c, g, or t

<400> SEQUENCE: 72
nnnnnnnnnn nnnnnnnnnn nnnnnnatag agatcgnnnn nnnnnnnnnn nnnnnnnctc    60
gagnnnnnnn nnnnnnnnnn nnnnttttg taccgagctc ggatccacta gtccagtgtg    120
ggcatgctgc gttgacattg att                                           143

<210> SEQ ID NO 73
<211> LENGTH: 26
<212> TYPE: DNA
<213> ORGANISM: Artificial
<220> FEATURE:
<223> OTHER INFORMATION: Forward primer for human CD95L

<400> SEQUENCE: 73
tggctttata tatctcccta tcagtg                                         26

<210> SEQ ID NO 74
<211> LENGTH: 26
<212> TYPE: DNA
<213> ORGANISM: Artificial
<220> FEATURE:
<223> OTHER INFORMATION: Forward primer for human CD95L

<400> SEQUENCE: 74
ggtcgtccta tctattatta ttcacg                                         26

<210> SEQ ID NO 75
<211> LENGTH: 26
<212> TYPE: DNA
<213> ORGANISM: Artificial
<220> FEATURE:
<223> OTHER INFORMATION: Forward primer for human CD95

<400> SEQUENCE: 75
tcttgtgtcc agaccaattt atttcg                                         26

<210> SEQ ID NO 76
<211> LENGTH: 26
<212> TYPE: DNA
<213> ORGANISM: Artificial
<220> FEATURE:
<223> OTHER INFORMATION: Forward primer for human CD95
```

```
<400> SEQUENCE: 76
ctcattgact atcgttttag ctactg                                          26

<210> SEQ ID NO 77
<211> LENGTH: 26
<212> TYPE: DNA
<213> ORGANISM: Artificial
<220> FEATURE:
<223> OTHER INFORMATION: Forward primer for Venus control

<400> SEQUENCE: 77
tatcatcttt catgatgact ttccgg                                          26

<210> SEQ ID NO 78
<211> LENGTH: 20
<212> TYPE: DNA
<213> ORGANISM: Artificial
<220> FEATURE:
<223> OTHER INFORMATION: Reverse primer for generating shRNA libraries
      for human CD95 or for CD95L or for Venus control

<400> SEQUENCE: 78
aatcaatgtc aacgcagcat                                                 20

<210> SEQ ID NO 79
<211> LENGTH: 27
<212> TYPE: DNA
<213> ORGANISM: Artificial
<220> FEATURE:
<223> OTHER INFORMATION: Forward primer for human CD95L

<400> SEQUENCE: 79
ttggctttat atatctccct atcagtg                                         27

<210> SEQ ID NO 80
<211> LENGTH: 21
<212> TYPE: DNA
<213> ORGANISM: Artificial
<220> FEATURE:
<223> OTHER INFORMATION: Reverse primer for human CD95L

<400> SEQUENCE: 80
taatcaatgt caacgcagca t                                               21

<210> SEQ ID NO 81
<211> LENGTH: 28
<212> TYPE: DNA
<213> ORGANISM: Artificial
<220> FEATURE:
<223> OTHER INFORMATION: Forward primer for human CD95L

<400> SEQUENCE: 81
cttggcttta tatctcccc tatcagtg                                         28

<210> SEQ ID NO 82
<211> LENGTH: 22
<212> TYPE: DNA
<213> ORGANISM: Artificial
<220> FEATURE:
<223> OTHER INFORMATION: Reverse primer for human CD95L

<400> SEQUENCE: 82
ataatcaatg tcaacgcagc at                                              22
```

```
<210> SEQ ID NO 83
<211> LENGTH: 29
<212> TYPE: DNA
<213> ORGANISM: Artificial
<220> FEATURE:
<223> OTHER INFORMATION: Forward primer for human CD95L

<400> SEQUENCE: 83
tcttggcttt atatatctcc ctatcagtg                                29

<210> SEQ ID NO 84
<211> LENGTH: 23
<212> TYPE: DNA
<213> ORGANISM: Artificial
<220> FEATURE:
<223> OTHER INFORMATION: Reverse primer for human CD95L

<400> SEQUENCE: 84
aataatcaat gtcaacgcag cat                                      23

<210> SEQ ID NO 85
<211> LENGTH: 21
<212> TYPE: DNA
<213> ORGANISM: Homo sapiens

<400> SEQUENCE: 85
tgaccattaa actatgggat t                                        21

<210> SEQ ID NO 86
<211> LENGTH: 21
<212> TYPE: DNA
<213> ORGANISM: Homo sapiens

<400> SEQUENCE: 86
cgtatgggat tacaagaaca a                                        21

<210> SEQ ID NO 87
<211> LENGTH: 21
<212> TYPE: DNA
<213> ORGANISM: Homo sapiens

<400> SEQUENCE: 87
cctccagaac aagacctcat a                                        21

<210> SEQ ID NO 88
<211> LENGTH: 21
<212> TYPE: DNA
<213> ORGANISM: Homo sapiens

<400> SEQUENCE: 88
gcctacggct actaccagga t                                        21

<210> SEQ ID NO 89
<211> LENGTH: 21
<212> TYPE: DNA
<213> ORGANISM: Homo sapiens

<400> SEQUENCE: 89
gtgaggtcga aacaggataa a                                        21

<210> SEQ ID NO 90
<211> LENGTH: 21
<212> TYPE: DNA
<213> ORGANISM: Homo sapiens
```

```
<400> SEQUENCE: 90
cgacaggctc acattctact t                                              21

<210> SEQ ID NO 91
<211> LENGTH: 21
<212> TYPE: DNA
<213> ORGANISM: Homo sapiens

<400> SEQUENCE: 91
gcccaattta acgacacaga a                                              21

<210> SEQ ID NO 92
<211> LENGTH: 21
<212> TYPE: DNA
<213> ORGANISM: Homo sapiens

<400> SEQUENCE: 92
gactgaagtt atactcctta a                                              21

<210> SEQ ID NO 93
<211> LENGTH: 21
<212> TYPE: DNA
<213> ORGANISM: Homo sapiens

<400> SEQUENCE: 93
gagaccaaca aatagctgta t                                              21

<210> SEQ ID NO 94
<211> LENGTH: 21
<212> TYPE: DNA
<213> ORGANISM: Homo sapiens

<400> SEQUENCE: 94
cgcggcacaa acaccaagga t                                              21

<210> SEQ ID NO 95
<211> LENGTH: 21
<212> TYPE: DNA
<213> ORGANISM: Homo sapiens

<400> SEQUENCE: 95
catgccaatt tcagtgccat a                                              21

<210> SEQ ID NO 96
<211> LENGTH: 21
<212> TYPE: DNA
<213> ORGANISM: Homo sapiens

<400> SEQUENCE: 96
gccaatttca gtgccataca a                                              21

<210> SEQ ID NO 97
<211> LENGTH: 21
<212> TYPE: DNA
<213> ORGANISM: Homo sapiens

<400> SEQUENCE: 97
gacagaatag agccagacat a                                              21

<210> SEQ ID NO 98
<211> LENGTH: 21
<212> TYPE: DNA
<213> ORGANISM: Homo sapiens
```

```
<400> SEQUENCE: 98
gcccacatgt cctgatcata t                                              21

<210> SEQ ID NO 99
<211> LENGTH: 21
<212> TYPE: DNA
<213> ORGANISM: Homo sapiens

<400> SEQUENCE: 99
gctgcattac accaaggaga a                                              21

<210> SEQ ID NO 100
<211> LENGTH: 21
<212> TYPE: DNA
<213> ORGANISM: Homo sapiens

<400> SEQUENCE: 100
cgtactcaca tccatcaaca a                                              21

<210> SEQ ID NO 101
<211> LENGTH: 21
<212> TYPE: DNA
<213> ORGANISM: Homo sapiens

<400> SEQUENCE: 101
gcacatgctt cacagttaca t                                              21

<210> SEQ ID NO 102
<211> LENGTH: 21
<212> TYPE: DNA
<213> ORGANISM: Homo sapiens

<400> SEQUENCE: 102
gctttagttg atcaccatga t                                              21

<210> SEQ ID NO 103
<211> LENGTH: 21
<212> TYPE: DNA
<213> ORGANISM: Homo sapiens

<400> SEQUENCE: 103
ctcaagttca tgctgacgaa t                                              21

<210> SEQ ID NO 104
<211> LENGTH: 21
<212> TYPE: DNA
<213> ORGANISM: Homo sapiens

<400> SEQUENCE: 104
gcttgggtgt cctcacaatt t                                              21

<210> SEQ ID NO 105
<211> LENGTH: 21
<212> TYPE: DNA
<213> ORGANISM: Homo sapiens

<400> SEQUENCE: 105
cggagtgatt acgatggcat t                                              21

<210> SEQ ID NO 106
<211> LENGTH: 21
<212> TYPE: DNA
```

```
<213> ORGANISM: Homo sapiens

<400> SEQUENCE: 106
cgtagaatag tcgaacaaga t                                              21

<210> SEQ ID NO 107
<211> LENGTH: 21
<212> TYPE: DNA
<213> ORGANISM: Homo sapiens

<400> SEQUENCE: 107
gccatgagaa taccagcagt t                                              21

<210> SEQ ID NO 108
<211> LENGTH: 21
<212> TYPE: DNA
<213> ORGANISM: Homo sapiens

<400> SEQUENCE: 108
cgaaccaact tcaccagcaa a                                              21

<210> SEQ ID NO 109
<211> LENGTH: 21
<212> TYPE: DNA
<213> ORGANISM: Homo sapiens

<400> SEQUENCE: 109
cccagaaatc actgtgaaat t                                              21

<210> SEQ ID NO 110
<211> LENGTH: 21
<212> TYPE: DNA
<213> ORGANISM: Homo sapiens

<400> SEQUENCE: 110
gagttcacag aagcggtgga a                                              21

<210> SEQ ID NO 111
<211> LENGTH: 21
<212> TYPE: DNA
<213> ORGANISM: Homo sapiens

<400> SEQUENCE: 111
ccacctggac tcctatgaga a                                              21

<210> SEQ ID NO 112
<211> LENGTH: 21
<212> TYPE: DNA
<213> ORGANISM: Homo sapiens

<400> SEQUENCE: 112
cggcttctac tggagcgcag t                                              21

<210> SEQ ID NO 113
<211> LENGTH: 21
<212> TYPE: DNA
<213> ORGANISM: Homo sapiens

<400> SEQUENCE: 113
aggcagttca aatatagctt t                                              21

<210> SEQ ID NO 114
<211> LENGTH: 21
```

```
<212> TYPE: DNA
<213> ORGANISM: Homo sapiens

<400> SEQUENCE: 114
gcccacaaag atgccctata a                                           21

<210> SEQ ID NO 115
<211> LENGTH: 21
<212> TYPE: DNA
<213> ORGANISM: Homo sapiens

<400> SEQUENCE: 115
gcggcactgt cacttgttaa a                                           21

<210> SEQ ID NO 116
<211> LENGTH: 21
<212> TYPE: DNA
<213> ORGANISM: Homo sapiens

<400> SEQUENCE: 116
cagtatcaat tggactcaga a                                           21

<210> SEQ ID NO 117
<211> LENGTH: 21
<212> TYPE: DNA
<213> ORGANISM: Homo sapiens

<400> SEQUENCE: 117
cgacatgata gtcactgaca a                                           21

<210> SEQ ID NO 118
<211> LENGTH: 21
<212> TYPE: DNA
<213> ORGANISM: Homo sapiens

<400> SEQUENCE: 118
gacctcaaga gctccaatat c                                           21

<210> SEQ ID NO 119
<211> LENGTH: 21
<212> TYPE: DNA
<213> ORGANISM: Homo sapiens

<400> SEQUENCE: 119
actgggctgt actttgtata t                                           21

<210> SEQ ID NO 120
<211> LENGTH: 21
<212> TYPE: DNA
<213> ORGANISM: Homo sapiens

<400> SEQUENCE: 120
ggcacaagag gccctagatt t                                           21

<210> SEQ ID NO 121
<211> LENGTH: 21
<212> TYPE: DNA
<213> ORGANISM: Homo sapiens

<400> SEQUENCE: 121
acagtagagg agccgtcaaa t                                           21

<210> SEQ ID NO 122
```

```
<211> LENGTH: 21
<212> TYPE: DNA
<213> ORGANISM: Homo sapiens

<400> SEQUENCE: 122
gacttagact tgacctatat t                                              21

<210> SEQ ID NO 123
<211> LENGTH: 21
<212> TYPE: DNA
<213> ORGANISM: Homo sapiens

<400> SEQUENCE: 123
gacgaactgg tgtaatgata t                                              21

<210> SEQ ID NO 124
<211> LENGTH: 21
<212> TYPE: DNA
<213> ORGANISM: Homo sapiens

<400> SEQUENCE: 124
acattatgac accgccaaat t                                              21

<210> SEQ ID NO 125
<211> LENGTH: 21
<212> TYPE: DNA
<213> ORGANISM: Homo sapiens

<400> SEQUENCE: 125
caccatccac tacaactaca t                                              21

<210> SEQ ID NO 126
<211> LENGTH: 21
<212> TYPE: DNA
<213> ORGANISM: Homo sapiens

<400> SEQUENCE: 126
cggcgcacag aggaagagaa t                                              21

<210> SEQ ID NO 127
<211> LENGTH: 21
<212> TYPE: DNA
<213> ORGANISM: Homo sapiens

<400> SEQUENCE: 127
tcagacctat ggaaactact t                                              21

<210> SEQ ID NO 128
<211> LENGTH: 21
<212> TYPE: DNA
<213> ORGANISM: Homo sapiens

<400> SEQUENCE: 128
gtccagatga agctcccaga a                                              21

<210> SEQ ID NO 129
<211> LENGTH: 56
<212> TYPE: DNA
<213> ORGANISM: Artificial
<220> FEATURE:
<223> OTHER INFORMATION: Mutated siL3 sense sequence for human CD95L

<400> SEQUENCE: 129
ctcgagagct gccgtgcagc aggacttcaa ctagacatct ccccagatct actggg        56
```

<210> SEQ ID NO 130
<211> LENGTH: 57
<212> TYPE: DNA
<213> ORGANISM: Artificial
<220> FEATURE:
<223> OTHER INFORMATION: shRNA control sequence non-targeted to human
      CD95 and human CD95L

<400> SEQUENCE: 130
ccggcaacaa gatgaagagc accaactcga gttggtgctc ttcatcttgt tgttttt        57

<210> SEQ ID NO 131
<211> LENGTH: 58
<212> TYPE: DNA
<213> ORGANISM: Artificial
<220> FEATURE:
<223> OTHER INFORMATION: shRNA sequence for targeting human CD95L

<400> SEQUENCE: 131
ccggactggg ctgtactttg tatatctcga gatatacaaa gtacagccca gttttttg       58

<210> SEQ ID NO 132
<211> LENGTH: 58
<212> TYPE: DNA
<213> ORGANISM: Artificial
<220> FEATURE:
<223> OTHER INFORMATION: shRNA sequence for targeting human CD95

<400> SEQUENCE: 132
ccgggtgcag atgtaaacca aacttctcga gaagtttggt ttacatctgc acttttg        58

<210> SEQ ID NO 133
<211> LENGTH: 22
<212> TYPE: DNA
<213> ORGANISM: Artificial
<220> FEATURE:
<223> OTHER INFORMATION: 5' guide sequence for performing knock-out of
      human CD95L via CRISPR

<400> SEQUENCE: 133
ttgtgggcgg aaacttccag gg                                              22

<210> SEQ ID NO 134
<211> LENGTH: 22
<212> TYPE: DNA
<213> ORGANISM: Artificial
<220> FEATURE:
<223> OTHER INFORMATION: 3' guide sequence for performing knock-out of
      human CD95L via CRISPR

<400> SEQUENCE: 134
gtactgccta tgtaagcact gg                                              22

<210> SEQ ID NO 135
<211> LENGTH: 455
<212> TYPE: DNA
<213> ORGANISM: Artificial
<220> FEATURE:
<223> OTHER INFORMATION: G-block sequence encoding 5' guide sequence for
      performing knock-out of human CD95L via CRISPR

<400> SEQUENCE: 135
tgtacaaaaa agcaggcttt aaaggaacca attcagtcga ctggatccgg taccaaggtc     60
gggcaggaag agggcctatt tcccatgatt ccttcatatt tgcatatacg atacaaggct    120

```
gttagagaga taattagaat taatttgact gtaaacacaa agatattagt acaaaatacg      180
tgacgtagaa agtaataatt tcttgggtag tttgcagttt taaaattatg ttttaaaatg      240
gactatcata tgcttaccgt aacttgaaag tatttcgatt tcttggcttt atatatcttg      300
tggaaaggac gaaacaccgt tgtgggcgga aacttccagt tttagagcta gaaatagcaa      360
gttaaaataa ggctagtccg ttatcaactt gaaaaagtgg caccgagtcg gtgcttttt      420 tctagaccca gctttcttgt acaaagttgg catta                                455
```

```
<210> SEQ ID NO 136
<211> LENGTH: 455
<212> TYPE: DNA
<213> ORGANISM: Artificial
<220> FEATURE:
<223> OTHER INFORMATION: G-block sequence encoding 3' guide sequence for
      performing knock-out of human CD95L via CRISPR

<400> SEQUENCE: 136
tgtacaaaaa agcaggcttt aaaggaacca attcagtcga ctggatccgg taccaaggtc       60
gggcaggaag agggcctatt tcccatgatt ccttcatatt tgcatatacg atacaaggct      120
gttagagaga taattagaat taatttgact gtaaacacaa agatattagt acaaaatacg      180
tgacgtagaa agtaataatt tcttgggtag tttgcagttt taaaattatg ttttaaaatg      240
gactatcata tgcttaccgt aacttgaaag tatttcgatt tcttggcttt atatatcttg      300
tggaaaggac gaaacaccgt aatagagtgg cttagtaggt tttagagcta gaaatagcaa      360
gttaaaataa ggctagtccg ttatcaactt gaaaaagtgg caccgagtcg gtgcttttt      420 tctagaccca gctttcttgt acaaagttgg catta                                455
```

```
<210> SEQ ID NO 137
<211> LENGTH: 24
<212> TYPE: DNA
<213> ORGANISM: Artificial
<220> FEATURE:
<223> OTHER INFORMATION: Forward primer for detecting deletion of human
      CD95L

<400> SEQUENCE: 137
cataaaatta tagccccact gacc                                              24
```

```
<210> SEQ ID NO 138
<211> LENGTH: 24
<212> TYPE: DNA
<213> ORGANISM: Artificial
<220> FEATURE:
<223> OTHER INFORMATION: Reverse primer for detecting delection of human
      CD95L

<400> SEQUENCE: 138
ctgggatgac agcttaaaga aaat                                              24
```

```
<210> SEQ ID NO 139
<211> LENGTH: 24
<212> TYPE: DNA
<213> ORGANISM: Artificial
<220> FEATURE:
<223> OTHER INFORMATION: Forward primer for detecting deletion of human
      CD95L

<400> SEQUENCE: 139
gtggtaggct attgtccctg gaat                                              24
```

<210> SEQ ID NO 140
<211> LENGTH: 24
<212> TYPE: DNA
<213> ORGANISM: Artificial
<220> FEATURE:
<223> OTHER INFORMATION: Reverse primer for detecting deletion of human
      CD95L

<400> SEQUENCE: 140
tgcaagattg accccggaag tata                                            24

<210> SEQ ID NO 141
<211> LENGTH: 19
<212> TYPE: RNA
<213> ORGANISM: Artificial
<220> FEATURE:
<223> OTHER INFORMATION: Non-targeting siRNA sequence for mammalian
      cells

<400> SEQUENCE: 141
ugguuuacau gucgacuaa                                                  19

<210> SEQ ID NO 142
<211> LENGTH: 19
<212> TYPE: RNA
<213> ORGANISM: Homo sapiens

<400> SEQUENCE: 142
caacguaucu gagcucucu                                                  19

<210> SEQ ID NO 143
<211> LENGTH: 19
<212> TYPE: RNA
<213> ORGANISM: Homo sapiens

<400> SEQUENCE: 143
gcccuucaau uacccauau                                                  19

<210> SEQ ID NO 144
<211> LENGTH: 19
<212> TYPE: RNA
<213> ORGANISM: Artificial
<220> FEATURE:
<223> OTHER INFORMATION: siRNA sequence for targeting human CD95L with 6
      mutations

<400> SEQUENCE: 144
ggacuucaac uagacaucu                                                  19

<210> SEQ ID NO 145
<211> LENGTH: 7
<212> TYPE: PRT
<213> ORGANISM: Homo sapiens

<400> SEQUENCE: 145

Ala Ser Ser Leu Glu Lys Gln
1               5

<210> SEQ ID NO 146
<211> LENGTH: 7
<212> TYPE: PRT
<213> ORGANISM: Homo sapiens

<400> SEQUENCE: 146

Thr Gly Leu Tyr Phe Val Tyr
1               5

<210> SEQ ID NO 147
<211> LENGTH: 21
<212> TYPE: DNA
<213> ORGANISM: Artificial
<220> FEATURE:
<223> OTHER INFORMATION: Mutated sequence from human CD95L

<400> SEQUENCE: 147
gcctcgtccc tagaaaaaca g                                           21

<210> SEQ ID NO 148
<211> LENGTH: 21
<212> TYPE: DNA
<213> ORGANISM: Artificial
<220> FEATURE:
<223> OTHER INFORMATION: Mutated sequence from human CD95L

<400> SEQUENCE: 148
accggattat atttcgtgta c                                           21

<210> SEQ ID NO 149
<211> LENGTH: 21
<212> TYPE: DNA
<213> ORGANISM: Homo sapiens

<400> SEQUENCE: 149
gtgcagatgt aaaccaaact t                                           21

<210> SEQ ID NO 150
<211> LENGTH: 7
<212> TYPE: PRT
<213> ORGANISM: Homo sapiens

<400> SEQUENCE: 150

Cys Arg Cys Lys Pro Asn Phe
1               5

<210> SEQ ID NO 151
<211> LENGTH: 22
<212> TYPE: DNA
<213> ORGANISM: Artificial
<220> FEATURE:
<223> OTHER INFORMATION: DNA encoding gRNA targeting human CD95L

<400> SEQUENCE: 151
taaaaccgtt tgctggggct gg                                          22

<210> SEQ ID NO 152
<211> LENGTH: 22
<212> TYPE: DNA
<213> ORGANISM: Artificial
<220> FEATURE:
<223> OTHER INFORMATION: DNA encoding gRNA targeting human CD95L

<400> SEQUENCE: 152
tatccccaga tctactgggt gg                                          22

<210> SEQ ID NO 153
<211> LENGTH: 22
<212> TYPE: DNA
<213> ORGANISM: Artificial
<220> FEATURE:
<223> OTHER INFORMATION: DNA encoding gRNA targeting human CD95L

<400> SEQUENCE: 153
ccttgtgatc aatgaaactg gg                                          22

<210> SEQ ID NO 154
<211> LENGTH: 22
<212> TYPE: DNA
<213> ORGANISM: Artificial
<220> FEATURE:
<223> OTHER INFORMATION: DNA encoding gRNA targeting human CD95L

<400> SEQUENCE: 154
cccgggtcaa tcttgcaaca ac                                          22

<210> SEQ ID NO 155
<211> LENGTH: 22
<212> TYPE: DNA
<213> ORGANISM: Artificial
<220> FEATURE:
<223> OTHER INFORMATION: DNA encoding gRNA targeting human CD95

<400> SEQUENCE: 155
ccggacccag aataccaagt gc                                          22

<210> SEQ ID NO 156
<211> LENGTH: 22
<212> TYPE: DNA
<213> ORGANISM: Artificial
<220> FEATURE:
<223> OTHER INFORMATION: DNA encoding gRNA targeting human CD95

<400> SEQUENCE: 156
tgtttgctca tttaaacact gg                                          22

<210> SEQ ID NO 157
<211> LENGTH: 19
<212> TYPE: RNA
<213> ORGANISM: Artificial
<220> FEATURE:
<223> OTHER INFORMATION: Antisense guide strand for siRNA targeting
      human CD95L with passenger strand of SEQ ID NO:143

<400> SEQUENCE: 157
auauggguaa uugaagggc                                              19

<210> SEQ ID NO 158
<211> LENGTH: 19
<212> TYPE: RNA
<213> ORGANISM: Artificial
<220> FEATURE:
<223> OTHER INFORMATION: Guide strand for control siRNA including
      scrambled sequence of SEQ ID NO:37

<400> SEQUENCE: 158
ucaaacaaca uguaaacca                                              19

<210> SEQ ID NO 159
<211> LENGTH: 57
<212> TYPE: DNA
<213> ORGANISM: Artificial
<220> FEATURE:
<223> OTHER INFORMATION: DNA encoding shRNA targeting human CD95L

<400> SEQUENCE: 159
ccggactggg ctgtactttg tatatctcga gatatacaaa gtacagccca gtttttt    57

<210> SEQ ID NO 160

```
<211> LENGTH: 58
<212> TYPE: DNA
<213> ORGANISM: Artificial
<220> FEATURE:
<223> OTHER INFORMATION: DNA encoding shRNA targeting human CD95

<400> SEQUENCE: 160
ccgggtgcag atgtaaacca aacttctcga gaagtttggt ttacatctgc acttttttg      58

<210> SEQ ID NO 161
<211> LENGTH: 21
<212> TYPE: DNA
<213> ORGANISM: Artificial
<220> FEATURE:
<223> OTHER INFORMATION: Sequence of passenger strand for non-toxic
      scaffold of siRNA library
<220> FEATURE:
<221> NAME/KEY: misc_feature
<222> LOCATION: (13)..(18)
<223> OTHER INFORMATION: n is a, c, g, t or u

<400> SEQUENCE: 161
cgguuuacau gunnnnnnat t                                               21

<210> SEQ ID NO 162
<211> LENGTH: 21
<212> TYPE: DNA
<213> ORGANISM: Artificial
<220> FEATURE:
<223> OTHER INFORMATION: Sequence of guide strand for non-toxic scaffold
      of siRNA library
<220> FEATURE:
<221> NAME/KEY: misc_feature
<222> LOCATION: (2)..(7)
<223> OTHER INFORMATION: n is a, c, g, t or u

<400> SEQUENCE: 162
unnnnnnaca uguaaaccga a                                               21

<210> SEQ ID NO 163
<211> LENGTH: 19
<212> TYPE: DNA
<213> ORGANISM: Homo sapien

<400> SEQUENCE: 163
tcagtgcact acagaactt                                                  19

<210> SEQ ID NO 164
<211> LENGTH: 19
<212> TYPE: DNA
<213> ORGANISM: Homo sapiens

<400> SEQUENCE: 164
tcagtgcact acagaactt                                                  19

<210> SEQ ID NO 165
<211> LENGTH: 19
<212> TYPE: DNA
<213> ORGANISM: Homo sapiens

<400> SEQUENCE: 165
tgagatgaag cactgtagc                                                  19

<210> SEQ ID NO 166
<211> LENGTH: 19
<212> TYPE: DNA
<213> ORGANISM: Homo sapiens
```

```
<400> SEQUENCE: 166
tgagatgaag cactgtagc                                              19

<210> SEQ ID NO 167
<211> LENGTH: 19
<212> TYPE: DNA
<213> ORGANISM: Homo sapiens

<400> SEQUENCE: 167
gagcttatca gactgatgt                                              19

<210> SEQ ID NO 168
<211> LENGTH: 19
<212> TYPE: DNA
<213> ORGANISM: Homo sapiens

<400> SEQUENCE: 168
gagcttatca gactgatgt                                              19

<210> SEQ ID NO 169
<211> LENGTH: 19
<212> TYPE: DNA
<213> ORGANISM: Homo sapiens

<400> SEQUENCE: 169
aagctgggtt gagagggcg                                              19

<210> SEQ ID NO 170
<211> LENGTH: 19
<212> TYPE: DNA
<213> ORGANISM: Homo sapiens

<400> SEQUENCE: 170
aaaagctggg ttgagaggg                                              19

<210> SEQ ID NO 171
<211> LENGTH: 19
<212> TYPE: DNA
<213> ORGANISM: Homo sapiens

<400> SEQUENCE: 171
aagctgggtt gagagggcg                                              19

<210> SEQ ID NO 172
<211> LENGTH: 19
<212> TYPE: DNA
<213> ORGANISM: Homo sapiens

<400> SEQUENCE: 172
aaaagctggg ttgagaggg                                              19
```